US009090632B2

(12) United States Patent
Conn et al.

(10) Patent No.: US 9,090,632 B2
(45) Date of Patent: Jul. 28, 2015

(54) BICYCLIC OXAZOLE AND THIAZOLE COMPOUNDS AND THEIR USE AS ALLOSTERIC MODULATORS OF MGLUR5 RECEPTORS

(75) Inventors: P. Jeffrey Conn, Brentwood, TN (US); Craig W. Lindsley, Brentwood, TN (US); Shaun R. Stauffer, Brentwood, TN (US); Carrie K. Jones, Nashville, TN (US); Jose Manuel Bartolome-Nebreda, Toledo (ES); Susana Conde-Ceide, Toledo (ES); Gregor James Macdonald, Boorse (BE); Manuel Jesus Alcazar Vaca, Toledo (ES)

(73) Assignee: Vanderbilt University, Nashville, TN (US)

( * ) Notice: Subject to any disclaimer, the term of this patent is extended or adjusted under 35 U.S.C. 154(b) by 113 days.

(21) Appl. No.: 13/819,273

(22) PCT Filed: Aug. 31, 2011

(86) PCT No.: PCT/US2011/050066
§ 371 (c)(1),
(2), (4) Date: May 13, 2013

(87) PCT Pub. No.: WO2012/031024
PCT Pub. Date: Mar. 8, 2012

(65) Prior Publication Data
US 2013/0261107 A1    Oct. 3, 2013

Related U.S. Application Data

(60) Provisional application No. 61/378,805, filed on Aug. 31, 2010, provisional application No. 61/497,512, filed on Jun. 15, 2011.

(51) Int. Cl.
*C07D 513/04* (2006.01)
*C07D 498/04* (2006.01)

(52) U.S. Cl.
CPC ............ *C07D 513/04* (2013.01); *C07D 498/04* (2013.01)

(58) Field of Classification Search
CPC ..................................................... C07D 513/04
See application file for complete search history.

(56) References Cited

U.S. PATENT DOCUMENTS

2006/0128713 A1*  6/2006  Jolidon et al. ............... 514/250
2009/0270362 A1   10/2009  Conn et al.
2010/0081690 A1   4/2010   Le Poul et al.

FOREIGN PATENT DOCUMENTS

| CA | 2806103 | 3/2012 |
|---|---|---|
| EP | 2611298 | 7/2013 |
| WO | WO-2006/074884 A1 | 7/2006 |
| WO | WO-2008/012010 A1 | 1/2008 |
| WO | WO-2010/114971 A1 | 10/2010 |
| WO | WO-2012/031024 | 3/2012 |

OTHER PUBLICATIONS

U.S. Appl. No. 61/378,805, Conn et al.
U.S. Appl. No. 61/497,512, Conn et al.
Almarasson O, et al. (2004) Crystal Engineering of the Composition of Pharmaceutical Phases. Do Pharmaceutical Co-crystals Represent a New Path to Improved Medicines? Chem. Comm., 17: 1889-1896.
Awad H, et al. (2000) Activation of Metabotropic Glutamate Receptor 5 Has Direct Excitatory Effects and Potentiates NMDA Receptor Currents in Neurons of the Subthalamic Nucleus. The Journal of Neuroscience, 20(21): 7871-7879.
Chavez-Noriega L, et al. (2002) Metabotropic Glutamate Receptors: Potential Drug Targets for the Treatment of Schizophrenia. Current Drug Targets—CNS & Neurological Disorders, 1: 261-281.
Chiamulera C, et al. (2001) Reinforcing and locomotor stimulant effects of cocaine are absent in mGluR5 null mutant mice. Nature, 4(9): 873-874.
Collison CG, et al. (2006) The First Total Synthesis of the Proposed Structure of Montiporyne E. Synthesis, 14: 2319-2322.
Kew JN, et al. (2005) Ionotropic and metabotropic glutamate receptor structure and pharmacology. Psychopharmacol., 179: 4-29.
Kinney G, et al. (2005) A Novel Selective Positive Allosteric Modulator of Metabotropic Glutamate Receptor Subtype 5 Has in Vivo Activity and Antipsychotic-Like Effects in Rat Behavioral Models. The Journal of Pharmacology and Experimental Therapeutics, 313(1): 199-206.
Malherbe, et al. (2003) Mutational Analysis and Molecular Modeling of the Binding Pocket of the Metabotropic Glutamate 5 Receptor Negative modulator 2-Methyl-6-(phenylethynyl)-pyridine. Mol. Pharmacol., 64: 823-832. http://molpharm.aspetjournals.org/content/64/4/823.full.pdf.
Mannaioni G, et al. (2001) Metabotropic Glutamate Receptors 1 and 5 Differentially Regulate CA1 Pyramidal Cell Function. J. Neurosci., 21(6): 5925-5934.
Mutel V, et al. (2002) Therapeutic potential of non-competitive, subtype-selective metabotropic glutamate receptor ligands. Expert Opin. Ther. Patents, 12(12): 79-110.

(Continued)

*Primary Examiner* — David K O Dell
(74) *Attorney, Agent, or Firm* — Ballard Spahr LLP

(57) ABSTRACT

In one aspect, the invention relates to novel bicyclic oxazole and thiazole compounds which are positive allosteric modulators of the metabotropic glutamate receptor subtype 5 ("mGluR5"); synthetic methods for making the compounds; pharmaceutical compositions comprising the compounds; methods of treating neurological and psychiatric disorders associated with glutamate dysfunction using the compounds and compositions; and methods for the treatment or prevention of disorders associated with glutamate dysfunction and diseases in which the mGluR5 subtype of receptors is involved. This abstract is intended as a scanning tool for purposes of searching in the particular art and is not intended to be limiting of the present invention.

7 Claims, 5 Drawing Sheets

(56) References Cited

OTHER PUBLICATIONS

Ossowska K, et al. (2001) Blockade of the metabotropic glutamate receptor subtype 5 (mGluR5) produces antiparkinsonian-like effects in rats. Neuropharmacology 41: 413-420.

Salt T, et al. (2000) Contributions of mGlu1 and mGlu5 Receptors to Interactions with N-Methyl-D-Aspartate Receptor-Mediated Responses and Nociceptive Sensory Responses of Rat Thalamic Neurons. Neuroscience, 100(2): 375-380.

Schoepp DD, et al. (1999) Pharmacological agents acting at subtypes of metabotropic glutamate receptors. Neuropharmacology, 38(10): 1431-1476.

Spooren W, et al. (2000) Anxiolytic-Like Effects of the Prototypical Metabotropic Glutamate Receptor 5 Antagonist 2-Methyl-6-(phenylethynyl)pyridine in Rodents. J Pharmacol Exp Ther, 295(3): 1267-1275.

Tatarczynska E, et al. (2001) Potential anxiolytic- and antidepressant-like effects of MPEP, a potent, selective and systemically active mGLu5 receptor antagonist. British Journal of Pharmacology, 132: 1423-1430.

International Preliminary Report on Patentability issued on Mar. 5, 2013 for PCT/US2011/050066 filed on Aug. 31, 2011 and published as WO 2012/031024 on Mar. 8, 2012 (Applicant—Vanderbilt University; Inventors—Conn, et al.) (6 pages).

International Search Report mailed on Feb. 1, 2012 for PCT/US2011/050066 filed on Aug. 31, 2011 and published as WO 2012/031024 on Mar. 8, 2012 (Applicant—Vanderbilt University; Inventors—Conn, et al.) (2 pages).

Written Opinion mailed on Feb. 1, 2012 for PCT/US2011/050066 filed on Aug. 31, 2011 and published as WO 2012/031024 on Mar. 8, 2012 (Applicant—Vanderbilt University; Inventors—Conn, et al.) (5 pages).

\* cited by examiner

BICYCLIC OXAZOLE AND THIAZOLE COMPOUNDS AND THEIR USE AS ALLOSTERIC MODULATORS OF MGLUR5 RECEPTORS

CROSS-REFERENCE TO RELATED APPLICATIONS

The present application is a U.S. National Phase Application of International Application No. PCT/US2011/050066, filed Aug. 31, 2011, which claims the benefit of U.S. Provisional Application No. 61/378,805, filed Aug. 31, 2010, and U.S. Provisional Application No. 61/497,512, filed Jun. 15, 2011, all of which applications are incorporated herein fully by this reference.

BACKGROUND

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), and the NMDA, AMPA and kainate receptors which are responsible for fast excitatory transmission (Kew and Kemp Psychopharmacol., (2005), 179:4-29). In addition, glutamate activates metabotropic glutamate receptors (mGluRs) which have a more modulatory role that contributes to the fine tuning of synaptic efficacy.

Glutamate activates the mGluRs through binding to the large extracellular amino terminal domain of the receptor, herein called the orthosteric binding site. This binding induces a conformational change in the receptor which results in the activation of the G protein and intracellular signaling pathways. mGluR5 and NMDA receptors are co-expressed in hippocampus, cortex and striatum. mGluR5 potentiates NMDA receptor function via a PKC- and Src-dependent mechanism. Blockade of mGluR5 or NMDA receptors impairs cognitive function whereas activation of mGluR5 or NMDA receptors normalizes amphetamine-disrupted prepulse inhibition (PPI). Stimulation of mGluR5 receptors is postulated to normalize the NMDA receptor hypofunction which is hypothesised to occur in schizophrenia. An mGluR5 positive allosteric modulator (PAM) may have beneficial effects on cognition and positive and negative symptoms of schizophrenia, and cognitive deficits in various forms of dementia and mild cognitive impairment.

To date, most of the available pharmacological tools targeting mGluRs are orthosteric ligands which cross-react with several members of the family as they are structural analogs of glutamate and have limited bioavailability (Schoepp D. D. et al. Neuropharmacology (1999), 38(10), 1431-1476). A new avenue for developing selective compounds acting at mGluRs is to identify molecules that act through allosteric mechanisms, modulating the receptor by binding to a site different from the highly conserved glutamate binding site. Positive allosteric modulators of mGluRs have emerged recently as novel pharmacological entities offering this attractive alternative. This type of molecule has been discovered for several mGluRs (reviewed in Mutel (2002) Expert Opin. Ther. Patents 12:1-8).

WO 2008/012010 A1 (UCB Pharma, S.A.) published on Jan. 31, 2008 discloses fused oxazoles and thiazoles as Histamine H3-receptor ligands and US 2010/0081690 (Addex Pharma, S.A.) published on Apr. 1, 2010 discloses oxazole derivatives as positive allosteric modulators of mGluR5.

Unfortunately, there is a scarcity of selective positive allosteric modulators for the mGluR5 receptor. Further, conventional mGluR5 receptor modulators typically lack satisfactory aqueous solubility and exhibit poor oral bioavailability. Therefore, there remains a need for methods and compositions that overcome these deficiencies and that effectively provide selective positive allosteric modulators for the mGluR5 receptor.

SUMMARY

It is the object of the present invention to provide novel compounds with an improved balance of properties over the prior compounds, in particular, the novel compounds according to the invention are selective positive allosteric modulators of mGluR5 and display advantageous properties such as satisfactory aqueous solubility, and oral bioavailability, central penetration, and/or improved pharmacokinetic and metabolism and excretion (ADME) properties. In accordance with the purpose(s) of the invention, as embodied and broadly described herein, the invention, in one aspect, relates to compounds useful as positive allosteric modulators (e.g., potentiators) of the metabotropic glutamate receptor subtype 5 (mGluR5), methods of making same, pharmaceutical compositions comprising same, and methods of treating neurological and psychiatric disorders associated with glutamate dysfunction using same.

Disclosed are compounds having a structure represented by a Formula (I):

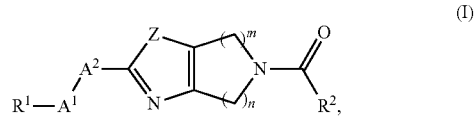

wherein Z is O or S; wherein each of m and n is independently selected from 1, 2, and 3; wherein -$A^1$-$A^2$- is selected from —$OCH_2$—, —$CH_2O$—, —$CH_2CH_2$—, and —CH=CH—; wherein $R^1$ is aryl or heteroaryl and substituted with 0, 1, 2, or 3 groups each independently selected from cyano, halo, hydroxyl, trialkylsiloxyl, $C_{1-4}$-alkyl, $C_{1-4}$-alkyloxy, monohalo-$C_{1-4}$-alkyl, and polyhalo-$C_{1-4}$-alkyl; wherein $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, —$NH_2$, $C_{1-4}$-alkyl, $C_{1-4}$-alkyloxy, monohalo-$C_{1-4}$-alkyl, polyhalo-$C_{1-4}$-alkyl, $C_{1-4}$-alkyloxycarbonylamino, aryloxy-$C_{1-4}$-alkyl, aryloxy-$C_{1-4}$-alkyl, aryl-$C_{3-8}$-cycloalkyl, polyhalo-$C_{1-4}$-alkyloxy, $C_{1-4}$-alkyloxy-$C_{1-4}$-alkyl, $C_{1-4}$-alkyloxy-$C_{1-4}$-alkylheterocyclyl, and heterocyclyl substituted with carbonyl; or wherein $R^2$ is selected from $Ar^1$, $Ar^1$—$C_{1-6}$-alkyl-, $Ar^1$-$C_{3-8}$-cycloalkyl-, $Ar^1$-oxy-$C_{1-4}$-alkyl; $Ar^2$, $Ar^2$-$C_{1-6}$-alkyl-, $Ar^2$-$C_{3-8}$-cycloalkyl-, $Ar^2$-oxy-$C_{1-4}$-alkyl; $Ar^3$, $Ar^3$-$C_{1-6}$-alkyl-, $Ar^1$-oxy-$C_{1-4}$-alkyl; $Ar^3$-$C_{3-8}$-cycloalkyl-, and $Ar^3$-oxy-$C_{1-4}$-alkyl; wherein $Ar^1$, when present, is phenyl substituted with 0, 1, 2, or 3 groups each independently selected from halo, cyano, —$NH_2$, monoalkylamino, dialkylamino, $C_{1-4}$-alkyl, $C_{1-4}$-alkyloxy, $C_{1-4}$-alkyloxy-$C_{1-4}$-alkyl, monohalo-$C_{1-4}$-alkyl, polyhalo-$C_{1-4}$-alkyl, polyhalo-$C_{1-4}$-alkyloxy, and pentafluorosulfanyl; wherein $Ar^2$, when present, is monocyclic heterocyclyl substituted with 0, 1, 2, or 3 groups each independently selected from halo, cyano, —$NH_2$, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $Ar^3$, when present, is bicyclic heterocyclyl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $R^3$ is selected from $Ar^4$ and $Ar^4$-$C_{1-6}$-alkyl-; wherein $Ar^4$, when present, is phenyl substituted with 0, 1, 2, or 3 groups each independently selected from halo, cyano, $C_{1-4}$-alkyl, $C_{1-4}$-alkyloxy, monohalo-$C_{1-4}$-alkyl, and polyhalo-$C_{1-4}$-alkyl; or a pharmaceutically acceptable salt, hydrate, solvate, or polymorph thereof.

Also disclosed are compounds having a structure represented by a Formula (I):

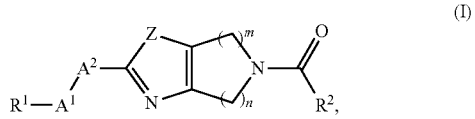

wherein Z is O or S; wherein each of m and n is independently selected from 1, 2, and 3; wherein -$A^1$-$A^2$- is selected from —$OCH_2$—, —$CH_2O$—, —$CH_2CH_2$—, and —CH═CH—; wherein $R^1$ is six-membered monocyclic aryl or six-membered monocyclic heteroaryl (e.g., phenyl, pyridinyl, pyrazinyl, pyridazinyl, or pyrimidinyl) and substituted with 0, 1, 2, or 3 groups each independently selected from cyano, halo, hydroxyl, trialkylsiloxyl, $C_{1-4}$-alkyl, $C_{1-4}$-alkyloxy, monohalo-$C_{1-4}$-alkyl, and polyhalo-$C_{1-4}$-alkyl; wherein $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, —$NH_2$, $C_{1-4}$-alkyl, $C_{1-4}$-alkyloxy, monohalo-$C_{1-4}$-alkyl, polyhalo-$C_{1-4}$-alkyl, $C_{1-4}$-alkyloxycarbonylamino, aryloxy-$C_{1-4}$-alkyl, aryloxy-$C_{1-4}$-alkyl, aryl-$C_{3-8}$-cycloalkyl, polyhalo-$C_{1-4}$-alkyloxy, $C_{1-4}$-alkyloxy-$C_{1-4}$-alkyl, $C_{1-4}$-alkyloxy-$C_{1-4}$-alkylheterocyclyl, and heterocyclyl substituted with carbonyl; or wherein $R^2$ is selected from $Ar^1$, $Ar^1$-$C_{1-6}$-alkyl-, $Ar^1$-$C_{3-8}$-cycloalkyl-, $Ar^1$-oxy-$C_{1-4}$-alkyl; $Ar^2$, $Ar^2$-$C_{1-6}$-alkyl-, $Ar^2$-$C_{3-8}$-cycloalkyl-, $Ar^2$-oxy-$C_{1-4}$-alkyl; $Ar^3$, $Ar^3$-$C_{1-6}$-alkyl-, $Ar^1$-oxy-$C_{1-4}$-alkyl; $Ar^3$-$C_{3-8}$-cycloalkyl-, and $Ar^3$-oxy-$C_{1-4}$-alkyl; wherein $Ar^1$, when present, is phenyl substituted with 0, 1, 2, or 3 groups each independently selected from halo, cyano, —$NH_2$, monoalkylamino, dialkylamino, $C_{1-4}$-alkyl, $C_{1-4}$-alkyloxy, $C_{1-4}$-alkyloxy-$C_{1-4}$-alkyl, monohalo-$C_{1-4}$-alkyl, polyhalo-$C_{1-4}$-alkyl, polyhalo-$C_{1-4}$-alkyloxy, and pentafluorosulfanyl; wherein $Ar^2$, when present, is monocyclic heterocyclyl substituted with 0, 1, 2, or 3 groups each independently selected from halo, cyano, —$NH_2$, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $Ar^3$, when present, is bicyclic heterocyclyl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $R^3$ is selected from $Ar^4$ and $Ar^4$-$C_{1-6}$-alkyl-; wherein $Ar^4$, when present, is phenyl substituted with 0, 1, 2, or 3 groups each independently selected from halo, cyano, $C_{1-4}$-alkyl, $C_{1-4}$-alkyloxy, monohalo-$C_{1-4}$-alkyl, and polyhalo-$C_{1-4}$-alkyl; or a pharmaceutically acceptable salt, hydrate, solvate, or polymorph thereof.

Also disclosed are pharmaceutical compositions comprising a therapeutically effective amount of one or more disclosed compounds, or pharmaceutically acceptable salt, hydrate, solvate, or polymorph thereof, and a pharmaceutically acceptable carrier.

Also disclosed are methods for the treatment of a neurological and/or psychiatric disorder associated with glutamate dysfunction in a mammal comprising the step of administering to the mammal a therapeutically effective amount of at least one disclosed compound or pharmaceutically acceptable salt, hydrate, solvate, or polymorph thereof.

Also disclosed are methods for enhancing cognition in a mammal comprising the step of administering to the mammal an effective amount of at least one disclosed compound or pharmaceutically acceptable salt, hydrate, solvate, or polymorph thereof.

Also disclosed are methods for modulating mGluR5 activity in a mammal comprising the step of administering to the mammal an effective amount of at least one disclosed compound or pharmaceutically acceptable salt, hydrate, solvate, or polymorph thereof.

Also disclosed are methods modulating mGluR5 activity in at least one cell, comprising the step of contacting the at least one cell with an effective amount of at least one disclosed compound or pharmaceutically acceptable salt, hydrate, solvate, or polymorph thereof.

Also disclosed are kits comprising at least one disclosed compound, or pharmaceutically acceptable salt, hydrate, solvate, or polymorph thereof, and one or more of: (a) at least one agent known to increase mGluR5 activity; (b) at least one agent known to decrease mGluR5 activity; (c) at least one agent known to treat a neurological and/or psychiatric disorder; (d) at least one agent known to treat a disease of uncontrolled cellular proliferation; or (e) instructions for treating a disorder associated with glutamate dysfunction.

Also disclosed are methods for manufacturing a medicament comprising combining at least one disclosed compound, or pharmaceutically acceptable salt, hydrate, solvate, or polymorph thereof, or at least one disclosed product with a pharmaceutically acceptable carrier or diluent.

Also disclosed are uses of a disclosed compound, or pharmaceutically acceptable salt, hydrate, solvate, or polymorph thereof, or a disclosed product in the manufacture of a medicament for the treatment of a disorder associated with glutamate dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
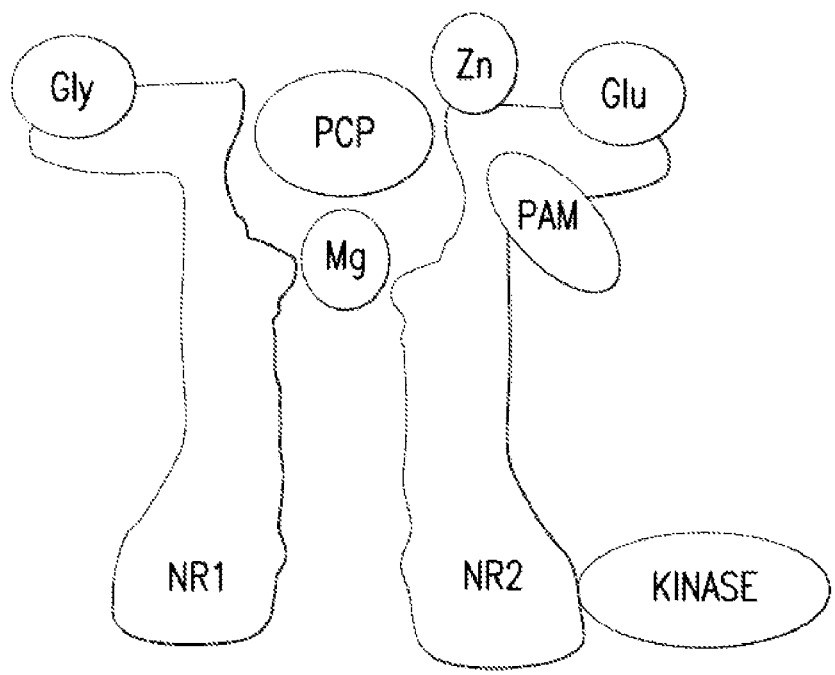
FIG. 1 shows a schematic of the NMDA receptor.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ software (Cambridgesoft Corporation, U.S.A.), or ACD/Name software (ACD/Name product version 10.01.0.14105, October 2006 or product version 10.01; Build 15494, 1 Dec. 2006, Advanced Chemical Development, Inc., Toronto, Canada).

The chemical names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006). In case of tautomeric forms, the name of the depicted tautomeric form of the structure was generated. However, it should be clear that the other non-depicted tautomeric form is also included within the scope of the present invention.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "orthosteric site" refers to the primary binding site on a receptor that is recognized by the endogenous ligand or agonist for that receptor. For example, the orthosteric site in the mGluR5 receptor is the site that glutamate binds.

As used herein, the term "mGluR5 receptor positive allosteric modulator" refers to any exogenously administered compound or agent that directly or indirectly augments the activity of the mGluR5 receptor in the presence or in the absence of glutamate in an animal, in particular a mammal, for example a human. In one aspect, a mGluR5 receptor positive allosteric modulator increases the activity of the mGluR5 receptor in a cell in the presence of extracellular glutamate. The cell can be human embryonic kidney cells transfected with human mGluR5. The cell can be human embryonic kidney cells transfected with rat mGluR5. The cell can be human embryonic kidney cells transfected with a mammalian mGluR5 The term "mGluR5 receptor positive allosteric modulator" includes a compound that is a "mGluR5 receptor allosteric potentiator" or a "mGluR5 receptor allosteric agonist," as well as a compound that has mixed activity comprising pharmacology of both an "mGluR5 receptor allosteric potentiator" and an "mGluR5 receptor allosteric agonist". The term "mGluR5 receptor positive allosteric modulator also includes a compound that is a "mGluR5 receptor allosteric enhancer."

As used herein, the term "mGluR5 receptor allosteric potentiator" refers to any exogenously administered compound or agent that directly or indirectly augments the response produced by the endogenous ligand (such as glutamate) when the endogenous ligand binds to the orthosteric site of the mGluR5 receptor in an animal, in particular a mammal, for example a human. The mGluR5 receptor allosteric potentiator binds to a site other than the orthosteric site, that is, an allosteric site, and positively augments the response of the receptor to an agonist or the endogenous ligand. In one aspect, an allosteric potentiator does not induce desensitization of the receptor, activity of a compound as an mGluR5 receptor allosteric potentiator provides advantages over the use of a pure mGluR5 receptor allosteric agonist. Such advantages can include, for example, increased safety margin, higher tolerability, diminished potential for abuse, and reduced toxicity.

As used herein, the term "mGluR5 receptor allosteric enhancer" refers to any exogenously administered compound or agent that directly or indirectly augments the response produced by the endogenous ligand in an animal, in particular a mammal, for example a human. In one aspect, the allosteric enhancer increases the affinity of the natural ligand or agonist for the orthosteric site. In another aspect, an allosteric enhancer increases the agonist efficacy. The mGluR5 receptor allosteric potentiator binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

As used herein, the term "mGluR5 receptor allosteric agonist" refers to any exogenously administered compound or agent that directly augments the activity of the mGluR5 receptor in the absence of the endogenous ligand (such as glutamate) in an animal, in particular a mammal, for example a human. The mGluR5 receptor allosteric agonist binds to a site that is distinct from the orthosteric glutamate site of the mGluR5 receptor and influences the binding of an agonist or the natural ligand to the orthosteric site of the mGluR5 receptor. Because it does not require the presence of the endogenous ligand, activity of a compound as an mGluR5 receptor allosteric agonist provides advantages over the use of a pure mGluR5 receptor allosteric potentiator, such as more rapid onset of action.

As used herein, the term "mGluR5 receptor neutral allosteric ligand" refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for positive allosteric modulation of metabotropic glutamate receptor activity prior to the administering step. In some aspects of the disclosed method, the subject has been diagnosed with a need for partial agonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mGluR5" means having been subjected to a physical examination by a person of skill, for example, a physician, and found to have a condition that can be diagnosed or treated by a compound or composition that can modulate mGluR5. As a further example, "diagnosed with a need for modulation of mGluR5" refers to having been subjected to a physical examination by a person of skill, for example, a physician, and found to have a condition characterized by mGluR5 activity. Such a diagnosis can be in reference to a disorder, such as a neurodegenerative disease, and the like, as discussed herein. For example, the term "diagnosed with a need for positive allosteric modulation of metabotropic glutamate receptor activity" refers to having been subjected to a physical examination by a person of skill, for example, a physician, and found to have a condition that can be diagnosed or treated by positive allosteric modulation of metabotropic glutamate receptor activity. For example, "diagnosed with a need for partial agonism of metabotropic glutamate receptor activity" means having been subjected to a physical examination by a person of skill, for example, a physician, and found to have a condition that can be diagnosed or treated by partial agonism of metabotropic glutamate receptor activity. For example, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR5 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target metabotropic glutamate receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response. In a yet further aspect, the response is in vitro. In a still further aspect, the response is in a human embryonic kidney cell transfected with human mGluR5. In a yet further aspect, the response is a human embryonic kidney cell transfected with rat mGluR5. In an even further aspect, the response is in a human embryonic kidney cell transfected with a mammalian mGluR5.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance. In a yet further aspect, the inhibition is measured in vitro. In a still further aspect, the inhibition is measured in a human embryonic kidney cell transfected with human mGluR5. In a yet further aspect, the inhibition is measured in a human embryonic kidney cell transfected with rat mGluR5. In an even further aspect, the inhibition is measured in a human embryonic kidney cell transfected with a mammalian mGluR5.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as poly-lactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and non-aromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$Q^1$," "$Q^2$," "$Q^3$," and "$Q^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" refers to a non-aromatic carbon-based moiety. Aliphatic can include both acyclic or cyclic moieties (e.g., alkyl and cycloalkyl) and can include both saturated and unsaturated moieties (e.g., alkyl, alkenyl, and alkynyl).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms.

Examples of cycloalkyl groups include, but are not limited to, cyclopropyl, cyclobutyl, cyclopentyl, cyclohexyl, norbornyl, and the like. The cycloalkyl group can be substituted or unsubstituted. The cycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl group bonded through an ether linkage; that is, an "alkoxy" group can be defined as —$OQ^1$ where $Q^1$ is alkyl or cycloalkyl as defined above. "Alkoxy" also includes polymers of alkoxy groups as just described; that is, an alkoxy can be a polyether such as —$OQ^1$-$OQ^2$ or —$OQ^1$-$(OQ^2)_a$-$OQ^3$, where "a" is an integer of from 1 to 200 and $Q^1$, $Q^2$, and $Q^3$ are alkyl and/or cycloalkyl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "amine" or "amino" as used herein are represented by the formula —$NQ^1Q^2$, where $Q^1$ and $Q^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "halide" or "halo" or "halogen", which can be used interchangeably and as used herein alone or as part of another chemical group refers fluorine, chlorine, bromine, and iodine. The term includes a single member, a subset, or collectively all of the foregoing.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, 1,2-oxazol-4-yl, 1,2-oxazol-5-yl, 1,3-oxazolyl, 1,2,4-oxadiazol-5-yl, 1,2,3-triazolyl, 1,3-thiazol-4-yl, pyridinyl, and pyrimidin-5-yl.

The term "monocyclic heterocyclyl," as used herein refers to a ring system in which at least one of the ring members is other than carbon. Monocyclic heterocyclyl encompasses aromatic and non-aromatic ring systems. Exemplary aromatic monocyclic heterocyclic groups include, but are not limited to, pyrrolyl, pyrazolyl, furanyl, 1,2-oxazol-4-yl, 1,2-oxazol-5-yl, 1,3-oxazolyl, 1,2,4-oxadiazol-5-yl, 1,2,3-triazolyl, thienyl, 1,3-thiazol-4-yl, pyridinyl, pyrimidin-5-yl. Exemplary non-aromatic monocyclic heterocyclic groups include, but are not limited to 5-oxo-pyrrolidinyl. In a particular embodiment, the aromatic monocyclic heterocyclic groups are selected from the group consisting of pyrrolyl, furanyl, 1,2-oxazol-5-yl, and pyridinyl.

The term "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. In particular, bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Exemplary bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl. In a particular embodiment, the aromatic bicyclic heterocyclic groups are selected from the group consisting of 3-indolyl, indazolyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "hydroxyl" as used herein is represented by the formula —OH.

"$R^1$," "$R^2$," "$R^3$," "IV," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph, which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$\circ$)N(R$^\circ$)C(O)NR$^\circ$$_2$; —N(R$^\circ$)$^{N(R\circ)}$C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched)alkenyl)O—N(R$^\circ$)$_2$; or —(C$_{1-4}$ straight or branched)alkenyl)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkenyl)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, ═O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, •NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 6 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the following structure:

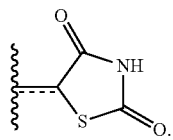

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Stereoisomeric forms of the compounds of Formula (I) are embraced within the scope of this invention. The invention also embraces each of the individual isomeric forms of the compounds of Formula (I) and their salts and solvates, substantially free, i.e. associated with less than about 10%, less than about 5%, less than about 2% and less than about 1% of the other isomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, at an enantiomeric excess of greater than or equal to about 90%, at an enantiomeric excess of greater than or equal to about 95%, at an enantiomeric excess of greater than or equal to about 98%, and at an enantiomeric excess of greater than or equal to about 99%. Similarly, wherein the compound is present as a diastereomer, the diastereomer is present at a diastereomeric excess of greater than or equal to about 80%, at a diastereomeric excess of greater than or equal to about 90%, at a diastereomeric excess of greater than or equal to about 95%, at a diastereomeric excess of greater than or equal to about 98%, and at a diastereomeric excess of greater than or equal to about 99%.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

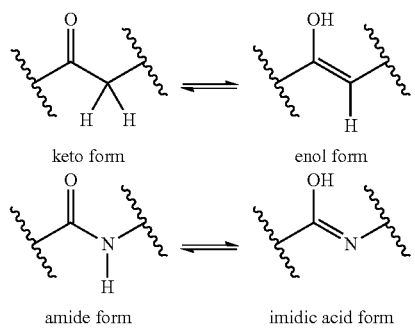

keto form     enol form amide form     imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

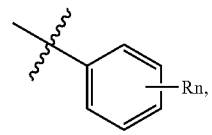

which is understood to be equivalent to a formula:

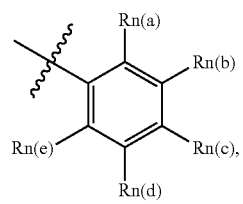

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as positive allosteric modulators of the metabotropic glutamate receptor subtype 5 (mGluR5). More specifically, in one aspect, the present invention relates to compounds that allosterically modulate mGluR5 receptor activity, affecting the sensitivity of mGluR5 receptors to agonists without acting as orthosteric agonists themselves. The compounds can, in one aspect, exhibit subtype selectivity.

In one aspect, the compounds of the invention are useful in the treatment neurological and psychiatric disorders associated with glutamate dysfunction and other diseases in which metabotropic glutamate receptors are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. STRUCTURE

In one aspect, the invention relates to a compound having a structure represented by Formula (I):

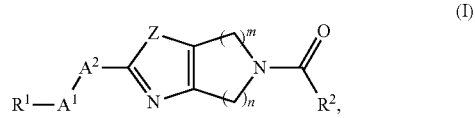

wherein Z is O or S; wherein each of m and n is independently selected from 1, 2, and 3; wherein -$A^1$-$A^2$- is selected from —$OCH_2$—, —$CH_2O$—, —$CH_2CH_2$—, and —CH═CH—; wherein $R^1$ is aryl or heteroaryl and substituted with 0, 1, 2, or 3 groups each independently selected from cyano, halo, hydroxyl, trialkylsiloxyl, $C_{1-4}$-alkyl, $C_{1-4}$-alkyloxy, monohalo-$C_{1-4}$-alkyl, and polyhalo-$C_{1-4}$-alkyl; wherein $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, —$NH_2$, $C_{1-4}$-alkyl, $C_{1-4}$-alkyloxy, monohalo-$C_{1-4}$-alkyl, polyhalo-$C_{1-4}$-alkyl, $C_{1-4}$-alkyloxycarbonylamino, aryloxy-$C_{1-4}$-alkyl, aryloxy-$C_{1-4}$-alkyl, aryl-$C_{3-8}$-cycloalkyl, polyhalo-$C_{1-4}$-alkyloxy, $C_{1-4}$-alkyloxy-$C_{1-4}$-alkyl, $C_{1-4}$-alkyloxy-$C_{1-4}$-alkylheterocyclyl, and heterocyclyl substituted with carbonyl; or wherein $R^2$ is selected from $Ar^1$, $Ar^1$-$C_{1-6}$-alkyl-, $Ar^1$-$C_{3-8}$-cycloalkyl-, $Ar^1$-oxy-$C_{1-4}$-alkyl; $Ar^2$, $Ar^2$-$C_{1-6}$-alkyl-, $Ar^2$-$C_{3-8}$-cycloalkyl-, $Ar^2$-oxy-$C_{1-4}$-alkyl; $Ar^3$, $Ar^3$-$C_{1-6}$-alkyl-, $Ar^3$-oxy-$C_{1-4}$-alkyl; $Ar^3$-$C_{3-8}$-cycloalkyl-, and $Ar^3$-oxy-$C_{1-4}$-alkyl; wherein $Ar^1$, when present, is phenyl substituted with 0, 1, 2, or 3 groups each independently selected from halo, cyano, —$NH_2$, monoalkylamino, dialkylamino, $C_{1-4}$-alkyl, $C_{1-4}$-alkyloxy, $C_{1-4}$-alkyloxy-$C_{1-4}$-alkyl, monohalo-$C_{1-4}$-alkyl, polyhalo-$C_{1-4}$-alkyl, polyhalo-$C_{1-4}$-alkyloxy, and pentafluorosulfanyl; wherein $Ar^2$, when present, is monocyclic heterocyclyl substituted with 0, 1, 2, or 3 groups each independently selected from halo, cyano, —$NH_2$, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $Ar^3$, when present, is bicyclic heterocyclyl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $R^3$ is selected from $Ar^4$ and $Ar^4$-$C_{1-6}$-alkyl-; wherein $Ar^4$, when present, is phenyl substituted with 0, 1, 2, or 3 groups each independently selected from halo, cyano, $C_{1-4}$-alkyl, $C_{1-4}$-alkyloxy, monohalo-$C_{1-4}$-alkyl, and polyhalo-$C_{1-4}$-alkyl; or a pharmaceutically acceptable salt, hydrate, solvate, or polymorph thereof.

In a further aspect, the invention relates to a compound having a structure represented by Formula (I):

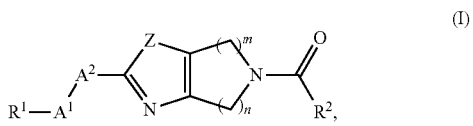

wherein Z is O or S; wherein each of m and n is independently selected from 1, 2, and 3; wherein -$A^1$-$A^2$- is selected from —$OCH_2$—, —$CH_2O$—, —$CH_2CH_2$—, and —CH═CH—; wherein $R^1$ is six-membered monocyclic aryl or six-membered monocyclic heteroaryl and substituted with 0, 1, 2, or 3 groups each independently selected from cyano, halo, hydroxyl, trialkylsiloxyl, $C_{1-4}$-alkyl, $C_{1-4}$-alkyloxy, monohalo-$C_{1-4}$-alkyl, and polyhalo-$C_{1-4}$-alkyl; wherein $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, —$NH_2$, $C_{1-4}$-alkyl, $C_{1-4}$-alkyloxy, monohalo-$C_{1-4}$-alkyl, polyhalo-$C_{1-4}$-alkyl, $C_{1-4}$-alkyloxycarbonylamino, aryloxy-$C_{1-4}$-alkyl, aryloxy-$C_{1-4}$-alkyl, aryl-$C_{3-8}$-cycloalkyl, polyhalo-$C_{1-4}$-alkyloxy, $C_{1-4}$-alkyloxy-$C_{1-4}$-alkyl, $C_{1-4}$-alkyloxy-$C_{1-4}$-alkylheterocyclyl, and heterocyclyl substituted with carbonyl; or wherein $R^2$ is selected from $Ar^1$, $Ar^1$-$C_{1-6}$-alkyl-, $Ar^1$-$C_{3-8}$-cycloalkyl-, $Ar^1$-oxy-$C_{1-4}$-alkyl; $Ar^2$, $Ar^2$-$C_{1-6}$-alkyl-, $Ar^2$-$C_{3-8}$-cycloalkyl-, $Ar^2$-oxy-$C_{1-4}$-alkyl; $Ar^3$, Ar³-C₁₋₆-alkyl-, Ar¹-oxy-C₁₋₄-alkyl; Ar³-C₃₋₈-cycloalkyl-, and Ar³-oxy-C₁₋₄-alkyl; wherein Ar¹, when present, is phenyl substituted with 0, 1, 2, or 3 groups each independently selected from halo, cyano, —NH₂, monoalkylamino, dialkylamino, C₁₋₄-alkyl, C₁₋₄-alkyloxy, C₁₋₄-alkyloxy-C₁₋₄-alkyl, monohalo-C₁₋₄-alkyl, polyhalo-C₁₋₄-alkyl, polyhalo-C₁₋₄-alkyloxy, and pentafluorosulfanyl; wherein Ar², when present, is monocyclic heterocyclyl substituted with 0, 1, 2, or 3 groups each independently selected from halo, cyano, —NH₂, monoalkylamino, dialkylamino, C₁₋₄-alkyl, C₁₋₄-alkyloxy, and monohalo-C₁₋₄-alkyl, polyhalo-C₁₋₄-alkyl, and pentafluorosulfanyl; wherein Ar³, when present, is bicyclic heterocyclyl substituted with 0, 1, 2, or 3 groups each independently selected from halo, cyano, amino, monoalkylamino, dialkylamino, C₁₋₄-alkyl, C₁₋₄-alkyloxy, and monohalo-C₁₋₄-alkyl, polyhalo-C₁₋₄-alkyl, and pentafluorosulfanyl; wherein R³ is selected from Ar⁴ and Ar⁴-C₁₋₆-alkyl-; wherein Ar⁴, when present, is phenyl substituted with 0, 1, 2, or 3 groups each independently selected from halo, cyano, C₁₋₄-alkyl, C₁₋₄-alkyloxy, monohalo-C₁₋₄-alkyl, and polyhalo-C₁₋₄-alkyl; or a pharmaceutically acceptable salt, hydrate, solvate, or polymorph thereof.

In a further aspect, the invention relates to a compound having a structure represented by Formula (I), wherein R¹ is phenyl optionally substituted with 1, 2, or 3 independently selected halo substituents; -A¹-A²- is selected from —OCH₂—, —CH₂—CH₂— and —CH=CH—; m is selected from 1 and 2; R² is selected from C₁₋₆alkyl, (C₃₋₈cycloalkyl)C₁₋₆alkyl, —OR³, Ar¹ and Ar²; Ar¹ is phenyl optionally substituted with 1, 2, or 3 independently selected halo substituents; R³ is Ar⁴C₁₋₆alkyl-, wherein Ar⁴ is unsubstituted phenyl; and Ar², when present, is pyridinyl optionally substituted with 1, 2, or 3 substituents each independently selected from halo and C₁₋₄alkyl, and wherein Z, m, n, and R³ are as previously defined.

In a further aspect, the invention relates to a compound having a structure represented by Formula (I), wherein R¹ is phenyl substituted with 0, 1, 2, or 3 groups each independently selected from the group consisting of halo, C₁₋₄alkyl, C₁₋₄alkyloxy, and mono- and poly-haloC₁₋₄alkyl; R² is selected from the group consisting of C₁₋₆alkyl, (C₁₋₆alkyloxy)C₁₋₆alkyl, mono- and polyhalo-C₁₋₆alkyl, C₃₋₈cycloalkyl, (C₃₋₈cycloalkyl)C₁₋₆alkyl, —OR³, Ar¹, and Ar²; R³ is selected from the group consisting of Ar⁴ and Ar⁴C₁₋₆alkyl-; Ar¹ is phenyl substituted with 0, 1, 2, or 3 groups each independently selected from the group consisting of halo, cyano, C₁₋₄alkyl, C₁₋₄alkyloxy, and mono- and polyhalo-C₁₋₄alkyl; Arᵉ is pyridinyl substituted with 0, 1, 2, or 3 groups each independently selected from the group consisting of halo, C₁₋₄alkyl, cyano, C₁₋₄alkyloxy and mono- and poly-halo-C₁₋₄alkyl; and Ar⁴ is phenyl substituted with 0, 1, 2, or 3 substituents each independently selected from the group consisting of halo, cyano, C₁₋₄alkyl, C₁₋₄alkyloxy, and mono- and polyhalo-C₁₋₄alkyl; or a pharmaceutically acceptable salt, solvate, or polymorph thereof.

In a further aspect, the invention relates to a compound having a structure represented by Formula (I), wherein Z is O or S; R¹ is phenyl substituted with 0, 1, 2, or 3 independently selected halo substituents; -A¹-A²- is selected from the group consisting of —OCH₂—, —CH₂—CH₂— and —CH=CH—; m is selected from 1 and 2; n is selected from the group consisting of 1, 2 and 3; R² is selected from the group consisting of C₁₋₆alkyl, (C₃₋₈cycloalkyl)C₁₋₆alkyl, —OR³, Ar¹ and Ar²; R³ is Ar⁴C₁₋₆alkyl-; Ar¹ is phenyl optionally substituted with one, one or three independently selected halo substituents; Ar² is pyridinyl substituted with 0, 1, 2, or 3 groups each independently selected from halo and C₁₋₄alkyl; and Ar⁴ is phenyl; or a pharmaceutically acceptable salt, solvate, or polymorph thereof.

In a further aspect, the invention relates to a compound having a structure represented by Formula (I), wherein Z is O or S; R¹ is phenyl substituted with 0, 1, 2, or 3 independently selected halo substituents; -A¹-A²- is selected from the group consisting of —OCH₂—, —CH₂—CH₂— and —CH=CH—; m is selected from 1 and 2; n is selected from the group consisting of 1, 2 and 3; R² is selected from the group consisting of C₁₋₆alkyl, (C₃₋₈cycloalkyl)C₁₋₆alkyl, —OR³ and Ar¹; R³ is Ar⁴C₁₋₆alkyl-; Ar¹ is phenyl optionally substituted with one, two or three independently selected halo substituents; and Ar⁴ is phenyl; or a pharmaceutically acceptable salt, solvate, or polymorph thereof.

In a further aspect, the invention relates to a compound having a structure represented by Formula (I), wherein R² is selected from the group consisting of C₁₋₆alkyl, (C₃₋₈cycloalkyl)C₁₋₆alkyl, —OR³ and Ar¹; or a pharmaceutically acceptable salt, solvate, or polymorph thereof.

In a further aspect, the invention relates to a compound having a structure represented by Formula (I), wherein Z is O or S; R¹ is phenyl optionally substituted with one or two fluoro substituents; -A¹-A²- is —OCH₂—; n is selected from the group consisting of 1, 2 and 3 when m is 1; or n is 2 when m is 2; and R² is phenyl optionally substituted with one or two fluoro substituents; or a pharmaceutically acceptable salt, solvate, or polymorph thereof.

In a further aspect, the invention relates to a compound having a structure represented by Formula (I), wherein Z is O or S; R¹ is unsubstituted phenyl; -A¹-A²- is —OCH₂—; m is 1; n is selected from the group consisting of 1, 2 and 3; and R² is 4-fluorophenyl; or a pharmaceutically acceptable salt, solvate, or polymorph thereof.

In a further aspect, the invention relates to a compound having a structure represented by Formula (I), wherein -A¹-A²- is selected from —OCH₂—, —CH₂—CH₂— and —CH=CH—.

In a further aspect, the invention relates to a compound having a structure represented by Formula (I), wherein Z is O; m is 1 and n is 2; R¹ is selected from phenyl, 3-fluoro-phenyl and 4-fluoro-phenyl; and R² is selected from 3-fluoro-phenyl and 4-fluoro-phenyl.

In a further aspect, the invention relates to a compound of Formula (I), or a stereoisomeric form thereof, wherein Z is O or S; R¹ is phenyl optionally substituted with one, two or three independently selected halo substituents; -A¹-A²- is selected from the group consisting of —OCH₂—, —CH₂—CH₂— and —CH=CH—; m is selected from 1 and 2; n is selected from the group consisting of 1, 2 and 3; R² is selected from the group consisting of C₁₋₆alkyl, (C₃₋₈cycloalkyl)C₁₋₆ alkyl, —OR³, Ar¹ and Ar²; R³ is Ar⁴C₁₋₆alkyl-; Ar¹ is phenyl optionally substituted with one, two or three independently selected halo substituents; and Ar², when present, is pyridinyl optionally substituted with one, two or three substituents each independently selected from halo and C₁₋₄alkyl; and Ar⁴ is unsubstituted phenyl; or a pharmaceutically acceptable addition salt thereof.

In a further aspect, the invention relates to a compound of Formula (I), or a stereoisomeric form thereof, wherein Z is O or S; R¹ is phenyl optionally substituted with one or two independently selected halo substituents; -A¹-A²- is selected from the group consisting of —OCH₂— and —CH=CH—; m is selected from the group consisting of 1 and 2; n is selected from the group consisting of 1, 2 and 3; R² is selected from the group consisting of C₁₋₆alkyl, (C₃₋₈cycloalkyl)C₁₋₆ alkyl, —OR³, Ar¹, Ar² and Ar³; wherein R³ is Ar⁴C₁₋₆alkyl-; Ar¹ is phenyl optionally substituted with one or two independently selected halo substituents; $Ar^2$, when present, is pyridinyl; and $Ar^4$ is phenyl; or a pharmaceutically acceptable addition salt thereof.

In a further aspect, the invention relates to a compound of Formula (I), or a stereoisomeric form thereof, wherein Z is O or S; $R^1$ is selected from the group consisting of phenyl, 2-fluorophenyl, 3-fluorophenyl, 4-fluorophenyl and 3,4-difluorophenyl; -$A^1$-$A^2$- is selected from the group consisting of —$OCH_2$— and —CH=CH—; m is selected from the group consisting of 1 and 2; n is selected from the group consisting of 1, 2 and 3; $R^2$ is selected from the group consisting of methyl, cyclopropylmethyl, benzyloxy, $Ar^1$, $Ar^2$, and $Ar^3$; wherein $Ar^1$ is selected from the group consisting of phenyl, 2-fluorophenyl, 3-fluorophenyl, 4-fluorophenyl, 2,3-difluorophenyl, 2,4-difluorophenyl, 2,6-difluorophenyl, 3,4-difluorophenyl and 3,5-difluorophenyl; and heteroaryl is selected from the group consisting of 2-pyridinyl, 3-pyridinyl and 4-pyridinyl; or a pharmaceutically acceptable addition salt thereof.

In a further aspect, m is 2 and n is 2. In an additional embodiment, the invention relates to a compound of Formula (I), or a stereoisomeric form thereof, wherein Z is O or S; $R^1$ is phenyl optionally substituted with one or two fluoro substituents; -$A^1$-$A^2$- is —$OCH_2$—; n is selected from the group consisting of 1, 2 and 3 when m is 1; or n is 2 when m is 2; and $R^2$ is phenyl optionally substituted with one or two fluoro substituents; or a pharmaceutically acceptable addition salt thereof.

In a further aspect, the invention relates to a compound of Formula (I), or a stereoisomeric form thereof, wherein Z is O or S; $R^1$ is phenyl optionally substituted with one or two fluoro substituents; -$A^1$-$A^2$- is —$OCH_2$—; m is 1; n is selected from the group consisting of 1, 2 and 3; and $R^2$ is phenyl optionally substituted with one or two fluoro substituents; or a pharmaceutically acceptable addition salt thereof.

In a further aspect, the invention relates to a compound of Formula (I), or a stereoisomeric form thereof, wherein Z is O or S; $R^1$ is selected from the group consisting of phenyl, 2-fluorophenyl, 3-fluorophenyl, 4-fluorophenyl and 3,4-difluorophenyl; -$A^1$-$A^2$- is —$OCH_2$—; m is 1; n is selected from the group consisting of 1, 2 and 3; and $R^2$ is selected from the group consisting of phenyl, 2-fluorophenyl, 3-fluorophenyl, 4-fluorophenyl, 2,3-difluorophenyl, 2,4-difluorophenyl, 2,6-difluorophenyl, 3,4-difluorophenyl and 3,5-difluorophenyl; or a pharmaceutically acceptable addition salt thereof.

In a further aspect, the invention relates to a compound of Formula (I), or a stereoisomeric form thereof, wherein Z is O or S; $R^1$ is unsubstituted phenyl; -$A^1$-$A^2$- is —$OCH_2$—; m is 1; n is selected from the group consisting of 1, 2 and 3; and $R^2$ is 4-fluorophenyl; or a pharmaceutically acceptable addition salt thereof.

In one aspect, the invention relates to a compound having a structure represented by Formula (I):

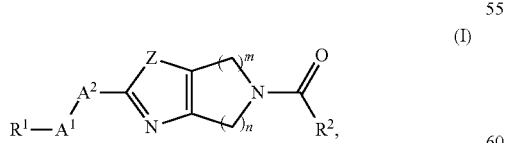

(I)

wherein Z is O or S; wherein each of m and n is independently selected from 1, 2, and 3; wherein -$A^1$-$A^2$- is selected from —$OCH_2$—, —$CH_2O$—, —$CH_2CH_2$—, and —CH=CH—; wherein $R^1$ is aryl or heteroaryl and substituted with 0, 1, 2, or 3 groups each independently selected from hydroxyl, trialkylsiloxyl, halo, $C_{1-4}$-alkyl, $C_{1-4}$-alkyloxy, monohalo-$C_{1-4}$-alkyl, and polyhalo-$C_{1-4}$-alkyl; wherein $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, $C_{1-4}$-alkyl, $C_{1-4}$-alkyloxy, monohalo-$C_{1-4}$-alkyl, and polyhalo-$C_{1-4}$-alkyl; or wherein $R^2$ is selected from $Ar^1$, $Ar^1$-$C_{1-6}$-alkyl-, $Ar^2$, $Ar^2$-$C_{1-6}$-alkyl-, $Ar^3$, and $Ar^3$-$C_{1-6}$-alkyl-; wherein $Ar^1$, when present, is phenyl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $Ar^2$, when present, is monocyclic heteroaryl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $Ar^3$, when present, is bicyclic heteroaryl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl; wherein $R^3$ is selected from $Ar^4$ and $Ar^4$-$C_{1-6}$-alkyl-; wherein $Ar^4$, when present, is phenyl substituted with 0, 1, 2, or 3 groups each independently selected from halo, cyano, $C_{1-4}$-alkyl, $C_{1-4}$-alkyloxy, monohalo-$C_{1-4}$-alkyl, and polyhalo-$C_{1-4}$-alkyl; or a pharmaceutically acceptable salt, hydrate, solvate, or polymorph thereof.

In a further aspect, $R^1$ is phenyl substituted with 0, 1, 2, or 3 groups each independently selected from halo, $C_{1-4}$alkyl, $C_{1-4}$alkyloxy, and mono- and poly-halo$C_{1-4}$alkyl; $R^2$ is selected from $C_{1-6}$alkyl, ($C_{1-6}$alkyloxy)$C_{1-6}$alkyl, mono- and polyhalo-$C_{1-6}$alkyl, $C_{3-8}$cycloalkyl, ($C_{3-8}$cycloalkyl)$C_{1-6}$alkyl, —$OR^3$, $Ar^1$, and heteroaryl; $Ar^1$, when present, is phenyl substituted with 0, 1, 2, or 3 groups each independently selected from halo, cyano, $C_{1-4}$alkyl, $C_{1-4}$alkyloxy, and mono- and polyhalo-$C_{1-4}$alkyl; and heteroaryl is pyridinyl; and optionally substituted with 1, 2 or 3 groups each independently selected from halo, $C_{1-4}$alkyl, cyano, $C_{1-4}$alkyloxy and mono- and polyhalo-$C_{1-4}$alkyl.

In a further aspect, $R^1$ is phenyl optionally substituted with 1, 2, or 3 independently selected halo substituents; -$A^1$-$A^2$- is selected from —$OCH_2$—, —$CH_2$—$CH_2$— and —CH=CH—; m is selected from 1 and 2; $R^2$ is selected from $C_{1-6}$alkyl, ($C_{3-8}$cycloalkyl)$C_{1-6}$alkyl, —$OR^3$, $Ar^1$, and heteroaryl; $Ar^1$ is phenyl optionally substituted with 1, 2, or 3 independently selected halo substituents; $R^3$ is $Ar^4C_{1-6}$alkyl-, wherein $Ar^4$ is phenyl; and heteroaryl is pyridinyl optionally substituted with 1, 2, or 3 substituents each independently selected from halo and $C_{1-4}$alkyl.

In one aspect, the invention relates to a compound having a structure represented by Formula (I):

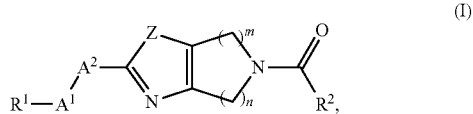

(I)

wherein Z is O or S; $R^1$ is phenyl optionally substituted with one, two or three substituents each independently selected from the group consisting of halo, $C_{1-4}$alkyl, $C_{1-4}$alkyloxy, and mono- and poly-halo$C_{1-4}$alkyl; -$A^1$-$A^2$- is selected from the group consisting of —$OCH_2$—, —$CH_2O$—, —$CH_2CH_2$—, and —CH=CH—; m and n are each independently selected from the group consisting of 1, 2 and 3; $R^2$ is selected from the group consisting of $C_{1-6}$alkyl, ($C_{1-6}$alkyloxy)$C_{1-6}$alkyl, mono- and polyhalo-$C_{1-6}$alkyl, $C_{3-8}$cycloalkyl, ($C_{3-8}$cycloalkyl)$C_{1-6}$alkyl, —$OR^3$, $Ar^1$, and heteroaryl; $R^3$ is selected from the group consisting of phenyl and phenyl-$C_{1-6}$alkyl-; wherein the phenyl is optionally substituted with one, two or three substituents each independently selected from the group consisting of halo, cyano, $C_{1-4}$alkyl, $C_{1-4}$alkyloxy, and mono- and polyhalo-$C_{1-4}$alkyl; heteroaryl is pyridinyl optionally substituted with one, two or three substituents each independently selected from the group consisting of halo, $C_{1-4}$alkyl, cyano, $C_{1-4}$alkyloxy and mono- and polyhalo-$C_{1-4}$alkyl; $Ar^1$ is phenyl optionally substituted with one, two or three substituents each independently selected from the group consisting of halo, cyano, $C_{1-4}$alkyl, $C_{1-4}$alkyloxy, and mono- and polyhalo-$C_{1-4}$alkyl; and pharmaceutically acceptable addition salts thereof.

In a further aspect, the invention relates to a compound of Formula (I), or a stereoisomeric form thereof, wherein Z is O or S; $R^1$ is phenyl optionally substituted with one, two or three independently selected halo substituents; -$A^1$-$A^2$- is selected from the group consisting of —$OCH_2$—, —$CH_2$—$CH_2$— and —CH=CH—; m is selected from 1 and 2; n is selected from the group consisting of 1, 2 and 3; $R^2$ is selected from the group consisting of $C_{1-6}$alkyl, ($C_{3-8}$cycloalkyl)$C_{1-6}$alkyl, —$OR^3$, $Ar^1$ and heteroaryl; $R^3$ is phenyl-$C_{1-6}$alkyl-, wherein the phenyl is unsubstituted; $Ar^1$ is phenyl optionally substituted with one, two or three independently selected halo substituents; and heteroaryl is pyridinyl optionally substituted with one, two or three substituents each independently selected from halo and $C_{1-4}$alkyl; or a pharmaceutically acceptable addition salt thereof.

In a further aspect, the invention relates to a compound of Formula (I), or a stereoisomeric form thereof, wherein Z is O or S; $R^1$ is phenyl optionally substituted with one or two independently selected halo substituents; -$A^1$-$A^2$- is selected from the group consisting of —$OCH_2$— and —CH=CH—; m is selected from the group consisting of 1 and 2; n is selected from the group consisting of 1, 2 and 3; $R^2$ is selected from the group consisting of $C_{1-6}$alkyl, ($C_{3-8}$cycloalkyl)$C_{1-6}$alkyl, —$OR^3$, $Ar^1$ and heteroaryl; wherein $R^3$ is phenyl-$C_{1-6}$alkyl-; $Ar^1$ is phenyl optionally substituted with one or two independently selected halo substituents; and heteroaryl is pyridinyl; or a pharmaceutically acceptable addition salt thereof.

In a further aspect, the invention relates to a compound of Formula (I), or a stereoisomeric form thereof, wherein Z is O or S; $R^1$ is selected from the group consisting of phenyl, 2-fluorophenyl, 3-fluorophenyl, 4-fluorophenyl and 3,4-difluorophenyl; -$A^1$-$A^2$- is selected from the group consisting of —$OCH_2$— and —CH=CH—; m is selected from the group consisting of 1 and 2; n is selected from the group consisting of 1, 2 and 3; $R^2$ is selected from the group consisting of methyl, cyclopropylmethyl, benzyloxy, $Ar^1$ and heteroaryl; wherein $Ar^1$ is selected from the group consisting of phenyl, 2-fluorophenyl, 3-fluorophenyl, 4-fluorophenyl, 2,3-difluorophenyl, 2,4-difluorophenyl, 2,6-difluorophenyl, 3,4-difluorophenyl and 3,5-difluorophenyl; and heteroaryl is selected from the group consisting of 2-pyridinyl, 3-pyridinyl and 4-pyridinyl; or a pharmaceutically acceptable addition salt thereof.

In a further aspect, the invention relates to a compound of Formula (I), or a stereoisomeric form thereof, wherein Z is O or S; $R^1$ is phenyl optionally substituted with one or two fluoro substituents; -$A^1$-$A^2$- is —$OCH_2$—; n is selected from the group consisting of 1, 2 and 3 when m is 1; or n is 2 when m is 2; and $R^2$ is phenyl optionally substituted with one or two fluoro substituents; or a pharmaceutically acceptable addition salt thereof.

In a further aspect, the invention relates to a compound of Formula (I), or a stereoisomeric form thereof, wherein Z is O or S; $R^1$ is phenyl optionally substituted with one or two fluoro substituents; -$A^1$-$A^2$- is —$OCH_2$—; m is 1; n is selected from the group consisting of 1, 2 and 3; and $R^2$ is phenyl optionally substituted with one or two fluoro substituents; or a pharmaceutically acceptable addition salt thereof.

In a further aspect, the invention relates to a compound of Formula (I), or a stereoisomeric form thereof, wherein Z is O or S; $R^1$ is selected from the group consisting of phenyl, 2-fluorophenyl, 3-fluorophenyl, 4-fluorophenyl and 3,4-difluorophenyl; -$A^1$-$A^2$- is —$OCH_2$—; m is 1; n is selected from the group consisting of 1, 2 and 3; and $R^2$ is selected from the group consisting of phenyl, 2-fluorophenyl, 3-fluorophenyl, 4-fluorophenyl, 2,3-difluorophenyl, 2,4-difluorophenyl, 2,6-difluorophenyl, 3,4-difluorophenyl and 3,5-difluorophenyl; or a pharmaceutically acceptable addition salt thereof.

In a further aspect, the invention relates to a compound of Formula (I), or a stereoisomeric form thereof, wherein Z is O or S; $R^1$ is unsubstituted phenyl; -$A^1$-$A^2$- is —$OCH_2$—; m is 1; n is selected from the group consisting of 1, 2 and 3; and $R^2$ is 4-fluorophenyl; or a pharmaceutically acceptable addition salt thereof.

In a further aspect, the compound has a structure represented by a formula, wherein $R^1$ and $R^2$ are defined as hereinbefore and hereinafter, selected from:

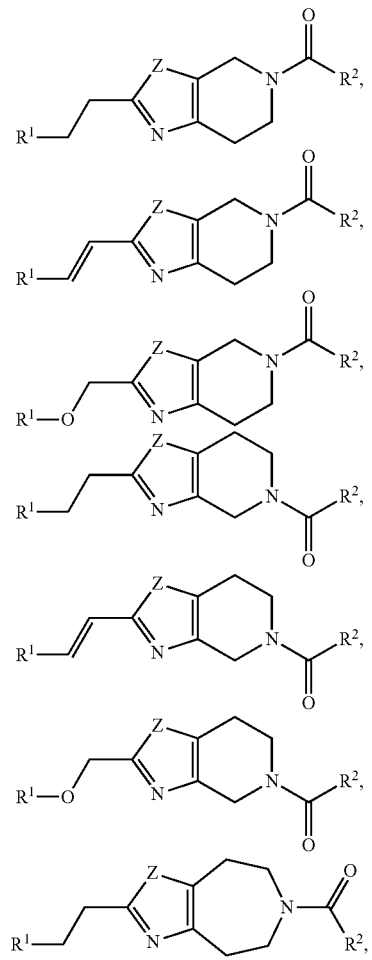

-continued
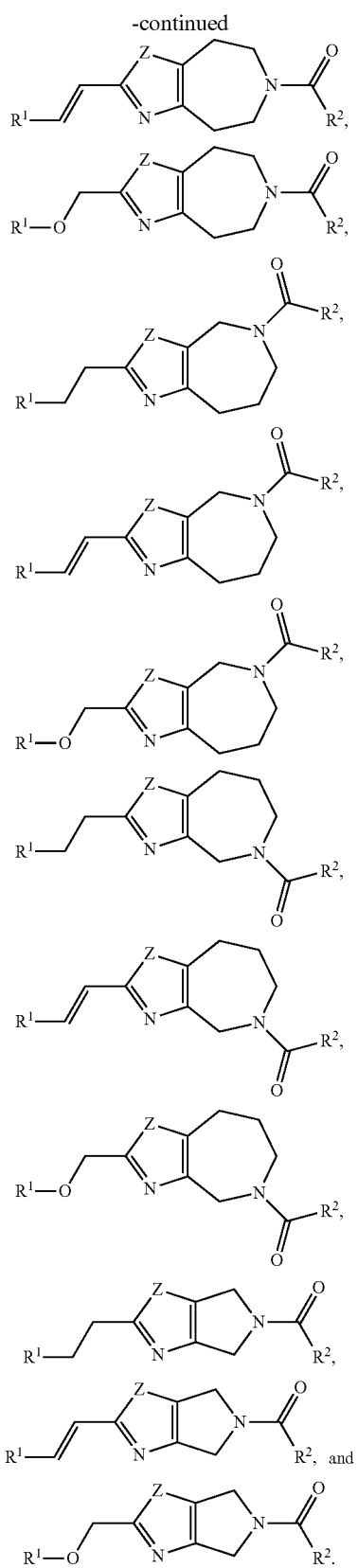
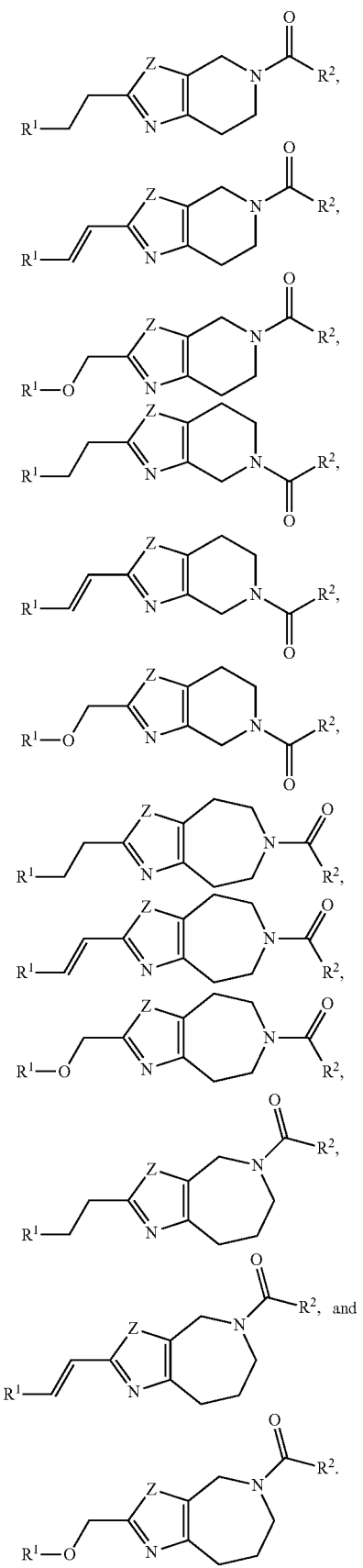
In a further aspect, the compound has a structure, wherein $R^1$ and $R^2$ are defined as hereinbefore and hereinafter, represented by a formula selected from:

In a further aspect, the compound has a structure, wherein $R^1$ and $R^2$ are defined as hereinbefore and hereinafter, represented by a formula selected from:

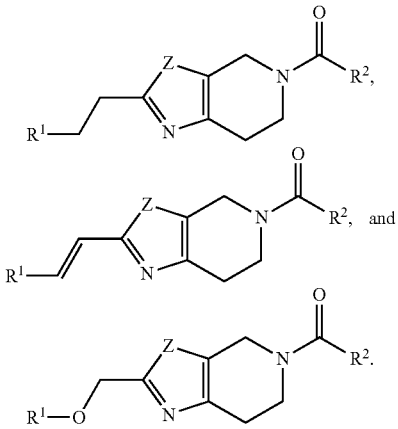

In a further aspect, the compound has a structure, wherein $R^1$ and $R^2$ are defined as hereinbefore and hereinafter, represented by a formula selected from:

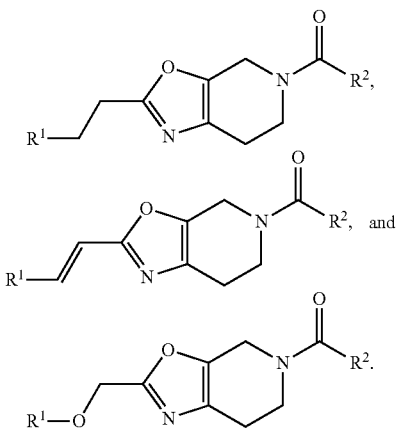

In a further aspect, the compound has a structure, wherein $R^1$ and $R^2$ are defined as hereinbefore and hereinafter, represented by a formula:

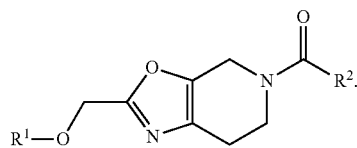

In a further aspect, the invention relates to compounds according to any of the previous aspects, wherein one or more of the following substituent definitions below apply, as defined in sections (a) to (o) below.

a. M GROUPS

In one aspect, m is selected from 1, 2, and 3. In a further aspect, m is selected from 1 and 2. In a further aspect, m is selected from 2 and 3. In a further aspect, m is 1. In a further aspect, m is 2. In a further aspect, m is 3.

b. N GROUPS

In one aspect, n is selected from 1, 2, and 3. In a further aspect, n is selected from 1 and 2. In a further aspect, n is selected from 2 and 3. In a further aspect, n is 1. In a further aspect, n is 2. In a further aspect, n is 3.

In one aspect, m is 1 and n is 1, thereby forming a five-membered ring. In a further aspect, m is 1 and n is 2, thereby forming a six-membered ring. In a further aspect, m is 2 and n is 1, thereby forming a six-membered ring. In a further aspect, m is 2 and n is 2, thereby forming a seven-membered ring. In a further aspect, m is 1 and n is 3, thereby forming a seven-membered ring. In a further aspect, m is 3 and n is 1, thereby forming a seven-membered ring. In a still further aspect, m is selected from 1 and 2, and n is selected from the group consisting of 1, 2 and 3. In a further aspect, n is selected from the group consisting of 1, 2 and 3 when m is 1; or n is 2 when m is 2. In a yet further aspect, m is 1, and n is selected from the group consisting of 1, 2 and 3.

c. Z GROUPS

In one aspect, Z is O or S. For example, Z can be selected to be 0. In a further example, Z can be selected to be S.

d. -$A^1$-$A^2$- GROUPS

In one aspect, -$A^1$-$A^2$- is selected from —OCH$_2$—, —CH$_2$O—, —CH$_2$CH$_2$—, and —CH═CH—. In a further aspect, -$A^1$-$A^2$- is selected from —OCH$_2$—, —CH$_2$CH$_2$— and —CH═CH—. In a further aspect, -$A^1$-$A^2$- is selected from —CH$_2$—CH$_2$— and —CH═CH—. In a further aspect, -$A^1$-$A^2$- is —OCH$_2$—. In a yet further aspect, -$A^1$-$A^2$- is —CH$_2$—CH$_2$. In a still further aspect, -$A^1$-$A^2$- is —CH═CH—. In an even further aspect, -$A^1$-$A^2$- is selected from the group consisting of —OCH$_2$— and —CH═CH—. In a yet further aspect, $A^1$-$A^2$- is selected from the group consisting of —OCH$_2$— and —CH$_2$—CH$_2$—.

For the avoidance of doubt, -$A^1$-$A^2$- corresponds to a bivalent linker of formula —O—CH$_2$—, —CH$_2$O—, —CH$_2$—CH$_2$— and —CH═CH— as previously defined, wherein the part corresponding to -$A^1$- is bound to $R^1$ and the part -$A^2$- is bound to the rest of the molecule. Thus, when -$A^1$-$A^2$- is —O—CH$_2$—, the —O— is bound to $R^1$ and —CH$_2$— is attached directly to the bicycle.

e. $R^1$ GROUPS

In one aspect, $R^1$ is aryl or heteroaryl and substituted with 0, 1, 2, or 3 groups each independently selected from cyano, halo, hydroxyl, trialkylsiloxyl, $C_{1-4}$-alkyl, $C_{1-4}$-alkyloxy, monohalo-$C_{1-4}$-alkyl, and polyhalo-$C_{1-4}$-alky. In a yet further aspect, $R^1$ is aryl or heteroaryl and substituted with 0, 1, 2, or 3 groups each independently selected from hydroxyl, trialkylsiloxyl, halo, $C_{1-4}$-alkyl, $C_{1-4}$-alkyloxy, monohalo-$C_{1-4}$-alkyl, and polyhalo-$C_{1-4}$-alkyl. In a further aspect, $R^1$ is aryl or heteroaryl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a further aspect, $R^1$ is aryl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a further aspect, $R^1$ is phenyl substituted with 0, 1, 2, or 3 groups each independently selected from halo, $C_{1-4}$alkyl, $C_{1-4}$alkyloxy, and mono- and poly-halo$C_{1-4}$alkyl. In a further aspect, $R^1$ is phenyl optionally substituted with 1, 2, or 3 independently selected halo substituents.

In a further aspect, $R^1$ is six-membered monocyclic aryl or six-membered monocyclic heteroaryl.

In a yet further aspect, $R^1$ is heteroaryl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a further aspect, $R^1$ is heteroaryl optionally substituted with 1, 2, or 3 independently selected halo substituents.

In various aspects, $R^1$ is aryl (e.g., phenyl), which can be substituted with, for example, 0, 1, 2, or 3 groups, with 1-3 groups, with 1-2 groups, with 0-1 groups, or with 0 groups. In various further aspects, $R^1$ is heteroaryl (e.g., pyridinyl), which can be substituted with, for example, 0, 1, 2, or 3 groups, with 1-3 groups, with 1-2 groups, with 0-1 groups, or with 0 groups.

In a further aspect, $R^1$ is selected from phenyl, pyridinyl, pyrazinyl, pyridazinyl and pyrimidinyl, and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a still further aspect, $R^1$ is selected from phenyl, pyridinyl, and pyrimidinyl, and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a yet further aspect, $R^1$ is selected from phenyl and pyridinyl, and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In an even further aspect, $R^1$ is selected from phenyl and pyrimidinyl, and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl.

In a further aspect, $R^1$ is phenyl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a yet further aspect, $R^1$ is pyridinyl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a still further aspect, $R^1$ is pyrazinyl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In an even further aspect, $R^1$ is pyridazinyl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl. In a yet further aspect, $R^1$ is pyrimidinyl and substituted with 0, 1, 2, or 3 groups each independently selected from halo, $C_{1-4}$-alkyl, $C_{1-4}$-alkyloxy, monohalo-$C_{1-4}$-alkyl, and polyhalo-$C_{1-4}$-alkyl.

In a further aspect, $R^1$ is selected from unsubstituted phenyl, pyridinyl, pyrazinyl, pyridazinyl and pyrimidinyl. In a still further aspect, $R^1$ is selected from unsubstituted phenyl, pyridinyl, and pyrimidinyl. In a yet further aspect, $R^1$ is selected from unsubstituted phenyl and pyridinyl. In an even further aspect, $R^1$ is selected from unsubstituted phenyl and pyrimidinyl.

In a further aspect, $R^1$ is unsubstituted phenyl. In a yet further aspect, $R^1$ is unsubstituted pyridinyl. In a still further aspect, $R^1$ is unsubstituted pyrazinyl. In an even further aspect, $R^1$ is unsubstituted pyridazinyl. In a yet further aspect, $R^1$ is unsubstituted pyrimidinyl.

In one aspect, $R^1$ is phenyl optionally substituted with one, two or three substituents each independently selected from the group consisting of halo, $C_{1-4}$alkyl, $C_{1-4}$alkyloxy, and mono- and poly-halo$C_{1-4}$alkyl. In a further aspect, $R^1$ is selected from the group consisting of phenyl, 2-fluorophenyl, 3-fluorophenyl, 4-fluorophenyl and 3,4-difluorophenyl. In a still further aspect, $R^1$ is selected from the group consisting of phenyl, 2-fluorophenyl, 3-fluorophenyl, 4-fluorophenyl and 3,4-difluorophenyl.

f. $R^2$ GROUPS

In one aspect, $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, —$NH_2$, $C_{1-4}$alkyl, $C_{1-4}$-alkyloxy, monohalo-$C_{1-4}$-alkyl, polyhalo-$C_{1-4}$-alkyl, $C_{1-4}$-alkyloxycarbonylamino, aryloxy-$C_{1-4}$-alkyl, aryloxy-$C_{1-4}$-alkyl, aryl-$C_{3-8}$-cycloalkyl, polyhalo-$C_{1-4}$-alkyloxy, $C_{1-4}$-alkyloxy-$C_{1-4}$-alkyl, $C_{1-4}$-alkyloxy-$C_{1-4}$-alkylheterocyclyl, and heterocyclyl substituted with carbonyl; or wherein $R^2$ is selected from $Ar^1$, $Ar^1$—$C_{1-6}$-alkyl-, $Ar^1$-$C_{3-8}$-cycloalkyl-, $Ar^1$-oxy-$C_{1-4}$-alkyl; $Ar^2$, $Ar^2$-$C_{1-6}$-alkyl-, $Ar^2$-$C_{3-8}$-cycloalkyl-, $Ar^2$-oxy-$C_{1-4}$-alkyl; $Ar^3$, $Ar^3$—$C_{1-6}$-alkyl-, $Ar^1$-oxy-$C_{1-4}$-alkyl; $Ar^3$-$C_{3-8}$-cycloalkyl-, and $Ar^3$-oxy-$C_{1-4}$-alkyl.

In a further aspect, $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, —$NH_2$, $C_{1-4}$-alkyl, $C_{1-4}$-alkyloxy, monohalo-$C_{1-4}$-alkyl, polyhalo-$C_{1-4}$-alkyl, $C_{1-4}$-alkyloxycarbonylamino, aryloxy-$C_{1-4}$-alkyl, aryloxy-$C_{1-4}$-alkyl, aryl-$C_{3-8}$-cycloalkyl, polyhalo-$C_{1-4}$-alkyloxy, $C_{1-4}$-alkyloxy-$C_{1-4}$-alkylheterocyclyl, and heterocyclyl substituted with carbonyl; or $R^2$ is selected from $Ar^1$, $Ar^1$—$C_{1-6}$-alkyl-, $Ar^2$, $Ar^2$-$C_{1-6}$-alkyl-, $Ar^3$, and $Ar^3$-$C_{1-6}$-alkyl-.

In a further aspect, $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, $C_{1-4}$-alkyl, $C_{1-4}$-alkyloxy, monohalo-$C_{1-4}$-alkyl, and polyhalo-$C_{1-4}$-alkyl. In a further aspect, $R^2$ is selected from $Ar^1$, $Ar^1$-$C_{1-6}$-alkyl-, $Ar^2$, $Ar^2$-$C_{1-6}$-alkyl-, $Ar^3$, and $Ar^3$-$C_{1-6}$-alkyl-.

In a further aspect, $R^2$ is selected from $C_{1-6}$alkyl, ($C_{1-6}$alkyloxy)$C_{1-6}$alkyl, mono- and polyhalo-$C_{1-6}$alkyl, $C_{3-8}$cycloalkyl, ($C_{3-8}$cycloalkyl)$C_{1-6}$alkyl, —$OR^3$, $Ar^1$, and heteroaryl. In further aspect, $R^2$ is selected from $C_{1-6}$alkyl, ($C_{3-8}$cycloalkyl)$C_{1-6}$alkyl, —$OR^3$, $Ar^1$, and heteroaryl.

In a further aspect, $R^2$, when present, is substituted with 1, 2, or 3 substituents each independently selected from halo, $C_{1-4}$-alkyl, $C_{1-4}$-alkyloxy, monohalo-$C_{1-4}$-alkyl, and polyhalo-$C_{1-4}$-alkyl.

In one aspect, $R^2$ is selected from the group consisting of $C_{1-6}$alkyl, ($C_{1-6}$alkyloxy)$C_{1-6}$alkyl, mono- and polyhalo-$C_{1-6}$alkyl, $C_{3-8}$cycloalkyl, ($C_{3-8}$cycloalkyl)$C_{1-6}$alkyl, —$OR^3$, $Ar^1$, and heteroaryl. In a further aspect, $R^2$ is selected from the group consisting of $C_{1-6}$alkyl, ($C_{3-8}$cycloalkyl)$C_{1-6}$alkyl, —$OR^3$, $Ar^1$ and heteroaryl. In a still further aspect, $R^2$ is selected from the group consisting of methyl, cyclopropylmethyl, benzyloxy, $Ar^1$ and heteroaryl. In an even further aspect, $R^2$ is selected from the group consisting of phenyl, 2-fluorophenyl, 3-fluorophenyl, 4-fluorophenyl, 2,3-difluorophenyl, 2,4-difluorophenyl, 2,6-difluorophenyl, 3,4-difluorophenyl and 3,5-difluorophenyl. In a still further aspect, $R^2$ is phenyl optionally substituted with one or two fluoro substituents. In an even further aspect, $R^2$ is 4-fluorophenyl.

g. R³ GROUPS

In one aspect, R³ is selected from Ar⁴ and Ar⁴-$C_{1-6}$-alkyl-. For example, R³ can be Ar⁴. In a further example, R³ can be Ar⁴-$C_{1-6}$-alkyl-.

In one aspect, R³ is selected from the group consisting of phenyl and phenyl-$C_{1-6}$alkyl-; wherein the phenyl is optionally substituted with one, two or three substituents each independently selected from the group consisting of halo, cyano, $C_{1-4}$alkyl, $C_{1-4}$alkyloxy, and mono- and polyhalo-$C_{1-4}$alkyl. In a further aspect, R³ is selected from phenyl and phenyl-$C_{1-6}$alkyl-, wherein the phenyl is unsubstituted. In a still further aspect, R³ is unsubstituted phenyl. In a yet further aspect, R³ is phenyl-$C_{1-6}$alkyl-, wherein the phenyl is unsubstituted.

h. AR¹ GROUPS

In one aspect, Ar¹, when present, is phenyl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl. In a further aspect, Ar¹, when present, is phenyl substituted with 0, 1, 2, or 3 groups each independently selected from halo, cyano, $C_{1-4}$alkyl, $C_{1-4}$alkyloxy, and mono- and polyhalo-$C_{1-4}$alkyl.

In one aspect, Ar¹, when present, is phenyl optionally substituted with one, two or three substituents each independently selected from the group consisting of halo, cyano, $C_{1-4}$alkyl, $C_{1-4}$alkyloxy, and mono- and polyhalo-$C_{1-4}$alkyl. In a further aspect, Ar¹, when present, is phenyl optionally substituted with one, two or three independently selected halo substituents. In a yet further aspect, Ar¹, when present, is phenyl optionally substituted with one or two independently selected halo substituents. In an even further aspect, Ar¹ is selected from the group consisting of phenyl, 2-fluorophenyl, 3-fluorophenyl, 4-fluorophenyl, 2,3-difluorophenyl, 2,4-difluorophenyl, 2,6-difluorophenyl, 3,4-difluorophenyl and 3,5-difluorophenyl.

i. AR² GROUPS

In one aspect, Ar², when present, is monocyclic heteroaryl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl. In a further aspect, Ar², when present, is substituted with 1, 2, or 3 groups each independently selected from halo, cyano, $C_{1-4}$-alkyl, $C_{1-4}$-alkyloxy, and monohalo-$C_{1-4}$-alkyl, polyhalo-$C_{1-4}$-alkyl, and pentafluorosulfanyl.

In one aspect, Ar², when present, is monocyclic heterocyclyl substituted with 0, 1, 2, or 3 groups each independently selected from selected from halo, cyano, amino, mono-$C_{1-4}$-alkylamino, di-$C_{1-4}$-alkylamino, $C_{1-4}$-alkyl, $C_{1-4}$-alkyloxy, ($C_{1-6}$-alkyloxy)-$C_{1-4}$-alkyl, monohalo-$C_{1-4}$-alkyl, polyhalo-$C_{1-4}$-alkyl, and pentafluorosulfanyl. In a further aspect, Ar², when present, is substituted with 1, 2, or 3 groups each independently selected from halo, cyano, amino, mono-$C_{1-4}$-alkylamino, di-$C_{1-4}$-alkylamino, $C_{1-4}$-alkyl, $C_{1-4}$-alkyloxy, ($C_{1-6}$-alkyloxy)-$C_{1-4}$-alkyl, monohalo-$C_{1-4}$-alkyl, polyhalo-$C_{1-4}$-alkyl, and pentafluorosulfanyl.

In a further aspect, Ar², when present, is selected from furanyl, imidazolyl, isoxazolyl (1,3-oxazolyl), oxazolyl, 1,2,4-oxadiazolyl, pyrazinyl, pyrazolyl, pyridazinyl, pyridinyl, pyridin-2(1H)-onyl, pyrimidinyl, pyrrolyl, pyrrolidin-2-only (oxo-pyrrolidinyl), thioenyl, thiazolyl, and 1,2,3-triazolyl, and substituted with 0, 1, 2, or 3 groups each independently selected from selected from halo, cyano, amino, mono-$C_{1-4}$-alkylamino, di-$C_{1-4}$-alkylamino, $C_{1-4}$-alkyl, $C_{1-4}$-alkyloxy, ($C_{1-6}$-alkyloxy)-$C_{1-4}$-alkyl, monohalo-$C_{1-4}$-alkyl, polyhalo-$C_{1-4}$-alkyl, and pentafluorosulfanyl.

In a further aspect, Ar², when present, is selected from furanyl, imidazolyl, isoxazolyl (1,3-oxazolyl), oxazolyl, 1,2,4-oxadiazolyl, pyrazinyl, pyrazolyl, pyridazinyl, pyridinyl, pyridin-2(1H)-onyl, pyrimidinyl, pyrrolyl, pyrrolidin-2-only (oxo-pyrrolidinyl), thioenyl, thiazolyl, and 1,2,3-triazolyl, wherein the heterocyclyl is unsubstituted.

In a further aspect, Ar², when present, is selected from furan-2-yl, imidazol-2-yl, imidazol-4-yl, imidazol-5-yl, isoxazol-3-yl, isoxazol-4-yl, isoxazol-5-yl, oxazol-2-yl, 1,2-oxazol-4-yl (oxazol-4-yl), 1,2-oxazol-5-yl (oxazol-5-yl), 1,2,4-oxadiazol-3-yl, 1,2,4-oxadiazol-5-yl, pyrazin-2-yl, pyrazol-3-yl, pyrazol-4-yl, pyridazin-3-yl, pyridazin-4-yl, pyridin-2-yl, pyridin-3-yl, pyridin-4-yl, pyridin-2(1H)-on-5-yl, pyrimidin-2-yl, pyrimidin-5-ylpyrrol-2-yl, pyrrolidin-2-on-5-yl, thien-2-yl, thiazol-2-yl, 1,3-thiazol-4-yl (thiazol-4-yl), and 1,2,3-triazol-5-yl, and substituted with 0, 1, 2, or 3 groups each independently selected from selected from halo, cyano, amino, mono-$C_{1-4}$-alkylamino, di-$C_{1-4}$-alkylamino, $C_{1-4}$-alkyl, $C_{1-4}$-alkyloxy, ($C_{1-6}$-alkyloxy)-$C_{1-4}$-alkyl, monohalo-$C_{1-4}$-alkyl, polyhalo-$C_{1-4}$-alkyl, and pentafluorosulfanyl.

In a further aspect, Ar², when present, is selected from furan-2-yl, imidazol-2-yl, imidazol-4-yl, imidazol-5-yl, isoxazol-3-yl, isoxazol-4-yl, isoxazol-5-yl, oxazol-2-yl, 1,2-oxazol-4-yl (oxazol-4-yl), 1,2-oxazol-5-yl (oxazol-5-yl), 1,2,4-oxadiazol-3-yl, 1,2,4-oxadiazol-5-yl, pyrazin-2-yl, pyrazol-3-yl, pyrazol-4-yl, pyridazin-3-yl, pyridazin-4-yl, pyridin-2-yl, pyridin-3-yl, pyridin-4-yl, pyridin-2(1H)-on-5-yl, pyrimidin-2-yl, pyrimidin-5-ylpyrrol-2-yl, pyrrolidin-2-on-5-yl, thien-2-yl, thiazol-2-yl, 1,3-thiazol-4-yl (thiazol-4-yl), and 1,2,3-triazol-5-yl, wherein the heterocyclyl is unsubstituted.

In a further aspect, Ar², when present, is selected from pyrrol-2-yl, pyrazolyl, pyrazin-2-yl, pyrazol-3-yl, pyrazol-4-yl, furan-2-yl, 1,2-oxazol-4-yl, 1,2-oxazol-5-yl, 1,3-oxazolyl, 1,2,4-oxadiazol-5-yl, 1,2,3-triazolyl, thien-2-yl, 1,3-thiazol-4-yl, pyridin-2-yl, pyridin-3-yl, pyridin-4-yl, pyrrolidin-2-on-5-yl, and pyrimidin-5-yl, and substituted with 0, 1, 2, or 3 groups each independently selected from selected from halo, cyano, amino, mono-$C_{1-4}$-alkylamino, di-$C_{1-4}$-alkylamino, $C_{1-4}$-alkyl, $C_{1-4}$-alkyloxy, ($C_{1-6}$-alkyloxy)-$C_{1-4}$-alkyl, monohalo-$C_{1-4}$-alkyl, polyhalo-$C_{1-4}$-alkyl, and pentafluorosulfanyl.

In a further aspect, Ar², when present, is selected from pyrrol-2-yl, pyrazolyl, pyrazin-2-yl, pyrazol-3-yl, pyrazol-4-yl, furan-2-yl, 1,2-oxazol-4-yl, 1,2-oxazol-5-yl, 1,3-oxazolyl, 1,2,4-oxadiazol-5-yl, 1,2,3-triazolyl, thien-2-yl, 1,3-thiazol-4-yl, pyridin-2-yl, pyridin-3-yl, pyridin-4-yl, pyrrolidin-2-on-5-yl, and pyrimidin-5-yl, wherein the heterocyclyl is unsubstituted.

In a further aspect, Ar², when present, is 2-pyridyl, 3-pyridyl, or 4-pyridyl and substituted with 0, 1, 2, or 3 groups each independently selected from halo, $C_{1-4}$alkyl, cyano, $C_{1-4}$alkyloxy and mono- and polyhalo-$C_{1-4}$alkyl. In a still further aspect, Ar², when present, is selected from pyrrolyl, furanyl, 1,2-oxazol-5-yl, and pyridinyl. In a still further aspect, Ar², when present, is oxo-pyrrolidinyl.

j. AR³ GROUPS

In one aspect, Ar³, when present, is bicyclic heteroaryl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl. In a further aspect, Ar$^3$, when present, is bicyclic heteroaryl substituted with 0, 1, 2, or 3 groups each independently selected from halo, cyano, $C_{1-4}$-alkyl, $C_{1-4}$-alkyloxy, and monohalo-$C_{1-4}$-alkyl, polyhalo-$C_{1-4}$-alkyl, and pentafluorosulfanyl.

In one aspect, Ar$^3$, when present, is bicyclic heterocyclyl substituted with 0, 1, 2, or 3 groups each independently selected from halo, cyano, amino, mono-$C_{1-4}$-alkylamino, di-$C_{1-4}$-alkylamino, $C_{1-4}$-alkyl, $C_{1-4}$-alkyloxy, monohalo-$C_{1-4}$-alkyl, polyhalo-$C_{1-4}$-alkyl, and pentafluorosulfanyl. In a further aspect, Ar$^3$, when present, is bicyclic heterocyclyl substituted with 1, 2, or 3 groups each independently selected from halo, cyano, amino, mono-$C_{1-4}$-alkylamino, di-$C_{1-4}$-alkylamino, $C_{1-4}$-alkyl, $C_{1-4}$-alkyloxy, monohalo-$C_{1-4}$-alkyl, polyhalo-$C_{1-4}$-alkyl, and pentafluorosulfanyl.

In a further aspect, Ar$^3$, when present, is selected from benzo[d][1,3]dioxolyl (1,3-benzodioxolyl), benzo[b][1,4]dioxinyl (2,3-dihydro-1,4-benzodioxinyl), benzofuranyl, benzo[d]imidazolyl, chromanyl, 3,4-dihydro-2H-chromenyl, indazolyl, indolyl, quinolinyl, quinoxalinyl, pyrazolo[1,5-a]pyridinyl, pyrrolo[3,2-b]pyridinyl, pyrazolo[3,4-b]pyridinyl, pyrazolo[4,3-b]pyridinyl, and pyrazolo[4,3-c]pyridinyl, and substituted with 0, 1, 2, or 3 groups each independently selected from halo, cyano, amino, mono-$C_{1-4}$-alkylamino, di-$C_{1-4}$-alkylamino, $C_{1-4}$-alkyl, $C_{1-4}$-alkyloxy, monohalo-$C_{1-4}$-alkyl, polyhalo-$C_{1-4}$-alkyl, and pentafluorosulfanyl.

In a further aspect, Ar$^3$, when present, is selected from benzo[d][1,3]dioxolyl (1,3-benzodioxolyl), benzo[b][1,4]dioxinyl (2,3-dihydro-1,4-benzodioxinyl), benzofuranyl, benzo[d]imidazolyl, chromanyl, 3,4-dihydro-2H-chromenyl, indazolyl, indolyl, quinolinyl, quinoxalinyl, pyrazolo[1,5-a]pyridinyl, pyrrolo[3,2-b]pyridinyl, pyrazolo[3,4-b]pyridinyl, pyrazolo[4,3-b]pyridinyl, pyrazolo[4,3-c]pyridinyl, and the bicyclic heterocyclyl is unsubstituted.

In a further aspect, Ar$^3$, when present, is selected from benzo[d][1,3]dioxol-5-yl, benzo[b][1,4]dioxin-6-yl, benzofuran-3-yl, benzo[d]imidazol-5-yl, chroman-2-yl, indazol-3-yl, indol-2-yl, indol-3-yl, quinolin-2-yl, quinoxalin-2-yl, quinoxalin-6-yl, pyrazolo[1,5-a]pyridin-3-yl, pyrrolo[3,2-b]pyridin-3-yl, pyrazolo[3,4-b]pyridin-3-yl, pyrazolo[4,3-b]pyridin-3-yl, and pyrazolo[4,3-c]pyridin-3-yl, and substituted with 0, 1, 2, or 3 groups each independently selected from halo, cyano, amino, mono-$C_{1-4}$-alkylamino, di-$C_{1-4}$-alkylamino, $C_{1-4}$-alkyl, $C_{1-4}$-alkyloxy, monohalo-$C_{1-4}$-alkyl, polyhalo-$C_{1-4}$-alkyl, and pentafluorosulfanyl.

In a further aspect, Ar$^3$, when present, is selected from benzo[d][1,3]dioxol-5-yl, benzo[b][1,4]dioxin-6-yl, benzofuran-3-yl, benzo[d]imidazol-5-yl, chroman-2-yl, indazol-3-yl, indol-2-yl, indol-3-yl, quinolin-2-yl, quinoxalin-2-yl, quinoxalin-6-yl, pyrazolo[1,5-a]pyridin-3-yl, pyrrolo[3,2-b]pyridin-3-yl, pyrazolo[3,4-b]pyridin-3-yl, pyrazolo[4,3-b]pyridin-3-yl, and pyrazolo[4,3-c]pyridin-3-yl, and the bicyclic heterocyclyl is unsubstituted.

In a further aspect, Ar$^a$, when present, is selected from benzo[d][1,3]dioxolyl (1,3-benzodioxolyl), benzo[b][1,4]dioxinyl (2,3-dihydro-1,4-benzodioxinyl), benzofuranyl, benzo[d]imidazolyl, chromanyl, 3,4-dihydro-2H-chromenyl, indazolyl, indolyl, quinolinyl, quinoxalinyl, pyrazolo[1,5-a]pyridinyl, pyrrolo[3,2-b]pyridinyl, pyrazolo[3,4-b]pyridinyl, pyrazolo[4,3-b]pyridinyl, pyrazolo[4,3-c]pyridinyl, and substituted with 0, 1, 2, or 3 groups each independently selected from halo, cyano, amino, mono-$C_{1-4}$-alkylamino, di-$C_{1-4}$-alkylamino, $C_{1-4}$-alkyl, $C_{1-4}$-alkyloxy, monohalo-$C_{1-4}$-alkyl, polyhalo-$C_{1-4}$-alkyl, and pentafluorosulfanyl.

k. AR$^4$ GROUPS

In one aspect, Ar$^4$, when present, is monocyclic heteroaryl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl. In a further aspect, Ar$^4$, when present, is phenyl substituted with 0, 1, 2, or 3 groups each independently selected from halo, cyano, $C_{1-4}$-alkyl, $C_{1-4}$-alkyloxy, monohalo-$C_{1-4}$-alkyl, and polyhalo-$C_{1-4}$-alkyl.

l. HETEROARYL GROUPS

In one aspect, heteroaryl is selected from monocyclic heteroaryl and bicyclic heteroaryl. In a further aspect, heteroaryl is a monocyclic heteroaryl. In a yet further aspect, heteroaryl is bicyclic heteroaryl.

In one aspect, heteroaryl can be pyridinyl; optionally substituted with 1, 2, or 3 groups each independently selected from halo, $C_{1-4}$alkyl, cyano, $C_{1-4}$alkyloxy and mono- and polyhalo-$C_{1-4}$alkyl. In a further aspect, heteroaryl is selected from the group consisting of 2-pyridinyl, 3-pyridinyl and 4-pyridinyl.

In a further aspect, heteroaryl is a monocyclic heteroaryl selected pyridinyl, pyrazinyl, pyridazinyl and pyrimidinyl. In a yet further aspect, heteroaryl is selected from pyridinyl, and pyrimidinyl. In a yet further aspect, heteroaryl is pyridinyl. In a still further aspect, heteroaryl is pyrazinyl. In an even further aspect, heteroaryl is pyridazinyl. In a yet further aspect, heteroaryl is pyrimidinyl.

m. MONOCYCLIC HETEROCYCLYL GROUPS

In one aspect, monocyclic heterocyclyl encompasses aromatic and non-aromatic ring systems. In a further aspect, aromatic monocyclic heterocyclic groups include, but are not limited to, pyrrolyl, pyrazolyl, furanyl, 1,2-oxazol-4-yl, 1,2-oxazol-5-yl, 1,3-oxazolyl, 1,2,4-oxadiazol-5-yl, 1,2,3-triazolyl, thienyl, 1,3-thiazol-4-yl, pyridinyl, and pyrimidin-5-yl. Exemplary non-aromatic monocyclic heterocyclic groups include, but are not limited to 5-oxo-pyrrolidinyl. In a particular embodiment, the aromatic monocyclic heterocyclic groups are selected from the group consisting of pyrrolyl, furanyl, 1,2-oxazol-5-yl, and pyridinyl.

n. BICYCLIC HETEROCYCLYL GROUPS

In one aspect, bicyclic heterocyclyl encompasses ring systems in which at least one of the ring members is other than carbon. In a further aspect, bicyclic heterocyclyl further encompass ring systems wherein an aromatic ring is fused with another aromatic ring, or wherein an aromatic ring is fused with a non-aromatic ring. In a still further aspect, bicyclic heterocyclyl groups include, but are not limited to, ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Exemplary bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, and 3,4-dihydro-2H-chromenyl. In a yet further aspect, the aromatic bicyclic heterocyclic groups are selected from the group consisting of 3-indolyl, indazolyl, quinolinyl, quinoxalinyl, 1,3-benzodioxolyl, 2,3-dihydro-1,4-benzodioxinyl, and 3,4-dihydro-2H-chromenyl.

o. HALOGEN (X)

In one aspect, halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.
2. EXAMPLE COMPOUNDS
In one aspect, a compound can be present as one or more of:
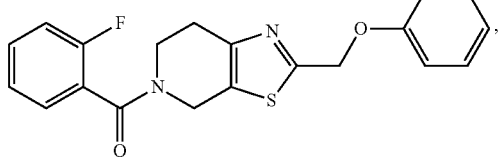
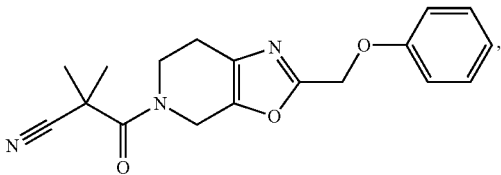
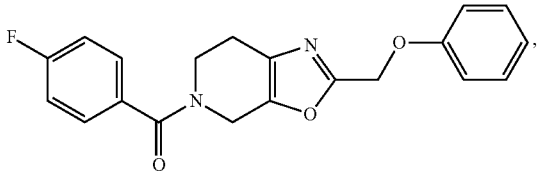
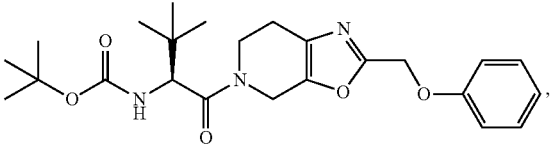
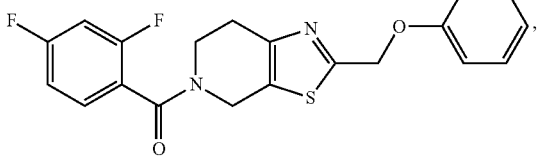
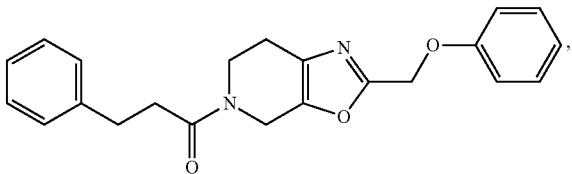
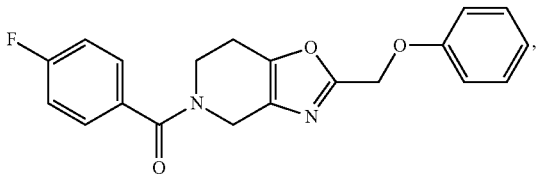
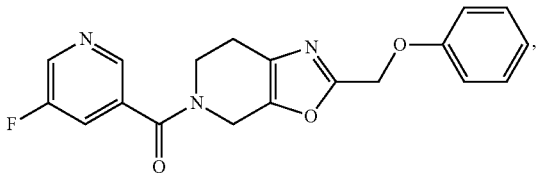
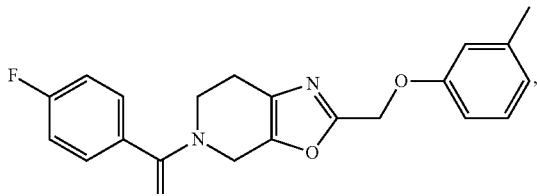
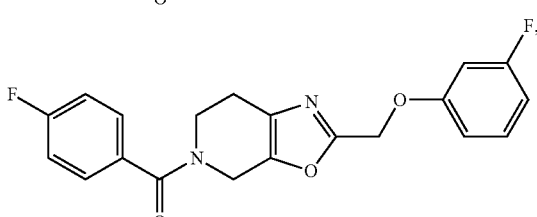
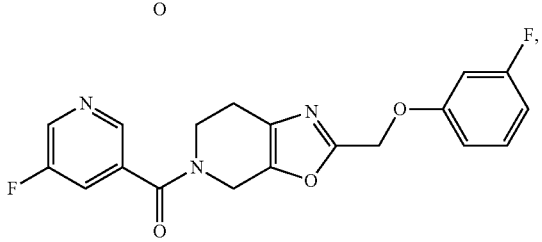
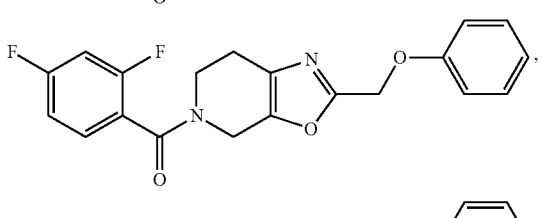
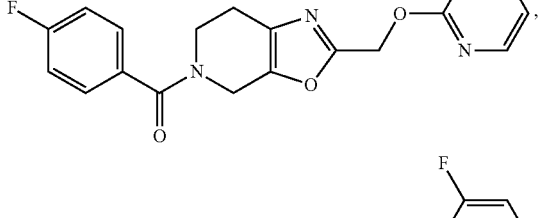
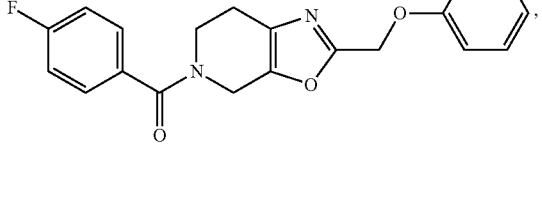
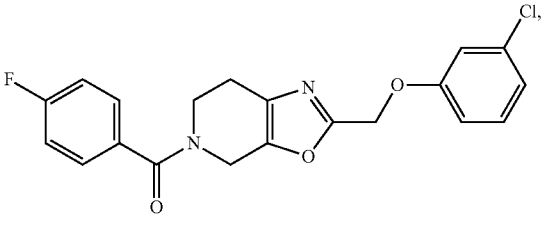

-continued
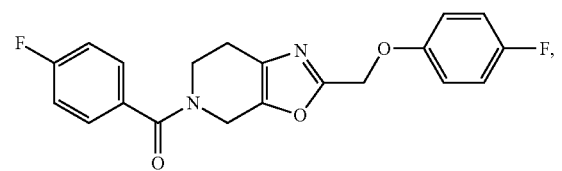
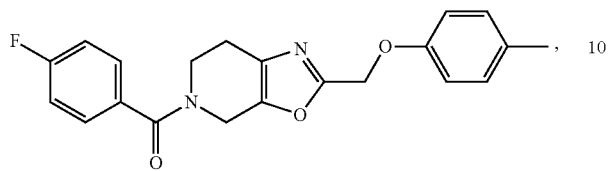
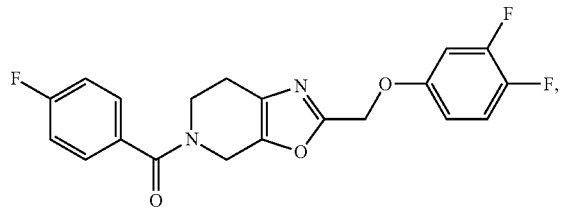
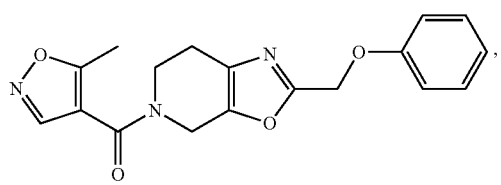
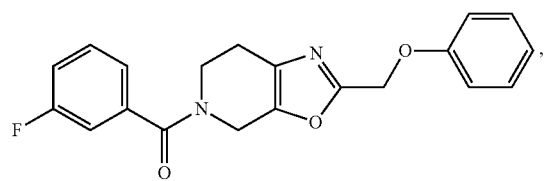
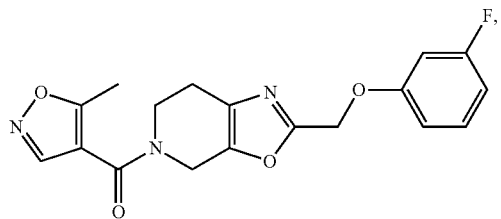
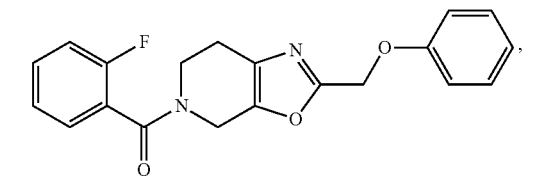
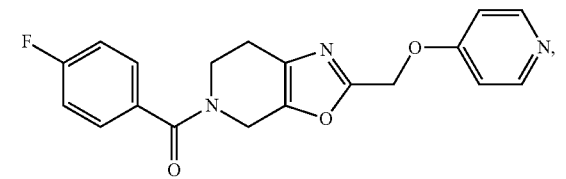
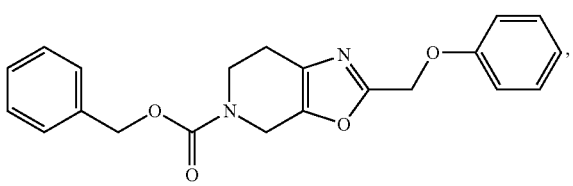
-continued
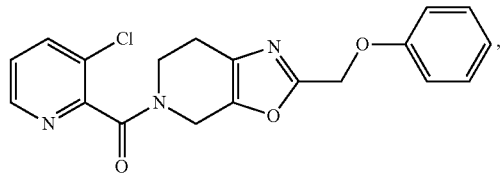
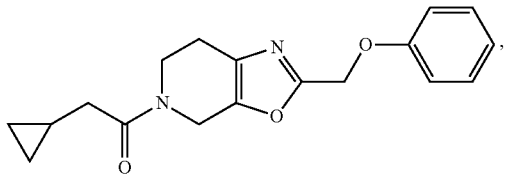
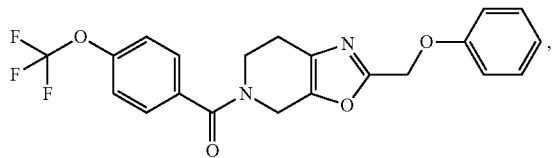
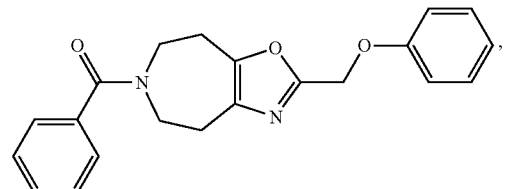
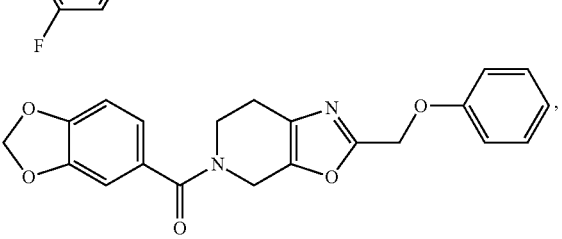
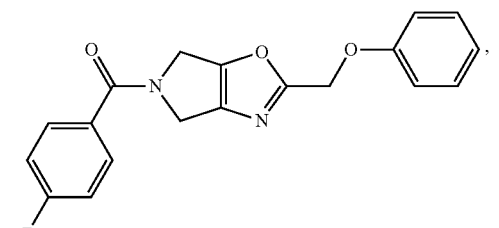
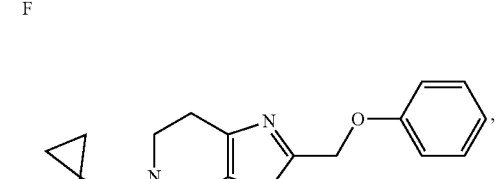
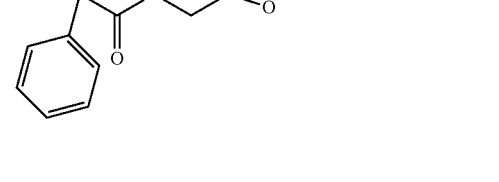
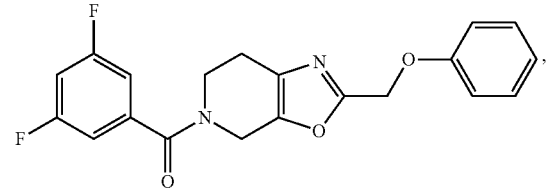

-continued
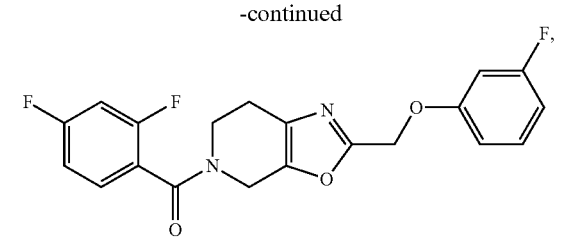
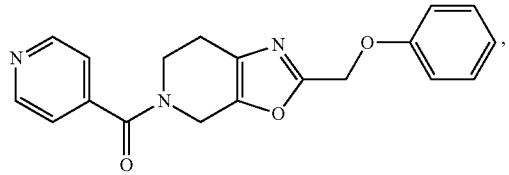
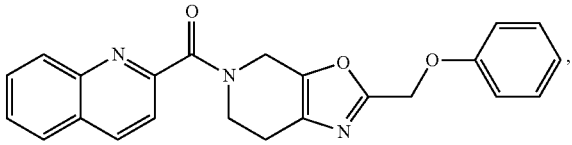
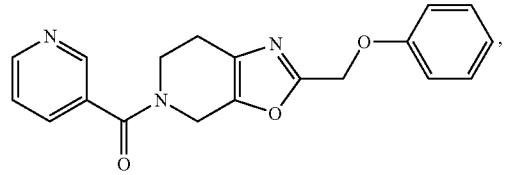
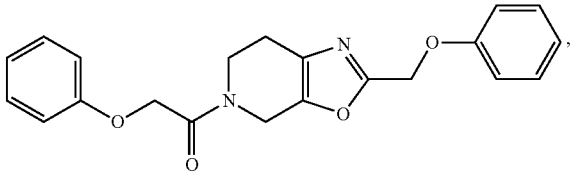
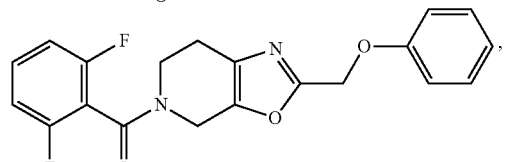
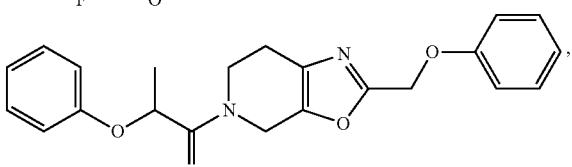
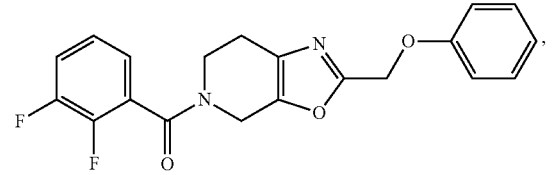
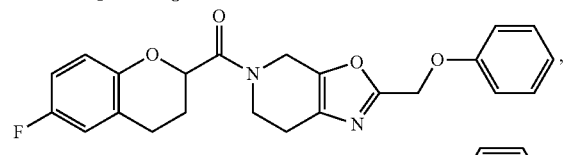
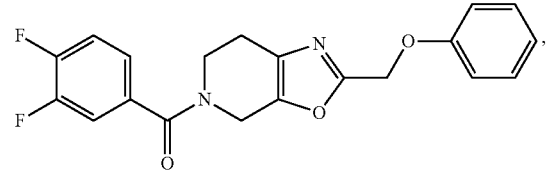
-continued
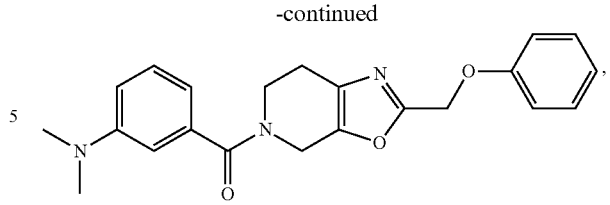
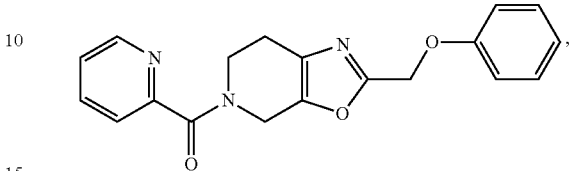
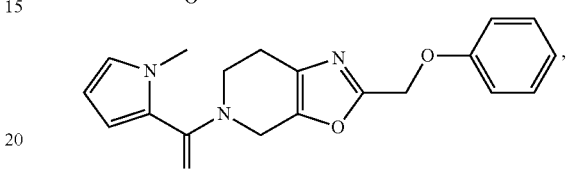
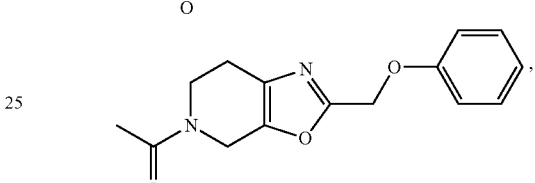
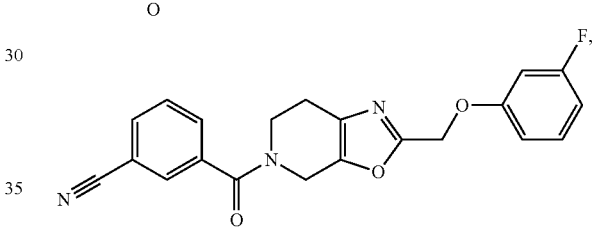
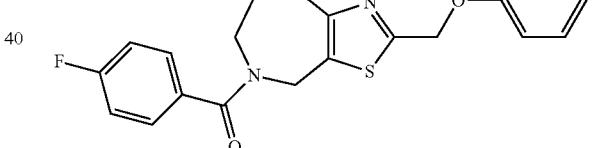
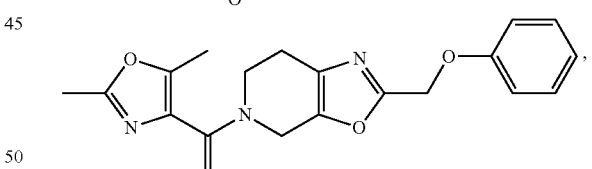
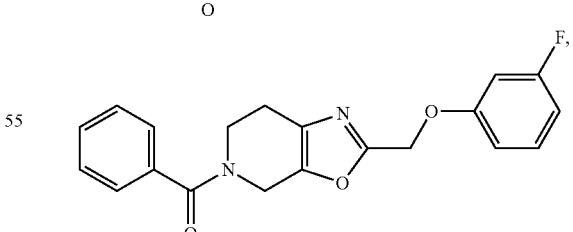
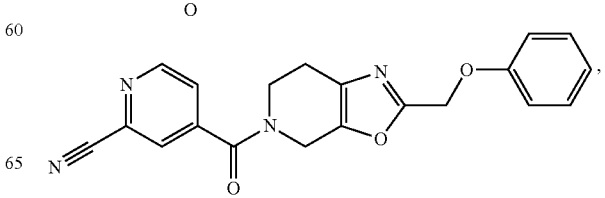

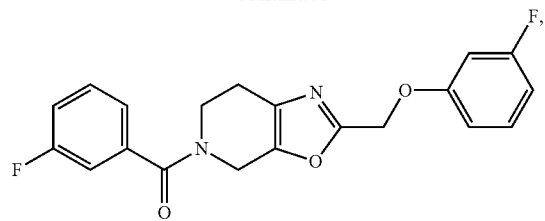
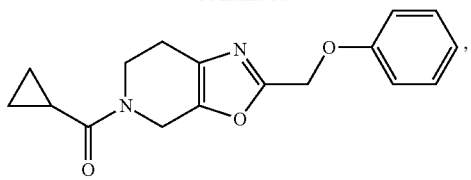
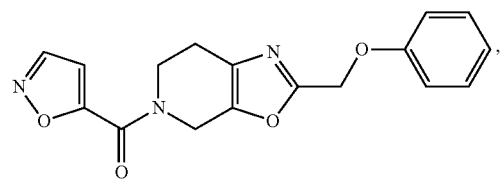
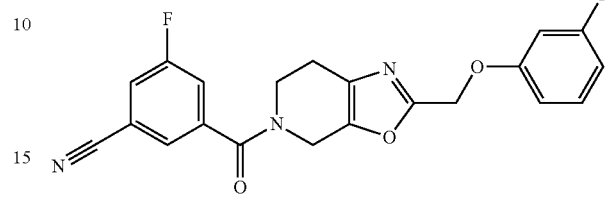
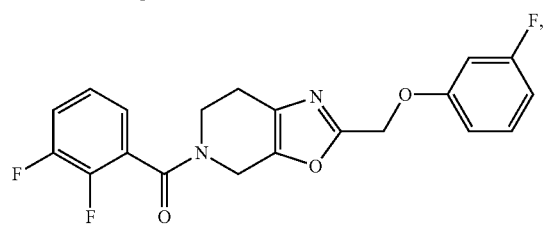
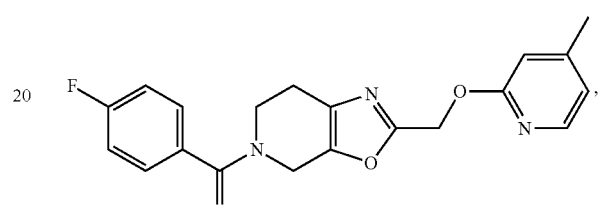
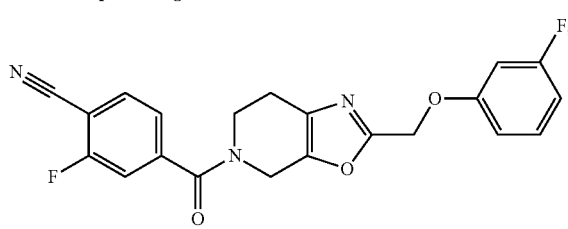
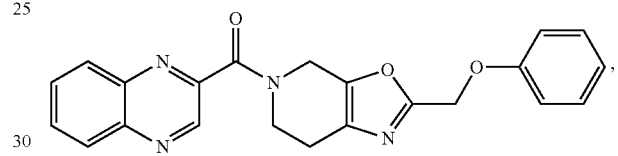
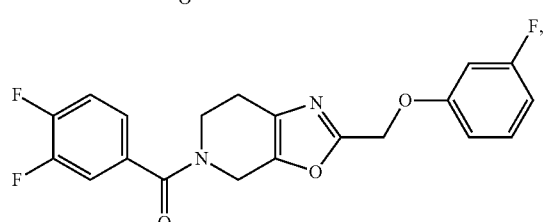
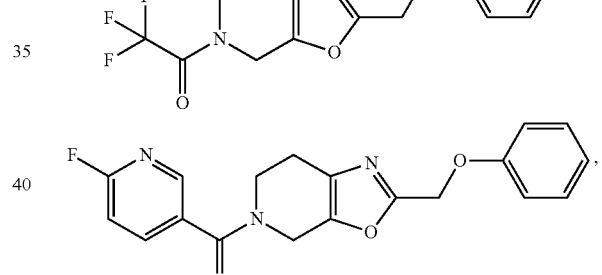
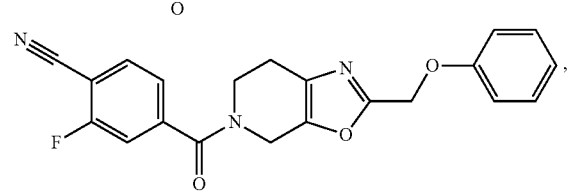
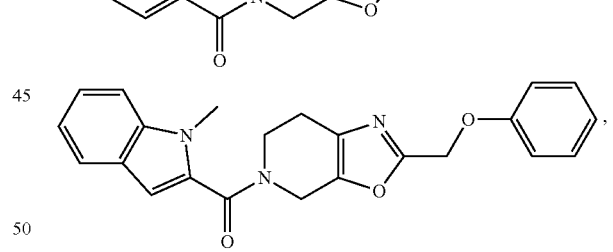
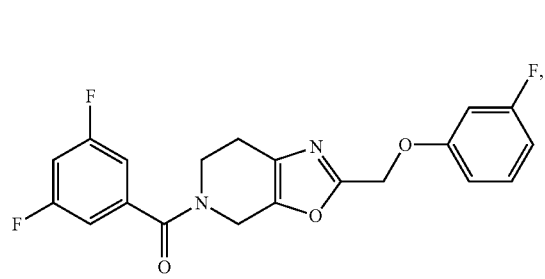
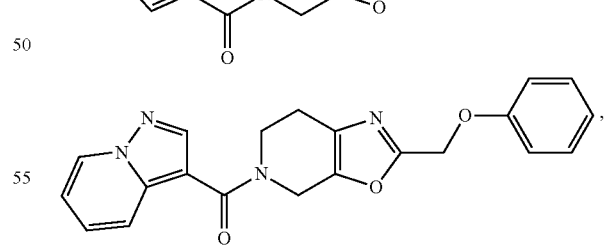
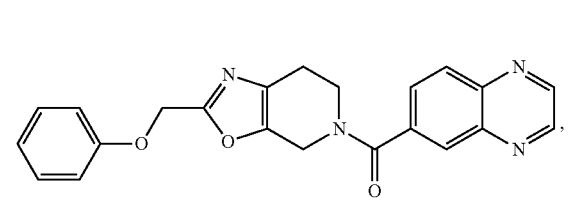
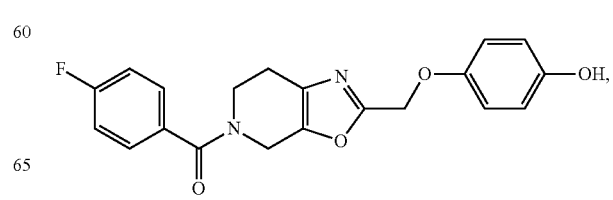

47
-continued
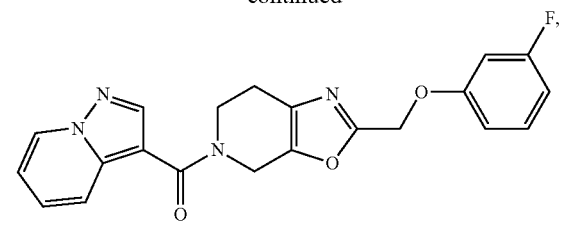
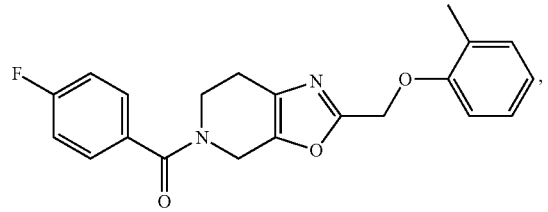
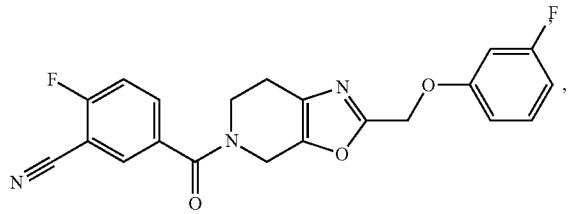
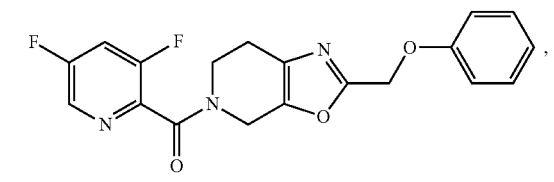
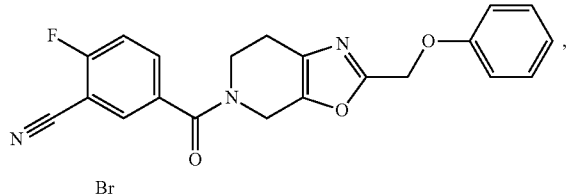
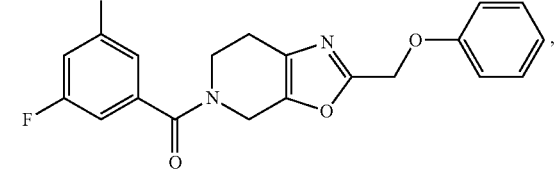
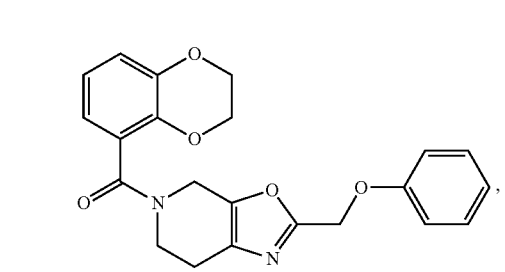
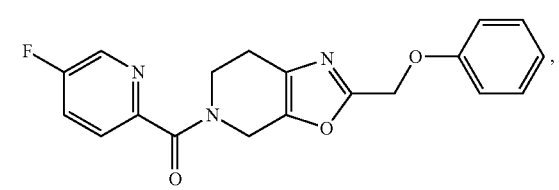
48
-continued
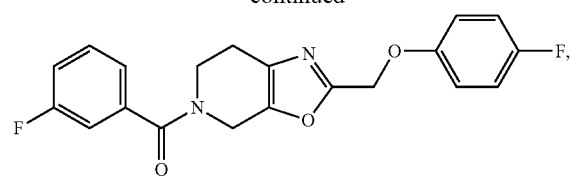
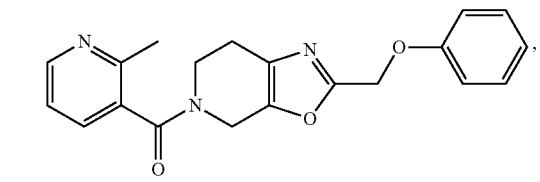
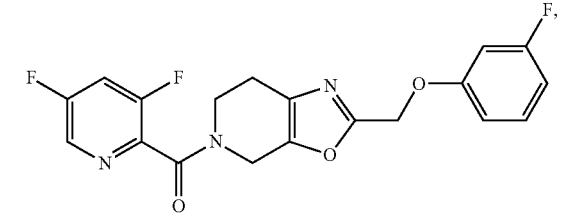
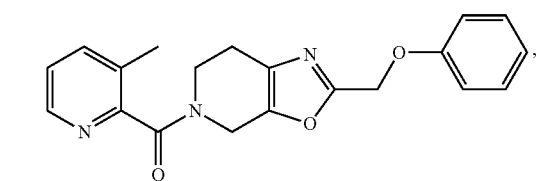
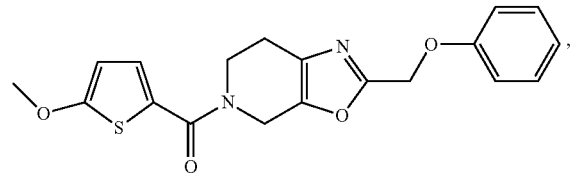
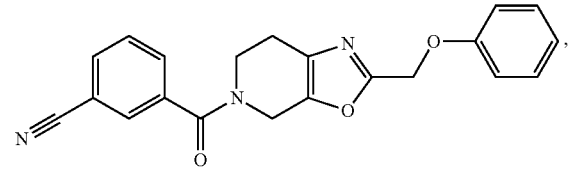
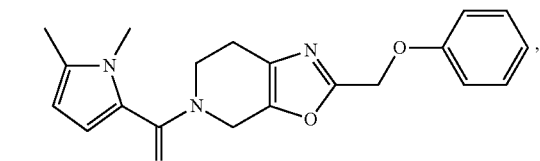
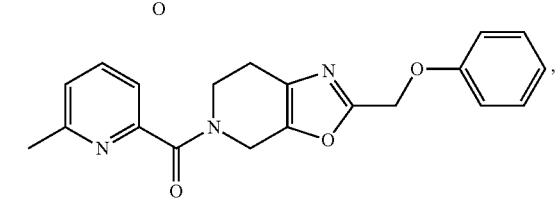
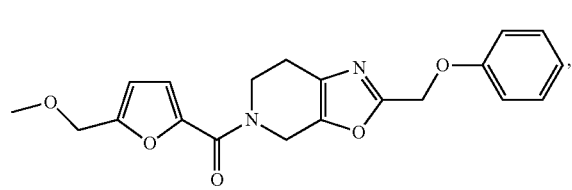

49
-continued
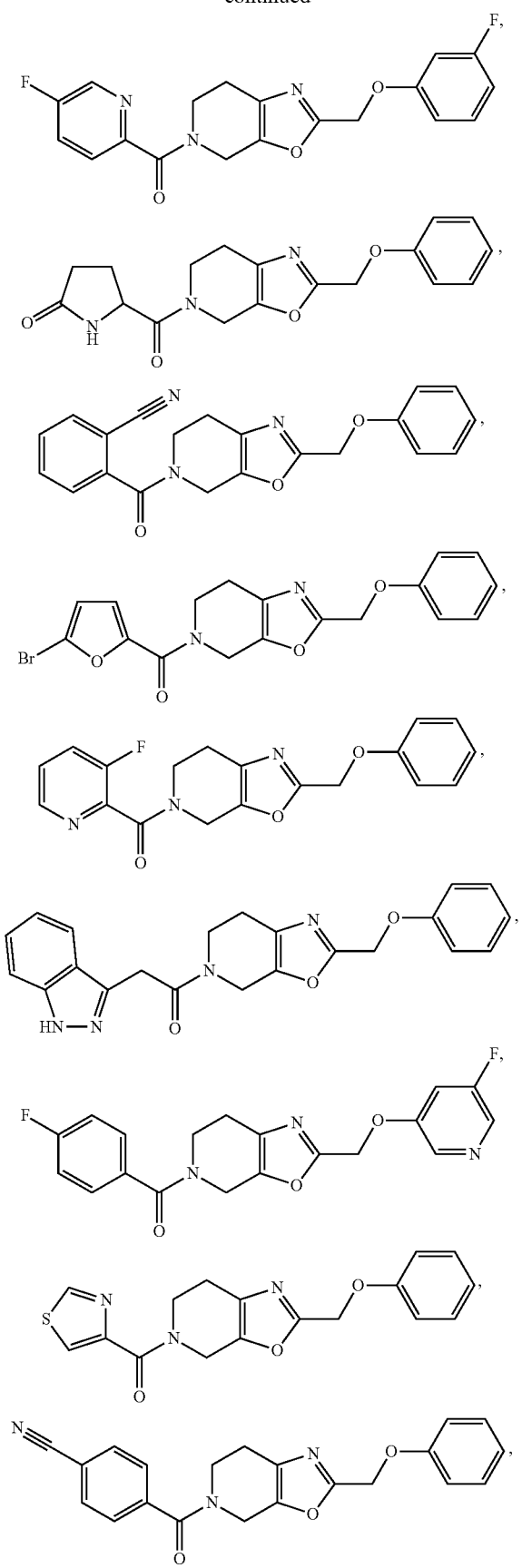
50
-continued
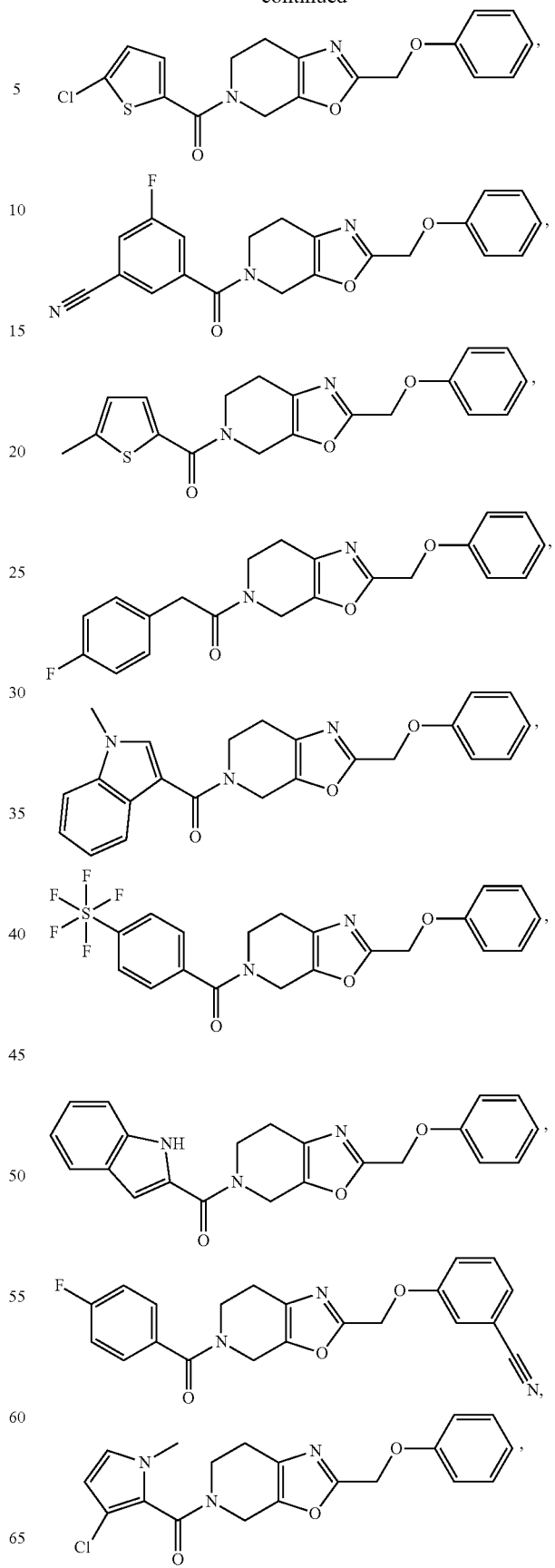

51
-continued
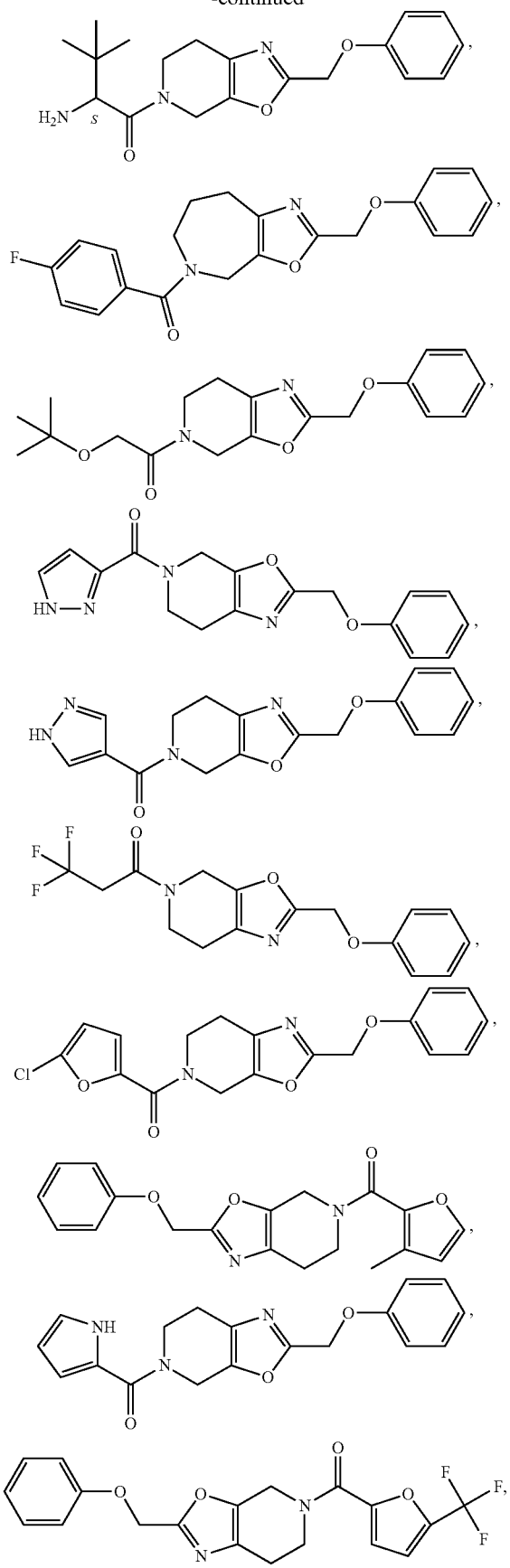
52
-continued
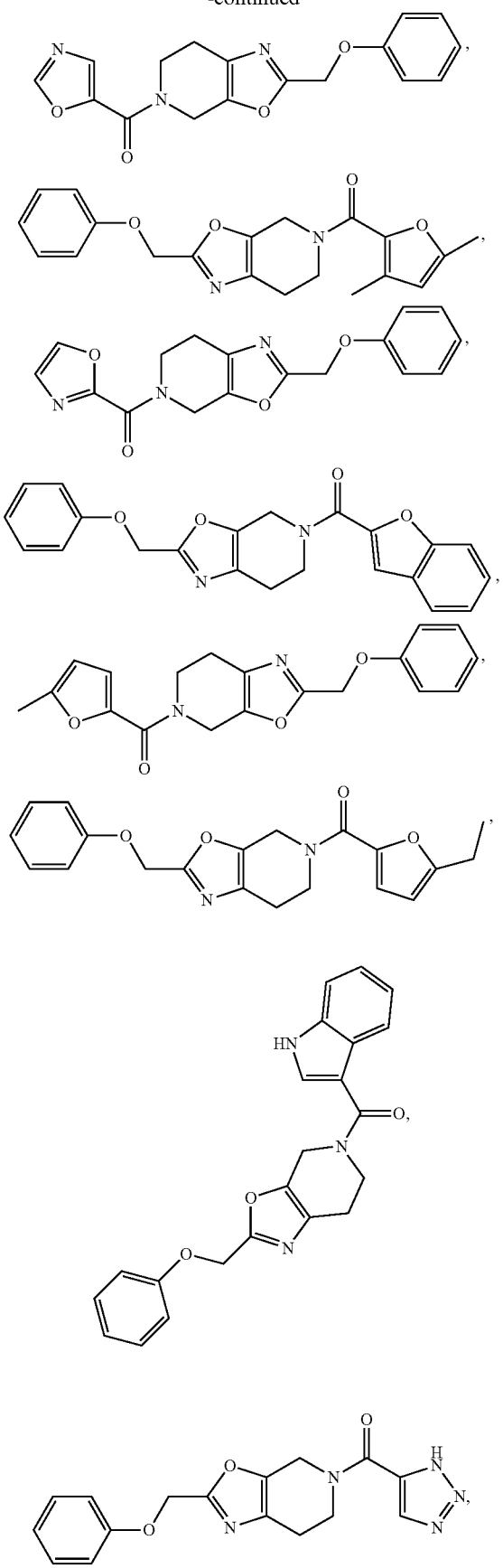

53
-continued
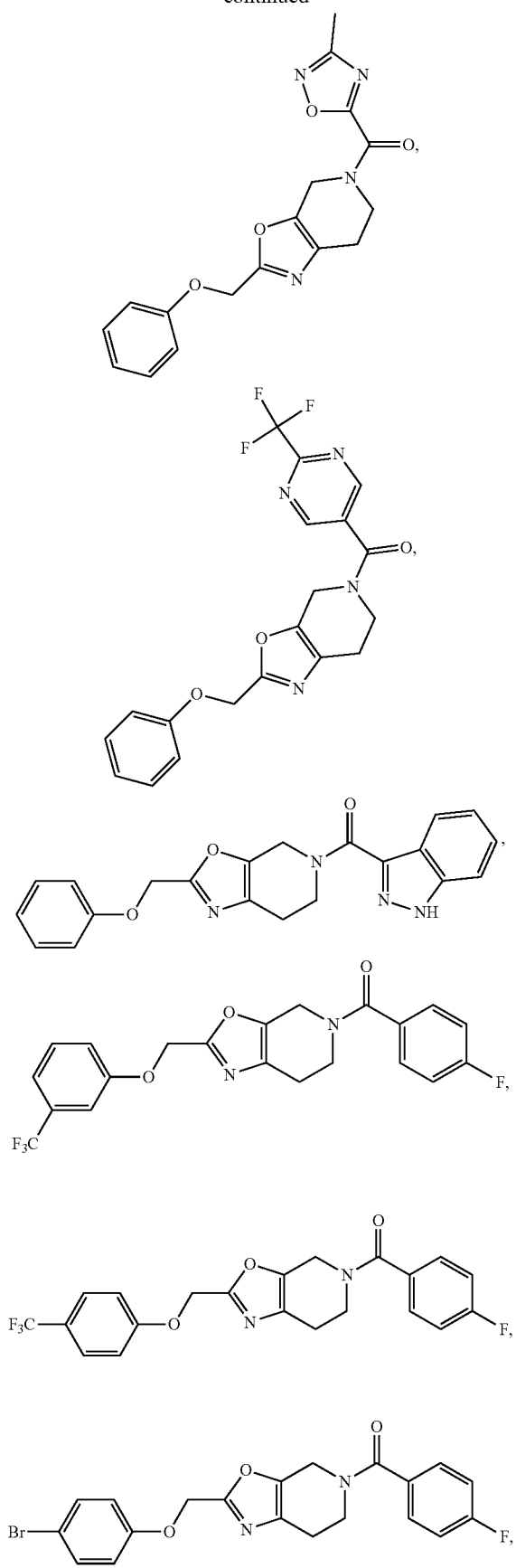
54
-continued
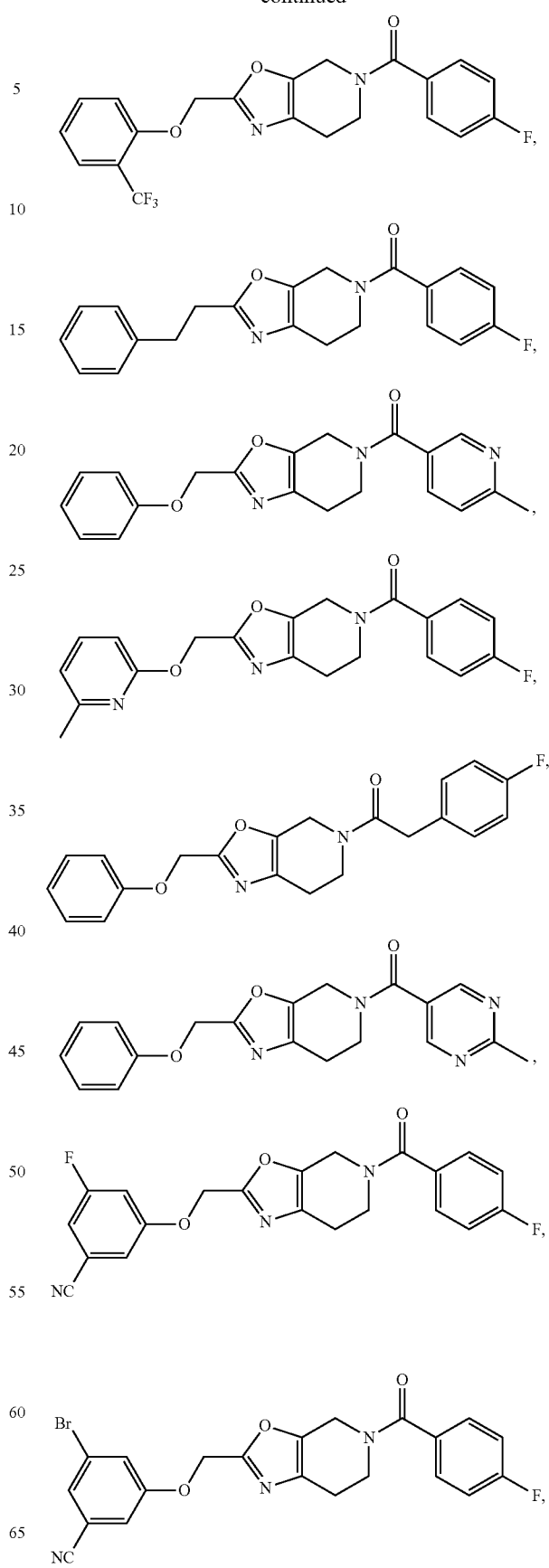

55
-continued
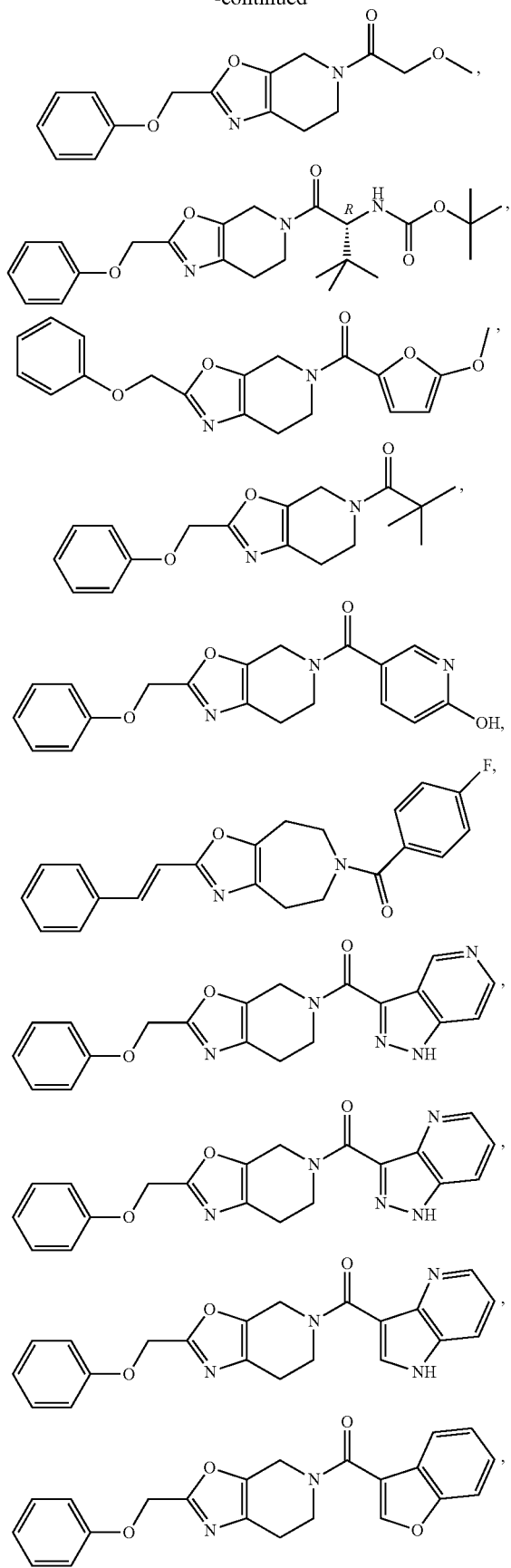
56
-continued
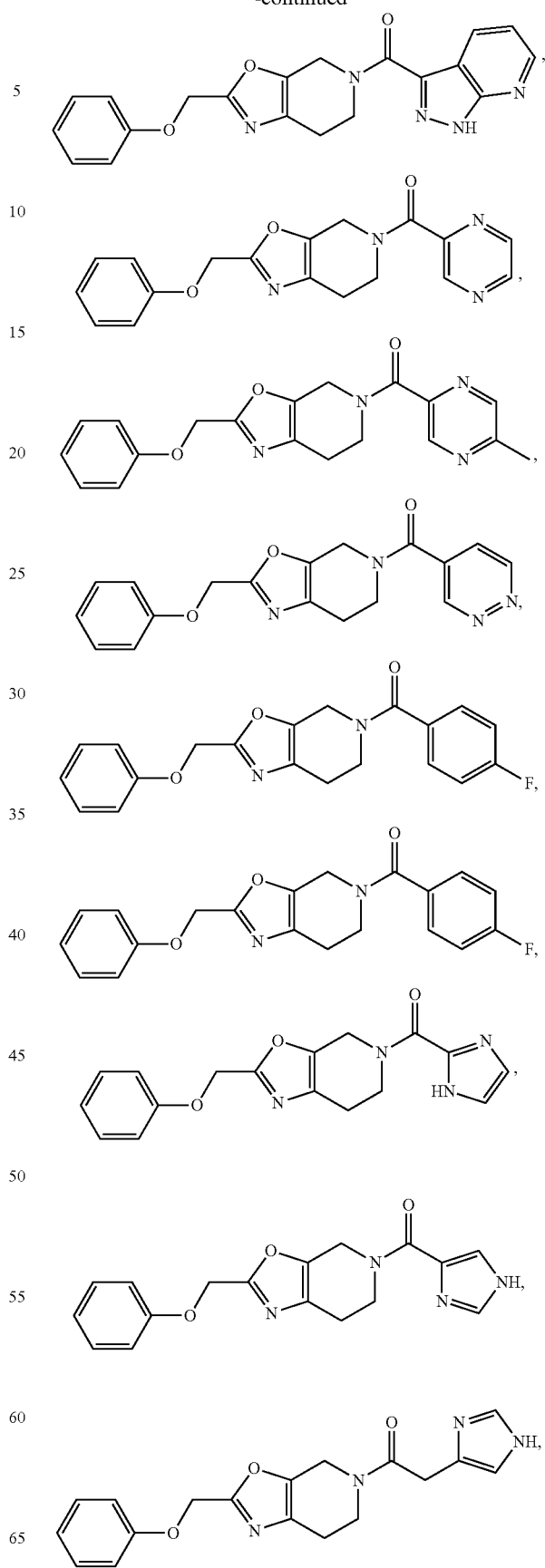

-continued

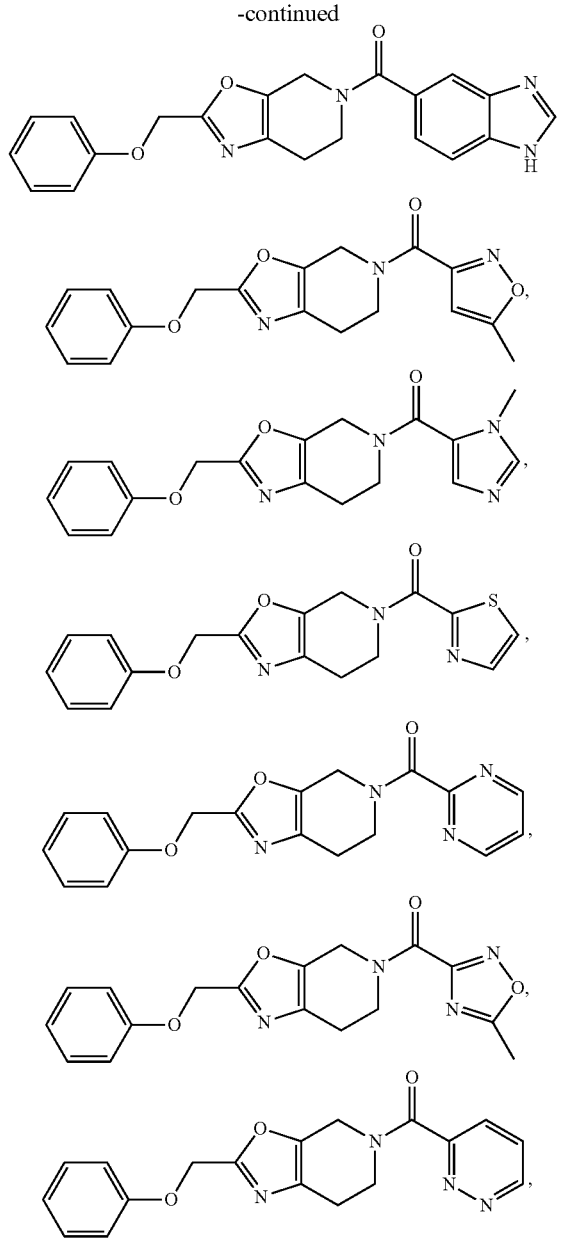

or a subgroup thereof.

In one aspect, a compound can be present as one or more of:

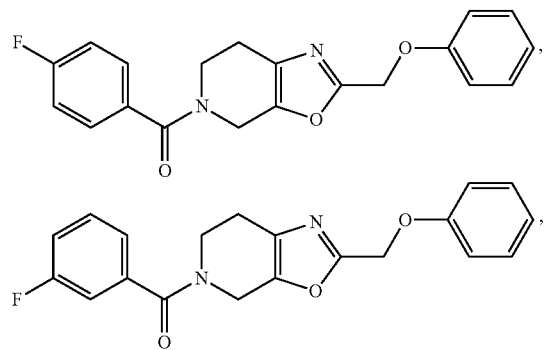

-continued

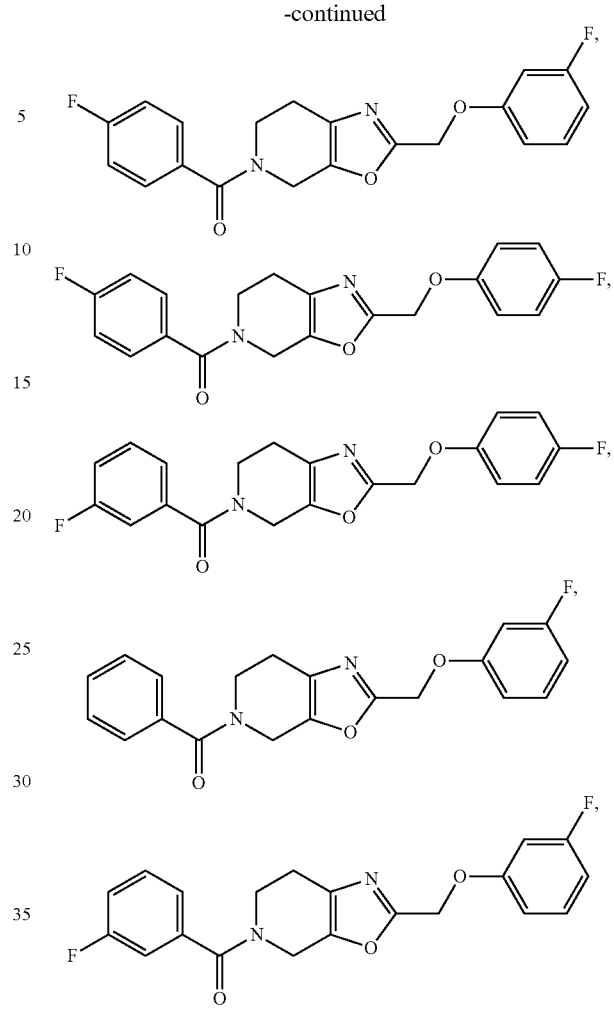

or a subgroup thereof.

Compounds are shown above are depicted having a basic group or acidic group and named as the free base acid. Depending on the reaction and purification conditions, various compounds having a basic group were isolated in either the free base form, or as a salt (such as HCl salt), or in both free base and salt forms.

In one aspect, a compound can be present as: 5-(2-fluorobenzoyl)-4,5,6,7-tetrahydro-2-(phenoxymethyl)-thiazolo[5,4-c]pyridine, 5-(4-fluorobenzoyl)-4,5,6,7-tetrahydro-2-(phenoxymethyl)-oxazolo[5,4-c]pyridine, 5-(2,4-difluorobenzoyl)-4,5,6,7-tetrahydro-2-(phenoxymethyl)-thiazolo[5,4-c]pyridine, 5-(4-fluorobenzoyl)-4,5,6,7-tetrahydro-2-(phenoxymethyl)-oxazolo[4,5-c]pyridine, 5-(4-fluorobenzoyl)-4,5,6,7-tetrahydro-2-[(E)-2-phenylethenyl]-oxazolo[5,4-c]pyridine, 5-(4-fluorobenzoyl)-2-[(3-fluorophenoxy)methyl]-4,5,6,7-tetrahydro-oxazolo[5,4-c]pyridine, 5-(2,4-difluorobenzoyl)-4,5,6,7-tetrahydro-2-(phenoxymethyl)-oxazolo[5,4-c]pyridine, 5-(4-fluorobenzoyl)-2-[(2-fluorophenoxy)methyl]-4,5,6,7-tetrahydro-oxazolo[5,4-c]pyridine, 5-(4-fluorobenzoyl)-2-[(4-fluorophenoxy)methyl]-4,5,6,7-tetrahydro-oxazolo[5,4-c]pyridine, 2-[(3,4-difluorophenoxy)methyl]-5-(4-fluorobenzoyl)-4,5,6,7-tetrahydro-oxazolo[5,4-c]pyridine, 5-(3-fluorobenzoyl)-4,5,6,7-tetrahydro-2-(phenoxymethyl)-oxazolo[5,4-c]pyridine, 5-(2-fluorobenzoyl)-4,5,6,7-tetrahydro-2-(phenoxymethyl)-oxazolo[5,4-c]pyridine, 6-[(4- fluorophenyl)carbonyl]-2-[(E)-2-phenylethenyl]-5,6,7,8-tetrahydro-4H-[1,3]oxazolo[4,5-d]azepine, 6,7-dihydro-2-(phenoxymethyl)-oxazolo[5,4-c]pyridine-5(4H)-carboxylic acid phenylmethyl ester, 5-(cyclopropylacetyl)-4,5,6,7-tetrahydro-2-(phenoxymethyl)-oxazolo[5,4-c]pyridine, 6-(4-fluorobenzoyl)-5,6,7,8-tetrahydro-2-(phenoxymethyl)-4H-oxazolo[4,5-d]azepine, 5-(4-fluorobenzoyl)-5,6-dihydro-2-(phenoxymethyl)-4H-pyrrolo[3,4-d]oxazole, 5-(3,5-difluorobenzoyl)-4,5,6,7-tetrahydro-2-(phenoxymethyl)-oxazolo[5,4-c]pyridine, 4,5,6,7-tetrahydro-2-(phenoxymethyl)-5-(4-pyridinylcarbonyl)-oxazolo[5,4-c]pyridine, 4,5,6,7-tetrahydro-2-(phenoxymethyl)-5-(3-pyridinylcarbonyl)-oxazolo[5,4-c]pyridine, 5-(2,6-difluorobenzoyl)-4,5,6,7-tetrahydro-2-(phenoxymethyl)-oxazolo[5,4-c]pyridine, 5-(2,3-difluorobenzoyl)-4,5,6,7-tetrahydro-2-(phenoxymethyl)-oxazolo[5,4-c]pyridine, 5-(3,4-difluorobenzoyl)-4,5,6,7-tetrahydro-2-(phenoxymethyl)-oxazolo[5,4-c]pyridine, 4,5,6,7-tetrahydro-2-(phenoxymethyl)-5-(2-pyridinylcarbonyl)-oxazolo[5,4-c]pyridine, 5-acetyl-4,5,6,7-tetrahydro-2-(phenoxymethyl)-oxazolo[5,4-c]pyridine, 5-(4-fluorobenzoyl)-5,6,7,8-tetrahydro-2-(phenoxymethyl)-4H-thiazolo[5,4-c]azepine, 5-benzoyl-2-[(3-fluorophenoxy)methyl]-4,5,6,7-tetrahydro-oxazolo[5,4-c]pyridine, 5-(3-fluorobenzoyl)-2-[(3-fluorophenoxy)methyl]-4,5,6,7-tetrahydro-oxazolo[5,4-c]pyridine, 5-(2,3-difluorobenzoyl)-2-[(3-fluorophenoxy)methyl]-4,5,6,7-tetrahydro-oxazolo[5,4-c]pyridine, 5-(3,4-difluorobenzoyl)-2-[(3-fluorophenoxy)methyl]-4,5,6,7-tetrahydro-oxazolo[5,4-c]pyridine, 5-(3,5-difluorobenzoyl)-2-[(3-fluorophenoxy)methyl]-4,5,6,7-tetrahydro-oxazolo[5,4-c]pyridine, 5-(cyclopropylcarbonyl)-4,5,6,7-tetrahydro-2-(phenoxymethyl)-oxazolo[5,4-c]pyridine, 5-[(4-Fluorophenyl)carbonyl]-2-{[(4-methylpyridin-2-yl)oxy]methyl}-4,5,6,7-tetrahydro[1,3]oxazolo[5,4-c]pyridine, 2-(Phenoxymethyl)-5-(trifluoroacetyl)-4,5,6,7-tetrahydro[1,3]oxazolo[5,4-c]pyridine, 4-({5-[(4-Fluorophenyl)carbonyl]-4,5,6,7-tetrahydro[1,3]oxazolo[5,4-c]pyridin-2-yl}methoxy)phenol, 5-[(1-Methyl-1H-indol-2-yl)carbonyl]-2-(phenoxymethyl)-4,5,6,7-tetrahydro[1,3]oxazolo[5,4-c]pyridine, 5-[(4-Fluorophenyl)carbonyl]-2-[(2-methylphenoxy)methyl]-4,5,6,7-tetrahydro[1,3]oxazolo[5,4-c]pyridine, 5-[(3,5-Difluoropyridin-2-yl)carbonyl]-2-(phenoxymethyl)-4,5,6,7-tetrahydro[1,3]oxazolo[5,4-c]pyridine, 5-[(3-Bromo-5-fluorophenyl)carbonyl]-2-(phenoxymethyl)-4,5,6,7-tetrahydro[1,3]oxazolo[5,4-c]pyridine, 5-[(5-Fluoropyridin-2-yl)carbonyl]-2-(phenoxymethyl)-4,5,6,7-tetrahydro[1,3]oxazolo[5,4-c]pyridine, 5-[(2-Methylpyridin-3-yl)carbonyl]-2-(phenoxymethyl)-4,5,6,7-tetrahydro[1,3]oxazolo[5,4-c]pyridine, 5-[(3-Methylpyridin-2-yl)carbonyl]-2-(phenoxymethyl)-4,5,6,7-tetrahydro[1,3]oxazolo[5,4-c]pyridine, 3-{[2-(Phenoxymethyl)-6,7-dihydro[1,3]oxazolo[5,4-c]pyridin-5(4H)-yl]carbonyl}benzonitrile, 5-[(6-Methylpyridin-2-yl)carbonyl]-2-(phenoxymethyl)-4,5,6,7-tetrahydro[1,3]oxazolo[5,4-c]pyridine, 2-[(3-Fluorophenoxy)methyl]-5-[(5-fluoropyridin-2-yl)carbonyl]-4,5,6,7-tetrahydro[1,3]oxazolo[5,4-c]pyridine, 2-{[2-(Phenoxymethyl)-6,7-dihydro[1,3]oxazolo[5,4-c]pyridin-5(4H)-yl]carbonyl}benzonitrile, 5-[(3-Fluoropyridin-2-yl)carbonyl]-2-(phenoxymethyl)-4,5,6,7-tetrahydro[1,3]oxazolo[5,4-c]pyridine, 5-[(4-Fluorophenyl)carbonyl]-2-{[(5-fluoropyridin-3-yl)oxy]methyl}-4,5,6,7-tetrahydro[1,3]oxazolo[5,4-c]pyridine, 4-{[2-(Phenoxymethyl)-6,7-dihydro[1,3]oxazolo[5,4-c]pyridin-5(4H)-yl]carbonyl}benzonitrile, 3-Fluoro-5-{[2-(phenoxymethyl)-6,7-dihydro[1,3]oxazolo[5,4-c]pyridin-5(4H)-yl]carbonyl}benzonitrile, 5-[(4-Fluorophenyl)acetyl]-2-(phenoxymethyl)-4,5,6,7-tetrahydro[1,3]oxazolo[5,4-c]pyridine, 5-{[4-(Pentafluoro-lambda$^6$-sulfanyl)phenyl]carbonyl}-2-(phenoxymethyl)-4,5,6,7-tetrahydro[1,3]oxazolo[5,4-c]pyridine, 3-({5-[(4-Fluorophenyl)carbonyl]-4,5,6,7-tetrahydro[1,3]oxazolo[5,4-c]pyridin-2-yl}methoxy)benzonitrile, (2S)-3,3-Dimethyl-1-oxo-1-[2-(phenoxymethyl)-6,7-dihydro[1,3]oxazolo[5,4-c]pyridin-5(4H)-yl]butan-2-amine, 5-(tert-Butoxyacetyl)-2-(phenoxymethyl)-4,5,6,7-tetrahydro[1,3]oxazolo[5,4-c]pyridine, 2-(Phenoxymethyl)-5-(1H-pyrazol-4-ylcarbonyl)-4,5,6,7-tetrahydro[1,3]oxazolo[5,4-c]pyridine, 5-[(5-Chlorofuran-2-yl)carbonyl]-2-(phenoxymethyl)-4,5,6,7-tetrahydro[1,3]oxazolo[5,4-c]pyridine, 2-(Phenoxymethyl)-5-(1H-pyrrol-2-ylcarbonyl)-4,5,6,7-tetrahydro[1,3]oxazolo[5,4-c]pyridine, 5-(1,3-Oxazol-5-ylcarbonyl)-2-(phenoxymethyl)-4,5,6,7-tetrahydro[1,3]oxazolo[5,4-c]pyridine, 5-(1,3-Oxazol-2-ylcarbonyl)-2-(phenoxymethyl)-4,5,6,7-tetrahydro[1,3]oxazolo[5,4-c]pyridine, 5-[(5-Methylfuran-2-yl)carbonyl]-2-(phenoxymethyl)-4,5,6,7-tetrahydro[1,3]oxazolo[5,4-c]pyridine, 2,2-Dimethyl-3-oxo-3-[2-(phenoxymethyl)-6,7-dihydro[1,3]oxazolo[5,4-c]pyridin-5(4H)-yl]propanenitrile, tert-Butyl[(1S)-2,2-dimethyl-1-{[2-(phenoxymethyl)-6,7-dihydro[1,3]oxazolo[5,4-c]pyridin-5(4H)-yl]carbonyl}propyl]carbamate, 2-(Phenoxymethyl)-5-(3-phenylpropanoyl)-4,5,6,7-tetrahydro[1,3]oxazolo[5,4-c]pyridine, 5-[(5-Fluoropyridin-3-yl)carbonyl]-2-(phenoxymethyl)-4,5,6,7-tetrahydro[1,3]oxazolo[5,4-c]pyridine, 5-[(4-Fluorophenyl)carbonyl]-2-[(3-methylphenoxy)methyl]-4,5,6,7-tetrahydro[1,3]oxazolo[5,4-c]pyridine, 2-[(3-Fluorophenoxy)methyl]-5-[(5-fluoropyridin-3-yl)carbonyl]-4,5,6,7-tetrahydro[1,3]oxazolo[5,4-c]pyridine, 5-[(4-Fluorophenyl)carbonyl]-2-[(pyridin-2-yloxy)methyl]-4,5,6,7-tetrahydro[1,3]oxazolo[5,4-c]pyridine, 2-[(3-Chlorophenoxy)methyl]-5-[(4-fluorophenyl)carbonyl]-4,5,6,7-tetrahydro[1,3]oxazolo[5,4-c]pyridine, 5-[(4-Fluorophenyl)carbonyl]-2-[(4-methylphenoxy)methyl]-4,5,6,7-tetrahydro[1,3]oxazolo[5,4-c]pyridine, 5-[(5-Methylisoxazol-4-yl)carbonyl]-2-(phenoxymethyl)-4,5,6,7-tetrahydro[1,3]oxazolo[5,4-c]pyridine, 2-[(3-Fluorophenoxy)methyl]-5-[(5-methylisoxazol-4-yl)carbonyl]-4,5,6,7-tetrahydro[1,3]oxazolo[5,4-c]pyridine, 5-[(4-Fluorophenyl)carbonyl]-2-[(pyridin-4-yloxy)methyl]-4,5,6,7-tetrahydro[1,3]oxazolo[5,4-c]pyridine, 5-[(3-Chloropyridin-2-yl)carbonyl]-2-(phenoxymethyl)-4,5,6,7-tetrahydro[1,3]oxazolo[5,4-c]pyridine, 2-(Phenoxymethyl)-5-1 [4-(trifluoromethoxy)phenyl]carbonyl}-4,5,6,7-tetrahydro[1,3]oxazolo[5,4-c]pyridine, 5-(1,3-Benzodioxol-5-ylcarbonyl)-2-(phenoxymethyl)-4,5,6,7-tetrahydro[1,3]oxazolo[5,4-c]pyridine, 2-(Phenoxymethyl)-5-[(1-phenylcyclopropyl)carbonyl]-4,5,6,7-tetrahydro[1,3]oxazolo[5,4-c]pyridine, 5-[(2,4-Difluorophenyl)carbonyl]-2-[(3-fluorophenoxy)methyl]-4,5,6,7-tetrahydro[1,3]oxazolo[5,4-c]pyridine, 2-{[2-(Phenoxymethyl)-6,7-dihydro[1,3]oxazolo[5,4-c]pyridin-5 (4H)-yl]carbonyl}quinoline, 5-(Phenoxyacetyl)-2-(phenoxymethyl)-4,5,6,7-tetrahydro[1,3]oxazolo[5,4-c]pyridine, 2-(Phenoxymethyl)-5-(2-phenoxypropanoyl)-4,5,6,7-tetrahydro[1,3]oxazolo[5,4-c]pyridine, 5-[(6-Fluoro-3,4-dihydro-2H-chromen-2-yl)carbonyl]-2-(phenoxymethyl)-4,5,6,7-tetrahydro[1,3]oxazolo[5,4-c]pyridine, N,N-Dimethyl-3-1 [2-(phenoxymethyl)-6,7-dihydro[1,3]oxazolo[5,4-c]pyridin-5 (4H)-yl]carbonyl}aniline, 5-[(1-Methyl-1H-pyrrol-2-yl)carbonyl]-2-(phenoxymethyl)-4,5,6,7-tetrahydro[1,3]oxazolo[5,4-c]pyridine, 3-({2-[(3-Fluorophenoxy)

methyl]-6,7-dihydro[1,3]oxazolo[5,4-c]pyridin-5 (4H)-yl}carbonyl)benzonitrile, 5-[(2,5-Dimethyl-1,3-oxazol-4-yl)carbonyl]-2-(phenoxymethyl)-4,5,6,7-tetrahydro[1,3]oxazolo[5,4-c]pyridine, 4-{[2-(Phenoxymethyl)-6,7-dihydro[1,3]oxazolo[5,4-c]pyridin-5 (4H)-yl]carbonyl}pyridine-2-carbonitrile, 5-(isoxazol-5-ylcarbonyl)-2-(phenoxymethyl)-4,5,6,7-tetrahydro[1,3]oxazolo[5,4-c]pyridine, 2-Fluoro-4-({2-[(3-fluorophenoxy)methyl]-6,7-dihydro[1,3]oxazolo[5,4-c]pyridin-5 (4H)-yl}carbonyl)benzonitrile, 2-Fluoro-4-{[2-(phenoxymethyl)-6,7-dihydro[1,3]oxazolo[5,4-c]pyridin-5 (4H)-yl]carbonyl}benzonitrile, 6-{[2-(Phenoxymethyl)-6,7-dihydro[1,3]oxazolo[5,4-c]pyridin-5 (4H)-yl]carbonyl}quinoxaline, 3-Fluoro-5-({2-[(3-fluorophenoxy)methyl]-6,7-dihydro[1,3]oxazolo[5,4-c]pyridin-5 (4H)-yl}carbonyl)benzonitrile, 2-{[2-(Phenoxymethyl)-6,7-dihydro[1,3]oxazolo[5,4-c]pyridin-5(4H)-yl]carbonyl}quinoxaline, 5-[(6-Fluoropyridin-3-yl)carbonyl]-2-(phenoxymethyl)-4,5,6,7-tetrahydro[1,3]oxazolo[5,4-c]pyridine, 2-(Phenoxymethyl)-5-(pyrazolo[1,5-a]pyridin-3-ylcarbonyl)-4,5,6,7-tetrahydro[1,3]oxazolo[5,4-c]pyridine, 2-[(3-Fluorophenoxy)methyl]-5-(pyrazolo[1,5-a]pyridin-3-ylcarbonyl)-4,5,6,7-tetrahydro[1,3]oxazolo[5,4-c]pyridine, 2-Fluoro-5-({2-[(3-fluorophenoxy)methyl]-6,7-dihydro[1,3]oxazolo[5,4-c]pyridin-5 (4H)-yl}carbonyl)benzonitrile, 2-Fluoro-5-{[2-(phenoxymethyl)-6,7-dihydro[1,3]oxazolo[5,4-c]pyridin-5 (4H)-yl]carbonyl}benzonitrile, 5-(2,3-Dihydro-1,4-benzodioxin-5-ylcarbonyl)-2-(phenoxymethyl)-4,5,6,7-tetrahydro[1,3]oxazolo[5,4-c]pyridine, 2-[(4-Fluorophenoxy)methyl]-5-[(3-fluorophenyl)carbonyl]-4,5,6,7-tetrahydro[1,3]oxazolo[5,4-c]pyridine, 5-[(3,5-Difluoropyridin-2-yl)carbonyl]-2-[(3-fluorophenoxy)methyl]-4,5,6,7-tetrahydro[1,3]oxazolo[5,4-c]pyridine, 5-[(5-Methoxythiophen-2-yl)carbonyl]-2-(phenoxymethyl)-4,5,6,7-tetrahydro[1,3]oxazolo[5,4-c]pyridine, 5-[(1,5-Dimethyl-1H-pyrrol-2-yl)carbonyl]-2-(phenoxymethyl)-4,5,6,7-tetrahydro[1,3]oxazolo[5,4-c]pyridine, 5-1 [5-(Methoxymethyl)furan-2-yl]carbonyl}-2-(phenoxymethyl)-4,5,6,7-tetrahydro[1,3]oxazolo[5,4-c]pyridine, 5-{[2-(Phenoxymethyl)-6,7-dihydro[1,3]oxazolo[5,4-c]pyridin-5(4H)-yl]carbonyl}pyrrolidin-2-one, 5-[(5-Bromofuran-2-yl)carbonyl]-2-(phenoxymethyl)-4,5,6,7-tetrahydro[1,3]oxazolo[5,4-c]pyridine, 5-(1H-Indazol-3-ylacetyl)-2-(phenoxymethyl)-4,5,6,7-tetrahydro[1,3]oxazolo[5,4-c]pyridine, 2-(Phenoxymethyl)-5-(1,3-thiazol-4-ylcarbonyl)-4,5,6,7-tetrahydro[1,3]oxazolo[5,4-c]pyridine, 5-[(5-Chlorothiophen-2-yl)carbonyl]-2-(phenoxymethyl)-4,5,6,7-tetrahydro[1,3]oxazolo[5,4-c]pyridine, 5-[(5-Methylthiophen-2-yl)carbonyl]-2-(phenoxymethyl)-4,5,6,7-tetrahydro[1,3]oxazolo[5,4-c]pyridine, 5-[(1-Methyl-1H-indol-3-yl)carbonyl]-2-(phenoxymethyl)-4,5,6,7-tetrahydro[1,3]oxazolo[5,4-c]pyridine, 5-(1H-Indol-2-ylcarbonyl)-2-(phenoxymethyl)-4,5,6,7-tetrahydro[1,3]oxazolo[5,4-c]pyridine, 5-[(3-Chloro-1-methyl-1H-pyrrol-2-yl)carbonyl]-2-(phenoxymethyl)-4,5,6,7-tetrahydro[1,3]oxazolo[5,4-c]pyridine, 5-[(4-Fluorophenyl)carbonyl]-2-(phenoxymethyl)-5,6,7,8-tetrahydro-4H-[1,3]oxazolo[5,4-c]azepine, 2-(Phenoxymethyl)-5-(1H-pyrazol-3-ylcarbonyl)-4,5,6,7-tetrahydro[1,3]oxazolo[5,4-c]pyridine, 2-(Phenoxymethyl)-5-(3,3,3-trifluoropropanoyl)-4,5,6,7-tetrahydro[1,3]oxazolo[5,4-c]pyridine, 5-(1H-Indol-3-ylcarbonyl)-2-(phenoxymethyl)-4,5,6,7-tetrahydro[1,3]oxazolo[5,4-c]pyridine, 2-(Phenoxymethyl)-5-1 [2-(trifluoromethyl)pyrimidin-5-yl]carbonyl}-4,5,6,7-tetrahydro[1,3]oxazolo[5,4-c]pyridine, 5-[(3-Methyl-1,2,4-oxadiazol-5-yl)carbonyl]-2-(phenoxymethyl)-4,5,6,7-tetrahydro[1,3]oxazolo[5,4-c]pyridine, 5-(1-Benzofuran-2-ylcarbonyl)-2-(phenoxymethyl)-4,5,6,7-tetrahydro[1,3]oxazolo[5,4-c]pyridine, 5-[(3-Methylfuran-2-yl)carbonyl]-2-(phenoxymethyl)-4,5,6,7-tetrahydro[1,3]oxazolo[5,4-c]pyridine, 2-(Phenoxymethyl)-5-1 [5-(trifluoromethyl)furan-2-yl]carbonyl}-4,5,6,7-tetrahydro[1,3]oxazolo[5,4-c]pyridine, 5-[(3,5-Dimethylfuran-2-yl)carbonyl]-2-(phenoxymethyl)-4,5,6,7-tetrahydro[1,3]oxazolo[5,4-c]pyridine, 5-[(5-Ethylfuran-2-yl)carbonyl]-2-(phenoxymethyl)-4,5,6,7-tetrahydro[1,3]oxazolo[5,4-c]pyridine, 2-(Phenoxymethyl)-5-(1H-1,2,3-triazol-5-ylcarbonyl)-4,5,6,7-tetrahydro[1,3]oxazolo[5,4-c]pyridine, 5-(1H-Indazol-3-ylcarbonyl)-2-(phenoxymethyl)-4,5,6,7-tetrahydro[1,3]oxazolo[5,4-c]pyridine, 5-[(4-Fluorophenyl)carbonyl]-2-{[3-(trifluoromethyl)phenoxy]methyl}-4,5,6,7-tetrahydro[1,3]oxazolo[5,4-c]pyridine, 5-[(4-Fluorophenyl)carbonyl]-2-[(4-(trifluoromethyl)phenoxy]methyl}-4,5,6,7-tetrahydro[1,3]oxazolo[5,4-c]pyridine, 2-[(4-Bromophenoxy)methyl]-5-[(4-fluorophenyl)carbonyl]-4,5,6,7-tetrahydro[1,3]oxazolo[5,4-c]pyridine, 5-[(4-Fluorophenyl)carbonyl]-2-{[2-(trifluoromethyl)phenoxy]methyl}-4,5,6,7-tetrahydro[1,3]oxazolo[5,4-c]pyridine, 5-[(4-Fluorophenyl)carbonyl]-2-(2-phenylethyl)-4,5,6,7-tetrahydro[1,3]oxazolo[5,4-c]pyridine, 5-[(6-Methylpyridin-3-yl)carbonyl]-2-(phenoxymethyl)-4,5,6,7-tetrahydro[1,3]oxazolo[5,4-c]pyridine, 5-[(4-Fluorophenyl)carbonyl]-2-{[(6-methylpyridin-2-yl)oxy]methyl}-4,5,6,7-tetrahydro[1,3]oxazolo[5,4-c]pyridine, 5-[(4-Fluorophenyl)acetyl]-2-(phenoxymethyl)-4,5,6,7-tetrahydro[1,3]oxazolo[5,4-c]pyridine, 5-[(2-Methylpyrimidin-5-yl)carbonyl]-2-(phenoxymethyl)-4,5,6,7-tetrahydro[1,3]oxazolo[5,4-c]pyridine, 3-Fluoro-5-({5-[(4-fluorophenyl)carbonyl]-4,5,6,7-tetrahydro[1,3]oxazolo[5,4-c]pyridin-2-yl}methoxy)benzonitrile, 3-Bromo-5-({5-[(4-fluorophenyl)carbonyl]-4,5,6,7-tetrahydro[1,3]oxazolo[5,4-c]pyridin-2-yl}methoxy)benzonitrile, 5-(Methoxyacetyl)-2-(phenoxymethyl)-4,5,6,7-tetrahydro[1,3]oxazolo[5,4-c]pyridine, 5-[2-(Phenoxymethyl)-6,7-dihydro[1,3]oxazolo[5,4-c]pyridin-5(4H)-yl]carbonyl}pyridin-2-ol, tert-Butyl[(1R)-2,2-dimethyl-1-{[2- (phenoxymethyl)-6,7-dihydro[1,3]oxazolo[5,4-c]pyridin-5(4H)-yl]carbonyl}propyl]carbamate, 5-[(5-Methoxyfuran-2-yl)carbonyl]-2-(phenoxymethyl)-4,5,6,7-tetrahydro[1,3]oxazolo[5,4-c]pyridine, and 5-(2,2-Dimethylpropanoyl)-2-(phenoxymethyl)-4,5,6,7-tetrahydro[1,3]oxazolo[5,4-c]pyridine, (2-(phenoxymethyl)-6,7-dihydrooxazolo[5,4-c]pyridin-5(4H)-yl)(1H-pyrazolo[4,3-c]pyridin-3-yl)methanone, (2-(phenoxymethyl)-6,7-dihydrooxazolo[5,4-c]pyridin-5(4H)-yl)(1H-pyrazolo[4,3-b]pyridin-3-yl)methanone, (2-(phenoxymethyl)-6,7-dihydrooxazolo[5,4-c]pyridin-5(4H)-yl)(1H-pyrrolo[3,2-b]pyridin-3-yl)methanone, benzofuran-3-yl(2-(phenoxymethyl)-6,7-dihydrooxazolo[5,4-c]pyridin-5(4H)-yl)methanone, (2-(phenoxymethyl)-6,7-dihydrooxazolo[5,4-c]pyridin-5(4H)-yl)(1H-pyrazolo[3,4-b]pyridin-3-yl)methanone, (2-(phenoxymethyl)-6,7-dihydrooxazolo[5,4-c]pyridin-5(4H)-yl)(pyrazin-2-yl)methanone, (5-methylpyrazin-2-yl)(2-(phenoxymethyl)-6,7-dihydrooxazolo[5,4-c]pyridin-5(4H)-yl)methanone, (2-(phenoxymethyl)-6,7-dihydrooxazolo[5,4-c]pyridin-5(4H)-yl)(pyridazin-4-yl)methanone, (4-fluorophenyl)(2-(phenoxymethyl)-6,7-dihydrooxazolo[5,4-c]pyridin-5(4H)-yl)methanone, (4-fluorophenyl)(2-(phenoxymethyl)-6,7-dihydrooxazolo

[5,4-c]pyridin-5(4H)-yl)methanone, (1H-imidazol-2-yl)(2-(phenoxymethyl)-6,7-dihydrooxazolo[5,4-c]pyridin-5(4H)-yl)methanone, (1H-imidazol-4-yl)(2-(phenoxymethyl)-6,7-dihydrooxazolo[5,4-c]pyridin-5(4H)-yl)methanone, 2-(1H-imidazol-4-yl)-1-(2-(phenoxymethyl)-6,7-dihydrooxazolo[5,4-c]pyridin-5(4H)-yl)ethanone, (1H-benzo[d]imidazol-5-yl)(2-(phenoxymethyl)-6,7-dihydrooxazolo[5,4-c]pyridin-5(4H)-yl)methanone, (5-methylisoxazol-3-yl)(2-(phenoxymethyl)-6,7-dihydrooxazolo[5,4-c]pyridin-5(4H)-yl)methanone, 1-methyl-1H-imidazol-5-yl)(2-(phenoxymethyl)-6,7-dihydrooxazolo[5,4-c]pyridin-5(4H)-yl)methanone, (2-(phenoxymethyl)-6,7-dihydrooxazolo[5,4-c]pyridin-5(4H)-yl)(thiazol-2-yl)methanone, (2-(phenoxymethyl)-6,7-dihydrooxazolo[5,4-c]pyridin-5(4H)-yl)(pyrimidin-2-yl)methanone, (5-methyl-1,2,4-oxadiazol-3-yl)(2-(phenoxymethyl)-6,7-dihydrooxazolo[5,4-c]pyridin-5(4H)-yl)methanone, (2-(phenoxymethyl)-6,7-dihydrooxazolo[5,4-c]pyridin-5(4H)-yl)(pyridazin-3-yl)methanone, or a subgroup thereof. Included within the scope of this list is stereoisomeric forms, the acid addition salts and the solvates thereof.

It is contemplated that one or more compounds can optionally be omitted from the disclosed invention.

C. METABOTROPIC GLUTAMATE RECEPTOR ACTIVITY

The utility of the disclosed compounds and products of disclosed methods of making, in accordance with the present invention as potentiators of metabotropic glutamate receptor activity, in particular mGluR5 activity, can be demonstrated by methodology known in the art. Human embryonic kidney (HEK) cells transfected with rat mGluR5 were plated in clear bottom assay plates for assay in a Functional Drug Screening System (FDSS). In the alternative assay, HEK cells transfected with human mGluR5 were plated for assay in the FDSS. In some cases the HEK cells transfected with human mGluR5 are the H10H cell line. Alternatively, the HEK cells transfected with human mGluR5 are the H12H cell line. Rat assay results were found to correlate well with human assay results. The cells were loaded with a $Ca^{2+}$-sensitive fluorescent dye (e.g., Fluo-4), and the plates were washed and placed in the FDSS instrument. After establishment of a fluorescence baseline for about three seconds, the compounds of the present invention were added to the cells, and the response in cells was measured. Five minutes later, an mGluR5 agonist (e.g., glutamate, 3,5-dihydroxyphenylglycine, or quisqualate) was added to the cells, and the response of the cells was measured. Potentiation of the agonist response of mGluR5 by the compounds in the present invention was observed as an increase in response to non-maximal concentrations of agonist (here, glutamate) in the presence of compound compared to the response to agonist in the absence of compound.

The above described assay can be operated in two modes. In the first mode, a range of concentrations of the present compounds were added to cells, followed by a single fixed concentration of agonist. If a compound acted as a potentiator, an $EC_{50}$ value for potentiation and a maximum extent of potentiation by the compound at this concentration of agonist was determined by non-linear curve fitting. In the second mode, several fixed concentrations of the present compounds were added to various wells on a plate, followed by a range of concentrations of agonist for each concentration of present compound; the $EC_{50}$ values for the agonist at each concentration of compound were determined by non-linear curve fitting. A decrease in the $EC_{50}$ value of the agonist with increasing concentrations of the present compounds (a leftward shift of the agonist concentration-response curve) is an indication of the degree of mGluR5 potentiation at a given concentration of the present compound. An increase in the $EC_{50}$ value of the agonist with increasing concentrations of the present compounds (a rightward shift of the agonist concentration-response curve) is an indication of the degree of mGluR5 antagonism at a given concentration of the present compound. The second mode also indicates whether the present compounds also affect the maximum response to mGluR5 to agonists.

In one aspect, the disclosed compounds and products of disclosed methods of making exhibit potentiation of mGluR5 response to glutamate as an increase in response to non-maximal concentrations of glutamate in human embryonic kidney cells transfected with a mammalian mGluR5 in the presence of the compound, compared to the response to glutamate in the absence of the compound. In a further aspect, the human embryonic kidney cells can be transfected with a mammalian GluR5. In a still further aspect, human embryonic kidney cells can be transfected with human mGluR5. In a yet further aspect, human embryonic kidney cells can be transfected with rat mGluR5. It is to be understood that "transfected with a mGluR5" (e.g. human mGluR5) refers to transfection of the indicated cells with an appropriate expression construct comprising the nucleic acid sequence coding for the indicated mGluR5. The nucleic acid sequence for an mGluR5 can be a cDNA sequence which is full-length or alternatively a partial cDNA sequence a subset of the full-length cDNA sequence. Appropriate expression constructs are available to one skilled in the art, as are methods for manipulation of the desired cDNA sequence.

In a further aspect, the disclosed compounds and products of disclosed methods of making are allosteric modulators of mGluR5, in particular, positive allosteric modulators of mGluR5. The disclosed compounds can potentiate glutamate responses by binding to an allosteric site other than the glutamate orthosteric binding site. The response of mGluR5 to a concentration of glutamate is increased when the disclosed compounds are present. In a further aspect, the disclosed compounds can have their effect substantially at mGluR5 by virtue of their ability to enhance the function of the receptor.

In particular, the disclosed compounds and products of disclosed methods of making exhibit activity in potentiating the mGluR5 receptor in the aforementioned assays, generally with an $EC_{50}$ for potentiation of less than about 10 μM. Preferred compounds within the present invention had activity in potentiating the mGluR5 receptor with an $EC_{50}$ for potentiation of less than about 500 nM. Preferred compounds further caused a leftward shift of the agonist $EC_{50}$ by greater than 3-fold. These compounds did not cause mGluR5 to respond in the absence of agonist, and they did not elicit a significant increase in the maximal response of mGluR5 to agonists. These compounds are selective positive allosteric modulators (potentiators) of human and rat mGluR5 compared to the other seven subtypes of metabotropic glutamate receptors.

In a further aspect, the disclosed compounds and products of disclosed methods of making can exhibit positive allosteric modulation of mGluR5 in the cell-based assay methods described herein, i.e. the disclosed compounds and disclosed products of making can exhibit positive allosteric modulation of mGluR5 response to glutamate as an increase in response to non-maximal concentrations of glutamate in human embryonic kidney cells transfected with a mGluR5 (e.g. a mammalian, a rat, or a human mGluR5) in the presence of the compound, compared to the response to glutamate in the absence of the compound. For example, the disclosed compounds and products of disclosed methods of making can exhibit positive allosteric modulation of mGluR5 in a aforementioned cell-based assay with an $EC_{50}$ of less than about 10,000 nM, of less than about 5,000 nM, of less than about 1,000 nM, of less than about 500 nM, or of less than about 100 nM. In a further aspect, the disclosed compounds and products of disclosed methods of making can exhibit positive allosteric modulation of human mGluR5 in the H10H cell-line with an $EC_{50}$ of less than about 10,000 nM, of less than about 5,000 nM. of less than about 1,000 nM, of less than about 500 nM, or of less than about 100 nM.

In vivo efficacy for disclosed compounds and products of disclosed methods of making can be measured in a number of preclinical rat behavioral model where known, clinically useful antipsychotics display similar positive responses. For example, disclosed compounds can reverse amphetamine-induced hyperlocomotion in male Sprague-Dawley rats at doses ranging from 1 to 100 mg/kg p.o.

D. METHODS Of MAKING THE COMPOUNDS

In one aspect, the invention relates to methods of making compounds useful as positive allosteric modulators of the metabotropic glutamate receptor subtype 5 (mGluR5), which can be useful in the treatment of neurological and psychiatric disorders associated with glutamate dysfunction and other diseases in which metabotropic glutamate receptors are involved.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

The compounds according to the invention can generally be prepared by a succession of steps, each of which is known to the skilled person. In particular, the compounds can be prepared according to the following synthesis methods. It is also contemplated that pseudohalogens (e.g. triflate, mesylate, brosylate, etc.) can be used as leaving groups in place of halogens in certain aspects.

The disclosed compounds may be synthesized in the form of racemic mixtures of enantiomers which can be separated from one another following art-known resolution procedures. The racemic compounds of disclosed compounds may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of disclosed compounds involves liquid chromatography using a chiral stationary phase. Said pure stereochemically isomeric forms may also be derived from the corresponding pure stereochemically isomeric forms of the appropriate starting materials, provided that the reaction occurs stereospecifically.

a. EXPERIMENTAL PROCEDURE 1

A compound of Formula (I) can be prepared by reacting a compound of Formula (II) with an acid halide derivative of Formula (III), where Y represents a chlorine or a bromine atom, in the presence of a suitable base, such as triethylamine, in a suitable inert solvent, such as dichloromethane, under suitable reaction conditions, such as at a convenient temperature, typically ranging between −10° C. and 25° C., for a period of time to ensure the completion of the reaction. Alternatively, a compound of Formula (I) can be prepared by reacting an intermediate of Formula (II) with a carboxylic acid of Formula (III), where Y represents a hydroxy group, in the presence of a suitable coupling reagent, such as 1-(3-dimethylaminopropyl)-3-ethylcarbodiimide hydrochloride (EDCI), in the presence of a suitable base, such as N,N-diisopropylethylamine, in a suitable inert solvent, such as N,N-dimethylformamide, under suitable reaction conditions, such as at a convenient temperature, typically ranging between 0° C. and 40° C., for a period of time to ensure the completion of the reaction. In Reaction Scheme (1), all variables are defined as in Formula (I).

Reaction Scheme 1

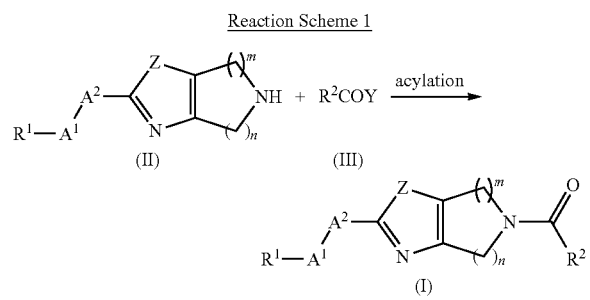

b. EXPERIMENTAL PROCEDURE 2

Alternatively, a compound of Formula (I), wherein -$A^1$-$A^2$- is —$OCH_2$—, hereby named (Ia), can be prepared by a Mitsunobu type reaction between a compound of Formula (IV) and an appropriate alcohol of Formula (V), in the presence of a suitable trialkyl or triaryl phosphine, such as triphenylphosphine and a suitable dialkyl azodicarboxylate reagent, such as di-tert-butyl azodicarboxylate (DTBAD), in a suitable inert solvent, such as tetrahydrofuran, under suitable reaction conditions, such as heating at a convenient temperature, typically ranging between 0° C. and 100° C., for a period of time to ensure the completion of the reaction. In Reaction Scheme (2), all variables are defined as in Formula (I).

Reaction Scheme 2

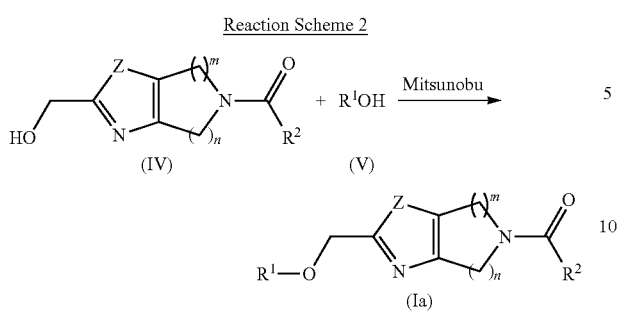

c. EXPERIMENTAL PROCEDURE 3

Alternatively, a compound of Formula (Ia) can be prepared by reacting an intermediate of Formula (VI) with an appropriate alcohol of Formula (V) in a suitable inert solvent, such as acetonitrile, in the presence of a suitable base, such as cesium carbonate, under suitable reaction conditions, such as heating at a convenient temperature, typically ranging between 60° C. and 100° C., for a period of time to ensure the completion of the reaction. In Reaction Scheme (3), all variables are as defined in Formula (I).

Reaction Scheme 3

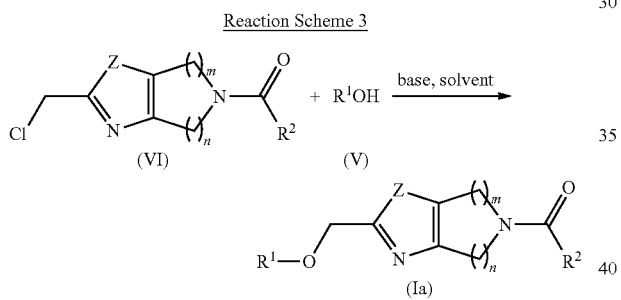

d. EXPERIMENTAL PROCEDURE 4

Alternatively, a compound of Formula (Ia) can be prepared by reacting an intermediate of Formula (IV) with an appropriate aryl or heteroaryl halide of Formula (VII) where X is Br or I, with a suitable coupling reagent, such as copper (I) iodide in the presence of a ligand, such as N,N-dimethylglycine, in the presence of a base, such as cesium carbonate, in a suitable inert solvent, such as 1,4-dioxane, under suitable reaction conditions, such as at a convenient temperature, typically ranging between 100° C. and 140° C., for a period of time to ensure the completion of the reaction. In Reaction Scheme (4), all variables are as defined in Formula (I).

Reaction Scheme 4

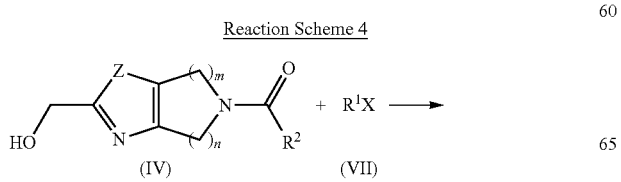

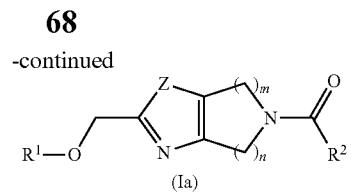

e. EXPERIMENTAL PROCEDURE 5

A compound of Formula (II), wherein Z is O, m is 1, n is 2 and -$A^1$-$A^2$- is —$OCH_2$—, hereby named (IIa), can be prepared by reacting an intermediate of Formula (VIII) with a suitable base, such as lithium hydroxide, in a suitable inert solvent, such as a mixture of water and 1,4-dioxane, under suitable reaction conditions, such as heating at a convenient temperature, either under conventional heating or by microwave irradiation, for a period of time to ensure the completion of the reaction. In Reaction Scheme (5), $R^1$ is defined as in Formula (I).

Reaction Scheme 5

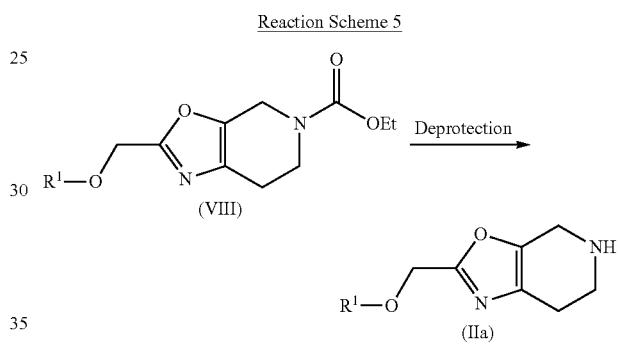

f. EXPERIMENTAL PROCEDURE 6

A compound of Formula (VIII) can be prepared by reacting a compound of Formula (IX) with a suitable dehydrating reagent, such as phosphorus oxychloride, in a suitable inert solvent, such as 1,4-dioxane, under suitable reaction conditions, such as heating at a convenient temperature, either by conventional heating or under microwave irradiation for a period of time to ensure the completion of the reaction. In Reaction Scheme (6), $R^1$ is defined as in Formula (I).

Reaction Scheme 6

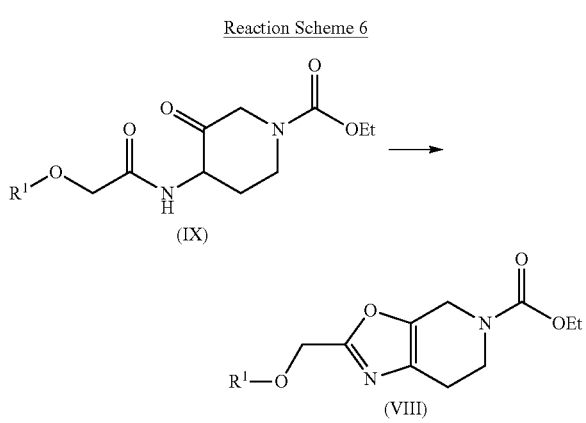

g. EXPERIMENTAL PROCEDURE 7

A compound of Formula (IX) can be prepared by oxidation of a compound of Formula (X) with a suitable oxidizing reagent, such as Dess-Martin periodinane, in a suitable inert solvent, such as dichloromethane, under suitable reaction conditions, such as heating at a convenient temperature, either by conventional heating or under microwave irradiation for a period of time to ensure the completion of the reaction. In Reaction Scheme (7), $R^1$ is defined as in Formula (I).

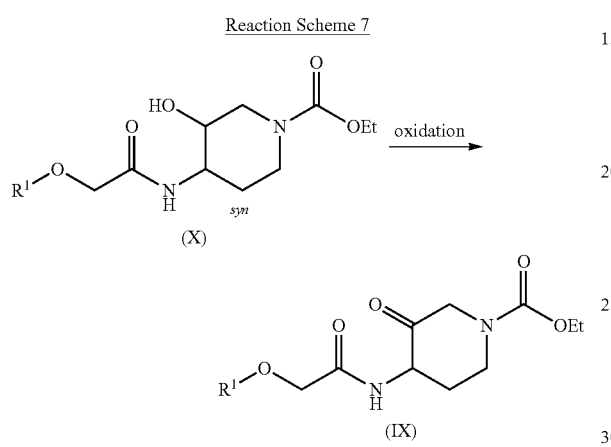

h. EXPERIMENTAL PROCEDURE 8

A compound of Formula (X) can be prepared by reacting a compound of Formula (XI) with an acid chloride derivative of Formula (XII), in the presence of a suitable base, such as triethylamine, in a suitable inert solvent, such as dichloromethane, under suitable reaction conditions, such as at a convenient temperature, typically ranging between 0° C. and 40° C. for a period of time to ensure the completion of the reaction. In Reaction Scheme (8), $R^1$ is defined as in Formula (I).

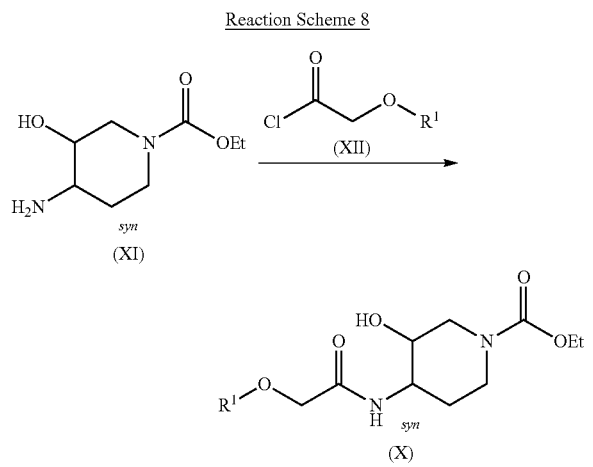

Compound of Formula (XII) can be obtained commercially and compound of Formula (XI) can be prepared following Drug Development Research, 8(1-4), 225-32; 1986.

i. EXPERIMENTAL PROCEDURE 9

A compound of Formula (II), wherein Z is O, m is 1, n is 1 and $-A^1-A^2-$ is $-OCH_2-$, hereby named (IIb), can be prepared by reacting an intermediate of Formula (XIII) with a suitable acid, such as trifluoroacetic acid, in a suitable inert solvent, such as dichloromethane, under suitable reaction conditions, such as at a convenient temperature, typically ranging between –10° C. and 40° C., for a period of time to ensure the completion of the reaction. In Reaction Scheme (9), $R^1$ is defined as in Formula (I).

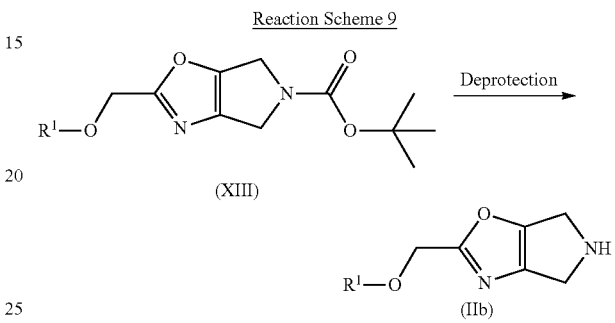

j. EXPERIMENTAL PROCEDURE 10

A compound of Formula (XIII) can be prepared by a Mitsunobu type reaction between a compound of Formula (XIV) and an appropriate alcohol of Formula (V), in the presence of a suitable trialkyl or triaryl phosphine, such as triphenylphosphine, and a suitable dialkyl azodicarboxylate reagent, such as di-tert-butyl azodicarboxylate (DTBAD), in a suitable inert solvent, such as tetrahydrofuran, under suitable reaction conditions, such as at a convenient temperature, typically ranging between 0° C. and 40° C., for a period of time to ensure the completion of the reaction. In Reaction Scheme (10), $R^1$ is defined as in Formula (I).

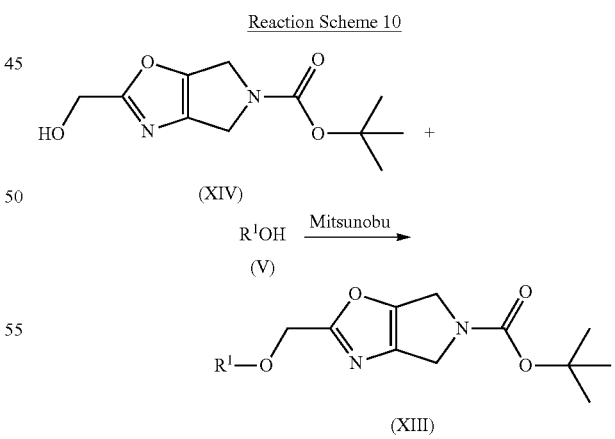

k. EXPERIMENTAL PROCEDURE 11

A compound of Formula (XIV) can be prepared by reacting a compound of Formula (XV) with a suitable reducing reagent, such as lithium borohydride, in a suitable inert solvent, such as a mixture of tetrahydrofuran and methanol,

Reaction Scheme 11

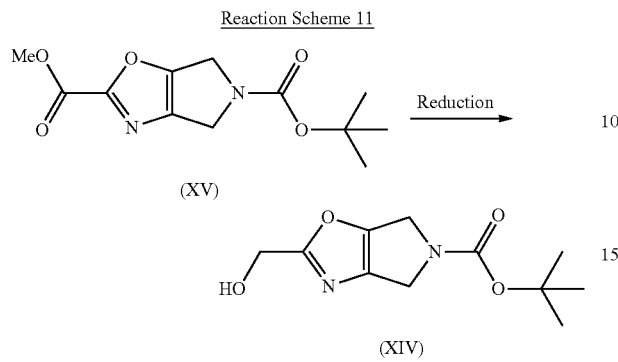

l. EXPERIMENTAL PROCEDURE 12

A compound of Formula (XV) can be prepared by reacting a compound of Formula (XVI) with an alkylating reagent, such as iodomethane, in the presence of a suitable base, such as potassium carbonate, in a suitable inert solvent, such as N,N-dimethylformamide, under suitable reaction conditions, such as heating at a convenient temperature, either by conventional heating or by microwave irradiation for a period of time to ensure the completion of the reaction.

Reaction Scheme 12

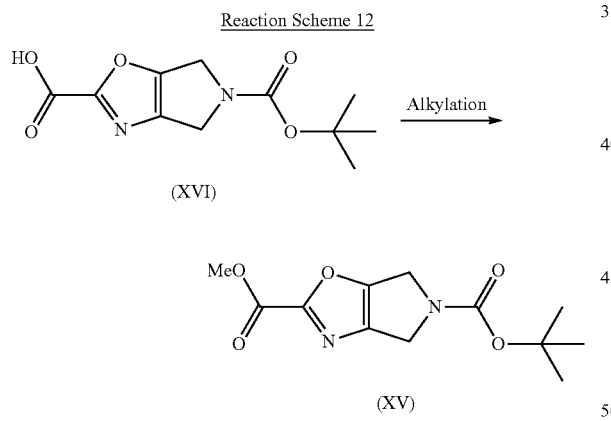

A compound of Formula (XVI) can be obtained commercially.

m. EXPERIMENTAL PROCEDURE 13

A compound of Formula (IV), wherein Z is O, m is 2, and n is 2, hereby named (IVa), can be prepared by reacting a compound of Formula (XVII) with a suitable reducing reagent, such as sodium borohydride, in a suitable inert solvent, such as methanol, under suitable reaction conditions, such as at a convenient temperature, typically ranging between -10° C. and 25° C., for a period of time to ensure the completion of the reaction. In Reaction Scheme (13), $R^2$ is defined as in Formula (I).

Reaction Scheme 13

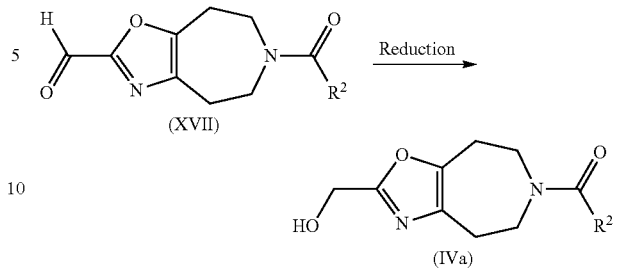

n. EXPERIMENTAL PROCEDURE 14

A compound of Formula (XVII) can be prepared by reacting a compound of Formula (I), wherein Z is O, m is 2, n is 2 and -$A^1$-$A^2$- is —CH=CH—, hereby named (Ib) with a suitable reagent, such as osmium tetraoxide, in a suitable inert solvent, such as a mixture of tetrahydrofuran, water and methanol, under suitable reaction conditions, such as heating at a convenient temperature, either by conventional heating or under microwave irradiation, for a period of time to ensure the completion of the reaction, followed by reaction with an oxidizing reagent, such as sodium periodate, in a suitable inert solvent, such as a mixture of tetrahydrofuran, water and methanol, under suitable reaction conditions, such as heating at a convenient temperature, either by conventional heating or under microwave irradiation, for a period of time to ensure the completion of the reaction. In Reaction Scheme (14), all variables are defined as in Formula (I).

Reaction Scheme 14

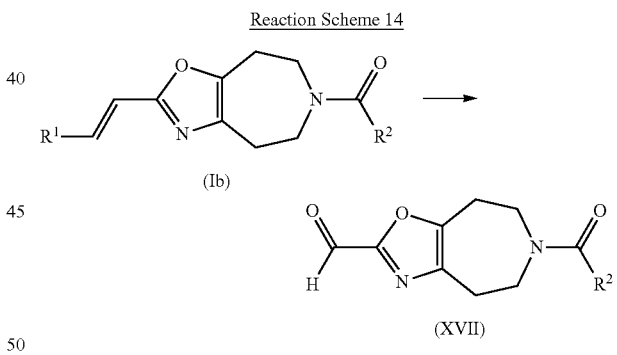

A compound of Formula (Ib), where Z is O, m is 2, n is 2 and -$A^1$-$A^2$- is —CH=CH—, can be prepared from a compound of Formula (II), wherein Z is O, m is 2, n is 2 and -$A^1$-$A^2$- is —CH=CH—, hereby named (IIc), following the conditions described in experimental procedure 1.

o. EXPERIMENTAL PROCEDURE 15

A compound of Formula (IIc) can be prepared by reacting an intermediate of Formula (XVIII) with an appropriate amide of Formula (XIX), in silica gel, under suitable reaction conditions, such as heating at a convenient temperature, typically ranging from 100° C. to 140° C., for a period of time to ensure the completion of the reaction. In Reaction Scheme (15), $R^1$ is defined as in Formula (I).

Reaction Scheme 15

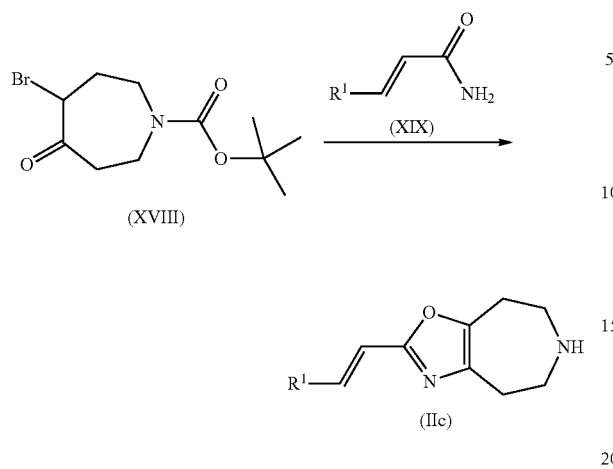

p. EXPERIMENTAL PROCEDURE 16

A compound of Formula (XVIII) can be prepared by reacting a compound of Formula (XX) with a suitable brominating reagent, such as tetra-N-butylammonium tribromide, in a suitable inert solvent, such as tetrahydrofuran, under suitable reaction conditions, such as at a convenient temperature, typically ranging from −10° C. to 25° C., for a period of time to ensure the completion of the reaction.

Reaction Scheme 16

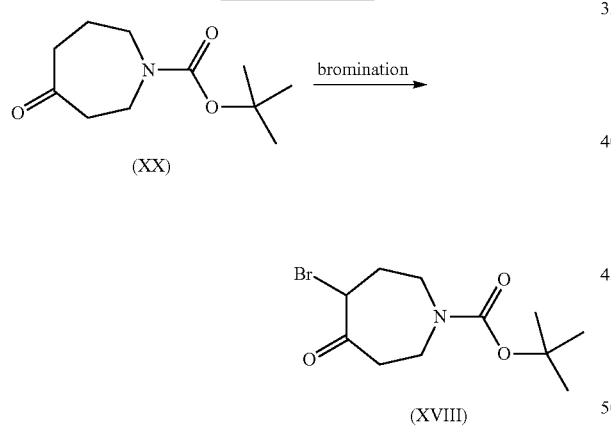

A compound of Formula (XX) can be obtained commercially.

q. EXPERIMENTAL PROCEDURE 17

A compound of Formula (II), wherein Z is O, m is 2, n is 1 and -$A^1$-$A^2$- is —$OCH_2$—, hereby named (IId), can be prepared by reacting an intermediate of Formula (XXI) with a suitable acid, such as trifluoroacetic acid, in a suitable inert solvent, such as dichloromethane, under suitable reaction conditions, such as at a convenient temperature, typically ranging between −10° C. and 40° C., for a period of time to ensure the completion of the reaction. In Reaction Scheme (17), $R^1$ is defined as in Formula (I).

Reaction Scheme 17

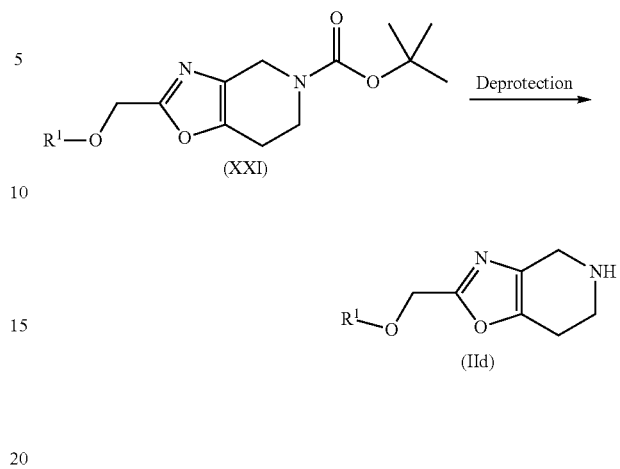

r. EXPERIMENTAL PROCEDURE 18

A compound of Formula (XXI) can be prepared by reacting a compound of Formula (XXII) with a suitable dehydrating reagent, such as the Burgess reagent, in a suitable inert solvent, such as tetrahydrofuran, under suitable reaction conditions, such as heating at a convenient temperature, either by conventional heating or under microwave irradiation for a period of time to ensure the completion of the reaction. In Reaction Scheme (18), $R^1$ is defined as in Formula (I).

Reaction Scheme 18

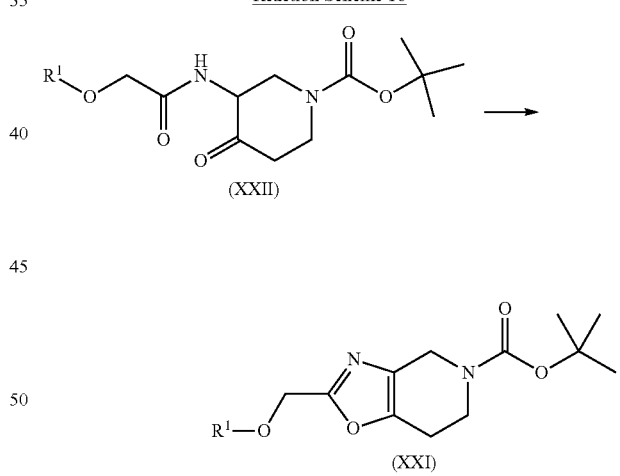

s. EXPERIMENTAL PROCEDURE 19

A compound of Formula (XXII) can be prepared by oxidation of a compound of Formula (XXIII) with a suitable oxidazing reagent, such as Des s-Martin periodinane, in a suitable inert solvent, such as dichloromethane, under suitable reaction conditions, such as heating at a convenient temperature, either by conventional heating or under microwave irradiation for a period of time to ensure the completion of the reaction. In Reaction Scheme (19), $R^1$ is defined as in Formula (I).

Reaction Scheme 19

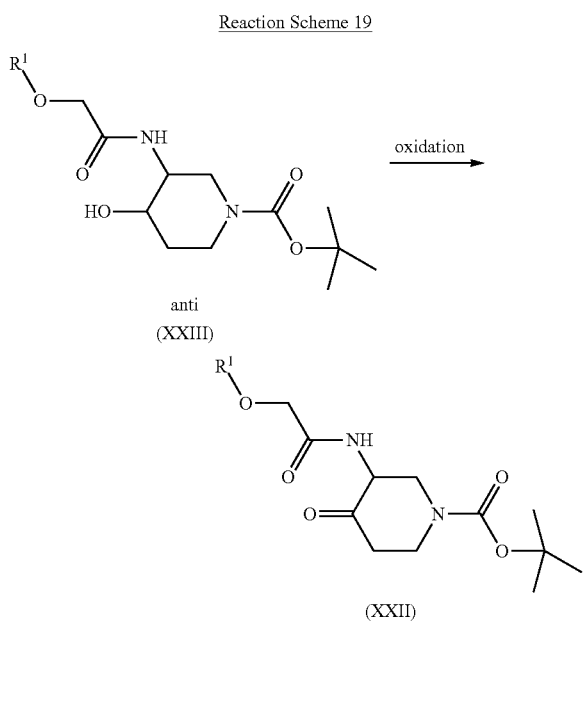

t. EXPERIMENTAL PROCEDURE 20

A compound of Formula (XXIII) can be prepared by reacting a compound of Formula (XXIV) with an acid chloride derivative of Formula (XXV), in the presence of a suitable base, such as triethylamine, in a suitable inert solvent, such as dichloromethane, under suitable reaction conditions, such as at a convenient temperature, typically ranging between 0° C. and 40° C. for a period of time to ensure the completion of the reaction. In Reaction Scheme (20), $R^1$ is defined as in Formula (I).

Reaction Scheme 20

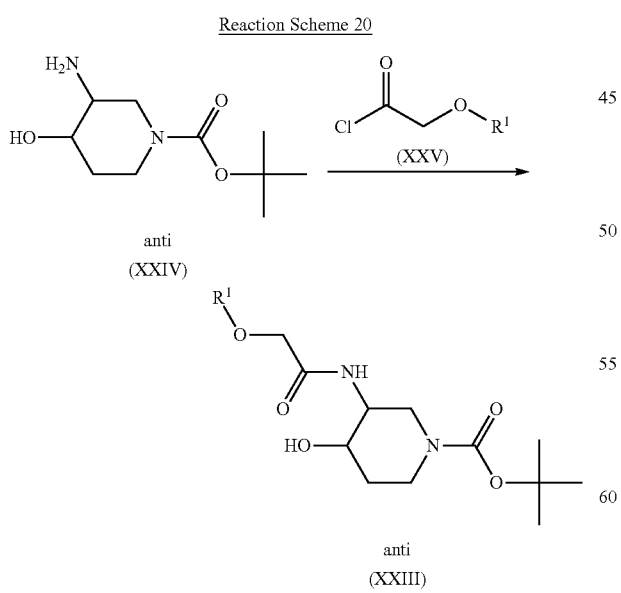

A compound of Formula (XXV) can be obtained commercially.

u. EXPERIMENTAL PROCEDURE 21

A compound of Formula (XXIV) can be prepared by reacting a compound of Formula (XXVI) with hydrogen in the presence of a suitable catalyst, such as 10% palladium on charcoal, in a suitable inert solvent, such as methanol, under suitable reaction conditions, such as heating at a convenient temperature, typically ranging between 40° C. and 60° C. for a period of time that allows the completion of the reaction.

Reaction Scheme 21

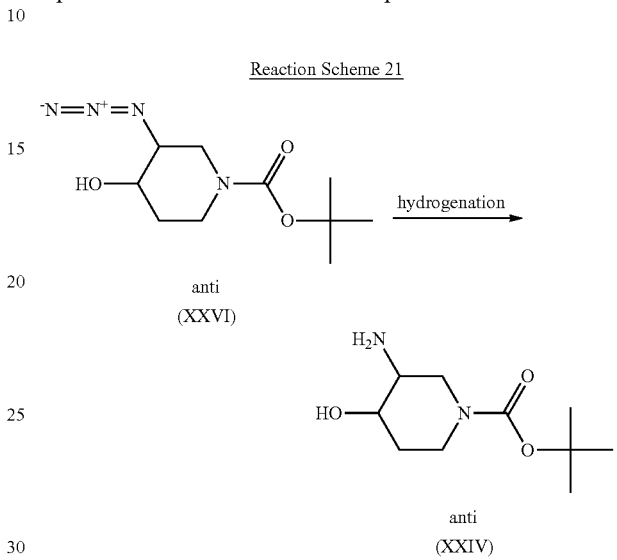

v. EXPERIMENTAL PROCEDURE 22

A compound of Formula (XXVI) can be prepared by reacting a compound of Formula (XXVII) with sodium azide, in a suitable inert solvent, such as a mixture of ethanol and water, under suitable reaction conditions, such as heating at a convenient temperature, either by conventional heating or under microwave irradiation for a period of time to ensure the completion of the reaction.

Reaction Scheme 22

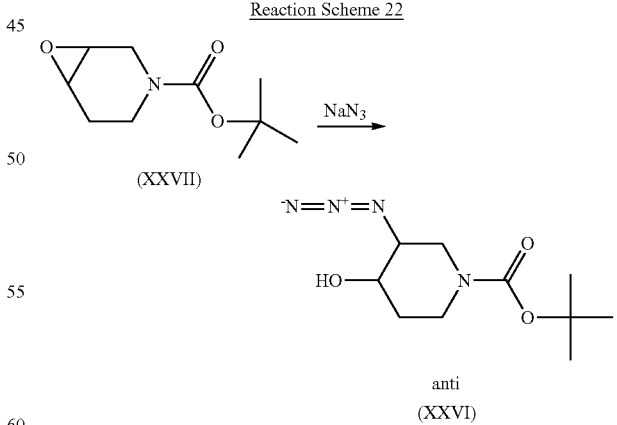

w. EXPERIMENTAL PROCEDURE 23

A compound of Formula (XXVII) can be prepared by reacting a compound of Formula (XXVIII) with a suitable oxidazing reagent, such as 3-chloroperoxybenzoic acid, in a suitable inert solvent, such as dichloromethane, under suitable reaction conditions, such as at a convenient temperature, typically ranging between 0° C. and 40° C. for a period of time to ensure the completion of the reaction.

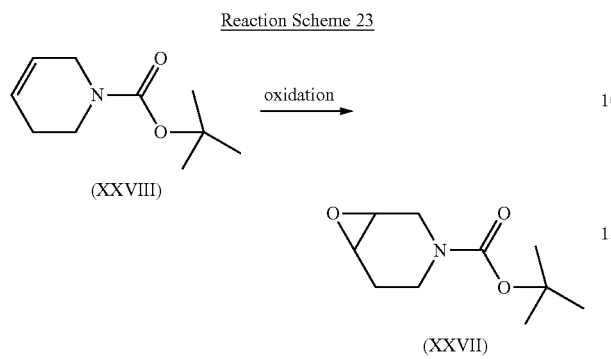

A compound of Formula (XXVIII) can be obtained commercially.

x. EXPERIMENTAL PROCEDURE 24

A compound of Formula (VI), wherein Z is S, m is 1, and n is 2, hereby named (VIa) can be prepared by reacting a compound of Formula (IV), wherein Z is S, m is 1, and n is 2, hereby named (IVb), with a suitable chlorinating reagent, such as thionyl chloride, in a suitable inert solvent, such as dichloromethane, under suitable reaction conditions, such as at a convenient temperature, typically ranging between 0° C. and 40° C. for a period of time to ensure the completion of the reaction. In Reaction Scheme (24), $R^1$ is defined as in Formula (I).

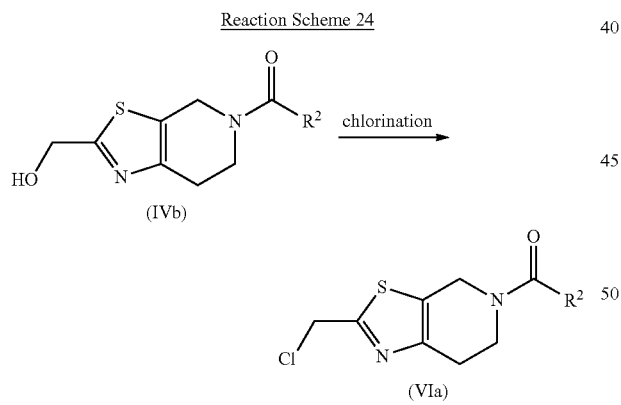

y. EXPERIMENTAL PROCEDURE 25

A compound of Formula (IVb) can be prepared by reacting a compound of Formula (XXIX) with a suitable reducing reagent, such as sodium borohydride, in a suitable inert solvent, such as methanol, under suitable reaction conditions, such as at a convenient temperature, typically ranging between 0° C. and 40° C. for a period of time to ensure the completion of the reaction. In Reaction Scheme (25), $R^2$ is defined as in Formula (I).

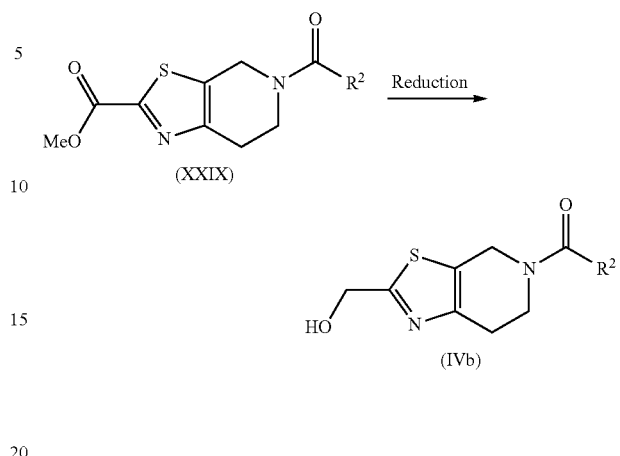

z. EXPERIMENTAL PROCEDURE 26

A compound of Formula (XXIX) can be prepared by reacting a compound of Formula (XXX) with carbon monoxide, in the presence of an appropriate alcohol, such as methanol, in the presence of a suitable palladium catalyst, such as 1,1'-bis (diphenylphosphino)ferrocenedichloro palladium (II), and under suitable reaction conditions, such as heating at a convenient temperature, typically ranging between 80° C. and 120° C. for a period of time to ensure the completion of the reaction. In Reaction Scheme (26), $R^2$ is defined as in Formula (I).

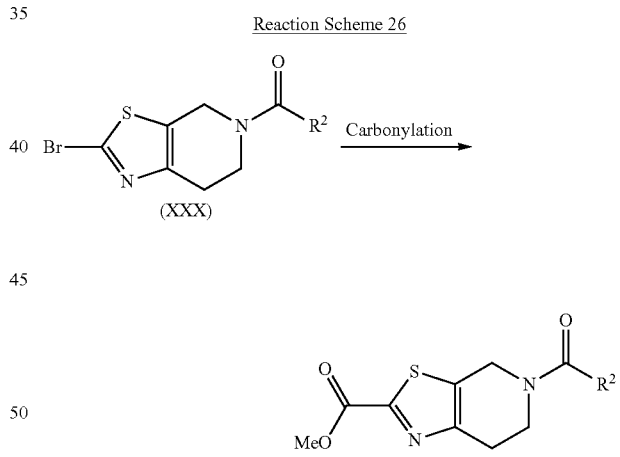

aa. EXPERIMENTAL PROCEDURE 27

A compound of Formula (XXX) can be prepared by reacting a compound of Formula (XXXI) with a suitable alkyl nitrite, such as isopentyl nitrite, in the presence of copper (II) bromide, in a suitable inert solvent, such as a mixture of methanol and tetrahydrofuran, under suitable reaction conditions, such as at a convenient temperature, typically ranging between 0° C. and 40° C. for a period of time to ensure the completion of the reaction. In Reaction Scheme (27), $R^2$ is defined as in Formula (I).

Reaction Scheme 27

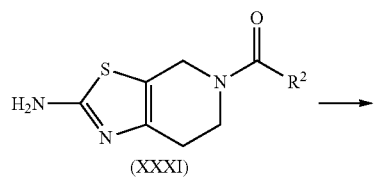

(XXXI)

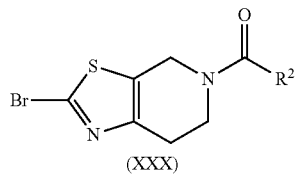

(XXX)

bb. EXPERIMENTAL PROCEDURE 28

A compound of Formula (XXXI) can be prepared by reacting a compound of Formula (XXXII) with thiourea, in the presence of a suitable base, such as sodium hydrogen carbonate, in a suitable inert solvent, such as ethanol, under suitable reaction conditions, such as heating at a convenient temperature, typically ranging between 60° C. and 100° C. for a period of time to ensure the completion of the reaction. In Reaction Scheme (28), $R^2$ is defined as in Formula (I).

Reaction Scheme 28

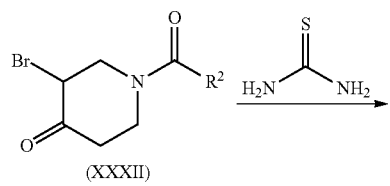

(XXXII)

(XXXI)

cc. EXPERIMENTAL PROCEDURE 29

A compound of Formula (XXXII) can be prepared by reacting a compound of Formula (XXXIII) with a suitable brominating reagent, such as tetra-N-butylammonium tribromide, in a suitable inert solvent, such as tetrahydrofuran, under suitable reaction conditions, such as heating at a convenient temperature, typically ranging between 60° C. and 100° C. for a period of time to ensure the completion of the reaction. In Reaction Scheme (29), $R^2$ is defined as in Formula (I).

Reaction Scheme 29

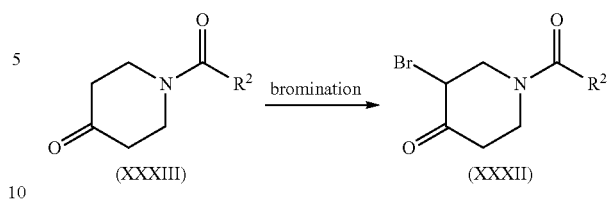

(XXXIII) (XXXII)

dd. EXPERIMENTAL PROCEDURE 30

A compound of Formula (XXXIII) can be prepared by reacting a compound of Formula (XXXIV) with an acid halide derivative of Formula (III), where Y represents a chlorine or a bromine atom, in the presence of a suitable base, such as N,N-diisopropylethylamine, in a suitable inert solvent, such as dichloromethane, under suitable reaction conditions, such as at a convenient temperature, typically ranging between 0° C. and 40° C. for a period of time to ensure the completion of the reaction. In Reaction Scheme (30), $R^2$ is defined as in Formula (I).

Reaction Scheme 30

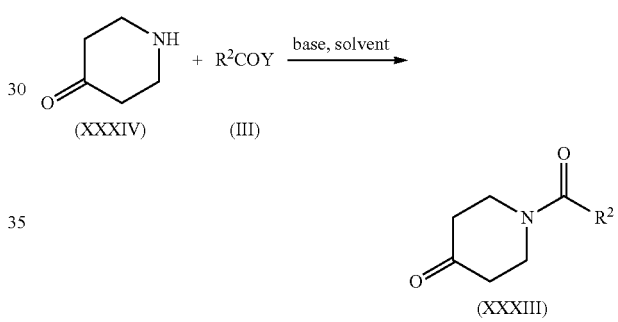

(XXXIV) (III)

(XXXIII)

A compound of Formula (XXXIV) can be obtained commercially.

ee. EXPERIMENTAL PROCEDURE 31

A compound of Formula (II), wherein Z is S, m is 1, n is 3 and -$A^1$-$A^2$- is —OCH$_2$—, hereby named (IIe), can be prepared by reacting a compound of Formula (XXXV) with 1-chloroethyl chloroformate, in the presence of a suitable base, such as N,N-diisopropylethylamine, in a suitable inert solvent, such as a mixture of dichloromethane and methanol, under suitable reaction conditions, such as at a convenient temperature, typically ranging between 0° C. and 40° C. for a period of time to ensure the completion of the reaction. In Reaction Scheme (31), $R^1$ is defined as in Formula (I).

Reaction Scheme 31

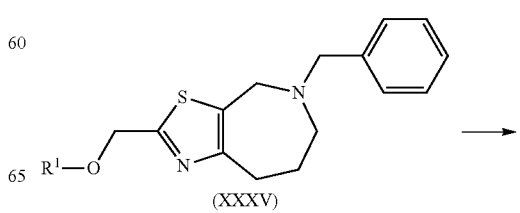

(XXXV)

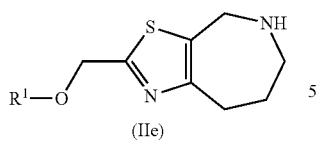

(IIe)

ff. EXPERIMENTAL PROCEDURE 32

A compound of Formula (XXXV) can be prepared by reacting a compound of Formula (XXXVI) with a reducing reagent, such as lithium aluminium hydride, in a suitable inert solvent, such as tetrahydrofuran, under suitable reaction conditions, such as at a convenient temperature, typically ranging between −10° C. and 25° C. for a period of time to ensure the completion of the reaction. In Reaction Scheme (32), $R^1$ is defined as in Formula (I).

Reaction Scheme 32

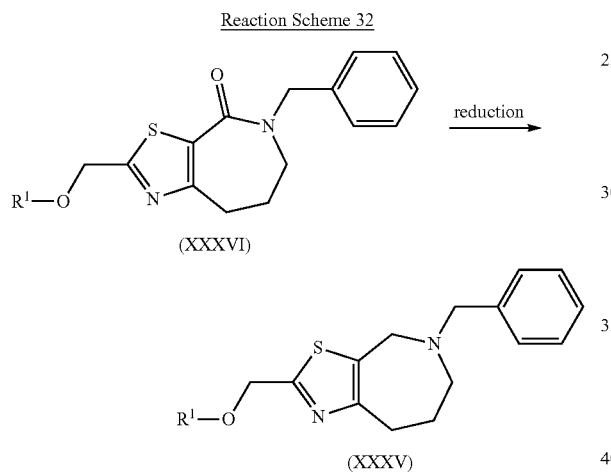

gg. EXPERIMENTAL PROCEDURE 33

A compound of Formula (XXXVI) can be prepared by reacting a compound of Formula (XXXVII) with an alkylating reagent, such as benzyl bromide, in the presence of a suitable base, such as sodium hydride, in a suitable inert solvent, such as N,N-dimethylformamide, under suitable reaction conditions, such as at a convenient temperature, typically ranging between −10° C. and 25° C. for a period of time to ensure the completion of the reaction. In Reaction Scheme (33), $R^1$ is defined as in Formula (I).

Reaction Scheme 33

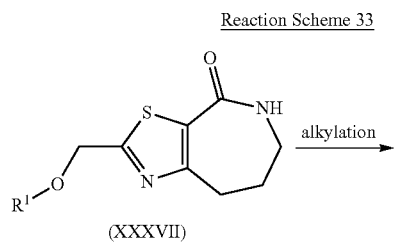

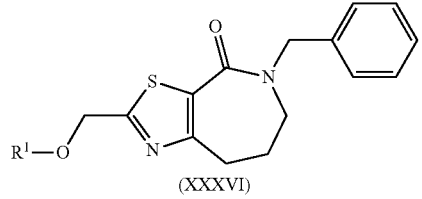

(XXXVI)

hh. EXPERIMENTAL PROCEDURE 34

A compound of Formula (XXXVII) can be prepared by reacting a compound of Formula (XXXVIII) with cerium ammonium (IV) nitrate, in a suitable inert solvent, such as a mixture of water and acetonitrile, under suitable reaction conditions, such as at a convenient temperature, typically ranging between 0° C. and 40° C. for a period of time to ensure the completion of the reaction. In Reaction Scheme (34), $R^1$ is defined as in Formula (I).

Reaction Scheme 34

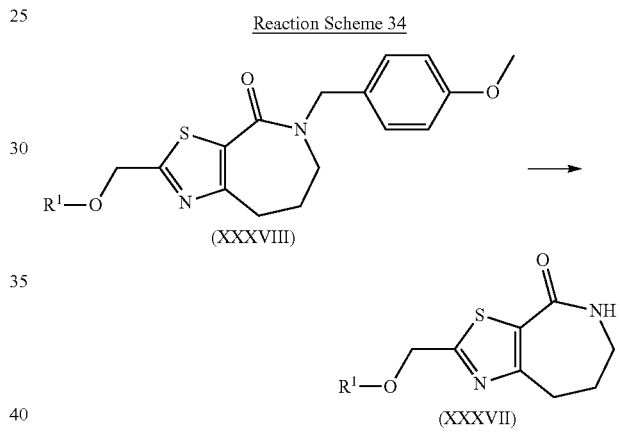

ii. EXPERIMENTAL PROCEDURE 35

A compound of Formula (XXXVIII) can be prepared by reacting a compound of Formula (XXXIX) with an appropriate thioamide of Formula (XL), in the presence of a suitable base, such as sodium hydrogen carbonate, in a suitable inert solvent, such as N,N-dimethylformamide, under suitable reaction conditions, such as heating at a convenient temperature, typically ranging between 80° C. and 120° C. for a period of time to ensure the completion of the reaction. In Reaction Scheme (35), $R^1$ is defined as in Formula (I).

Reaction Scheme 35

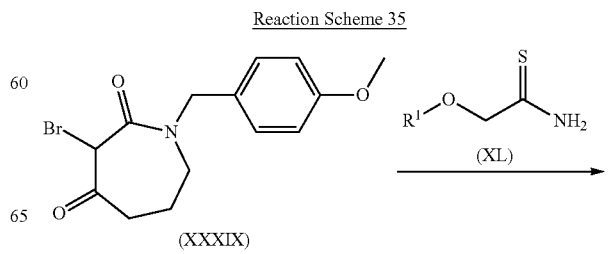

-continued

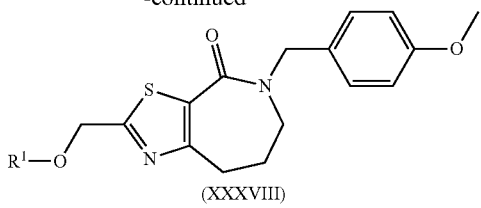

(XXXVIII)

A compound of Formula (XL) can be obtained commercially.

jj. EXPERIMENTAL PROCEDURE 36

A compound of Formula (XXXIX) can be prepared by reacting a compound of Formula (XLI) with a suitable brominating reagent, such as N-bromosuccinimide, in the presence of a suitable base, such as sodium hydrogen sulphate, in a suitable inert solvent, such as tetrahydrofuran, under suitable reaction conditions, such as heating at a convenient temperature, typically ranging between 0° C. and 40° C. for a period of time to ensure the completion of the reaction.

Reaction Scheme 36

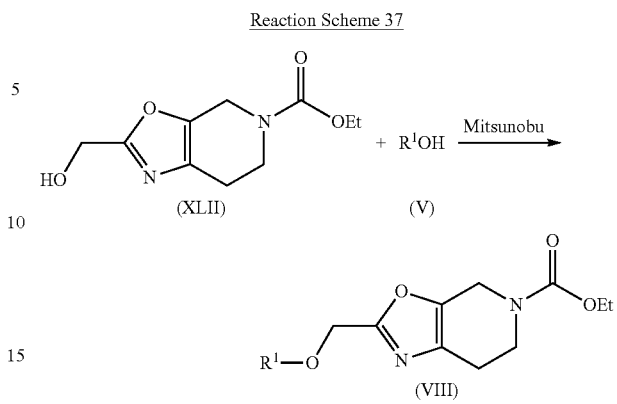

A compound of Formula (XLI) can be obtained commercially or alternatively, can also be prepared by procedures similar to those described in Collison, C. G. Synthesis, 2006, 2319-2322.

kk. EXPERIMENTAL PROCEDURE 37

Alternatively to EXPERIMENTAL PROCEDURE 6, a compound of Formula (VIII) can be prepared by a Mitsunobu type reaction between a compound of Formula (XLII) and an appropriate alcohol of Formula (V) in the presence of a suitable trialkyl or triaryl phosphine, such as triphenylphosphine, and a suitable dialkyl azodicarboxylate reagent, such as di-tert-butyl azodicarboxylate (DTBAD), in a suitable inert solvent, such as tetrahydrofuran, under suitable reaction conditions, such as at a convenient temperature, typically ranging between 0° C. and 40° C., for a period of time to ensure the completion of the reaction. In Reaction Scheme (37), $R^1$ is defined as in Formula (I).

Reaction Scheme 37

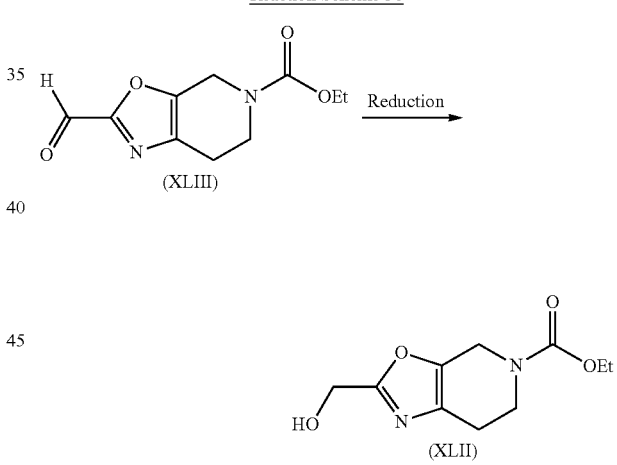

ll. EXPERIMENTAL PROCEDURE 38

A compound of Formula (XLII) can be prepared by reacting a compound of Formula (XLIII) with a suitable reducing reagent, such as sodium borohydride, in a suitable inert solvent, such as methanol, under suitable reaction conditions, such as at a convenient temperature, typically ranging between −10° C. and 25° C., for a period of time to ensure the completion of the reaction.

Reaction Scheme 38 mm. EXPERIMENTAL PROCEDURE 39

A compound of Formula (XLIII) can be prepared by reacting an intermediate of Formula (XLIV) with a suitable reagent, such as osmium tetraoxide, in a suitable inert solvent, such as a mixture of tetrahydrofuran, water and methanol, under suitable reaction conditions, such as at a convenient temperature, typically ranging from 0° C. to 40° C., for a period of time to ensure the completion of the reaction, followed by reaction with a suitable oxidazing reagent, such as sodium periodate, in a suitable inert solvent, such as a mixture of tetrahydrofuran, water and methanol, under suitable reaction conditions, such as at a convenient temperature, typically ranging from 0° C. to 40° C., for a period of time to ensure the completion of the reaction. In Reaction Scheme (39), $R^1$ is defined as in Formula (I).

Reaction Scheme 39

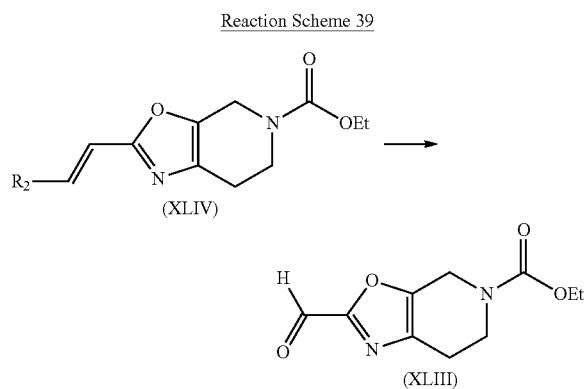

nn. EXPERIMENTAL PROCEDURE 40

A compound of Formula (XLIV) can be prepared by reacting an intermediate of Formula (XLV) with an appropriate amide of Formula (XIX), in silica gel, under suitable reaction conditions, such as heating at a convenient temperature, typically ranging from 100° C. to 140° C., for a period of time to ensure the completion of the reaction. In Reaction Scheme (40), $R^1$ is defined as in Formula (I).

Reaction Scheme 40

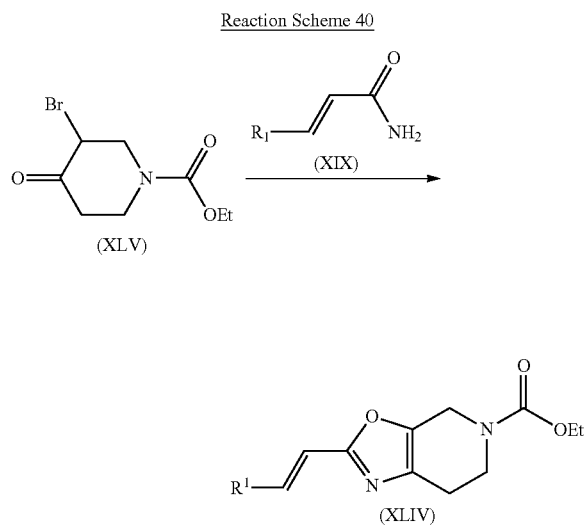

A compound of Formula (XIX) can be obtained commercially.

oo. EXPERIMENTAL PROCEDURE 41

A compound of Formula (XLV) can be obtained commercially or can be prepared by reacting a compound of Formula (XLVI) with a suitable brominating reagent, such as bromine, in the presence of a suitable acid catalyst, such as hydrobromic acid, in a suitable inert solvent, such as a mixture of water and tetrahydrofuran, under suitable reaction conditions, such as at a convenient temperature, typically ranging from −10° C. to 25° C., for a period of time to ensure the completion of the reaction.

Reaction Scheme 41

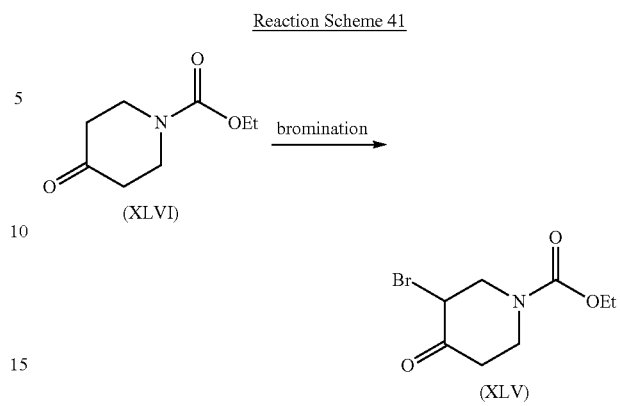

A compound of Formula (XLVI) can be obtained commercially.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

E. PHARMACEUTICAL COMPOSITIONS

In one aspect, the invention relates to pharmaceutical compositions comprising the disclosed compounds, or a product of a disclosed method of making, or a pharmaceutically acceptable salt, solvate, or polymorph thereof. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

For therapeutic use, salts of the compounds of Formula (I) are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require positive allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

The invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) in pharmaceutical compositions, it can be advantageous to employ α-, O— or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention relates to a pharmaceutical composition comprising a therapeutically effective amount of a compound according to the invention, and a pharmaceutically acceptable carrier. Additionally, the invention relates to a process for preparing such pharmaceutical composition, characterized in that a pharmaceutically acceptable carrier is intimately mixed with a therapeutically effective amount of a compound according to the invention.

As already mentioned, the invention also relates to a pharmaceutical composition comprising the compounds according to the invention and one or more other drugs in the treatment, prevention, control, amelioration, or reduction of risk of diseases or conditions for which compounds of Formula (I) or the other drugs may have utility as well as to the use of such a composition for the manufacture of a medicament. The present invention also relates to a combination of a compound according to the present invention and an mGluR5 orthosteric agonist. The present invention also relates to such a combination for use as a medicine. The present invention also relates to a product comprising (a) a compound according to the present invention, a pharmaceutically acceptable salt thereof or a solvate thereof, and (b) a mGluR5 orthosteric agonist, as a combined preparation for simultaneous, separate or sequential use in the treatment or prevention of a condition in a mammal, including a human, the treatment or prevention of which is affected or facilitated by the neuromodulatory effect of mGluR5 allosteric modulators, in particular positive mGluR5 allosteric modulators. The different drugs of such a combination or product may be combined in a single preparation together with pharmaceutically acceptable carriers or diluents, or they may each be present in a separate preparation together with pharmaceutically acceptable carriers or diluents.

F. METHODS OF USING THE COMPOUNDS AND COMPOSITIONS

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders, including, but not limited to, schizophrenia and other psychotic disorders and cognitive disorders, involving cognitive deficits, are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainite receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through $G\alpha q/11$ to increase inositol phosphate and metabolism and resultant increases in intracellular calcium. Group I mGluRs are primarily located post-synaptically and have a modulatory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to $G\alpha i$ and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et. al. J. Neurosci. 21:5925-5934 (2001)). Therefore, modulation of mGluRs is an approach to modulating glutamatergic transmission. Numerous reports indicate that mGluR5 plays a role in a number of disease states including anxiety (Spooren et. al. J. Pharmacol. Exp. Therapeut. 295:1267-1275 (2000), Tatarczynska et al. Br. J. Pharmaol. 132:1423-1430 (2001)), schizophrenia (reviewed in Chavez-Noriega et al. Curr. Drug Targets: CNS & Neurological Disorders 1:261-281 (2002), Kinney, G. G. et al. J. Pharmacol. Exp. Therapeut. 313:199-206 (2005)), addiction to cocaine (Chiamulera et al. Nature Neurosci. 4:873-874 (2001), Parkinson's disease (Awad et al. J. Neurosci. 20:7871-7879 (2000), Ossowska et al. Neuropharmacol. 41: 413-420 (2001), and pain (Salt and Binns Neurosci. 100: 375-380 (2001).

Figure 2:
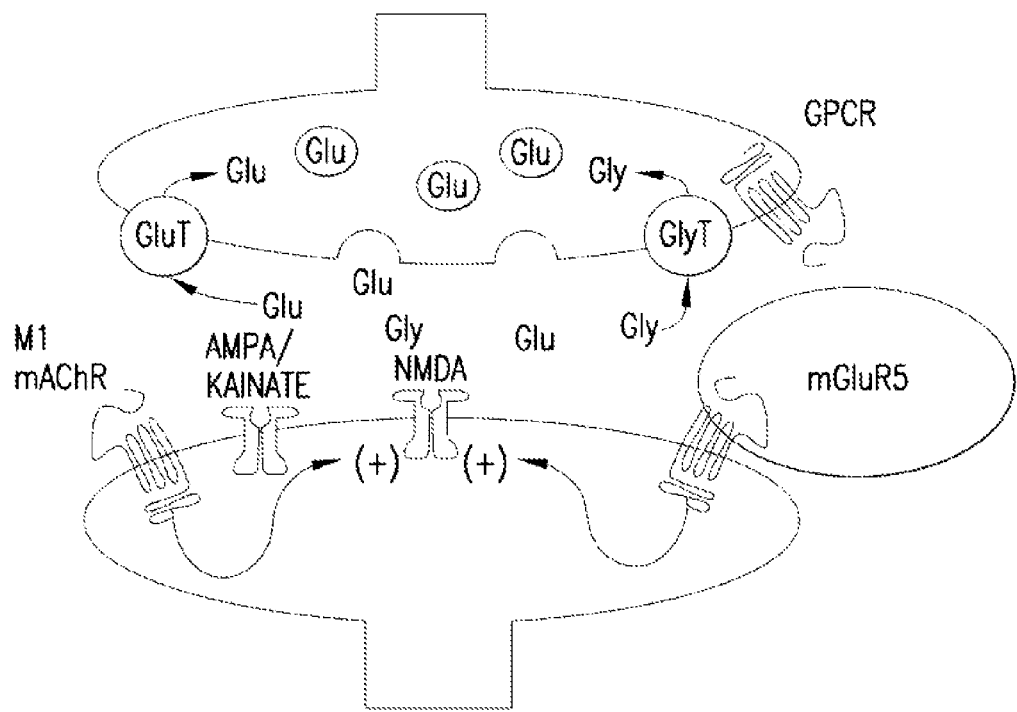
FIG. 2 shows a schematic illustrating that activation of mGluR5 potentiates NMDA receptor function.
Figure 3:
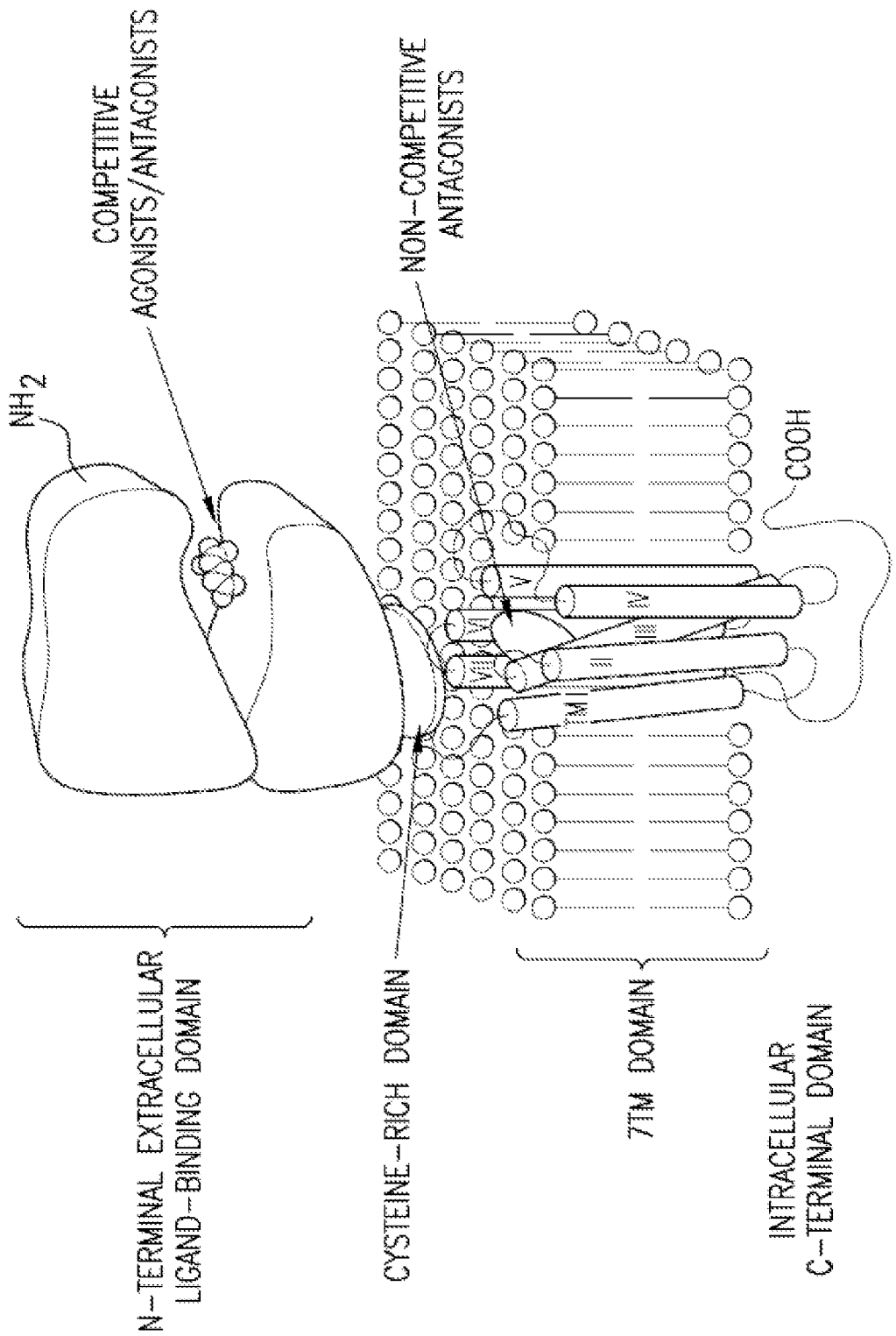
FIG. 3 shows a schematic illustrating structural features of mGluR5 and allosteric binding.

Phencyclidine (PCP) and other NMDA receptor antagonists induce a psychotic state in humans similar to schizophrenia. In schizophrenia patients, PCP and ketamine exacerbate/precipitate preexisting positive and negative symptoms in stable patients. Treatment with NMDA receptor co-agonists can improve positive and negative symptoms. A schematic of the NMDA receptor is shown in FIG. 1. Activation of mGluR5 potentiates NMDA receptor function as shown in FIG. 2. Orthosteric ligands lack subtype selectivity and can cause unwanted side effects. Allosteric modulators (see FIG. 3) that can target transmembrane domains offer a pharmacologically attractive alternative. In one aspect, transmembrane domains can be significantly less conserved than extracellular loop regions.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with anti-Alzheimer's agents, β-secretase inhibitors, γ-secretase inhibitors, muscarinic agonists, muscarinic potentiatorsHMG-CoA reductase inhibitors, NSAIDs and anti-amyloid antibodies.

In another aspect, the subject compounds can be administered in combination with sedatives, hypnotics, anxiolytics, antipsychotics, selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

In another aspect, the subject compound can be used in combination with levodopa (with or without a selective extracerebral decarboxylase inhibitor), anticholinergics such as biperiden, COMT inhibitors such as entacapone, A2a adenosine antagonists, cholinergic agonists, NMDA receptor antagonists and dopamine agonists.

The pharmaceutical compositions and methods of the present invention can further comprise other therapeutically active compounds as noted herein which are usually applied in the treatment of the above mentioned pathological conditions.

The compounds provided in this invention are allosteric modulators of metabotropic glutamate receptors, in particular they are positive allosteric modulators of mGluR5. The compounds of the present invention do not appear to bind to the glutamate recognition site, the orthosteric ligand site, but instead to an allosteric site. In the presence of glutamate or an agonist of mGluR5, the compounds of this invention increase the mGluR5 response. The compounds provided in this invention are expected to have their effect at mGluR5 by virtue of their ability to increase the response of such receptors to glutamate or mGluR5 agonists, enhancing the response of the receptor.

Hence, the present invention relates to a compound according to the present invention for use as a medicament, as well as to the use of a compound according to the invention or a pharmaceutical composition according to the invention for the manufacture of a medicament, in particular, for the manufacture of a medicament for treating or preventing, in particular treating, a condition in a mammal, including a human, the treatment or prevention of which is affected or facilitated by the neuromodulatory effect of allosteric modulators of mGluR5, in particular positive allosteric modulators thereof. The present invention also relates to a compound according to the present invention or a pharmaceutical composition according to the invention for use in the treatment or prevention of, in particular treatment of, a condition in a subject such as a mammal, including a human, the treatment or prevention of which is affected or facilitated by the neuromodulatory effect of allosteric modulators of mGluR5, in particular positive allosteric modulators thereof. The present invention also relates to the use of a compound according to the present invention or a pharmaceutical composition according to the invention for the manufacture of a medicament for treating or preventing, in particular treating, a condition in a subject such as a mammal, including a human, the treatment or prevention of which is affected or facilitated by the neuromodulatory effect of allosteric modulators of mGluR5, in particular positive allosteric modulators thereof. The present invention also relates to a compound according to the present invention or a pharmaceutical composition according to the invention for treating or preventing, in particular treating, a condition in a subject such as a mammal, including a human, the treatment or prevention of which is affected or facilitated by the neuromodulatory effect of allosteric modulators of mGluR5, in particular positive allosteric modulators thereof.

The present invention also relates to the use of a compound according to the invention or a pharmaceutical composition according to the invention for the manufacture of a medicament for treating, preventing, ameliorating, controlling or reducing the risk of various neurological and psychiatric disorders associated with glutamate dysfunction in a subject such as a mammal, including a human, the treatment or prevention of which is affected or facilitated by the neuromodulatory effect of allosteric modulators of mGluR5, in particular positive allosteric modulators thereof.

Also, the present invention relates to a compound according to the invention or a pharmaceutical composition according to the invention for use in the treatment, prevention, amelioration, control or reduction of the risk of various neurological and psychiatric disorders associated with glutamate dysfunction in a subject such as a mammal, including a human, the treatment or prevention of which is affected or facilitated by the neuromodulatory effect of allosteric modulators of mGluR5, in particular positive allosteric modulators thereof.

The present compounds are suitable for use as a medicine in the treatment or prevention of schizophrenia, including positive, negative and cognitive symptoms thereof, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified, psychosis associated with dementia, major depressive disorder, dysthymic disorder, premenstrual dysphoric disorder, depressive disorder not otherwise specified, bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder, mental retardation, pervasive developmental disorders, attention deficit disorders, attention-deficit/hyperactivity disorder, disruptive behaviour disorders, personality disorder of the paranoid type, personality disorder of the schizoid type, personality disorder of the schizotypical type, tic disorders, Tourette's syndrome, substance dependence, substance abuse, substance withdrawal, trichotillomania, conditions wherein cognition is impaired, Alzheimer's disease, Parkinson's disease, Huntington's disease, Lewy Body Dementia, dementia due to HIV disease, dementia due to Creutzfeldt-Jakob disease, amnestic disorders, mild cognitive impairment, and age-related cognitive decline, feeding disorders such as anorexia and bulimia, and obesity.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of schizophrenia and dementia are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound according to the general Formula (I), the stereoisomeric forms thereof and the pharmaceutically acceptable acid or base addition salts and the solvates thereof, for use in the treatment of any one of the diseases mentioned hereinbefore.

The invention also relates to a compound according to the general Formula (I), the stereoisomeric forms thereof and the pharmaceutically acceptable acid or base addition salts and the solvates thereof, for use in treating any one of the diseases mentioned hereinbefore.

The invention also relates to a compound according to the general Formula (I), the stereoisomeric forms thereof and the pharmaceutically acceptable acid or base addition salts and the solvates thereof, for the treatment or prevention, in particular treatment, of any one of the diseases mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, such as mammals including humans, suffering from any one of the diseases mentioned hereinbefore, and a method of preventing in warm-blooded animals, such as mammals including humans, any one of the diseases mentioned hereinbefore.

Said methods comprise the administration, i.e. the systemic or topical administration, preferably oral administration, of a therapeutically effective amount of a compound of Formula (I), a stereoisomeric form, a pharmaceutically acceptable salt or a solvate thereof, to warm-blooded animals, such as mammals including humans.

Therefore, the invention also relates to a method for the prevention and/or treatment of any one of the diseases mentioned hereinbefore comprising administering a therapeutically effective amount of compound according to the invention to a patient in need thereof.

Because such positive allosteric modulators of mGluR5, including compounds of Formula (I), enhance the response of mGluR5 to glutamate, it is an advantage that the present methods utilize endogenous glutamate.

Because positive allosteric modulators of mGluR5, including compounds of Formula (I), enhance the response of mGluR5 to agonists, it is understood that the present invention extends to the treatment of neurological and psychiatric disorders associated with glutamate dysfunction by administering an effective amount of a positive allosteric modulator of mGluR5, including compounds of Formula (I), in combination with an mGluR5 agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

In a further embodiment, the invention relates to a method for the treatment of a neurological and/or psychiatric disorder associated with glutamate dysfunction in a mammal comprising the step of administering to the mammal a therapeutically effective amount of least one disclosed compound, composition, or product. In a further embodiment, the mammal is a human. In a further embodiment, the mammal has been diagnosed with a need for treatment of the disorder prior to the administering step. In a further embodiment, the method further comprises the step of identifying a mammal in need of treatment of the disorder. In a further embodiment, the disorder is a neurological and/or psychiatric disorder associated with mGluR5 dysfunction. In a further embodiment, the disorder is selected from dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In a further embodiment, the invention relates to a method for potentiation of metabotropic glutamate receptor activity in a mammal comprising the step of administering to the mammal a therapeutically effective amount of least one disclosed compound, composition, or product. In a further embodiment, the mammal is a human. In a further embodiment, the mammal has been diagnosed with a need for potentiation of metabotropic glutamate receptor activity prior to the administering step. In a further embodiment, the method further comprises the step of identifying a mammal in need for potentiation of metabotropic glutamate receptor activity. In a further embodiment, the metabotropic glutamate receptor is mGluR5.

In a further embodiment, the invention relates to a method for partial agonism of metabotropic glutamate receptor activity in a mammal comprising the step of administering to the mammal a therapeutically effective amount of least one disclosed compound, composition, or product. In a further embodiment, the mammal is a human. In a further embodiment, the mammal has been diagnosed with a need for partial agonism of metabotropic glutamate receptor activity prior to the administering step. In a further embodiment, the method further comprises the step of identifying a mammal in need for partial agonism of metabotropic glutamate receptor activity. In a further embodiment, the metabotropic glutamate receptor is mGluR5.

In a further embodiment, the invention relates to a method for enhancing cognition in a mammal comprising the step of administering to the mammal an effective amount of least one disclosed compound, composition, or product. In a further embodiment, the mammal is a human. In a further embodiment, the cognition enhancement is a statistically significant increase in Novel Object Recognition. In a further embodiment, the cognition enhancement is a statistically significant increase in performance of the Wisconsin Card Sorting Test.

In a further embodiment, the invention relates to a method for modulating mGluR5 activity in a mammal comprising the step of administering to the mammal an effective amount of least one disclosed compound, composition, or product. In a further embodiment, modulating is increasing. In a further embodiment, modulating is potentiation. In a further embodiment, modulating is partial agonism. In a further embodiment, the mammal is a human. In a further embodiment, the mammal has been diagnosed with a need for modulating mGluR5 activity prior to the administering step. In a further embodiment, the method further comprises the step of identifying a mammal in need of decreasing mGluR5 activity. In a further embodiment, an effective amount is a therapeutically effective amount. In a further embodiment, the mammal has been diagnosed with a need for treatment of a disorder related to mGluR5 activity prior to the administering step. In a further embodiment, the disorder is a neurological and/or psychiatric disorder associated with mGluR5 dysfunction. In a further embodiment, the disorder is selected from dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In a further embodiment, the invention relates to a method for modulating mGluR5 activity in at least one cell, comprising the step of contacting the at least one cell with an effective amount of least one disclosed compound, composition, or product. In a further embodiment, modulating is increasing. In a further embodiment, modulating is potentiation. In a further embodiment, modulating is partial agonism. In a further embodiment, the cell is mammalian. In a further embodiment, the cell is human. In a further embodiment, the cell has been isolated from a mammal prior to the contacting step. In a further embodiment, contacting is via administration to a mammal. In a further embodiment, the mammal has been diagnosed with a need for modulating mGluR5 activity prior to the administering step. In a further embodiment, the mammal has been diagnosed with a need for treatment of a disorder related to mGluR5 activity prior to the administering step.

In a further embodiment, the invention relates to a kit comprising at least one disclosed compound, composition, or product and at least one agent selected from: (a) at least one agent known to increase mGluR5 activity; (b) at least one agent known to decrease mGluR5 activity; (c) at least one agent known to treat a neurological and/or psychiatric disorder; or (d) instructions for treating a disorder associated with glutamate dysfunction. In a further embodiment, the at least one compound, composition, or product and the at least one agent are co-formulated. In a further embodiment, the at least one compound, composition, or product and the at least one agent are co-packaged.

1. Treatment Methods

The compounds disclosed herein are useful for treating, preventing, ameliorating, controlling or reducing the risk of a variety of neurological and psychiatric disorders associated with glutamate dysfunction.

Examples of disorders associated with glutamate dysfunction include: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Thus, in some aspects of the disclosed method, the disorder is dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, psychotic depression.

Thus, provided is a method for treating or prevention schizophrenia, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including schizophrenia and related disorders.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

a. TREATMENT of a Neurological and/or Psychiatric Disorder Associated With Glutamate Dysfunction In one aspect, the invention relates to a method for the treatment of a neurological and/or psychiatric disorder associated with glutamate dysfunction in a mammal comprising the step of administering to the mammal a therapeutically effective amount of at least one compound, or a pharmaceutically acceptable salt, hydrate, solvate, or polymorph thereof, wherein the compound is a disclosed compound or a product of a disclosed method of making a compound.

In one aspect, the invention relates to a method for the treatment of a disorder associated with mGluR5 activity in a mammal comprising the step of administering to the mammal at least one disclosed compound or at least one disclosed product in a dosage and amount effective to treat the disorder in the mammal.

In a further aspect, the compound administered exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal that the compound is administered to is a human. In a further aspect, the mammal has been diagnosed with a need for treatment of the disorder prior to the administering step. In a further aspect, the method further comprises the step of identifying a mammal in need of treatment of the disorder.

In a further aspect, the disorder is a neurological and/or psychiatric disorder associated with mGluR5 dysfunction. In a further aspect, the disorder is selected from dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

b. Enhancing Cognition

In one aspect, the invention relates to a method for enhancing cognition in a mammal comprising the step of administering to the mammal an effective amount of at least one compound, or a pharmaceutically acceptable salt, hydrate, solvate, or polymorph thereof, wherein the compound is a disclosed compound or a product of a disclosed method of making a compound.

In one aspect, the invention relates to a method for enhancing cognition in a mammal comprising the step of administering to the mammal at least one disclosed compound or at least one disclosed product in a dosage and amount effective for enhancing cognition in the mammal either in the presence or absence of the endogenous ligand. In a further aspect, the method relates to a method for enhancing cognition in a mammal by contacting at least one cell in a mammal, comprising the step of contacting the at least one cell with at least one disclosed compound or at least one disclosed product in an amount effective enhance cognition in the mammal.

In a further aspect, the compound administered exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, the mammal is a human. In one aspect, the mammal has been diagnosed with a need for cognition enhancement prior to the administering step. In a still further aspect, the method further comprises the step of identifying a mammal in need of cognition enhancement prior to the administering step. In a further aspect, the cognition enhancement is a statistically significant increase in Novel Object Recognition. In a further aspect, the cognition enhancement is a statistically significant increase in performance of the Wisconsin Card Sorting Test. In a further aspect, the method further comprises the step of identifying a mammal in need of increasing mGluR5 activity.

c. Modulating mGluR5 Activity in Mammals

In one aspect, the invention relates to a method for modulating mGluR5 activity in a mammal comprising the step of administering to the mammal an effective amount of at least one compound, or a pharmaceutically acceptable salt, hydrate, solvate, or polymorph thereof, wherein the compound is a disclosed compound or a product of a disclosed method of making a compound.

In one aspect, the invention relates to a method for modulating mGluR5 activity in a mammal comprising the step of administering to the mammal at least one disclosed compound or at least one disclosed product in a dosage and amount effective for modulating mGluR5 activity in the mammal either in the presence or absence of the endogenous ligand. In a further aspect, the method relates to a method for modulation of metabotropic glutamate receptor activity in a mammal by contacting at least one cell in a mammal, comprising the step of contacting the at least one cell with at least one disclosed compound or at least one disclosed product in an amount effective to modulate mGluR5 activity in the at least one cell.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, modulating is increasing. In a further aspect, modulating is potentiation. In a yet further aspect, modulating is partial agonism.

In one aspect, the compound is a potentiator of mGluR5. In a further aspect, the compound is a partial agonist of modulating mGluR5. In a yet further aspect, the compound is a modulator of mGluR5. In a still further aspect, the compound is a partial allosteric modulator of mGluR5.

In one aspect, the mammal is a human. In a further aspect, the mammal has been diagnosed with a need for modulating mGluR5 activity prior to the administering step. In a further aspect, the mammal has been diagnosed with a need for treatment of a disorder related to mGluR5 activity prior to the administering step. In a further aspect, the method further comprises the step of identifying a mammal in need of increasing mGluR5 activity.

In one aspect, an effective amount is a therapeutically effective amount.

In one aspect, modulating mGluR5 activity in a mammal is associated with the treatment of a neurological and/or psychiatric disorder associated with mGluR5 dysfunction. In a further aspect, the disorder is selected from dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In one aspect, modulating mGluR5 activity in a mammal is associated with the treatment of a disorder associated with uncontrolled cellular proliferation. In a further aspect, the disorder is cancer. In a still further aspect, the cancer is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

d. Modulating mGluR5 Activity in Cells

In one aspect, the invention relates to a method for modulating mGluR5 activity in at least one cell, comprising the step of contacting the at least one cell with an effective amount of at least one compound, or a pharmaceutically acceptable salt, hydrate, solvate, or polymorph thereof, wherein the compound is a disclosed compound or a product of a disclosed method of making a compound.

In one aspect, the invention relates to a method for modulation of metabotropic glutamate receptor activity in a mammal by contacting at least one cell in a mammal, comprising the step of contacting the at least one cell with at least one disclosed compound or at least one disclosed product in an amount effective to modulate mGluR5 activity in the at least one cell.

In a further aspect, the compound administered is a disclosed compound or a product of a disclosed method of making a compound.

In a further aspect, the compound exhibits positive allosteric modulation of mGluR5 with an $EC_{50}$ of less than about 10,000 nM. In a still further aspect, the compound exhibits positive allosteric modulation of mGluR5 with an $EC_{50}$ of less than about 5,000 nM. In an even further aspect, the compound exhibits positive allosteric modulation of mGluR5 with an $EC_{50}$ of less than about 1,000 nM. In a further aspect, the compound exhibits positive allosteric modulation of mGluR5 with an $EC_{50}$ of less than about 500 nM. In a yet further aspect, the compound exhibits positive allosteric modulation of mGluR5 with an $EC_{50}$ of less than about 100 nM.

In one aspect, modulating is increasing. In a further aspect, modulating is potentiation. In a further aspect, modulating is partial agonism.

In one aspect, the cell is mammalian. In a further aspect, the cell is human. In a further aspect, the cell has been isolated from a mammal prior to the contacting step.

In a further aspect, contacting is via administration to a mammal. In a further aspect, the mammal has been diagnosed with a need for modulating mGluR5 activity prior to the administering step. In a further aspect, the mammal has been diagnosed with a need for treatment of a disorder related to mGluR5 activity prior to the administering step.

2. Manufacture of a Medicament

In one aspect, the invention relates to a method for the manufacture of a medicament for potentiation of metabotropic glutamate receptor activity in a mammal comprising combining a therapeutically effective amount of a disclosed compound or product of a disclosed method with a pharmaceutically acceptable carrier or diluent.

3. Use of Compounds

In one aspect, the invention relates to the use of a disclosed compound or a product of a disclosed method of making. In a further aspect, the use relates to the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation. In a further aspect, a use relates to treatment of a neurological and/or psychiatric disorder associated with glutamate dysfunction in a mammal.

In a further aspect, a use relates to potentiation of metabotropic glutamate receptor activity in a mammal. In a further aspect, a use relates to partial agonism of metabotropic glutamate receptor activity in a mammal. In a further aspect, a use relates to enhancing cognition in a mammal. In a further aspect, a use relates to modulating mGluR5 activity in a mammal. In a further aspect, a use relates to modulating mGluR5 activity in a cell.

In one aspect, a use is treatment of a neurological and/or psychiatric disorder associated with mGluR5 dysfunction. In a further aspect, the disorder is selected from dementia, delirium, amnestic disorders, age-related cognitive decline, schizophrenia, schizophreniform disorder, schizoaffective disorder, delusional disorder, brief psychotic disorder, substance-related disorder, movement disorders, epilepsy, chorea, pain, migraine, diabetes, dystonia, obesity, eating disorders, brain edema, sleep disorder, narcolepsy, anxiety, affective disorder, panic attacks, unipolar depression, bipolar disorder, and psychotic depression.

In one aspect, a use is associated with the treatment of a disorder associated with uncontrolled cellular proliferation. In a further aspect, the disorder is cancer. In a still further aspect, the cancer is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

In one aspect, the invention relates to the use of a disclosed compound or a disclosed product in the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation.

In one aspect, the invention relates to the use of a disclosed compound or a product of a disclosed method of making, or a pharmaceutically acceptable salt, solvate, or polymorph thereof, or a pharmaceutical composition for use in treating or preventing a central nervous system disorder selected from the group of psychotic disorders and conditions; anxiety disorders; movement disorders; drug abuse; mood disorders; neurodegenerative disorders; disorders or conditions comprising as a symptom a deficiency in attention and/or cognition; pain and diseases of uncontrolled cellular proliferation. In a further aspect, the invention relates to the use of a disclosed compound or a product of a disclosed method of making, or a pharmaceutically acceptable salt, solvate, or polymorph thereof, or a pharmaceutical composition for use wherein the psychotic disorders and conditions are selected from the group of schizophrenia; schizophreniform disorder; schizoaffective disorder; delusional disorder; substance-induced psychotic disorder; personality disorders of the paranoid type; and personality disorder of the schizoid type; the anxiety disorders are selected from the group of panic disorder; agoraphobia; specific phobia; social phobia; obsessive-compulsive disorder; post-traumatic stress disorder; acute stress disorder; and generalized anxiety disorder; the movement disorders are selected from the group of Huntington's disease; dyskinesia; Parkinson's disease; restless leg syndrome and essential tremor; Tourette's syndrome and other tic disorders; the substance-related disorders are selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal; the mood disorders are selected from depression, mania and bipolar disorder of types I and II; cyclothymic disorder; depression; dysthymic disorder; major depressive disorder and substance-induced mood disorder; the neurodegenerative disorders are selected from the group of Parkinson's disease; Huntington's disease; dementia such as for example Alzheimer's disease; multi-infarct dementia; AIDS-related dementia or frontotemporal dementia; the disorders or conditions comprising as a symptom a deficiency in attention and/or cognition are selected from the group of dementia, such as Alzheimer's disease; multi-infarct dementia; dementia due to Lewy body disease; alcoholic dementia or substance-induced persisting dementia; dementia associated with intracranial tumors or cerebral trauma; dementia associated with Huntington's disease; dementia associated with Parkinson's disease; AIDS-related dementia; dementia due to Pick's disease; dementia due to Creutzfeldt-Jakob disease; delirium; amnestic disorder; post-traumatic stress disorder; stroke; progressive supranuclear palsy; mental retardation; a learning disorder; attention-deficit/hyperactivity disorder (ADHD); mild cognitive disorder; Asperger's syndrome; and age-related cognitive impairment; pain includes acute and chronic states, severe pain, intractable pain, neuropathic pain and post-traumatic pain, cancer pain, non-cancer pain, pain disorder associated with psychological factors, pain disorder associated with a general medical condition or pain disorder associated with both psychological factors and a general medical condition; the diseases of uncontrolled cellular proliferation are selected from lymphoma, cancers of the brain, genitourinary tract cancer, lymphatic cancer, stomach cancer, larynx cancer, lung cancer, pancreatic cancer, breast cancer, and malignant melanoma.

In one aspect, the invention relates to the use of a disclosed compound or a product of a disclosed method of making, or a pharmaceutically acceptable salt, solvate, or polymorph thereof, or a pharmaceutical composition, in combination with an additional pharmaceutical agent for use in the treatment or prevention of a central nervous system disorder selected from the group of psychotic disorders and conditions; anxiety disorders; movement disorders; drug abuse; mood disorders; neurodegenerative disorders; disorders or conditions comprising as a symptom a deficiency in attention and/or cognition; pain and diseases of uncontrolled cellular proliferation.

In one aspect, the invention relates to a process for preparing a pharmaceutical composition comprising a therapeutically effective amount of a disclosed compound or a product of a disclosed method of making, or a pharmaceutically acceptable salt, solvate, or polymorph thereof, characterized in that a pharmaceutically acceptable carrier is intimately mixed with a therapeutically effective amount of the compound or the product of a disclosed method of making.

In a further aspect, the invention relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

4. Kits

In one aspect, the invention relates to a kit comprising at least one compound, or a pharmaceutically acceptable salt, hydrate, solvate, or polymorph thereof, wherein the compound is a disclosed compound or a product of a disclosed method of making a compound; and one or more of: (a) at least one agent known to increase mGluR5 activity; (b) at least one agent known to decrease mGluR5 activity; (c) at least one agent known to treat a neurological and/or psychiatric disorder; (d) at least one agent known to treat a disease of uncontrolled cellular proliferation; or (e) instructions for treating a disorder associated with glutamate dysfunction.

In a further aspect, the at least one compound or the at least one product and the at least one agent are co-formulated. In a further aspect, the at least one compound or the at least one product and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient. It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of potentiators of mGluR5 related activity in laboratory animals such as cats, dogs, rabbits, monkeys, rats and mice, as part of the search for new therapeutic agents of mGluR5.

G. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. Abbreviations

The following abbreviations are used hereinafter: the term "ACN" means acetonitrile, "AcOEt" means ethyl acetate, AcOH means acetic acid, ACN means acetonitrile, "BCD" means beta cyclodextrin, "BOC" means tert-butoxycarbonyl, BuOH means 1-butanol, "DCM" means dichloromethane, "DIEA" means diisopropylethylamine,"DIPE" means diisopropylether, "DIPEA" means N,N-diisopropylethylamine, "DMF" means N,N-dimethylformamide, "DMSO" means dimethylsulfoxide, "EDC" means 1-ethyl-3-[3-dimethylaminopropyl]carbodiimide hydrochloride, "EI" means electronic impact, "EtOH" means ethanol, "GCMS" means gas chromatography/mass spectrometry, "h" means hours, "HOBt" means 1-hydroxybenzotriazole, "HPLC" means high-performance liquid chromatography, "i.p." or "ip" means intraperitoneal administration, "iPrOH" means 2-propanol, "LCMS" or "LC-MS" means liquid chromatography/mass spectrometry, "[M+H]+" means the protonated mass of the free base of the compound, "MeOH" means methanol, "min" means minutes, "M.p." means melting point, "NMR" means nuclear magnetic resonance, "p.o". or "po" means oral administration, "ppm" means parts per million, "RP" means reversed phase, "Rt" means retention time (in minutes), "RT" means Room temperature, "TEA" means triethylamine, "THF" means tetrahydrofuran, "TLC" means thin layer chromatography, and "TMEDA" means N,N,N',N'-tetramethylethylenediamine.

2. General Methods $^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard. Coupling constants (J-values) are expressed in Hz units.

Microwave assisted reactions were performed in a single-mode reactor: Emrys™ Optimizer microwave reactor (Personal Chemistry A.B., currently Biotage).

Hydrogenation reactions were performed in a continuous flow hydrogenator: H-CUBE® from ThalesNano Nanotechnology Inc.

Thin layer chromatography (TLC) was carried out on silica gel 60 F254 plates (Merck) using reagent grade solvents. Open column chromatography was performed on silica gel, particle size 60 Å, mesh=230-400 (Merck) under standard techniques. Flash column chromatography was performed using ready-to-connect cartridges from: (a) ISCO, on irregular silica gel, particle size 15-40 μm (normal layer disposable flash columns) on a Companion system from ISCO, Inc.; or, (b) Merck, on irregular silica gel, particle size 15-40 μm (normal layer disposable flash columns) on an SPOT or LAFLASH system from Armen Instrument.

Melting point values are peak values, and are obtained with experimental uncertainties that are commonly associated with this analytical method. For a number of compounds, melting points were determined in open capillary tubes either on a Mettler FP62 or on a Mettler FP81HT-FP90 apparatus. Melting points were measured with a temperature gradient of 10° C./minute. Maximum temperature was 300° C. The melting point was read from a digital display.

For a number of compounds, melting points were determined with a Diamond DSC (PerkinElmer). Melting points were measured with a temperature gradient of 10° C./minute. Maximum temperature was 300° C. Values are peak values.

For a number of compounds, melting points (m.p.) were determined with a WRS-2A melting point apparatus (Shanghai Precision and Scientific Instrument Co. Ltd.). Melting points were measured with a linear heating up rate of 0.2-5.0° C./minute. The reported values are melt ranges. The maximum temperature was 300° C.

Analytical HPLC was performed on an HP1100 with UV detection at 214 and 254 nm along with ELSD detection and low resolution mass spectra using an Agilent 1200 series 6130 mass spectrometer.

Preparative RP-HPLC purification was performed on a custom HP1100 automated purification system with collection triggered by mass detection or using a Gilson Inc. preparative UV-based system using a Phenomenex Luna C18 column (50×30 mm I.D., 5 µm) with an acetonitrile (unmodified)-water (0.1% TFA) custom gradient.

3. LC-MS Methods a. General Procedure A

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 L/min.

b. General Procedure B

The HPLC measurement was performed using an HP 1100 (Agilent Technologies) system comprising a pump (quaternary or binary) with degasser, an autosampler, a column oven, a diode-array detector (DAD) and a column as specified in the respective methods below. Flow from the column was split to the MS spectrometer. The MS detector was configured with either an electrospray ionization source or an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

c. General Procedure C

The HPLC measurement was performed using an HP 1100 (Agilent Technologies) system comprising a binary pump with degasser, an autosampler, a column oven, a diode-array detector (DAD) and a column as specified in the respective methods below. Flow from the column was split to a MS spectrometer. The MS detector was configured with an ESCI dual ionization source (electrospray combined with atmospheric pressure chemical ionization). Nitrogen was used as the nebulizer gas. The source temperature was maintained at 100° C. Data acquisition was performed with Chemsation-Agilent Data Browser software.

d. General Procedure D

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

e. General Procedure E

The HPLC measurement was performed using an Agilent 1200 system comprising a binary pump with degasser, an autosampler, a column oven, a diode-array detector (DAD) and a column as specified in the respective methods below. Flow from the column was split to a SQ mass spectrometer and Polymer Labs ELSD. The MS detector was configured with an ES ionization source. Nitrogen was used as the nebulizer gas. The source temperature was maintained at 350° C. Data acquisition was performed with Agilent Chemstation software.

f. LC-MS Method 1

In addition to general procedure A: Reversed phase HPLC was carried out on a YMC-Pack ODS-AQ, 50×2.0 mm 5 µm column with a flow rate of 0.8 mL/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive)

g. LC-MS Method 2

In addition to the general procedure B: Reversed phase HPLC was carried out on a Eclipse Plus-C18 column (3.5 2.1×30 mm) from Agilent, with a flow rate of 1.0 ml/min, at 60° C. The gradient conditions used are: 95% A (0.5 g/L ammonium acetate solution+5% acetonitrile), 5% B (acetonitrile), kept 0.2 minutes, to 100% B in 3.0 minutes, kept till 3.15 minutes and equilibrated to initial conditions at 3.3 minutes until 5.0 minutes. Injection volume 2 High-resolution mass spectra (Time of Flight, TOF detector) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

h. LC-MS Method 3

In addition to the general procedure C: Reversed phase HPLC was carried out on an Eclipse Plus-C18 column (3.5 2.1×30 mm) from Agilent, with a flow rate of 1.0 ml/min, at 60° C. The gradient conditions used are: 95% A (0.5 g/L ammonium acetate solution+5% acetonitrile), 5% B (aceto- i. LC-MS Method 4

In addition to the general procedure C: Reversed phase HPLC was carried out on an Eclipse Plus-C18 column (3.5 µm, 2.1×30 mm) from Agilent, with a flow rate of 1.0 mL/min, at 60° C. The gradient conditions used are: 95% A (0.5 g/L ammonium acetate solution+5% acetonitrile), 5% B (acetonitrile), kept 0.2 minutes, to 100% B in 3.0 minutes, kept till 3.15 minutes and equilibrated to initial conditions at 3.3 minutes until 5.0 minutes. Injection volume 2 µL. Low-resolution mass spectra (single quadrupole, MSD detector) were acquired in APCI mode by scanning from 100 to 1000 in 0.99 seconds, step size of 0.30 and peak width of 0.10 minutes. The capillary needle voltage was 3.0 kV, the fragmentor voltage was 70V for both positive and negative ionization modes and the Corona intensity was 4 µA.

j. LC-MS Method 5

In addition to the general procedure C: Reversed phase HPLC was carried out on an Eclipse Plus-C18 column (3.5 µm, 2.1×30 mm) from Agilent, with a flow rate of 1.0 mL/min, at 60° C. The gradient conditions used are: 95% A (0.5 g/L ammonium acetate solution+5% acetonitrile), 5% B (acetonitrile), kept 0.2 minutes, to 100% B in 1.0 minutes, kept till 1.15 minutes and equilibrated to initial conditions at 1.3 minutes until 3.0 minutes. Injection volume 2 µL. Low-resolution mass spectra (single quadrupole, MSD detector) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

k. LC-MS Method 6

In addition to the general procedure D: Reversed phase UPLC was carried out on a BEH-C18 column (1.7 µm, 2.1×50 mm) from Waters, with a flow rate of 1.0 mL/min, at 50° C. without split to the MS detector. The gradient conditions used are: 95% A (0.5 g/L ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2.0 µL. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

l. LC-MS Method 7

In addition to the general procedure D: Reversed phase UPLC was carried out on a BEH-C18 column (1.7 µm, 2.1×50 mm) from Waters, with a flow rate of 1.0 mL/min, at 50° C. without split to the MS detector. The gradient conditions used are: 95% A (0.5 g/l ammonium acetate solution+5% acetonitrile), 5% B (acetonitrile), to 40% A, 60% B in 1.2 minutes, to 5% A, 95% B in 1.8 minutes, kept till 2.0 minutes. Injection volume 2.0 µL. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

m. LC-MS Method 8

In addition to the general procedure D: Reversed phase UPLC was carried out on a HSS-C18 SB column (1.8 µm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2.0 µL. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

n. LC-MS Method 9

In addition to the general procedure B: Reversed phase HPLC was carried out on an Eclipse Plus-C18 column (3.5 µm, 2.1×30 mm) from Agilent, with a flow rate of 1.0 mL/min, at 60° C. without split to the MS detector. The gradient conditions used are: 95% A (0.5 g/l ammonium acetate solution+5% acetonitrile), 5% B (mixture of acetonitrile/methanol, 1/1), to 100% B in 5.0 minutes, kept till 5.15 minutes and equilibrated to initial conditions at 5.30 minutes until 7.0 minutes. Injection volume 2 µL. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V for positive ionization mode and 30 V for negative ionization mode.

o. LC-MS Method 10

In addition to the general procedure B: Reversed phase HPLC was carried out on a Eclipse Plus-C18 column (3.5 µm, 2.1×30 mm) from Agilent, with a flow rate of 1.0 mL/min, at 60° C. The gradient conditions used are: 95% A (0.5 g/L ammonium acetate solution+5% acetonitrile), 5% B (acetonitrile) to 100% B in 5.0 minutes, kept till 5.15 minutes and equilibrated to initial conditions at 5.3 minutes until 7.0 minutes. Injection volume 2 µL. MS: High-resolution mass spectra (Time of Flight, TOF detector) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

p. LC-MS Method 11

In addition to the general procedure B: Reversed phase HPLC was carried out on an Eclipse Plus-C18 column (3.5 µm, 2.1×30 mm) from Agilent, with a flow rate of 1.0 mL/min, at 60° C. without split to the MS detector. The gradient conditions used are: 95% A (0.5 g/L ammonium acetate solution+5% acetonitrile), 5% B (mixture of acetonitrile/methanol, 1/1), kept 0.2 minutes, to 100% B in 3.0 minutes, kept till 3.15 minutes and equilibrated to initial conditions at 3.30 minutes until 5.0 minutes. Injection volume 2 μL. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V and 50 V for positive ionization mode and 30 V for negative ionization mode.

q. LC-MS Method 12

In addition to the general procedure C: Reversed phase HPLC was carried out on an Eclipse Plus-C18 column (3.5 μm, 2.1×30 mm) from Agilent, with a flow rate of 1.0 ml/min, at 60° C. The gradient conditions used are: 95% A (0.5 g/l ammonium acetate solution+5% acetonitrile), 5% B (acetonitrile), to 100% B in 5.0 minutes, kept till 5.15 minutes and equilibrated to initial conditions at 5.3 minutes until 7.0 minutes. Injection volume 2 μl. Low-resolution mass spectra (single quadrupole, MSD detector) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

r. LC-MS Method 13

In addition to the general procedure D: Reversed phase HPLC was carried out on a Kinetex C18 column (2.6 μm, 2.1×30 μm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 μL. Low-resolution mass spectra (single quadrupole MSD detector) were acquired in electrospray mode by scanning from 100 to 700 in 0.25 seconds, step size of 0.1 and peak width of 0.03 minutes. The capillary needle voltage was 3.0 kV and the fragmentor voltage was 100V.

LC-MS Method 14

In addition to the general procedure B: Reversed phase HPLC was carried out on a Eclipse Plus-C18 column (3.5 μm, 2.1×30 mm) from Agilent, with a flow rate of 1.0 mL/min, at 60° C. The gradient conditions used are: 95% A (0.5 g/l ammonium acetate solution+5% of acetonitrile), 5% B (acetonitrile/ methanol, 1/1) to 100% B in 6.5 minutes, kept till 7.0 minutes and equilibrated to initial conditions at 7.3 minutes until 9.0 minutes. Injection volume 2 μL. MS: High-resolution mass spectra (Time of Flight, TOF detector) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

4. GC-MS Methods a. General Procedure E

The GC measurement was performed using a 6890 Series Gas Chromatograph (Agilent Technologies) system comprising a 7683 Series injector and autosampler, a column oven and a column as specified in the respective methods below, coupled to a 5973N MSD Mass Selective Detector (single quadrupole, Agilent Technologies). The MS detector was configured with an electronic impact ionization source/chemical ionization source (EI/CI). EI low-resolution mass spectra were acquired by scanning from 50 to 550 at a rate of 14.29 scans/s. The source temperature was maintained at 230° C. Helium was used as the nebulizer gas. Data acquisition was performed with Chemstation-Open Action software.

b. GC-MS Method 1

In addition to the general procedure E: GC was carried out on a J&W HP-5MS column (30 m×0.25 mm, 0.25 μm) from Agilent Technologies, with a flow rate of 1.2 mL/min. The temperature gradient applied was: initial temperature 50° C., hold for 3 min, then a 20° C./min ramp applied for 10 min until 250° C. and hold for 2 min in a 15 min run. Front inlet temperature was 250° C. Split injection mode was used, 1 μL injection volume, with a 50/1 ratio into the GC/MS system.

c. GC-MS Method 2

In addition to the general procedure E: GC was carried out on a J&W HP-5MS column (20 m×0.18 mm, 0.18 μm) from Agilent Technologies, with a flow rate of 0.7 mL/min. The temperature gradient applied was: initial temperature 50° C., hold for 0.8 min, then a 60° C./min ramp applied for 4.17 min until 300° C. and hold for 3.0 min in a 8 min run. Front inlet temperature was 250° C. Split injection mode was used, 0.2 μL injection volume, with a 50/1 ratio into the GC/MS system.

d. GC-MS Method 3

In addition to the general procedure E: GC was carried out on a J&W HP-5MS column (20 m×0.18 mm, 0.18 μm) from Agilent Technologies, with a flow rate of 0.7 mL/min. The temperature gradient applied was: initial temperature 50° C., hold for 2.0 min, then a 50° C./min ramp applied for 5.0 min until 300° C. and hold for 3.0 min in a 10 min run. Front inlet temperature was 250° C. Split injection mode was used, 0.2 μL injection volume, with a 50/1 ratio into the GC/MS system.

5. Preparation of Intermediates a. Preparation of 3-bromo-4-oxo-1-piperidinecarboxylic acid ethyl ester

Example A1

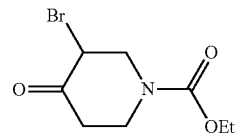

Bromine (2.83 mL, 55 mmol) was added dropwise to a stirred solution of N-carbethoxy-4-piperidone (7.54 mL, 50 mmol) and a 48% solution of HBr in $H_2O$ (1.41 mL) in THF (88 mL) at 0° C. The mixture was stirred at room temperature for 15 minutes and then quenched with a saturated solution of $Na_2S_2O_3$, basified with a saturated solution of $Na_2CO_3$ and extracted with diethyl ether. The organic layer was separated, dried ($Na_2SO_4$), filtered and the solvents evaporated in vacuo to yield 3-bromo-4-oxo-1-piperidinecarboxylic acid ethyl ester (13.5 g, 54% yield, 50% pure) as a dark brown oil that was used in the next step without further purification. $C_8H_{12}BrNO_3$ GCMS (EI): Rt 3.77, MW (theor) 249; m/z [M]+ 249 (using method, GC-MS Method 2).

b. Preparation of 6,7-dihydro-2-[(E)-2-phenylethenyl]-oxazolo[5,4-c]pyridine-5(4H)-carboxylic acid ethyl ester Example A2

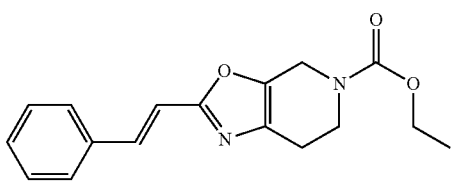 [SMILES: CCOC(=O)N1CCc2nc(/C=C/c3ccccc3)oc2C1]

A mixture of 3-bromo-4-oxo-1-piperidinecarboxylic acid ethyl ester (13.5 g, 26.99 mmol) and trans-cinnamamide (3.0 g, 20.7 mmol) was supported in silica gel (48 g) and mechanically stirred at 125° C. for 60 hours. The product was eluted from the silica gel with a 7M solution of ammonia in MeOH (3×140 mL). The filtrate was evaporated in vacuo and the crude product was basified with a saturated solution of NaHCO$_3$ and extracted with DCM. The organic layer was separated, dried (Na$_2$SO$_4$), filtered and the solvent evaporated in vacuo. The crude product was purified by flash column chromatography (silica; AcOEt in DCM 0/100 to 20/80). The desired fractions were collected and the solvents evaporated in vacuo to yield 6,7-dihydro-2-[(E)-2-phenylethenyl]-oxazolo[5,4-c]pyridine-5(4H)-carboxylic acid ethyl ester (1.65 g, 27% yield) as an orange oil. $C_{17}H_{18}N_2O_3$ LCMS: Rt 2.91, m/z 299 [M+H]+ (using method, LC-MS Method 6)

c. Preparation of 2-(1,2-dihydroxy-2-phenylethyl)-6,7-dihydro-oxazolo[5,4-c]pyridine-5(4H)-carboxylic acid ethyl ester Example A3

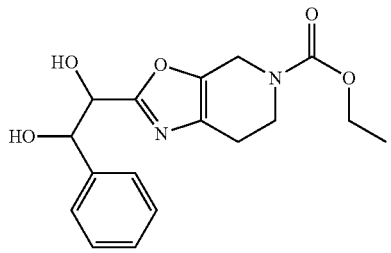 [SMILES: CCOC(=O)N1CCc2nc(C(O)C(O)c3ccccc3)oc2C1]

A 2.5% solution of osmium tetraoxide in tert-BuOH (3.36 mL, 0.26 mmol) was added to a stirred solution of 6,7-dihydro-2-[(E)-2-phenylethenyl]-oxazolo[5,4-c]pyridine-5(4H)-carboxylic acid ethyl ester (1.55 g, 5.19 mmol) and N-methylmorpholine-N-oxide (1.40 g, 10.4 mmol) in a mixture of THF (34 mL), MeOH (17 mL) and H$_2$O (8.5 mL). The mixture was stirred at room temperature for 16 hours, diluted with a saturated solution of Na$_2$S$_2$O$_3$ and extracted with AcOEt. The organic layer was separated, dried (Na$_2$SO$_4$), filtered and the solvents evaporated in vacuo to yield 2-(1,2-dihydroxy-2-phenylethyl)-6,7-dihydro-oxazolo[5,4-c]pyridine-5(4H)-carboxylic acid ethyl ester (1.77 g, 100% yield) as a dark oil that was used in the next step without further purification. $C_{17}H_{20}N_2O_5$ LCMS: Rt 2.00, m/z 333 [M+H]+ (using method, LC-MS Method 3).

d. Preparation of 2-formyl-6,7-dihydro-oxazolo[5,4-c]pyridine-5(4H)-carboxylic acid ethyl ester Example A4

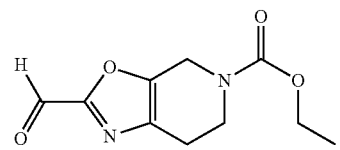 [SMILES: CCOC(=O)N1CCc2nc(C=O)oc2C1]

Sodium periodate (1.7 g, 7.8 mmol) was added to a stirred solution of 2-(1,2-dihydroxy-2-phenylethyl)-6,7-dihydro-oxazolo[5,4-c]pyridine-5(4H)-carboxylic acid ethyl ester (1.7 g, 5.2 mmol) in a mixture of THF (34 mL), MeOH (17 mL) and H$_2$O (8.5 mL). The mixture was stirred at room temperature for 2 hours, diluted with H$_2$O and extracted with AcOEt. The organic layer was separated, dried (Na$_2$SO$_4$), filtered and the solvents evaporated in vacuo to yield 2-formyl-6,7-dihydro-oxazolo[5,4-c]pyridine-5(4H)-carboxylic acid ethyl ester (1.2 g, 99% yield) as a dark oil that was used in the next step without further purification. $C_{10}H_{12}N_2O_4$ LCMS: Rt 1.13, m/z 243 [M+H$_2$O+H]+ (using method, LC-MS Method 3).

e. Preparation of 6,7-dihydro-2-(hydroxymethyl)-oxazolo[5,4-c]pyridine-5(4H)-carboxylic acid ethyl ester Example A5

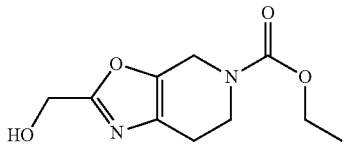 [SMILES: CCOC(=O)N1CCc2nc(CO)oc2C1]

Sodium borohydride (0.71 g, 18.8 mmol) was added to a stirred solution of 2-formyl-6,7-dihydro-oxazolo[5,4-c]pyridine-5(4H)-carboxylic acid ethyl ester (2.82 g, 12.6 mmol) in MeOH (140 mL) at 0° C. The mixture was stirred at room temperature for 20 minutes, diluted with brine and extracted with DCM. The organic layer was separated, dried (Na$_2$SO$_4$), filtered and the solvents evaporated in vacuo. The crude product was purified by flash column chromatography (silica; AcOEt in DCM 0/100 to 100/0 and then MeOH in AcOEt 15/85). The desired fractions were collected and evaporated in vacuo to yield 6,7-dihydro-2-(hydroxymethyl)-oxazolo[5,4-c]pyridine-5(4H)-carboxylic acid ethyl ester (1.8 g, 63% yield) as a colorless oil. $C_{10}H_{14}N_2O_4$ LCMS: Rt 0.72, m/z 227 [M+H]$^+$ (using method, LC-MS Method 6).

f. Preparation of 6,7-dihydro-2-(phenoxymethyl)-oxazolo[5,4-c]pyridine-5(4H)-carboxylic acid ethyl ester Example A6

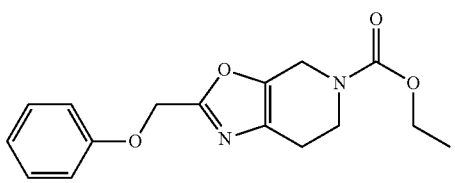 [SMILES: CCOC(=O)N1CCc2nc(COc3ccccc3)oc2C1]

Di-tert-butyl azodicarboxylate (2.20 g, 9.5 mmol) was added portionwise to a stirred solution of 6,7-dihydro-2-(hydroxymethyl)-oxazolo[5,4-c]pyridine-5(4H)-carboxylic acid ethyl ester (1.80 g, 7.95 mmol), phenol (0.90 g, 9.5 mmol) and triphenylphosphine (2.5 g, 9.5 mmol) in THF (40 mL) at 0° C. The mixture was stirred at room temperature for 20 minutes. The solvent was evaporated in vacuo and the crude product purified by flash column chromatography (silica; AcOEt in DCM 0/100 to 20/80). The desired fractions were collected and evaporated in vacuo. The crude product was dissolved with AcOEt and washed with a 10% solution of NaOH. The organic layer was separated, dried (Na$_2$SO$_4$), filtered and the solvents evaporated in vacuo to yield 6,7-dihydro-2-(phenoxymethyl)-oxazolo[5,4-c]pyridine-5(4H)-carboxylic acid ethyl ester (2.75 g, quantitative yield) that was used in the next step without further purification. $C_{16}H_{18}N_2O_4$ LCMS: Rt 2.43, m/z 303 [M+H]$^+$ (using method, LC-MS Method 6).

g. Preparation of 4,5,6,7-tetrahydro-2-(phenoxymethyl)-oxazolo[5,4-c]pyridine

Example A7

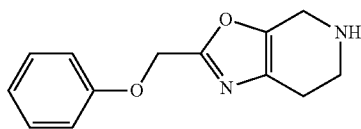 [SMILES: c1ccc(OCc2nc3c(o2)CNCC3)cc1]

Lithium hydroxide (0.66 g, 27.7 mmol) was added to a stirred solution of 6,7-dihydro-2-(phenoxymethyl)-oxazolo[5,4-c]pyridine-5(4H)-carboxylic acid ethyl ester (1.77 g, 5.55 mmol) in a mixture of H$_2$O (5 mL) and 1,4-dioxane (15 mL) under N$_2$. The mixture was stirred at 170° C. for 40 minutes under microwave irradiation, diluted with H$_2$O and extracted with DCM. The organic layer was separated, dried (Na$_2$SO$_4$), filtered and the solvents evaporated in vacuo to yield 4,5,6,7-tetrahydro-2-(phenoxymethyl)-oxazolo[5,4-c]pyridine (0.58 g, 45% yield) as a purple oil that was used in the next step without further purification. $C_{13}H_{14}N_2O_2$ LCMS: Rt 1.07, m/z 231 [M+H]$^+$ (using method, LC-MS Method 6).

Alternatively, the compound A7 can be prepared by conventional heating. Briefly, lithium hydroxide (CAS: 1310-65-2; 7.6 g, 320 mmol) was added to a stirred solution of 6,7-dihydro-2-(phenoxymethyl)-oxazolo[5,4-c]pyridine-5(4H)-carboxylic acid ethyl ester (19.2 g, 63.7 mmol) in a mixture of H$_2$O (70 mL) and 1,4-dioxane (200 mL) under N$_2$. The mixture was stirred at 125° C. for 90 hours and filtered through a pad of diatomaceous earth. The pad was washed with water and AcOEt. The organic layer was separated, dried (Na$_2$SO$_4$), filtered and the solvents evaporated in vacuo. The crude product was purified by short open column chromatography (silica; 7N solution of ammonia in methanol in dichloromethane, 0/100 to 3/97). The desired fractions were collected and evaporated in vacuo to yield 4,5,6,7-tetrahydro-2-(phenoxymethyl)-oxazolo[5,4-c]pyridine (6.4 g, 44% yield) as a brownish oil.

h. Preparation of 4,6-dihydro-5H-pyrrolo[3,4-d]oxazole-2,5-dicarboxylic acid 5-(1,1-dimethylethyl) 2-methyl ester Example A8

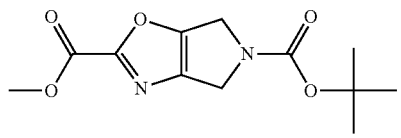 [SMILES: COC(=O)c1nc2c(o1)CN(C(=O)OC(C)(C)C)C2]

Iodomethane (0.098 mL, 1.58 mmol) was added to a stirred solution of 4,6-dihydro-pyrrolo[3,4-d]oxazole-2,5-dicarboxylic acid 5-tert-butyl ester (0.10 g, 0.39 mmol) and K$_2$CO$_3$ (0.10 g, 0.78 mmol) in DMF (2 mL). The mixture was stirred at 100° C. for 5 minutes under microwave irradiation, diluted with H$_2$O and extracted with AcOEt. The organic layer was separated, dried (Na$_2$SO$_4$), filtered and the solvents evaporated in vacuo to yield 4,6-dihydro-5H-pyrrolo[3,4-d]oxazole-2,5-dicarboxylic acid 5-(1,1-dimethylethyl) 2-methyl ester (0.055 g, 96% yield) as a pale yellow solid that was used in the next step without further purification. $C_{12}H_{16}N_2O_5$ LCMS: Rt 2.31, m/z 269 [M+H]$^+$ (using method, LC-MS Method 4).

i. Preparation of 4,6-dihydro-2-(hydroxymethyl)-5H-pyrrolo[3,4-d]oxazole-5-carboxylic acid 1,1-dimethylethyl ester Example A9

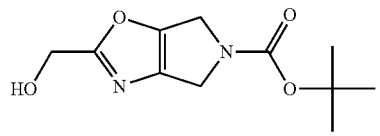 [SMILES: CC(C)(C)OC(=O)N1Cc2nc(CO)oc2C1]

Lithium borohydride (0.015 g, 0.72 mmol) was added to a stirred solution of 4,6-dihydro-5H-pyrrolo[3,4-d]oxazole-2,5-dicarboxylic acid 5-(1,1-dimethylethyl) 2-methyl ester (0.064 g, 0.24 mmol) in a mixture of MeOH (0.6 mL) and THF (1 mL) at 0° C. The mixture was stirred at room temperature for 30 minutes, diluted with a saturated solution of NH$_4$Cl and extracted with DCM. The organic layer was separated, dried (Na$_2$SO$_4$), and the solvents evaporated in vacuo to yield 4,6-dihydro-2-(hydroxymethyl)-5H-pyrrolo[3,4-d]oxazole-5-carboxylic acid 1,1-dimethylethyl ester (0.055 g, 96% yield) as a clear oil that was used in the next step without further purification. $C_{11}H_{16}N_2O_4$ LCMS: Rt 1.29, m/z 241 [M+H]$^+$ (using method, LC-MS Method 6).

j. Preparation of 4,6-dihydro-2-(phenoxymethyl)-5H-pyrrolo[3,4-d]oxazole-5-carboxylic acid 1,1-dimethylethyl ester Example A10

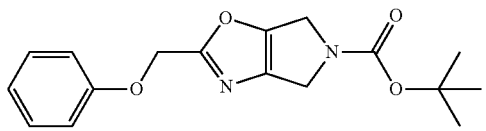 [SMILES: CC(C)(C)OC(=O)N1Cc2nc(COc3ccccc3)oc2C1]

Di-tert-butyl azodicarboxylate (0.079 g, 0.34 mmol) was added portionwise to a stirred solution of 4,6-dihydro-2-(hydroxymethyl)-5H-pyrrolo[3,4-d]oxazole-5-carboxylic acid 1,1-dimethylethyl ester (0.055 g, 0.23 mmol), phenol (0.032 g, 0.34 mmol) and triphenylphosphine (0.090 g, 034 mmol) in THF (1 mL) at 0° C. The mixture was stirred at room temperature for 10 minutes, diluted with MeOH and the solvent evaporated in vacuo. The crude product was purified by flash column chromatography (silica; AcOEt in DCM 0/100 to 10/90). The desired fractions were collected and evaporated in vacuo to yield 4,6-dihydro-2-(phenoxymethyl)-5H-pyrrolo[3,4-d]oxazole-5-carboxylic acid 1,1-dimethylethyl ester (0.073 g, quantitative yield) as a clear oil that was used in the next step without further purification. $C_{17}H_{20}N_2O_4$ LCMS: Rt 3.06, m/z 317 [M+H]$^+$ (using method, LC-MS Method 6).

k. Preparation of 5,6-dihydro-2-(phenoxymethyl)-4H-pyrrolo[3,4-d]oxazole

Example A11

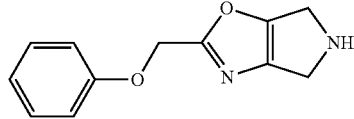

Trifluoroacetic acid (0.5 mL, 0.65 mmol) was added to a solution of 4,6-dihydro-2-(phenoxymethyl)-5H-pyrrolo[3,4-d]oxazole-5-carboxylic acid 1,1-dimethylethyl ester (0.075 g, 0.19 mmol) in DCM (0.5 mL). The mixture was stirred at room temperature for 15 minutes and diluted with a saturated solution of Na$_2$CO$_3$. The organic layer was separated, dried (Na$_2$SO$_4$), filtered and the solvents evaporated in vacuo to yield 5,6-dihydro-2-(phenoxymethyl)-4H-pyrrolo[3,4-d]oxazole (22 mg, 53% yield, 30% pure) as a clear oil that was used in the next step without further purification. $C_{12}H_{12}N_2O_2$ LCMS: Rt 1.04, m/z 217 [M+H]$^+$ (using method, LC-MS Method 6).

l. Preparation of a mixture of 4-bromohexahydro-5-oxo-1H-azepine-1-carboxylic acid 1,1-dimethylethyl ester and 3-bromohexahydro-4-oxo-1H-azepine-1-carboxylic acid 1,1-dimethylethyl ester Example A12

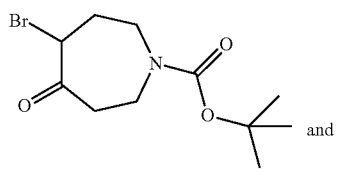

and

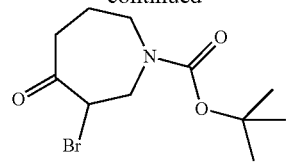

Tetra-N-butylammonium tribromide (0.82 g, 2.58 mmol) was added to a stirred suspension of 1-boc-hexahydro-4H-azepin-4-one (0.47 mL, 2.34 mmol) in THF (5 mL). The mixture was stirred at room temperature overnight and then a 10% solution of Na$_2$S$_2$O$_3$ was added. The mixture was diluted with a saturated solution of Na$_2$CO$_3$ and extracted with diethyl ether. The organic layer was separated and acidified with a 1N solution of HCl, separated, dried (Na$_2$SO$_4$), filtered and the solvents evaporated in vacuo to yield a mixture (60/40) of 4-bromohexahydro-5-oxo-1H-azepine-1-carboxylic acid 1,1-dimethylethyl ester and 3-bromohexahydro-4-oxo-1H-azepine-1-carboxylic acid 1,1-dimethylethyl ester (0.45 g, 66% yield) that was used in the next step without further purification. $C_{11}H_{18}BrNO_3$ GCMS (EI): Rt 5.63/5.67, MW (theor) 291; m/z [M]$^+$ 291 (using method, GC-MS Method 3).

m. Preparation of 5,6,7,8-tetrahydro-2-[(E)-2-phenylethenyl]-4H-oxazolo[4,5-d]azepine Example A13

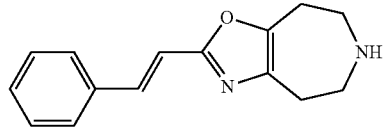 [SMILES: C(=C\c1nc2c(o1)CCNCC2)/c1ccccc1]

A mixture of 4-bromohexahydro-5-oxo-1H-azepine-1-carboxylic acid 1,1-dimethylethyl ester and 3-bromohexahydro-4-oxo-1H-azepine-1-carboxylic acid 1,1-dimethylethyl ester (0.22 g, 0.50 mmol) and trans-cinnamamide (0.06 g, 0.38 mmol) was supported in silica gel (1 g) and mechanically stirred at 120° C. for 3 days. The product was eluted from the silica gel with a 7M solution of ammonia in MeOH and the filtrate evaporated in vacuo. The crude product was basified with a saturated solution of NaHCO$_3$ and extracted with DCM. The organic layer was separated, dried (Na$_2$SO$_4$), filtered and the solvent evaporated in vacuo to yield 5,6,7,8-tetrahydro-2-[(E)-2-phenylethenyl]-4H-oxazolo[4,5-d]azepine (0.045 g, 15% yield, 32% pure) as a brown solid that was used in the next step without further purification. $C_{15}H_{16}N_2O$ LCMS: Rt 1.60, m/z 241 [M+H]$^+$ (method 5). The compound 3-bromohexahydro-4-oxo-1H-azepine-1-carboxylic acid 1,1-dimethylethyl ester was not observed in the crude of the reaction.

n. Preparation of 6-(4-fluorobenzoyl)-5,6,7,8-tetrahydro-4H-oxazolo[4,5-d]azepine-2-methanol Example A14

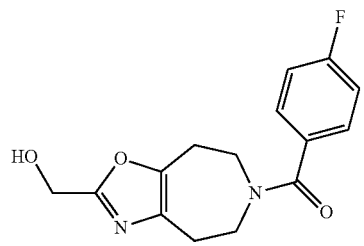 [SMILES: O=C(c1ccc(F)cc1)N1CCc2nc(CO)oc2CC1]

A 2.5% solution of osmium tetraoxide in tert-BuOH (0.064 mL, 0.005 mmol) was added to a stirred solution of 6-(4-fluorobenzoyl)-5,6,7,8-tetrahydro-2-[(E)-2-phenylethenyl]-4H-oxazolo[4,5-d]azepine (0.037 g, 0.10 mmol) and N-methylmorpholine-N-oxide (0.024 g, 0.20 mmol) in a mixture of THF (0.5 mL) and H₂O (0.10 mL). The mixture was stirred at 100° C. for 5 minutes under microwave irradiation. The solvent was evaporated in vacuo and the crude product dissolved in a mixture of MeOH (0.5 mL) and THF (0.5 mL). Then sodium periodate (0.087 g, 0.41 mmol) was added and the mixture stirred at 120° C. for 15 minutes. The mixture was cooled down to 0° C. and sodium borohydride (0.0.15 g, 0.41 mmol) was added portionwise. The mixture was stirred at room temperature for 15 minutes, diluted with a saturated solution of NH₄Cl and extracted with AcOEt. The organic layer was separated, dried (Na₂SO₄), filtered and the solvents evaporated in vacuo to yield 6-(4-fluorobenzoyl)-5,6,7,8-tetrahydro-4H-oxazolo[4,5-d]azepine-2-methanol (0.02 g, 67% yield) as a yellow oil that was used in the next step without further purification. $C_{15}H_{15}FN_2O_3$ LCMS: Rt 1.74, m/z 291 $[M+H]^+$ (using method, LC-MS Method 2).

o. Preparation of 7-oxa-3-azabicyclo[4.1.0]heptane-3-carboxylic acid 1,1-Dimethylethyl ester Example A15

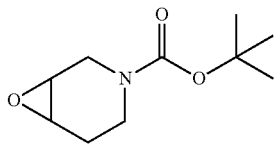

A solution of 3-chloroperoxybenzoic acid (2.96 g, 12.0 mmol) in DCM (20 mL) was added to a solution of N-boc-1,2,3,6-tetrahydropyridine (2.0 g, 10.9 mmol) in DCM (10 mL) at 0° C. The mixture was stirred at room temperature overnight and then a 10% solution of Na₂S₂O₃ was added and the mixture basified with a saturated solution of Na₂CO₃. The organic layer was separated, dried (Na₂SO₄), filtered and the solvent evaporated in vacuo to yield 7-oxa-3-azabicyclo [4.1.0]heptane-3-carboxylic acid 1,1-dimethylethyl ester (2.18 g, 100% yield) that was used in the next step without further purification. $C_{10}H_{17}NO_3$ GCMS (EI): Rt 8.96, MW (theor) 199; m/z [M]⁺ 199 (using method, GC-MS Method 1).

p. Preparation of a mixture of 4-azido-3-hydroxy-1-piperidinecarboxylic acid 1,1-dimethylethyl ester and 3-azido-4-hydroxy-1-piperidinecarboxylic acid 1,1-dimethylethyl ester Example A16

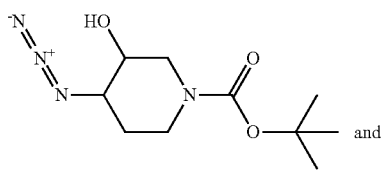

and

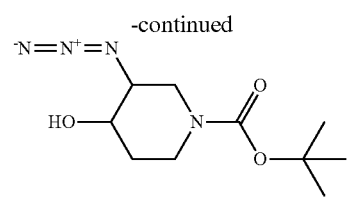

Sodium azide (0.94 g, 14.2 mmol) was added to a suspension of 7-oxa-3-azabicyclo[4.1.0]heptane-3-carboxylic acid 1,1-dimethylethyl ester (2.18 g, 10.9 mmol) and ammonium chloride (0.76 g, 14.2 mmol) in a mixture of EtOH (11 mL) and H₂O (11 mL). The mixture was stirred at 150° C. for 5 minutes under microwave irradiation. Then a saturated solution of NaHCO₃ was added and the mixture was extracted with DCM. The organic layer was separated, dried (Na₂SO₄), filtered and the solvent evaporated in vacuo. The crude product was purified by flash column chromatography (silica; AcOEt in Heptane 20/80 to 80/20). The desired fractions were collected and the solvents evaporated in vacuo to yield 4-azido-3-hydroxy-1-piperidinecarboxylic acid 1,1-dimethylethyl ester (0.93 g, 35% yield) and 3-azido-4-hydroxy-1-piperidinecarboxylic acid 1,1-dimethylethyl ester (0.26 g, 10% yield).

q. Preparation of 3-amino-4-hydroxy-1-piperidinecarboxylic acid 1,1-dimethylethyl ester Example A17

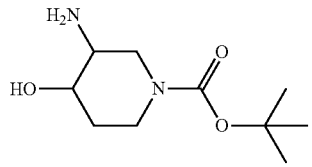

A solution of 3-azido-4-hydroxy-1-piperidinecarboxylic acid 1,1-dimethylethyl ester (0.25 g, 1.06 mmol) in EtOH (20 mL) was hydrogenated in an H-Cube reactor (1 mL/min flow, 30 mm Pd/C 10% cartridge, full H₂ mode, 50° C.). The solvent was evaporated in vacuo to yield 3-amino-4-hydroxy-1-piperidinecarboxylic acid 1,1-dimethylethyl ester (0.23 g, 100% yield) that was used in the next step without further purification. $C_{10}H_{20}N_2O_3$ LCMS: Rt 0.58, m/z 217 $[M+H]^+$ (using method, LC-MS Method 6).

r. Preparation of 4-hydroxy-3-[(phenoxyacetyl)amino]-1-piperidinecarboxylic acid 1,1-dimethylethyl ester Example A18

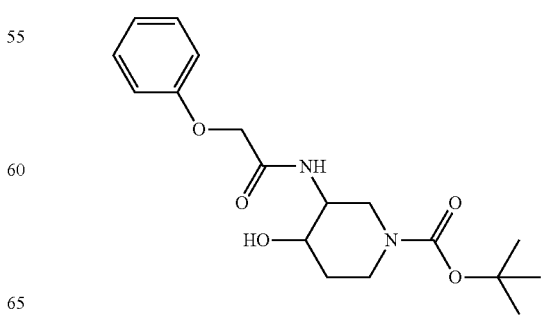

Phenoxyacetyl chloride (0.15 mL, 1.06 mmol) was added dropwise to a stirred solution of 3-amino-4-hydroxy-1-piperidinecarboxylic acid 1,1-dimethylethyl ester (0.23 g, 1.06 mmol) and TEA (0.18 mL, 1.27 mmol) in DCM (3 mL) at 0° C. The reaction mixture was stirred at room temperature for 15 minutes and a saturated solution of NaHCO$_3$ was added. The organic layer was separated, dried (Na$_2$SO$_4$), filtered and the solvent evaporated in vacuo to yield 4-hydroxy-3-[(phenoxyacetyl)amino]-1-piperidinecarboxylic acid 1,1-dimethylethyl ester (0.36 g, 98% yield) that was used in the next step without further purification. C$_{18}$H$_{26}$N$_2$O$_5$ LCMS: Rt 2.03, m/z 351 [M+H]$^+$ (using method, LC-MS Method 6).

s. Preparation of 4-oxo-3-[(phenoxyacetyl)amino]-1-piperidinecarboxylic acid 1,1-dimethylethyl ester Example A19

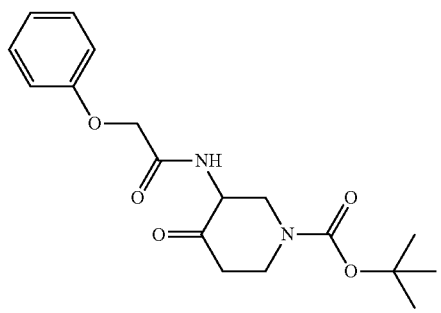 [SMILES: CC(C)(C)OC(=O)N1CCC(=O)C(NC(=O)COc2ccccc2)C1]

Dess-Martin periodinane (0.53 g, 1.25 mmol) was added to a stirred solution of 4-hydroxy-3-[(phenoxyacetyl)amino]-1-piperidinecarboxylic acid 1,1-dimethylethyl ester (0.36 g, 1.0 mmol) in DCM (4 mL). The mixture was stirred at 80° C. for 5 minutes under microwave irradiation and a saturated solution of Na$_2$CO$_3$ was added. The organic layer was separated, dried (Na$_2$SO$_4$), filtered and the solvent evaporated in vacuo to yield 4-oxo-3-[(phenoxyacetyl)amino]-1-piperidinecarboxylic acid 1,1-dimethylethyl ester (0.36 g, 100% yield, 28% pure) that was used in the next step without further purification. C$_{18}$H$_{24}$N$_2$O$_5$ LCMS: Rt 2.55, m/z 249 [M+H-BOC]$^+$ (using method, LC-MS Method 3).

t. Preparation of 6,7-dihydro-2-(phenoxymethyl)-oxazolo[4,5-c]pyridine-5(4H)-carboxylic acid 1,1-dimethylethyl ester Example A20

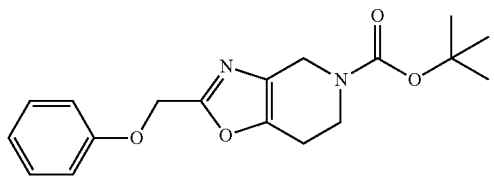 [SMILES: CC(C)(C)OC(=O)N1CCc2oc(COc3ccccc3)nc2C1]

A suspension of 4-oxo-3-[(phenoxyacetyl)amino]-1-piperidinecarboxylic acid 1,1-dimethylethyl ester (0.36 g, 1.0 mmol) and Burgess reagent (0.30 g, 1.25 mmol) in THF (4 mL) was stirred at 120° C. for 10 minutes under microwave irradiation. Then additional Burgess reagent (0.30 g, 1.25 mmol) was added and the mixture stirred at 150° C. for a further 5 minutes under microwave irradiation. The mixture was diluted with a saturated solution of NaHCO$_3$ and extracted with AcOEt. The organic layer was separated, dried (Na$_2$SO$_4$), filtered and the solvent evaporated in vacuo. The crude product was purified by flash column chromatography (silica; AcOEt in DCM 99/1 to 80/20). The desired fractions were collected and the solvents evaporated in vacuo to yield 6,7-dihydro-2-(phenoxymethyl)-oxazolo[4,5-c]pyridine-5 (4H)-carboxylic acid 1,1-dimethylethyl ester (0.11 mg, 33% yield). C$_{18}$H$_{22}$N$_2$O$_4$ LCMS: Rt 2.87, m/z 331 [M+H]$^+$ (using method, LC-MS Method 3).

u. Preparation of 4,5,6,7-tetrahydro-2-(phenoxymethyl)-oxazolo[4,5-c]pyridine

Example A21

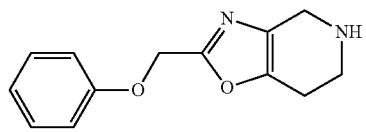 [SMILES: c1ccc(OCc2nc3c(o2)CCNC3)cc1]

Trifluoroacetic acid (1.0 mL, 13.0 mmol) was added to a solution of 6,7-dihydro-2-(phenoxymethyl)-oxazolo[4,5-c] pyridine-5(4H)-carboxylic acid 1,1-dimethylethyl ester (0.11 g, 0.35 mmol) in DCM (1 mL). The mixture was stirred at room temperature for 30 minutes and basified with a saturated solution of Na$_2$CO$_3$. The organic layer was separated, dried (Na$_2$SO$_4$), filtered and the solvents evaporated in vacuo to yield 4,5,6,7-tetrahydro-2-(phenoxymethyl)-oxazolo[4,5-c] pyridine (80 mg, 100% yield, 30% pure) that was used in the next step without further purification. C$_{13}$H$_{14}$N$_2$O$_2$ LCMS: Rt 0.65, m/z 231 [M+H]$^+$ (using method, LC-MS Method 7).

v. Preparation of 1-(2-fluorobenzoyl)-4-piperidinone

Example 22

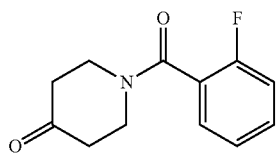 [SMILES: O=C1CCN(C(=O)c2ccccc2F)CC1]

2-Fluorobenzoyl chloride (10.5 g, 66.5 mmol) was added to a stirred solution of 4-piperidone hydrochloride (6.0 g, 60.5 mmol) and DIPEA (3.0 mL, 17.1 mmol) in DCM (150 mL). The mixture was stirred at room temperature for 2 hours and extracted with a 10% solution of citric acid, a saturated solution of Na$_2$CO$_3$ and H$_2$O. The organic layer was separated, dried (Na$_2$SO$_4$), filtered and the solvent evaporated in vacuo to yield 1-(2-fluorobenzoyl)-4-piperidinone (5.5 g, 41% yield) that was used in the next step without further purification.

w. Preparation of 3-bromo-1-(2-fluorobenzoyl)-4-piperidinone

Example A23

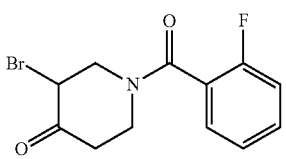 [SMILES: O=C1CCN(C(=O)c2ccccc2F)CC1Br]

Tetra-N-butylammonium tribromide (5.5 g, 11.3 mmol) was added to a stirred suspension of 1-(2-fluorobenzoyl)-4-piperidinone (2.5 g, 11.3 mmol) in THF (30 mL). The mixture was stirred at 80° C. for 16 hours and the solvent evaporated in vacuo. The crude product was diluted with H₂O and extracted with DCM. The organic layer was separated, dried (Na₂SO₄), filtered and the solvent evaporated in vacuo to yield 3-bromo-1-(2-fluorobenzoyl)-4-piperidinone (2.0 g, 59% yield) that was used in the next step without further purification.

x. Preparation of 5-(2-fluorobenzoyl)-4,5,6,7-tetrahydro-thiazolo[5,4-c]pyridin-2-amine

Example A24

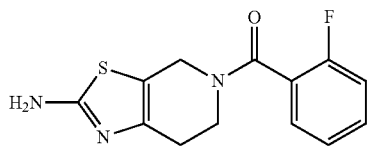 [SMILES: Nc1nc2c(s1)CN(C(=O)c1ccccc1F)CC2]

Thiourea (0.84 g, 6.7 mmol) was added to a stirred suspension of 3-bromo-1-(2-fluorobenzoyl)-4-piperidinone (2.0 g, 6.7 mmol) and NaHCO₃ (0.56 g, 6.7 mmol) in EtOH (50 mL). The mixture was stirred at 80° C. for 2 hours, cooled to room temperature and filtered. The filtrate was evaporated in vacuo to yield 5-(2-fluorobenzoyl)-4,5,6,7-tetrahydro-thiazolo[5,4-c]pyridin-2-amine (1.0 g, 54% yield) that was used in the next step without further purification.

y. Preparation of 2-bromo-5-(2-fluorobenzoyl)-4,5,6,7-tetrahydro-thiazolo[5,4-c]pyridine

Example A25

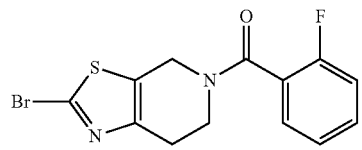 [SMILES: O=C(c1ccccc1F)N1CCc2nc(Br)sc2C1]

Isopentyl nitrite (0.63 g, 5.4 mmol) was added to a stirred suspension of 5-(2-fluorobenzoyl)-4,5,6,7-tetrahydro-thiazolo[5,4-c]pyridin-2-amine (1.0 g, 3.6 mmol) and copper (II) bromide (0.8 g, 3.6 mmol) in ACN (20 mL). The mixture was stirred at room temperature for 4 hours and the solvent evaporated in vacuo. The crude product was diluted with H₂O and extracted with AcOEt. The organic layer was separated, dried (Na₂SO₄), filtered and the solvents evaporated in vacuo. The crude product was purified by flash column chromatography (silica; AcOEt in petroleum ether 1/15 to 1/4). The desired fractions were collected and the solvents evaporated in vacuo to yield 2-bromo-5-(2-fluorobenzoyl)-4,5,6,7-tetrahydro-thiazolo[5,4-c]pyridine (0.60 g, 49% yield).

z. Preparation of 5-(2-fluorobenzoyl)-4,5,6,7-tetrahydro-thiazolo[5,4-c]pyridine-2-carboxylic acid methyl ester

Example A26

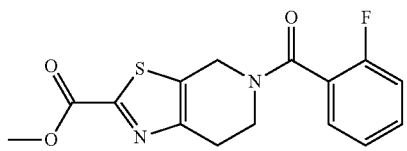 [SMILES: COC(=O)c1nc2c(s1)CN(C(=O)c1ccccc1F)CC2]

[1,1'-Bis(diphenylphosphino)ferrocene]dichloropalladium (II) (0.05 g, 0.068 mmol) was added to a stirred solution of 2-bromo-5-(2-fluorobenzoyl)-4,5,6,7-tetrahydro-thiazolo[5,4-c]pyridine (0.5 g, 1.60 mmol) in a mixture of MeOH (5 mL) and THF (5 mL). The mixture was stirred at 100° C. for 16 hours under CO atmosphere (3 MPa) and the solvent evaporated in vacuo. The crude product was purified by preparative TLC (AcOEt in petroleum ether 50/50) to yield 5-(2-fluorobenzoyl)-4,5,6,7-tetrahydro-thiazolo[5,4-c]pyridine-2-carboxylic acid methyl ester (0.25 g, 49% yield).

aa. Preparation of 5-(2-fluorobenzoyl)-4,5,6,7-tetrahydro-thiazolo[5,4-c]pyridine-2-methanol

Example A27

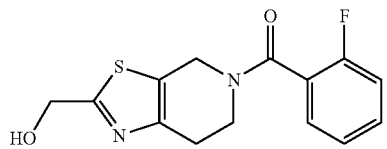 [SMILES: O=C(c1ccccc1F)N1CCc2nc(CO)sc2C1]

Sodium borohydride (0.035 g, 0.94 mmol) was added to a stirred suspension of 5-(2-fluorobenzoyl)-4,5,6,7-tetrahydro-thiazolo[5,4-c]pyridine-2-carboxylic acid methyl ester (0.25 g, 0.78 mmol) in MeOH (5 mL). The mixture was stirred at room temperature for 3 hours, diluted with H₂O and extracted with AcOEt. The organic layer was separated, dried (Na₂SO₄), filtered and the solvent evaporated in vacuo. The crude product was purified by preparative TLC (AcOEt in petroleum ether 50/50) to yield 5-(2-fluorobenzoyl)-4,5,6,7-tetrahydro-thiazolo[5,4-c]pyridine-2-methanol (0.18 g, 79% yield).

bb. Preparation of 2-(chloromethyl)-5-(2-fluorobenzoyl)-4,5,6,7-tetrahydro-thiazolo[5,4-c]pyridine Example A28

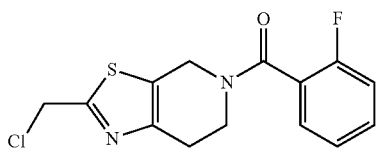 [SMILES: O=C(c1ccccc1F)N1CCc2nc(CCl)sc2C1]

Thionyl chloride (2 mL, 0.027 mmol) was added to a stirred suspension of 542-fluorobenzoyl)-4,5,6,7-tetrahydro-thiazolo[5,4-c]pyridine-2-methanol (0.18 g, 0.62 mmol) in DCM (2 mL). The mixture was stirred at room temperature for 2 hours and then the solvent evaporated in vacuo to yield 2-(chloromethyl)-5-(2-fluorobenzoyl)-4,5,6,7-tetrahydro-thiazolo[5,4-c]pyridine (0.19 g, 100% yield) that was used in the next step without further purification.

cc. Preparation of 3-bromodihydro-1-[(4-methoxyphenyl)methyl]-1H-azepine-2,4(3H,5H)-dione Example A29

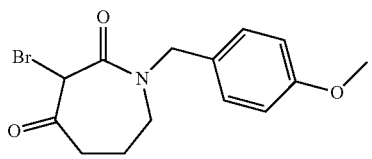 [SMILES: COc1ccc(CN2CCCC(=O)C(Br)C2=O)cc1]

N-Bromosuccinimide (2.88 g, 16.17 mmol) was added portionwise to a stirred solution of 1-(4-methoxy-benzyl)-azepane-2,4-dione (4.0 g, 16.17 mmol) and NaHSO$_4$.H$_2$O (0.67 g, 4.85 mmol) in THF anhydrous (80 mL) at 0° C. The reaction mixture was stirred at room temperature for 2.5 hours and the solvent evaporated in vacuo to yield 3-bromodihydro-1-[(4-methoxyphenyl)methyl]-1H-azepine-2,4(3H,5H)-dione (8 g, 91% yield, 60% pure) as a viscous orange oil which was used in the next step without further purification.

dd. Preparation of 5,6,7,8-tetrahydro-5-[(4-methoxyphenyl)methyl]-2-(phenoxymethyl)-4H-thiazolo[5,4-c]azepin-4-one Example A30

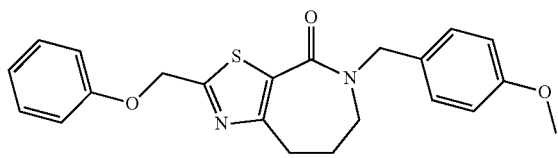 [SMILES: COc1ccc(CN2CCCc3nc(COc4ccccc4)sc3C2=O)cc1]

A mixture of 3-bromodihydro-1-[(4-methoxyphenyl)methyl]-1H-azepine-2,4(3H,5H)-dione (0.78 g, 2.38 mmol) and 2-phenoxythioacetamide (0.36 g, 2.14 mmol) in DMF (12.5 mL) was stirred at room temperature for 15 minutes. Then NaHCO$_3$ (0.32 g, 3.81 mmol) was added and the reaction was stirred at 100° C. for 30 minutes. The reaction was diluted with H$_2$O and extracted with AcOEt. The organic layer was separated, dried (Na$_2$SO$_4$), filtered and the solvents evaporated in vacuo. The crude product was purified by flash column chromatography (silica; DCM in Heptane 0/100 to 100/0). The desired fractions were collected and the solvents evaporated in vacuo to yield 5,6,7,8-tetrahydro-5-[(4-methoxyphenyl)methyl]-2-(phenoxymethyl)-4H-thiazolo[5,4-c]azepin-4-one (0.58 g, 62% yield) as an orange oil. C$_{22}$H$_{22}$N$_2$O$_3$S LCMS: Rt 3.01, m/z 395 [M+H]$^+$ (using method, LC-MS Method 6).

ee. Preparation of 5,6,7,8-tetrahydro-2-(phenoxymethyl)-4H-thiazolo[5,4-c]azepin-4-one Example A31

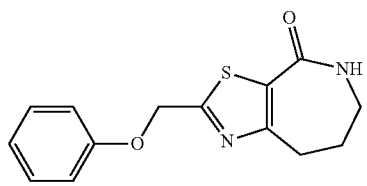 [SMILES: O=C1NCCCc2nc(COc3ccccc3)sc21]

A solution of ammonium cerium (IV) nitrate (1.08 g, 1.97 mmol) in H$_2$O (1.5 mL) was added to a stirred solution of 5,6,7,8-tetrahydro-5-[(4-methoxyphenyl)methyl]-2-(phenoxymethyl)-4H-thiazolo[5,4-c]azepin-4-one (0.22 g, 0.56 mmol) in ACN (5 mL). The mixture was stirred at room temperature for 16 hours and then diluted with H$_2$O and extracted with AcOEt. The organic layer was separated, dried (Na$_2$SO$_4$), filtered and the solvents evaporated in vacuo. The crude product was purified by flash column chromatography (silica; AcOEt in DCM 0/100 to 100/0). The desired fractions were collected and the solvents evaporated in vacuo to yield 5,6,7,8-tetrahydro-2-(phenoxymethyl)-4H-thiazolo[5,4-c]azepin-4-one (0.081 g, 52%) as a white solid. C$_{14}$H$_{14}$N$_2$O$_2$S LCMS: Rt 1.59, m/z 275 [M+H]$^+$ (using method, LC-MS Method 6).

ff. Preparation of 5,6,7,8-tetrahydro-2-(phenoxymethyl)-5-(phenylmethyl)-4H-thiazolo[5,4-c]azepin-4-one Example A32

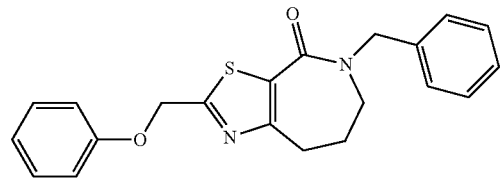 [SMILES: O=C1c2sc(COc3ccccc3)nc2CCCN1Cc1ccccc1]

A 60% dispersion of sodium hydride in mineral oils (0.014 g, 0.36 mmol) was added to a stirred solution of 5,6,7,8-tetrahydro-2-(phenoxymethyl)-4H-thiazolo[5,4-c]azepin-4-one (0.066 g, 0.24 mmol) in DMF anhydrous (1 mL) at 0° C. and the mixture was stirred at room temperature for 1 hour. Then, benzyl bromide (0.043 mL, 0.36 mmol) was added and the mixture was stirred at room temperature for 16 hours. The mixture was diluted with H$_2$O and extracted with DCM. The organic layer was separated, washed with brine, dried (Na₂SO₄), filtered and the solvents evaporated in vacuo. The crude product was purified by flash column chromatography (silica; AcOEt in heptane 0/100 to 100/0). The desired fractions were collected and the solvents evaporated in vacuo to yield 5,6,7,8-tetrahydro-2-(phenoxymethyl)-5-(phenylmethyl)-4H-thiazolo[5,4-c]azepin-4-one (0.084 g, 96% yield) as a colourless oil. $C_{21}H_{20}N_2O_2S$ LCMS: Rt 3.02, m/z 365 [M+H]⁺ (using method, LC-MS Method 6).

gg. Preparation of 5,6,7,8-tetrahydro-2-(phenoxymethyl)-5-(phenylmethyl)-4H-thiazolo[5,4-c]azepine Example A33

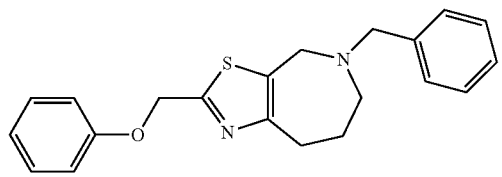 [SMILES: c1ccc(CN2CCCc3nc(COc4ccccc4)sc3C2)cc1]

A 1 M solution of lithium aluminium hydride in THF (0.28 mL, 0.28 mmol) was added dropwise to a stirred solution of 5,6,7,8-tetrahydro-2-(phenoxymethyl)-5-(phenylmethyl)-4H-thiazolo[5,4-c]azepin-4-one (0.084 g, 0.23 mmol) in THF (1.8 mL) under N₂ at 0° C. The mixture was stirred at room temperature for 1 hour and then quenched with a saturated solution of NH₄Cl, diluted with DCM and filtered through a pad of diatomaceous earth. The solvents were evaporated in vacuo to yield 5,6,7,8-tetrahydro-2-(phenoxymethyl)-5-(phenylmethyl)-4H-thiazolo[5,4-c]azepine (0.055 g, 68% yield) as a yellow oil that was used in the next step without further purification. $C_{21}H_{20}N_2O_2S$ LCMS: Rt 3.02, m/z 365 [M+H]⁺ (using method, LC-MS Method 6).

hh. Preparation of 5,6,7,8-tetrahydro-2-(phenoxymethyl)-4H-thiazolo[5,4-c]azepine Example A34

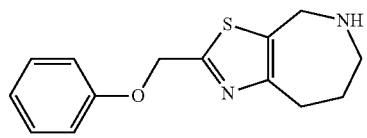 [SMILES: c1ccc(OCc2nc3c(s2)CNCCC3)cc1]

1-Chloroethyl chloroformate (0.034 mL, 0.31 mmol) was added to a stirred solution of 5,6,7,8-tetrahydro-2-(phenoxymethyl)-5-(phenylmethyl)-4H-thiazolo[5,4-c]azepine (0.055 mg, 0.16 mmol) and DIPEA (0.08 mL, 0.47 mmol) in DCM (1 mL). The mixture was stirred at room temperature for 1 hour. Then, the solvent was evaporated in vacuo and a solution of the crude product in MeOH (1 mL) was stirred at 70° C. for 1 hour. The mixture was treated with a 7M solution of ammonia in MeOH and the solvents evaporated in vacuo. The crude product was purified by flash column chromatography (silica; 7 M solution of ammonia in MeOH in DCM 0/100 to 3 /97). The desired fractions were collected and the solvents evaporated in vacuo to yield 5,6,7,8-tetrahydro-2-(phenoxymethyl)-4H-thiazolo[5,4-c]azepine (0.033 g, 81% yield) as a yellow oil. $C_{14}H_{16}N_2OS$ LCMS: Rt 1.13, m/z 302 [M+ACN+H]⁺ (using method, LC-MS Method 6).

ii. Preparation of 3-hydroxy-4-(2-phenoxy-acetylamino)-piperidine-1-carboxylic acid ethyl ester Example A35

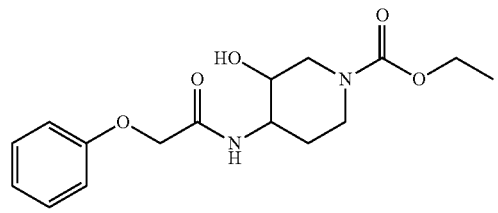 [SMILES: CCOC(=O)N1CCC(NC(=O)COc2ccccc2)C(O)C1]

Phenoxyacetyl chloride (19.3 mL, 139.5 mmol) was added dropwise to a stirred solution of cis-ethyl (3S,4R)-4-amino-3-hydroxypiperidine-1-carboxylate (25 g, 132.8 mmol) and TEA (22.1 mL, 159.4 mmol) in DCM (660 mL) at 0° C. The reaction mixture was stirred at room temperature for 1 hour and then a saturated solution of Na₂CO₃ was added. The organic layer was separated, dried (Na₂SO₄), filtered and the solvent evaporated in vacuo. The product was purified by flash column chromatography (7M solution of ammonia in MeOH in DCM 0/100 to 7/93). The desired fractions were collected and evaporated in vacuo to yield 3-hydroxy-4-(2-phenoxy-acetylamino)-piperidine-1-carboxylic acid ethyl ester (38 g, 89% yield) as a white solid. $C_{16}H_{22}N_2O_5$.

jj. Preparation of 3-oxo-4-(2-phenoxy-acetylamino)-piperidine-1-carboxylic acid ethyl ester Example A35A

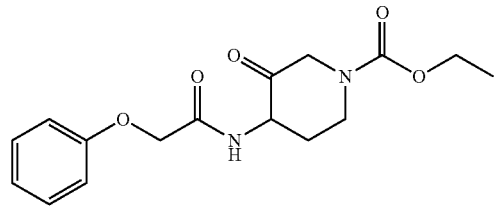 [SMILES: CCOC(=O)N1CCC(NC(=O)COc2ccccc2)C(=O)C1]

Dess-Martin periodinane (57.5 g, 135.5 mmol) was added to a stirred solution of 3-hydroxy-4-(2-phenoxy-acetylamino)-piperidine-1-carboxylic acid ethyl ester (38 g, 117.9 mmol) in DCM (590 mL). The mixture was stirred at room temperature for 16 hours and the solvent was evaporated in vacuo. The product was purified by flash column chromatography (AcOEt in DCM 0/100 to 100/0). The desired fractions were collected and evaporated in vacuo to yield 4-oxo-3-[(phenoxyacetyl)amino]-1-piperidinecarboxylic acid 1,1-dimethylethyl ester (30.6 g, 81% yield). $C_{16}H_{20}N_2O_5$.

kk. Preparation of 6,7-dihydro-2-(phenoxymethyl)-oxazolo[5,4-c]pyridine-5(4H)-carboxylic acid ethyl ester According to an Alternative Procedure Example A36

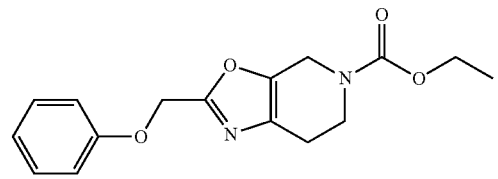 [SMILES: CCOC(=O)N1CCc2nc(COc3ccccc3)oc2C1]

Phosphorus oxychloride (9.3 mL, 99.9 mmol) was added to a stirred solution of 3-oxo-4-(2-phenoxy-acetylamino)-piperidine-1-carboxylic acid ethyl ester (30.3 g, 90.8 mmol) in 1,4-dioxane (454 mL). The mixture was stirred at 100° C. for 2 hours. The mixture was cooled at 0° C., treated with water and extracted with AcOEt. The organic layer was separated, dried (Na$_2$SO$_4$), filtered and the solvents evaporated in vacuo. The product was purified by flash column chromatography (AcOEt in DCM 0/100 to 30/70). The desired fractions were collected and evaporated in vacuo to yield 2-phenoxymethyl-6,7-dihydro-4H-oxazolo[5,4-c]pyridine-5-carboxylic acid ethyl ester (23.2 g, 84% yield) as a colourless oil.

ll. Preparation of 2-[(4-{[tert-butyl(dimethyl)silyl]oxy}phenoxy)methyl]-5-[(4-fluorophenyl)carbonyl]-4,5,6,7-tetrahydro[1,3]oxazolo[5,4-c]pyridine Example A37

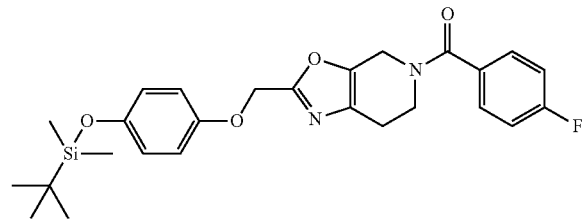 [SMILES: CC(C)(C)[Si](C)(C)Oc1ccc(OCc2nc3c(o2)CN(C(=O)c2ccc(F)cc2)CC3)cc1]

Di-tert-butyl azodicarboxylate (0.1 g, 0.43 mmol) was added to a stirred solution of 6-(4-fluorobenzoyl)-5,6,7,8-tetrahydro-4H-oxazolo[4,5-d]azepine-2-methanol (0.1 g, 0.36 mmol), 4-(tert-butyl-dimethyl-silanyloxy)-phenol (0.097 g, 0.43 mmol) and triphenylphosphine (0.114 g, 0.43 mmol) in THF (0.5 mL) at 0° C. The mixture was stirred at room temperature for 16 hours. Additional di-tert-butyl azodicarboxylate (0.1 g, 0.43 mmol), 4-(tert-butyl-dimethyl-silanyloxy)-phenol (0.097 g, 0.43 mmol) and triphenylphosphine (0.114 g, 0.43 mmol) were added at 0° C. The mixture was stirred at 120° C. for 20 minutes under microwave irradiation. The mixture was diluted with a 1M aqueous solution of NaOH and washed with AcOEt. The organic layer was separated, dried (MgSO$_4$), filtered and the solvents evaporated in vacuo. The crude product was purified by flash column chromatography (silica; AcOEt in DCM 0/100 to 30/70). The desired fractions were collected and the solvents evaporated in vacuo to yield 2-[(4-{[tert-butyl(dimethyl)silyl]oxy}phenoxy)methyl]-5-[(4-fluorophenyl)carbonyl]-4,5,6,7-tetrahydro[1,3]oxazolo[5,4-c]pyridine (264 mg, 66% purity, 99% yield) as a colorless oil. C$_{26}$H$_{31}$FN$_2$O$_4$Si.

mm. Preparation of 2-(phenoxymethyl)-5,6,7,8-tetrahydro-4H-[1,3]oxazolo[5,4-c]azepine Example A38

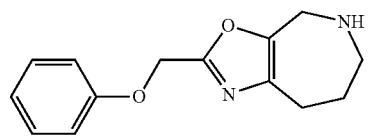

2-(Phenoxymethyl)-5,6,7,8-tetrahydro-4H-[1,3]oxazolo[5,4-c]azepine was prepared according to the experimental procedure described in patent WO2010/114971 A1.

6. Preparation of Final Compounds a. Preparation of 5-[(4-fluorophenyl)carbonyl]-2-(phenoxymethyl)-4,5,6,7-tetrahydro[1,3]oxazolo[5,4-c]pyridine Example B1

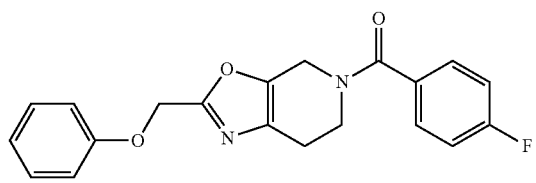 [SMILES: O=C(c1ccc(F)cc1)N1CCc2nc(COc3ccccc3)oc2C1]

4-Fluorobenzoyl chloride (0.25 mL, 2.12 mmol) was added dropwise to a stirred solution of 4,5,6,7-tetrahydro-2-(phenoxymethyl)-oxazolo[5,4-c]pyridine (0.37 g, 1.63 mmol) and TEA (0.34 mL, 2.44 mmol) in DCM (8.15 mL) at 0° C. The reaction mixture was stirred at room temperature for 15 minutes and then diluted with a saturated solution of NaHCO$_3$. The organic layer was separated, dried (Na$_2$SO$_4$), filtered and the solvent evaporated in vacuo. The crude product was purified by flash column chromatography (silica; AcOEt in DCM 0/100 to 30/70). The desired fractions were collected and the solvents evaporated in vacuo. The crude product was triturated with heptane to yield 5-(4-fluorobenzoyl)-4,5,6,7-tetrahydro-2-(phenoxymethyl)-oxazolo[5,4-c]pyridine (0.38 g, 67% yield) as a white solid. C$_{20}$H$_{17}$FN$_2$O$_3$. $^1$H NMR (400 MHz, CDCl$_3$) δ ppm 2.73 (br. s., 2 H), 3.69 (br. s., 1.4 H), 3.99 (br. s., 0.6 H), 4.57 (br. s., 0.6 H), 4.78 (br. s., 1.4 H), 5.12 (br. s., 2 H), 7.02 (d, J=7.4 Hz, 3 H), 7.14 (t, J=8.6 Hz, 2 H), 7.31 (t, J=7.7 Hz, 2 H), 7.43-7.51 (m, 2 H).

b. Preparation of 5-(cyclopropylacetyl)-2-(phenoxymethyl)-4,5,6,7-tetrahydro[1,3]oxazolo[5,4-c]pyridine Example B2

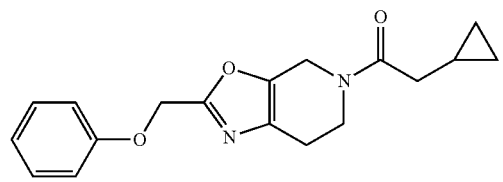 [SMILES: O=C(CC1CC1)N1CCc2nc(COc3ccccc3)oc2C1]

Cyclopropylacetic acid (0.019 mL, 0.25 mmol) was added portionwise to a stirred solution of 4,5,6,7-tetrahydro-2-(phenoxymethyl)-oxazolo[5,4-c]pyridine (0.047 g, 0.21 mmol), 2-(7-aza-1H-benzotriazole-1-yl)-1,1,3,3-tetramethyluronium hexafluorophosphate (0.078 g, 0.21 mmol), and triethylamine (0.043 mL, 0.31 mmol) in a mixture of THF (0.5 mL) and DMF (0.5 mL). The reaction mixture was stirred at room temperature for 15 hours and diluted with a saturated solution of NaHCO$_3$. The organic layer was separated, dried (Na$_2$SO$_4$), filtered and the solvent evaporated in vacuo. The crude product was purified by flash column chromatography (silica; AcOEt in DCM 0/100 to 50/50). The desired fractions were collected and the solvents evaporated in vacuo to yield 5-(cyclopropylacetyl)-4,5,6,7-tetrahydro-2-(phenoxymethyl)-oxazolo[5,4-c]pyridine (0.043 g, 67% yield) as an oil. $C_{18}H_{20}N_2O_3$. (mixture of rotamers 70:30) $^1$H NMR (400 MHz, CDCl$_3$) δ ppm 0.10-0.27 (m, 2 H), 0.50-0.66 (m, 2 H), 0.98-1.16 (m, 1 H), 2.33 (d, J=6.7 Hz, 0.6 H), 2.38 (d, J=6.7 Hz, 1.4 H), 2.59-2.82 (m, 2 H), 3.72 (t, J=5.7 Hz, 1.4 H), 3.92 (t, J=5.7 Hz, 0.6 H), 4.52 (br. s, 0.6 H), 4.71 (br. s, 1.4 H), 5.11 (s, 1.4 H), 5.12 (s, 0.6 H), 6.81-7.01 (m, 3 H), 7.02 (d, J=7.9 Hz, 2 H), 7.27-7.46 (m, 2 H).

c. Preparation of 5-[(3,5-difluorophenyl)carbonyl]-2-(phenoxymethyl)-4,5,6,7-tetrahydro[1,3]oxazolo[5,4-c]pyridine Example B3

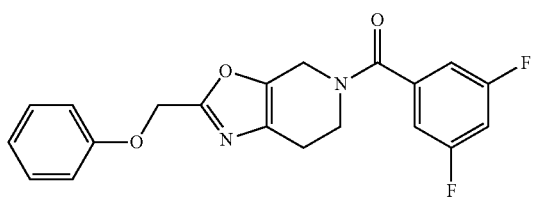 [SMILES: O=C(c1cc(F)cc(F)c1)N1CCc2nc(COc3ccccc3)oc2C1]

3,5-Difluorobenzoic acid (0.082 g, 0.52 mmol) was added to a stirred solution of 4,5,6,7-tetrahydro-2-(phenoxymethyl)-oxazolo[5,4-c]pyridine (0.10 g, 0.43 mmol), 1-(3-dimethylaminopropyl)-3-ethylcarbodiimide hydrochloride (0.10 g, 0.52 mmol), 1-hydroxybenzotriazole (0.070 g, 0.52 mmol) and N,N-diisopropylethylamine (0.15 mL, 0.87 mmol) in anhydrous DMF (2.2 mL) under N$_2$. The reaction mixture was stirred at room temperature for 16 hours, diluted with H$_2$O and extracted with AcOEt. The organic layer was separated, extracted with brine, dried (Na$_2$SO$_4$), filtered and the solvent evaporated in vacuo. The crude product was purified by flash column chromatography (silica; 7 N solution of ammonia in MeOH in DCM 0/100 to 5/95). The desired fractions were collected and the solvents evaporated in vacuo to yield 5-(3,5-difluorobenzoyl)-4,5,6,7-tetrahydro-2-(phenoxymethyl)-oxazolo[5,4-c]pyridine (0.086 g, 53% yield) as a colorless oil. $C_{20}H_{16}F_2N_2O_3$. (mixture of rotamers 65:35) $^1$H NMR (500 MHz, CDCl$_3$) δ ppm 2.71 (br. s., 1.3 H), 2.79 (br. s., 0.7 H), 3.66 (br. s., 1.3 H), 4.02 (br. s., 0.7 H), 4.50 (br. s., 0.7 H), 4.80 (br. s., 1.3 H), 5.13 (br. s., 2 H), 6.82-6.95 (m, 1 H), 6.95-7.09 (m, 5 H), 7.31 (t, J=7.8 Hz, 2 H).

d. Preparation of 6-[(4-fluorophenyl)carbonyl]-2-(phenoxymethyl)-5,6,7,8-tetrahydro-4H-[1,3]oxazolo[4,5-d]azepine Example B4

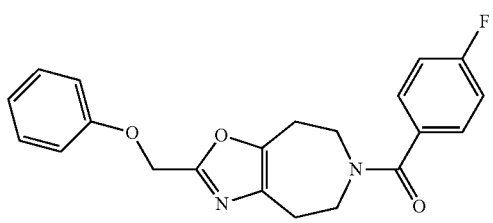 [SMILES: O=C(c1ccc(F)cc1)N1CCc2nc(COc3ccccc3)oc2CC1]

Di-tert-butyl azodicarboxylate (0.024 g, 0.10 mmol) was added portionwise to a stirred solution of 6-(4-fluorobenzoyl)-5,6,7,8-tetrahydro-4H-oxazolo[4,5-d]azepine-2-methanol (0.02 g, 0.069 mmol), phenol (0.01 g, 0.10 mmol) and triphenylphosphine (0.027 g, 0.10 mmol) in DCM (0.5 mL) at 0° C. The mixture was stirred at room temperature for 10 minutes and the solvent was evaporated in vacuo. The crude product was purified by flash column chromatography (silica; AcOEt in DCM 0/100 to 40/60). The desired fractions were collected and concentrated in vacuo. The product was further purified by flash column chromatography (silica; AcOEt in heptane 50/50 to 100/0). The desired fractions were collected and the solvents evaporated in vacuo and purified by reverse phase HPLC performed on a C18 XBridge 30×100 mm, 5 μm column (0.1% solution of ammonium formate/ammonium hydroxide buffer pH 9 in ethyl acetate 80/20 to 0/100) to yield 6-(4-fluorobenzoyl)-5,6,7,8-tetrahydro-2-(phenoxymethyl)-4H-oxazolo[4,5-d]azepine (2.07 mg, 8% yield) as an oil. $C_{21}H_{19}FN_2O_3$. (Mixture of rotamers ~60:40) $^1$H NMR (400 MHz, CDCl$_3$) δ ppm 2.66 (br. s., 1.2 H), 2.78 (br. s., 0.8 H), 3.00 (br. s., 0.8 H), 3.12 (br. s., 1.2 H), 3.62 (br. s., 2.1 H), 3.93 (br. s., 1.9 H), 5.05 (s, 2 H), 6.97-7.04 (m, 1 H), 7.02 (d, J=7.4 Hz, 2 H), 7.12 (t, J=8.7 Hz, 2 H), 7.31 (dd, J=9.1, 7.1 Hz, 2 H), 7.39 (dd, J=8.8, 5.3 Hz, 2 H).

e. Preparation of 5-[(2-fluorophenyl)carbonyl]-2-(phenoxymethyl)-4,5,6,7-tetrahydro[1,3]thiazolo[5,4-c]pyridine Example B5

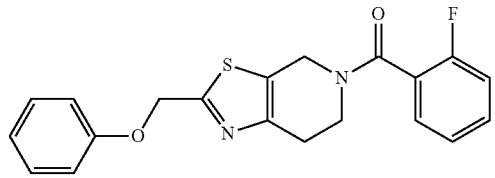 [SMILES: O=C(c1ccccc1F)N1CCc2nc(COc3ccccc3)sc2C1]

Phenol (0.12 g, 1.24 mmol) was added to a stirred solution of 2-(chloromethyl)-5-(2-fluorobenzoyl)-4,5,6,7-tetrahydro-thiazolo[5,4-c]pyridine (0.19 g, 0.62 mmol) and K$_2$CO$_3$ (0.25 g, 1.86 mmol) in ACN (5 mL). The reaction mixture was stirred at 80° C. for 16 hours, filtered and the solvent evaporated in vacuo. The crude product was purified by HPLC on a C18 XBridge 30×100 mm, 5 μm column (gradient elution: 0.1% TFA in ACN/0.1% TFA in H$_2$O). The desired fractions were collected and extracted with a saturated solution of NaHCO$_3$ and the aqueous layer extracted with AcOEt. The combined organic layers were dried (Na$_2$SO$_4$), filtered and the solvent evaporated in vacuo to yield 5-(2-fluorobenzoyl)-4,5,6,7-tetrahydro-2-(phenoxymethyl)-thiazolo[5,4-c]pyridine (95 mg, 42% yield) as a solid. $C_{20}H_{17}FN_2O_2S$. $^1$H NMR (DMSO-d$_6$, T=80° C.) δ ppm 2.81 (br. s., 2 H), 3.79 (br. s., 2 H), 4.76 (br. s., 2 H), 5.32 (s, 2 H), 6.85-7.09 (m, 3 H), 7.10-7.28 (m, 4 H), 7.30-7.39 (m, 1 H), 7.40-7.55 (m, 1 H).

f. Preparation of 6-(4-fluorobenzoyl)-5,6,7,8-tetrahydro-2-[(E)-2-phenylethenyl]-4H-oxazolo[4,5-d]azepine Example B31

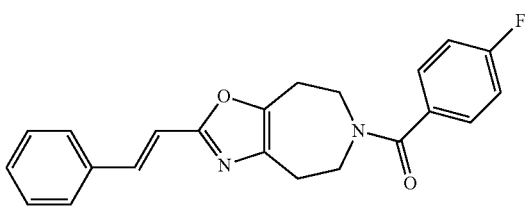 [SMILES: O=C(c1ccc(F)cc1)N1CCc2nc(/C=C/c3ccccc3)oc2CC1]

4-Fluorobenzoyl chloride (0.016 mL, 0.14 mmol) was added dropwise to a stirred solution of 5,6,7,8-tetrahydro-2-[(E)-2-phenylethenyl]-4H-oxazolo[4,5-d]azepine (95 mg, 0.13 mmol) and TEA (0.026 mL, 0.19 mmol) in DCM (1 mL) at 0° C. The reaction mixture was stirred at room temperature for 15 minutes and then diluted with a saturated solution of NaHCO$_3$. The organic layer was separated, dried (Na$_2$SO$_4$), filtered and the solvents evaporated in vacuo. The crude product was purified by flash column chromatography (silica; AcOEt in DCM 0/100 to 50/50). The desired fractions were collected and the solvents evaporated in vacuo. The crude product was triturated with DIPE to yield 6-(4-fluorobenzoyl)-5,6,7,8-tetrahydro-2-[(E)-2-phenylethenyl]-4H-oxazolo[4,5-d]azepine (37 mg, 80% yield) as a white solid. C$_{22}$H$_{19}$FN$_2$O$_2$.

g. Preparation of 5-[(4-fluorophenyl)carbonyl]-2-{[(4-methylpyridin-2-yl)oxy]methyl}-4,5,6,7-tetrahydro[1,3]oxazolo[5,4-c]pyridine Example B33

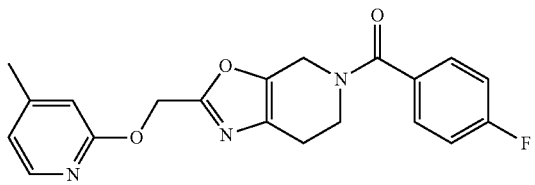 [SMILES: Cc1ccnc(OCc2nc3c(o2)CN(C(=O)c2ccc(F)cc2)CC3)c1]

Copper iodide (17 mg, 0.09 mmol) was added to a stirred suspension of {5-[(4-fluorophenyl)carbonyl]-4,5,6,7-tetrahydro[1,3]oxazolo[5,4-c]pyridin-2-yl}methanol (50 mg, 0.18 mmol), 2-bromo-4-methylpyridine (0.04 mL, 0.36 mmol), cesium carbonate (118 mg, 0.36 mmol) and N,N-dimethylglycine (18 mg, 0.18 mmol) in 1,4-dioxane (1 mL) in a sealed tube and under nitrogen. The mixture was stirred at 120° C. for 60 hours. The mixture was diluted with AcOEt and washed with a 16% aqueous solution of NH$_4$OH. The organic layer was separated, dried (Na$_2$SO$_4$), filtered and the solvents evaporated in vacuo. The crude product was purified by flash column chromatography (silica; 7N solution of ammonia in MeOH in DCM 0/100 to 4/96). The desired fractions were collected and the solvents evaporated in vacuo. The crude product was purified by RP HPLC on (C18 XBridge 19×100 5 um). Mobile phase (Gradient from 80% 0.1% NH$_4$CO$_3$H/NH$_4$OH pH 9 solution in Water, 20% ACN to 0% 0.1% NH$_4$CO$_3$H/NH$_4$OH pH 9 solution in Water, 100% ACN). The solvents were evaporated in vacuo to yield 5-[(4-fluorophenyl)carbonyl]-2-1[(4-methylpyridin-2-yl)oxy]methyl}-4,5,6,7-tetrahydro[1,3]oxazolo[5,4-c]pyridine (6.7 mg, 10% yield) as a colourless oil. C$_{20}$H$_{18}$FN$_3$O$_3$ $^1$H NMR (400 MHz, CDCl$_3$) δ ppm 2.30 (s, 3 H), 2.72 (br. s., 2 H), 3.69 (br.s., 2 H), 4.75 (br. s., 2 H), 5.43 (s, 2 H), 6.65 (s, 1 H), 6.75 (d, J=5.1 Hz, 1 H), 7.13 (t, J=8.4 Hz, 2 H), 7.40-7.52 (m, 2 H), 8.01 (d, J=5.1 Hz, 1 H).

h. Preparation of 2-(phenoxymethyl)-5-(trifluoroacetyl)-4,5,6,7-tetrahydro[1,3]oxazolo[5,4-c]pyridine Example B34

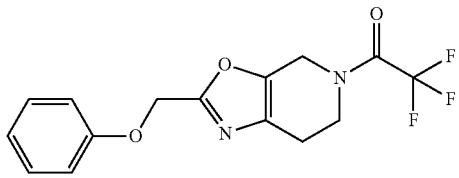 [SMILES: O=C(N1CCc2nc(COc3ccccc3)oc2C1)C(F)(F)F]

Trifluoroacetic anhydride (0.03 mL, 0.242 mmol) was added to a stirred solution of 2-(phenoxymethyl)-4,5,6,7-tetrahydro[1,3]oxazolo[5,4-c]pyridine (50 mg, 0.22 mmol) and triethylamine (0.045 mL, 0.73 mmol) in DCM (5 mL). The mixture was stirred at room temperature for 2 hours. Then additional trifluoroacetic anhydride (0.014 mL, 0.11 mmol) was added. The mixture was stirred at room temperature for 1 hour. The mixture was neutralized with a saturated solution of Na$_2$CO$_3$ and extracted with DCM. The organic layer was separated, dried (Na$_2$SO$_4$), filtered and the solvents evaporated in vacuo. The crude product was purified by short open column chromatography (silica; AcOEt in DCM 0/100 to 25/75). The desired fractions were collected and the solvents evaporated in vacuo and the crude product precipitated from DIPE/heptane to yield 2-(phenoxymethyl)-5-(trifluoroacetyl)-4,5,6,7-tetrahydro[1,3]oxazolo[5,4-c]pyridine (35 mg, 49% yield) as a white solid. (mixture of rotamers 70:30) C$_{15}$H$_{13}$F$_3$N$_2$O$_3$ $^1$H NMR (500 MHz, CDCl$_3$) δ ppm 2.70-2.89 (m, 2 H), 3.88 (t, J=5.5 Hz, 1.4 H), 3.99 (t, J=5.6 Hz, 0.6 H), 4.70 (br. s, 0.4 H), 4.76 (br. s, 1.6 H), 5.13 (s, 2 H), 6.99-7.04 (m, 3 H), 7.28-7.35 (m, 2 H).

i. Preparation of 4-({5-[(4-fluorophenyl)carbonyl]-4,5,6,7-tetrahydro[1,3]oxazolo[5,4-c]pyridin-2-yl}methoxy)phenol Example B35

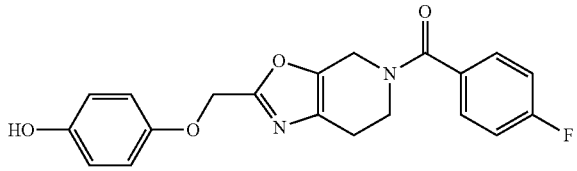 [SMILES: O=C(c1ccc(F)cc1)N1CCc2nc(COc3ccc(O)cc3)oc2C1]

1M solution of tetra-butylammonium fluoride in THF (0.54 mL, 0.54 mmol) was added to a stirred solution of 2-[(4-{[tert-butyl(dimethyl)silyl]oxy}phenoxy)methyl]-5-[(4-fluorophenyl)carbonyl]-4,5,6,7-tetrahydro[1,3]oxazolo[5,4-c]pyridine (264 mg, 0.36 mmol) in THF (2 mL). The mixture was stirred at room temperature for 16 hours. The mixture was treated with water and extracted with AcOEt. The organic layer was separated, dried (MgSO$_4$), filtered and the solvents evaporated in vacuo. The crude product was purified by flash column chromatography (silica; AcOEt in DCM 0/100 to 100/0). The desired fractions were collected and the solvents evaporated in vacuo. The product was triturated with DIPE to yield (4-({5-[(4-fluorophenyl)carbonyl]-4,5,6,7-tetrahydro[1,3]oxazolo[5,4-c]pyridin-2-yl}methoxy)phenol (60 mg, 45% yield) as a white solid. C$_{20}$H$_{17}$FN$_2$O$_4$ $^1$H NMR (400 MHz, CDCl$_3$) δ ppm 2.72 (br. s., 2 H), 3.69 (br. s, 2 H), 4.78 (br.s., 2 H), 5.05 (br. s., 2 H), 5.86 (br. s., 1 H), 6.74 (d, J=8.8 Hz, 2 H), 6.86 (d, J=8.8 Hz, 2 H), 7.09-7.18 (m, 2 H), 7.43-7.51 (m, 2 H).

j. Preparation of 5-[(1-methyl-1H-indol-2-yl)carbonyl]-2-(phenoxymethyl)-4,5,6,7-tetrahydro[1,3]oxazolo[5,4-c]pyridine Example B36

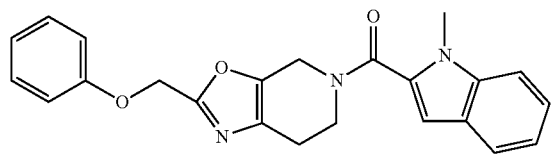 [SMILES: Cn1c(C(=O)N2CCc3nc(COc4ccccc4)oc3C2)cc2ccccc21]

Methyl iodide (0.01 mL, 0.161 mmol) was added to a suspension of a 60% dispersion of sodium hydride in mineral oils (3.85 mg, 0.096 mmol) and 5-(1H-Indol-2-ylcarbonyl)-2-(phenoxymethyl)-4,5,6,7-tetrahydro[1,3]oxazolo[5,4-c]pyridine (0.03 g, 0.08 mmol) in DMF (2 mL). The mixture was stirred under microwave irradiation at 100° C. for 10 minutes. Then a 60% dispersion of sodium hydride in mineral oils (3.86 mg, 0.096 mmol) and methyl iodide (0.01 mL, 0.161 mmol) were added. The crude product was washed with a saturated solution of sodium hydrogen carbonate and extracted with diethyl ether. The organic layer was separated, dried ($Na_2SO_4$), filtered and the solvents evaporated in vacuo. The crude product was purified by RP HPLC on (C18 XBridge 19×100 5 um). Mobile phase (Gradient from 80% 0.1% $NH_4CO_3H/NH_4OH$ pH 9 solution in Water, 20% ACN to 0% 0.1% $NH_4CO_3H/NH_4OH$ pH 9 solution in Water, 100% ACN). The solvents were evaporated to yield 5-[(1-methyl-1H-indol-2-yl)carbonyl]-2-(phenoxymethyl)-4,5,6,7-tetrahydro[1,3]oxazolo[5,4-c]pyridine (17.25 mg, 55% yield) as a white solid. $C_{23}H_{21}N_3O_3$ $^1H$ NMR (500 MHz, $CDCl_3$) δ ppm 2.82 (br. t, J=5.3 Hz, 2 H), 3.87 (s, 3 H), 4.05 (br. t, J=5.2 Hz, 2 H), 4.87 (s, 2 H), 5.14 (s, 2 H), 6.71 (s, 1 H), 6.98-7.07 (m, 3 H), 7.18 (t, J=7.4 Hz, 1 H), 7.29-7.37 (m, 3 H), 7.39 (d, J=8.4 Hz, 1 H), 7.66 (d, J=8.1 Hz, 1 H).

k. Preparation of 5-[(4-fluorophenyl)carbonyl]-2-(2-phenylethyl)-4,5,6,7-tetrahydro[1,3]oxazolo[5,4-c]pyridine Example B131

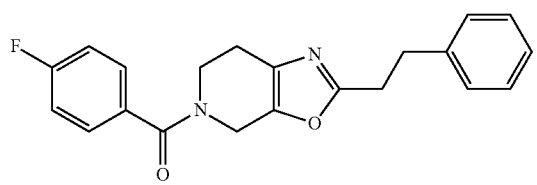 [SMILES: O=C(c1ccc(F)cc1)N1CCc2nc(CCc3ccccc3)oc2C1]

10% Palladium on charcoal (15 mg, 0.0144 mmol) was added to a stirred suspension of 5-[(4-fluorophenyl)carbonyl]-2-[(E)-2-phenylethenyl]-4,5,6,7-tetrahydro[1,3]oxazolo[5,4-c]pyridine (0.05 g, 0.144 mmol) and ammonium formate (54 mg, 0.86 mmol) in MeOH (0.5 mL) in a sealed tube and under nitrogen. The mixture was stirred at 100° C. for 1 hour. The mixture was filtered through a pad of diatomaceous earth and washed with DCM. The filtrate was treated with a saturated solution of sodium chloride and extracted with more DCM. The organic layer was separated, dried ($MgSO_4$), filtered and the solvents evaporated in vacuo. The crude product was purified by flash column chromatography (silica; 7 M solution of ammonia in MeOH in DCM 0/100 to 5/95). The desired fractions were collected and the solvents evaporated in vacuo to yield 5-[(4-fluorophenyl)carbonyl]-2-(2-phenylethyl)-4,5,6,7-tetrahydro[1,3]oxazolo[5,4-c]pyridine as a colourless oil.

7. Physico-Chemical Characterization of Exemplary Compounds

Compounds were synthesized represented by the formula:

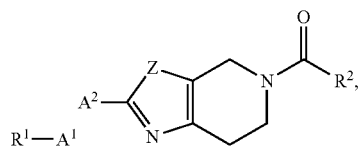

wherein $A_1$, $A_2$, Z, $R_1$, and $R_2$ were as described in Table I below. The synthetic methods used to prepare the indicated compound were as described in the preceding examples with a synthetic example method as noted in the table. The requisite starting materials were prepared as described herein, commercially available, described in the literature, or readily synthesized by one skilled in the art of organic synthesis.

Compounds were synthesized represented by the formula:

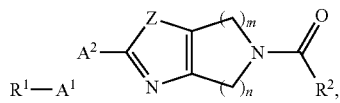

wherein m, n, $A_1$, $A_2$, Z, $R_1$, and $R_2$ were as described in Table II below. The synthetic methods used to prepare the indicated were as described in the preceding examples with a synthetic example method as noted in the table. The requisite starting materials were prepared as described herein, commercially available, described in the literature, or readily synthesized by one skilled in the art of organic synthesis.

Analytical data for the numbered compound in Table III corresponds to the compound number given in the first column of either Table I or Table II. LCMS: [M+H]+ means the protonated mass of the free base of the compound; Rt means retention time (in minutes); and Method refers to the LC-MS or GC-MS method used and as described above.

TABLE I

| No. | $R^1$ | $A^1—A^2$ | Z | $R^2$ | Synthetic Example* |
|---|---|---|---|---|---|
| B1 | phenyl | --O—$CH_2$-- | O | 4-fluorophenyl | B1 |
| B2 | phenyl | --O—$CH_2$-- | O | cyclopropyl | B2 |

TABLE I-continued
| No. | R¹ | A¹—A² | Z | R² | Synthetic Example* |
|---|---|---|---|---|---|
| B3 |  | --O—CH₂-- | O | 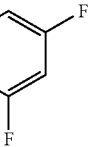 | B3 |
| B5 |  | --O—CH₂-- | S | 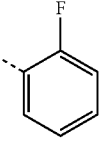 | B5 |
| B6 |  | --O—CH₂-- | O | 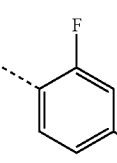 | B1 |
| B7 |  | --O—CH₂-- | O |  | B1 |
| B8 | 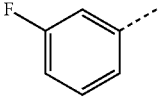 | --O—CH₂-- | O |  | B4 |
| B9 |  | --O—CH₂-- | O | 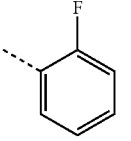 | B2 |
| B10 | 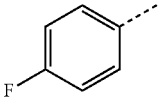 | --O—CH₂-- | O | 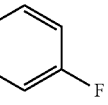 | B4 |
| B11 | 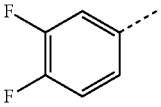 | --O—CH₂-- | O |  | B4 |
| B12 |  | --O—CH₂-- | S | 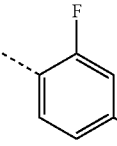 | B5 |
| B13 | 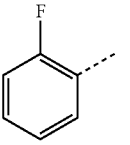 | --O—CH₂-- | O | 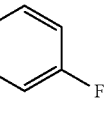 | B4 |
| B14 | 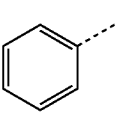 | --CH=CH-- | O | 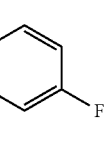 | B1 |

TABLE I-continued
| No. | R¹ | A¹—A² | Z | R² | Synthetic Example* |
|---|---|---|---|---|---|
| B15 |  | --O—CH₂-- | O | 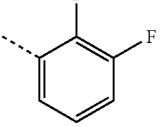 | B1 |
| B16 |  | --O—CH₂-- | O | 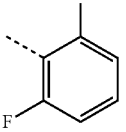 | B1 |
| B17 |  | --O—CH₂-- | O | 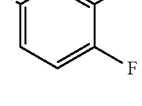 | B1 |
| B18 |  | --O—CH₂-- | O | 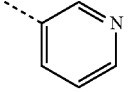 | B3 |
| B19 |  | --O—CH₂-- | O | 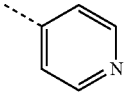 | B3 |
| B20 |  | --O—CH₂-- | O | 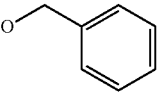 | B1 |
| B23 |  | --O—CH₂-- | O | 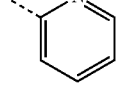 | B3 |
| B24 |  | --O—CH₂-- | O | —CH₃ | B1 |
| B26 | 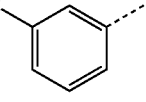 | --O—CH₂-- | O | 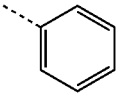 | B1 |
| B27 | 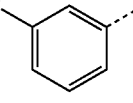 | --O—CH₂-- | O | 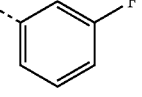 | B1 |
| B28 | 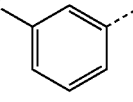 | --O—CH₂-- | O | 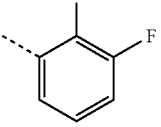 | B1 |
| B29 | 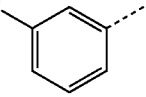 | --O—CH₂-- | O | 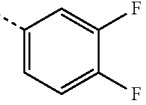 | B1 |

TABLE I-continued
| No. | R¹ | A¹—A² | Z | R² | Synthetic Example* |
|---|---|---|---|---|---|
| B30 | 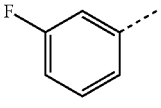 | --O—CH₂-- | O | 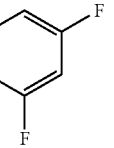 | B1 |
| B32 |  | --O—CH₂-- | O |  | B1 |
| B33 | 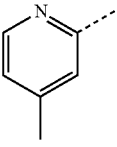 | --O—CH₂-- | O | 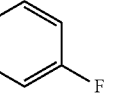 | B33 |
| B34 |  | --O—CH₂-- | O |  | B34 |
| B35 | 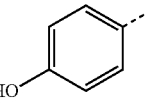 | --O—CH₂-- | O | 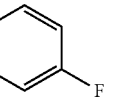 | B35 |
| B36 | 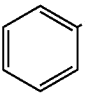 | --O—CH₂-- | O | 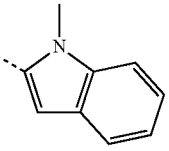 | B36 |
| B37 | 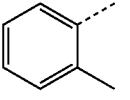 | --O—CH₂-- | O | 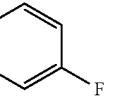 | B1 |
| B38 |  | --O—CH₂-- | O |  | B2 |
| B39 |  | --O—CH₂-- | O | 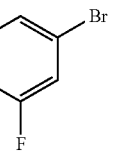 | B2 |
| B40 |  | --O—CH₂-- | O | 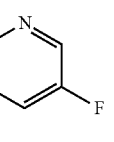 | B2 |
| B41 |  | --O—CH₂-- | O | 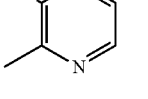 | B2 |

TABLE I-continued
| No. | R¹ | A¹—A² | Z | R² | Synthetic Example* |
|---|---|---|---|---|---|
| B42 |  | --O--CH₂-- | O | 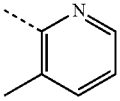 | B2 |
| B43 |  | --O--CH₂-- | O | 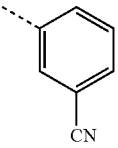 | B1 |
| B44 |  | --O--CH₂-- | O | 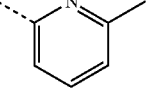 | B2 |
| B45 |  | --O--CH₂-- | O | 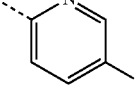 | B2 |
| B46 |  | --O--CH₂-- | O | 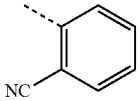 | B2 |
| B47 |  | --O--CH₂-- | O | 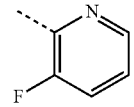 | B2 |
| B48 | 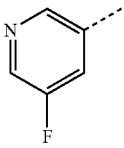 | --O--CH₂-- | O | 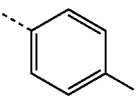 | B4 |
| B49 |  | --O--CH₂-- | O | 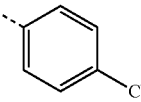 | B1 |
| B50 |  | --O--CH₂-- | O | 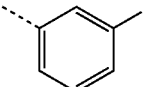 | B2 |
| B51 |  | --O--CH₂-- | O | 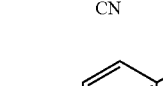 | B1 |
| B52 |  | --O--CH₂-- | O | 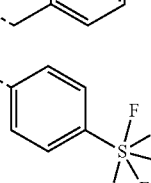 | B1 |

TABLE I-continued

| No. | R¹ | A¹—A² | Z | R² | Synthetic Example* |
|---|---|---|---|---|---|
| B53 | 3-cyanophenyl | --O—CH₂-- | O | 4-fluorophenyl | B4 |
| B54** | phenyl | --O—CH₂-- | O | (S)-1-amino-2,2-dimethylpropyl | B2 |
| B55 | phenyl | --O—CH₂-- | O | tert-butoxymethyl | B2 |
| B56 | phenyl | --O—CH₂-- | O | 1H-pyrazol-4-yl | B2 |
| B57 | phenyl | --O—CH₂-- | O | 5-chlorofuran-2-yl | B2 |
| B58 | phenyl | --O—CH₂-- | O | 1H-pyrrol-2-yl | B2 |
| B59 | phenyl | --O—CH₂-- | O | oxazol-5-yl | B2 |
| B60 | phenyl | --O—CH₂-- | O | oxazol-2-yl | B2 |
| B61 | phenyl | --O—CH₂-- | O | 5-methylfuran-2-yl | B2 |
| B62 | phenyl | --O—CH₂-- | O | 2-cyanopropan-2-yl | B2 |
| B63 | phenyl | --O—CH₂-- | O | (S)-1-(Boc-amino)-2,2-dimethylpropyl | B2 |
| B64 | phenyl | --O—CH₂-- | O | 2-phenylethyl | B1 |

TABLE I-continued
| No. | R¹ | A¹—A² | Z | R² | Synthetic Example* |
|---|---|---|---|---|---|
| B65 |  | --O—CH₂-- | O | 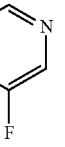 | B2 |
| B66 | 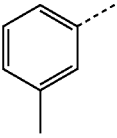 | --O—CH₂-- | O |  | B1 |
| B67 | 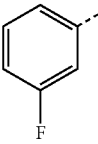 | --O—CH₂-- | O | 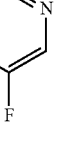 | B2 |
| B68 |  | --O—CH₂-- | O |  | B1 |
| B69 | 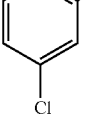 | --O—CH₂-- | O | 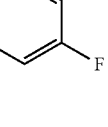 | B1 |
| B70 |  | --O—CH₂-- | O |  | B1 |
| B71 |  | --O—CH₂-- | O |  | B2 |
| B72 | 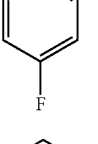 | --O—CH₂-- | O | 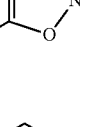 | B2 |
| B73 |  | --O—CH₂-- | O |  | B1 |
| B74 |  | --O—CH₂-- | O |  | B2 |
| B75 |  | --O—CH₂-- | O |  | B1 |
| B76 |  | --O—CH₂-- | O |  | B1 |

TABLE I-continued
| No. | R¹ | A¹—A² | Z | R² | Synthetic Example* |
|---|---|---|---|---|---|
| B77 |  | --O—CH₂-- | O | 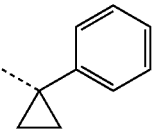 | B1 |
| B78 | 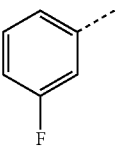 | --O—CH₂-- | O | 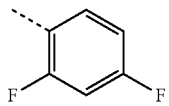 | B1 |
| B79 |  | --O—CH₂-- | O | 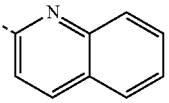 | B1 |
| B80 |  | --O—CH₂-- | O | 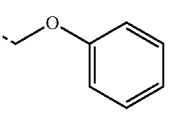 | B1 |
| B81 |  | --O—CH₂-- | O | 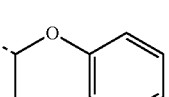 | B1 |
| B82 |  | --O—CH₂-- | O | 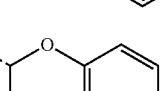 | B1 |
| B83 |  | --O—CH₂-- | O | 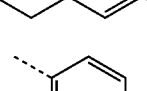 | B1 |
| B84 |  | --O—CH₂-- | O | 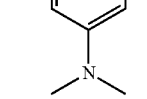 | B2 |
| B85 | 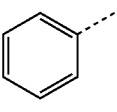 | --O—CH₂-- | O | 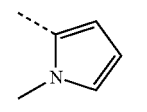 | B1 |
| B86 |  | --O—CH₂-- | O | 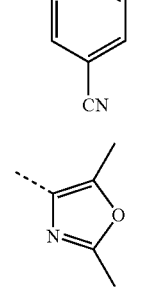 | B1 |
| B87 |  | --O—CH₂-- | O | 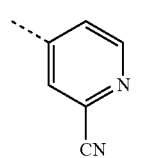 | B2 |

TABLE I-continued
| No. | R¹ | A¹—A² | Z | R² | Synthetic Example* |
|---|---|---|---|---|---|
| B88 |  | --O--CH₂-- | O |  | B2 |
| B89 | 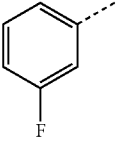 | --O--CH₂-- | O | 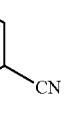 | B2 |
| B90 |  | --O--CH₂-- | O | 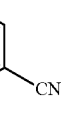 | B2 |
| B91 |  | --O--CH₂-- | O |  | B2 |
| B92 | 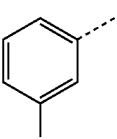 | --O--CH₂-- | O | 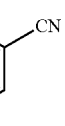 | B2 |
| B93 |  | --O--CH₂-- | O |  | B2 |
| B94 |  | --O--CH₂-- | O |  | B2 |
| B95 |  | --O--CH₂-- | O |  | B2 |
| B96 | 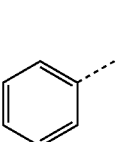 | --O--CH₂-- | O | 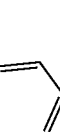 | B2 |
| B97 | 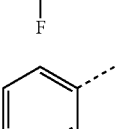 | --O--CH₂-- | O |  | B2 |
| B98 |  | --O--CH₂-- | O |  | B2 |

TABLE I-continued
| No. | R¹ | A¹—A² | Z | R² | Synthetic Example* |
|---|---|---|---|---|---|
| B99 |  | --O—CH₂-- | O | 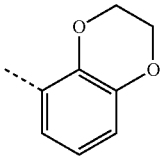 | B2 |
| B100 | 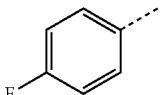 | --O—CH₂-- | O | 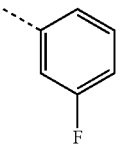 | B1 |
| B101 | 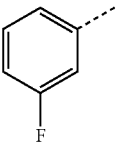 | --O—CH₂-- | O | 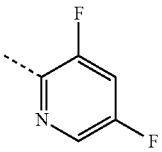 | B2 |
| B102 |  | --O—CH₂-- | O | 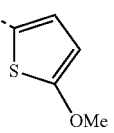 | B2 |
| B103 |  | --O—CH₂-- | O | 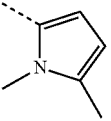 | B2 |
| B104 |  | --O—CH₂-- | O | 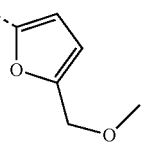 | B2 |
| B105 |  | --O—CH₂-- | O | 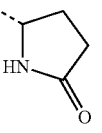 | B2 |
| B106 |  | --O—CH₂-- | O | 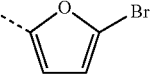 | B2 |
| B107 |  | --O—CH₂-- | O | 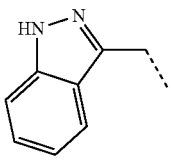 | B2 |
| B108 |  | --O—CH₂-- | O | 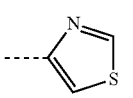 | B2 |
| B109 | 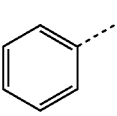 | --O—CH₂-- | O | 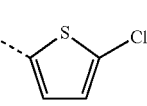 | B2 |

TABLE I-continued
| No. | R¹ | A¹—A² | Z | R² | Synthetic Example* |
|---|---|---|---|---|---|
| B110 | 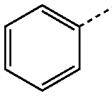 | --O—CH₂-- | O | 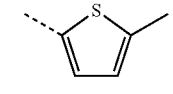 | B2 |
| B111 | 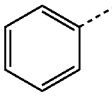 | --O—CH₂-- | O | 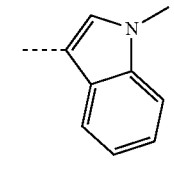 | B2 |
| B112 | 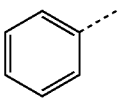 | --O—CH₂-- | O | 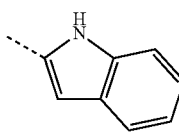 | B2 |
| B113 |  | --O—CH₂-- | O | 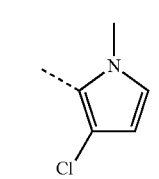 | B2 |
| B115 | 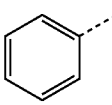 | --O—CH₂-- | O | 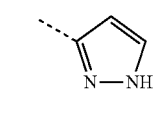 | B2 |
| B116 | 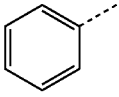 | --O—CH₂-- | O | 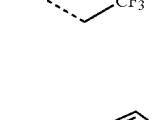 | B2 |
| B117 |  | --O—CH₂-- | O | 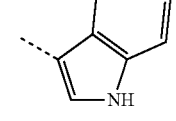 | B2 |
| B118 | 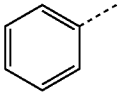 | --O—CH₂-- | O | 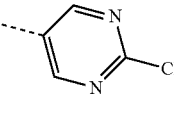 | B2 |
| B119 | 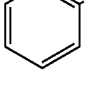 | --O—CH₂-- | O | 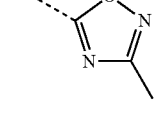 | B2 |
| B120 | 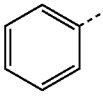 | --O—CH₂-- | O | 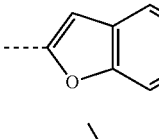 | B2 |
| B121 | 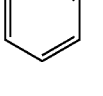 | --O—CH₂-- | O | 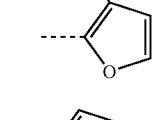 | B2 |
| B122 | 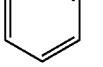 | --O—CH₂-- | O | 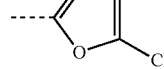 | B2 |

TABLE I-continued
| No. | R¹ | A¹—A² | Z | R² | Synthetic Example* |
|---|---|---|---|---|---|
| B123 |  | --O—CH₂-- | O | 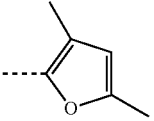 | B2 |
| B124 |  | --O—CH₂-- | O | 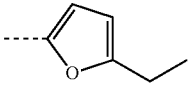 | B2 |
| B125 |  | --O—CH₂-- | O | 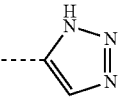 | B2 |
| B126 |  | --O—CH₂-- | O | 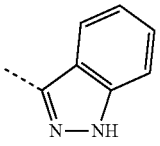 | B2 |
| B127 |  | --O—CH₂-- | --O-- | 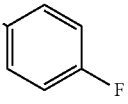 | B1 |
| B128 |  | --O—CH₂-- | --O-- | 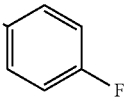 | B1 |
| B129 |  | --O—CH₂-- | --O-- | 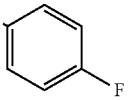 | B1 |
| B130 |  | --O—CH₂-- | --O-- | 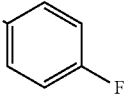 | B1 |
| B131 |  | --O—CH₂-- | --O-- | 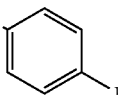 | B131 |
| B132 |  | --O—CH₂-- | --O-- | 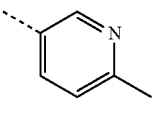 | B2 |
| B133 |  | --O—CH₂-- | --O-- | 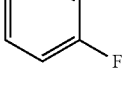 | B33 |
| B134 |  | --O—CH₂-- | --O-- | 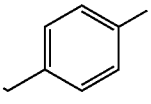 | B1 |

TABLE I-continued
| No. | R¹ | A¹—A² | Z | R² | Synthetic Example* |
|---|---|---|---|---|---|
| B135 |  | --O—CH₂-- | --O-- | 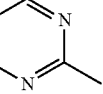 | B2 |
| B136 | 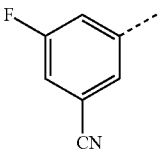 | --O—CH₂-- | --O-- | 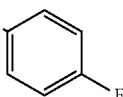 | B33 |
| B137 | 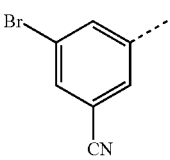 | --O—CH₂-- | --O-- | 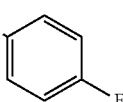 | B2 |
| B138 |  | --O—CH₂-- | --O-- |  | B2 |
| B139 |  | --O—CH₂-- | --O-- | 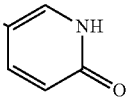 | B2 |
| B140 |  | --O—CH₂-- | --O-- | 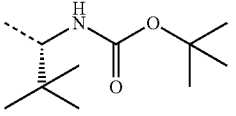 | B2 |
| B141 |  | --O—CH₂-- | --O-- | 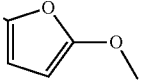 | B2 |
| B142 |  | --O—CH₂-- | --O-- |  | B1 |
| B143 |  | --O—CH₂-- | --O-- | 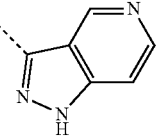 | B2 |
| B144 |  | --O—CH₂-- | --O-- | 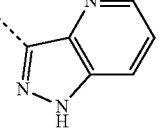 | B2 |
| B145 |  | --O—CH₂-- | --O-- | 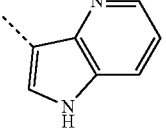 | B2 |

TABLE I-continued

| No. | R¹ | A¹—A² | Z | R² | Synthetic Example* |
|---|---|---|---|---|---|
| B146 | phenyl | --O—CH₂-- | --O-- | benzofuran-3-yl | B2 |
| B147 | phenyl | --O—CH₂-- | --O-- | 1H-pyrazolo[3,4-b]pyridin-3-yl | B2 |
| B148 | phenyl | --O—CH₂-- | --O-- | pyrimidin-5-yl | B2 |
| B149 | phenyl | --O—CH₂-- | --O-- | 5-methylpyrazin-2-yl | B2 |
| B150 | phenyl | --O—CH₂-- | --O-- | pyridazin-4-yl | B2 |
| B151 | pyrimidin-5-yl | --O—CH₂-- | --S-- | 4-fluorophenyl | B33 |
| B152 | pyrazin-2-yl | --O—CH₂-- | --O-- | 4-fluorophenyl | B33 |
| B153** | phenyl | --O—CH₂-- | --O-- | 1H-imidazol-2-yl | B2 |
| B154** | phenyl | --O—CH₂-- | --O-- | 1H-imidazol-4-yl | B2 |
| B155** | phenyl | --O—CH₂-- | --O-- | 1H-imidazol-5-ylmethyl | B2 |
| B156 | phenyl | --O—CH₂-- | --O-- | 1H-benzimidazol-5-yl | B1 |
| B157 | phenyl | --O—CH₂-- | --O-- | 5-methylisoxazol-3-yl | B1 |

TABLE I-continued

| No. | R¹ | A¹—A² | Z | R² | Synthetic Example* |
|---|---|---|---|---|---|
| B158 | phenyl | —O—CH₂— | —O— | N-methylimidazol-5-yl | B1 |
| B159 | phenyl | —O—CH₂— | —O— | thiazol-2-yl | B2 |
| B160 | phenyl | —O—CH₂— | —O— | pyrimidin-2-yl | B2 |
| B161 | phenyl | —O—CH₂— | —O— | 5-methyl-1,2,4-oxadiazol-3-yl | B2 |
| B162 | phenyl | —O—CH₂— | —O— | pyridazin-3-yl | B2 |

*Synthetic Example B1 is 5-[(4-fluorophenyl)carbonyl]-2-(phenoxymethyl)-4,5,6,7-tetrahydro[1,3]oxazolo[5,4-c]pyridine;

synthetic example B2 is 5-(cyclopropylacetyl)-2-(phenoxymethyl)-4,5,6,7-tetrahydro[1,3]oxazolo[5,4-c]pyridine;

synthetic example B3 is 5-[(3,5-difluorophenyl)carbonyl]-2-(phenoxymethyl)-4,5,6,7-tetrahydro[1,3]oxazolo[5,4-c]pyridine;

synthetic example B4 is 6-[(4-fluorophenyl)carbonyl]-2-(phenoxymethyl)-5,6,7,8-tetrahydro-4H-[1,3]oxazolo[4,5-d]azepine;

synthetic example B5 is 5-[(2-fluorophenyl)carbonyl]-2-(phenoxymethyl)-4,5,6,7-tetrahydro[1,3]thiazolo[5,4-c]pyridine;

synthetic example B31 is 6-(4-fluorobenzoyl)-5,6,7,8-tetrahydro-2-[(E)-2-phenylethenyl]-4H-oxazolo[4,5-d]azepine;

synthetic example B33 is 5-[(4-fluorophenyl)carbonyl]-2-{[(4-methylpyridin-2-yl)oxy]methyl}-4,5,6,7-tetrahydro[1,3]oxazolo[5,4-c]pyridine;

synthetic example B34 is 2-(phenoxymethyl)-5-(trifluoroacetyl)-4,5,6,7-tetrahydro[1,3]oxazolo[5,4-c]pyridine;

synthetic example B35 is 4-({5-[(4-fluorophenyl)carbonyl]-4,5,6,7-tetrahydro[1,3]oxazol[5,4-c]pyridin-2-yl}methoxy)phenol; and, synthetic example B36 is 5-[(1-methyl-1H-indol-2-yl)carbonyl]-2-(phenoxymethyl)-4,5,6,7-tetrahydro[1,3]oxazolo[5,4-c]pyridine.

**The indicated compounds were isolated as trifluoroacetate salts in a 1:1 stoichiometry of trifluoroacetate to the indicated compound.

TABLE II

| No. | R1 | A1—A2 | Z | m | n | R2 | Synthetic Example* |
|---|---|---|---|---|---|---|---|
| B4 | phenyl | —O—CH₂— | O | 2 | 2 | 4-fluorophenyl | B4 |
| B21 | phenyl | —O—CH₂— | O | 1 | 1 | 4-fluorophenyl | B1 |
| B22 | phenyl | —O—CH₂— | O | 2 | 1 | 4-fluorophenyl | B1 |
| B25 | phenyl | —O—CH₂— | S | 1 | 3 | 4-fluorophenyl | B1 |

TABLE II-continued

| No. | R1 | A1—A2 | Z | m | n | R2 | Synthetic Example* |
|---|---|---|---|---|---|---|---|
| B31 | phenyl | —CH=CH— | O | 2 | 2 | 4-fluorophenyl | B31 |
| B114 | phenyl | —O—CH₂— | O | 1 | 3 | 4-fluorophenyl | B1 |

*Synthetic Example B1 is 5-[(4-fluorophenyl)carbonyl]-2-(phenoxymethyl)-4,5,6,7-tetrahydro[1,3]oxazolo[5,4-c]pyridine;
synthetic example B4 is 6-[(4-fluorophenyl)carbonyl]-2-(phenoxymethyl)-5,6,7,8-tetrahydro-4H-[1,3]oxazolo[4,5-d]azepine; and
synthetic example B31 is 6-(4-fluorobenzoyl)-5,6,7,8-tetrahydro-2-[(E)-2-phenylethenyl]-4H-oxazolo[4,5-d]azepine.

TABLE III

| No. | (a) $[M + H]^+$ or (b) $[M − H]^-$ (as indicated) | $R_t$ | LC-MS Method | M.p. (° C.)* |
|---|---|---|---|---|
| B1 | 353 (a) | 2.82 | 2 | 103.7 |
| B2 | 313 (a) | 3.11 | 9 | n.d. |
| B3 | 371 (a) | 2.65 | 6 | n.d. |
| B4 | 367 (a) | 2.52 | 6 | n.d. |
| B5 | 369 (a) | 5.85 | 1 | 124.1-125.3 (WRS-2A) |
| B6 | 371 (a) | 2.57 | 6 | n.d. |
| B7 | 353 (a) | 3.43 | 10 | 66.0 |
| B8 | 371 (a) | 2.63 | 6 | 99.3 |
| B9 | 353 (a) | 3.36 | 10 | n.d. |
| B10 | 371 (a) | 2.78 | 11 | n.d. |
| B11 | 389 (a) | 3.60 | 9 | n.d. |
| B12 | 387 (a) | 5.94 | 1 | n.d. |
| B13 | 371 (a) | 2.51 | 6 | n.d. |
| B14 | 349 (a) | 2.88 | 6 | n.d. |
| B15 | 371 (a) | 2.57 | 6 | n.d. |
| B16 | 371 (a) | 2.51 | 6 | n.d. |
| B17 | 371 (a) | 2.62 | 6 | n.d. |
| B18 | 336 (a) | 1.67 | 6 | n.d. |
| B19 | 336 (a) | 1.67 | 6 | n.d. |
| B20 | 365 (a) | 3.94 | 9 | n.d. |
| B21 | 339 (a) | 2.51 | 6 | n.d. |
| B22 | 353 (a) | 2.57 | 6 | n.d. |
| B23 | 336 (a) | 1.86 | 6 | n.d. |
| B24 | 273 (a) | 1.49 | 6 | n.d. |
| B25 | 383 (a) | 2.72 | 6 | n.d. |
| B26 | 353 (a) | 2.54 | 6 | 204.7 |
| B27 | 371 (a) | 2.66 | 6 | 74.7 |
| B28 | 389 (a) | 2.73 | 6 | n.d. |
| B29 | 387 (b) | 2.77 | 6 | 139.2 |
| B30 | 389 (a) | 2.80 | 6 | 70 |
| B31 | 363 (a) | 3.06 | 8 | n.d. |
| B32 | 299 (a) | 1.97 | 6 | n.d. |
| B33 | 368 (a) | 2.43 | 6 | n.d. |
| B34 | 327 (a) | 2.75 | 8 | 71.8 |
| B35 | 369 (a) | 1.91 | 8 | 137.4 |
| B36 | 388 (a) | 3.29 | 8 | n.d. |
| B37 | 367 (a) | 3.42 | 12 | n.d. |
| B38 | 372 (a) | 2.20 | 6 | n.d. |
| B39 | 367 (a) | 3.42 | 6 | n.d. |
| B40 | 354 (a) | 2.15 | 6 | 113.1 |
| B41 | 350 (a) | 1.8 | 6 | n.d. |
| B42 | 350 (a) | 2.98 | 9 | n.d. |
| B43 | 360 (a) | 2.98 | 12 | 130.0 |
| B44 | 350 (a) | 3.14 | 9 | n.d. |
| B45 | 372 (a) | 2.31 | 6 | n.d. |
| B46 | 360 (a) | 2.25 | 6 | n.d. |
| B47 | 354 (a) | 1.97 | 6 | n.d. |
| B48 | 372 (a) | 1.93 | 6 | 141.8 |
| B49 | 360 (a) | 2.31 | 6 | 132.2 |
| B50 | 378 (a) | 2.47 | 6 | n.d. |
| B51 | 367 (a) | 2.82 | 8 | n.d. |
| B52 | 461 (a) | 0.85 | 13 | n.d. |
| B53 | 378 (a) | 2.52 | 8 | n.d. |
| B54 | 344 (a) | 0.65 | 13 | n.d. |
| B55 | 345 (a) | 0.78 | 13 | n.d. |
| B56 | 325 (a) | 0.69 | 13 | n.d. |
| B57 | 359 (a) | 0.79 | 13 | n.d. |
| B58 | 324 (a) | 0.74 | 13 | n.d. |
| B59 | 326 (a) | 0.69 | 13 | n.d. |
| B60 | 326 (a) | 0.72 | 13 | n.d. |
| B61 | 339 (a) | 0.77 | 13 | n.d. |
| B62 | 326 (a) | 0.76 | 13 | n.d. |
| B63 | 388 (a, M-56) | 0.86 | 13 | n.d. |
| B64 | 363 (a) | 3.69 | 10 | n.d. |
| B65 | 354 (a) | 2.73 | 12 | 98.3 |
| B66 | 367 (a) | 2.77 | 6 | n.d. |
| B67 | 372 (a) | 2.85 | 12 | >300 |
| B68 | 354 (a) | 2.1 | 6 | n.d. |
| B69 | 387 (a) | 2.91 | 6 | n.d. |
| B70 | 367 (a) | 2.79 | 6 | 137.2 |
| B71 | 340 (a) | 2.72 | 12 | 158.2 |
| B72 | 356 (a) | 2.1 | 6 | 102.6 |
| B73 | 354 (a) | 1.55 | 6 | n.d. |
| B74 | 370 (a) | 2.23 | 8 | n.d. |
| B75 | 419 (a) | 3.31 | 8 | >300 |
| B76 | 379 (a) | 3.36 | 9 | 121.3 |
| B77 | 375 (a) | 3.77 | 9 | 144.7 |
| B78 | 389 (a) | 3.62 | 10 | 90.1 |
| B79 | 386 (a) | 3.59 | 9 | 107.6 |
| B80 | 365 (a) | 2.76 | 8 | n.d. |
| B81 | 379 (a) | 2.95 | 8 | n.d. |
| B82 | 409 (a) | 3.22 | 8 | n.d. |
| B83 | 378 (a) | 2.95 | 8 | 102.9 |
| B84 | 338 (a) | 3.35 | 10 | 78.5 |
| B85 | 378 (a) | 2.60 | 8 | >300 |
| B86 | 354 (a) | 2.38 | 8 | 104.4 |
| B87 | 361 (a) | 2.21 | 8 | 156.4 |
| B88 | 326 (a) | 2.86 | 10 | 92.5 |
| B89 | 396 (a) | 3.48 | 10 | 102.9 |
| B90 | 378 (a) | 3.37 | 10 | 85 |
| B91 | 387 (a) | 2.11 | 8 | 156 |
| B92 | 396 (a) | 3.48 | 10 | 141.8 |
| B93 | 387 (a) | 2.7 | 8 | n.d. |
| B94 | 354 (a) | 2.97 | 10 | 128.7 |
| B95 | 375 (a) | 2.23 | 8 | 130.8 |
| B96 | 293 (a) | 2.37 | 8 | 143.3 |
| B97 | 396 (a) | 2.73 | 8 | 147.7 |
| B98 | 378 (a) | 2.60 | 8 | 128.2 |
| B99 | 393 (a) | 2.56 | 8 | 55.5 |
| B100 | 371 (a) | 2.62 | 6 | n.d. |
| B101 | 390 (a) | 2.35 | 6 | 109.8 |
| B102 | 371 (a) | 2.71 | 8 | n.d. |
| B103 | 352 (a) | 2.79 | 8 | n.d. |

TABLE III-continued

| No. | (a) [M + H]+ or (b) [M − H]− (as indicated) | $R_t$ | LC-MS Method | M.p. (° C.)* |
|---|---|---|---|---|
| B104 | 369 (a) | 2.34 | 8 | n.d. |
| B105 | 342 (a) | 1.37 | 8 | n.d. |
| B106 | 403 (a) | 0.82 | 13 | n.d. |
| B107 | 375 (a) | 0.73 | 13 | n.d. |
| B108 | 342 (a) | 0.72 | 13 | n.d. |
| B109 | 375 (a) | 3.10 | 8 | n.d. |
| B110 | 355 (a) | 2.83 | 8 | n.d. |
| B111 | 388 (a) | 2.92 | 8 | n.d. |
| B112 | 374 (a) | 0.81 | 13 | n.d. |
| B113 | 372 (a) | 2.98 | 8 | n.d. |
| B114 | 371 (a) | 2.57 | 6 | n.d. |
| B115 | 325 (a) | 0.68 | 13 | n.d. |
| B116 | 341 (a) | 0.75 | 13 | n.d. |
| B117 | 374 (a) | 0.77 | 13 | n.d. |
| B118 | 405 (a) | 0.78 | 13 | n.d. |
| B119 | 341 (a) | 0.76 | 13 | n.d. |
| B120 | 375 (a) | 0.85 | 13 | n.d. |
| B121 | 339 (a) | 0.81 | 13 | n.d. |
| B122 | 393 (a) | 0.85 | 13 | n.d. |
| B123 | 353 (a) | 0.82 | 13 | n.d. |
| B124 | 353 (a) | 0.83 | 13 | n.d. |
| B125 | 326 (a) | 0.60 | 13 | n.d. |
| B126 | 375 (a) | 0.73 | 13 | n.d. |
| B127 | 421 (a) | 2.86 | 3 | 78.9 |
| B128 | 421 (a) | 3.08 | 6 | 125.8 |
| B129 | 431 (a) | 3.54 | 12 | n.d. |
| B130 | 421 (a) | 2.99 | 6 | n.d. |
| B131 | 351 (a) | 2.73 | 6 | n.d. |
| B132 | 350 (a) | 1.92 | 6 | n.d. |
| B133 | 368 (a) | 2.52 | 6 | n.d. |
| B134 | 367 (a) | 2.82 | 6 | n.d. |
| B135 | 351 (a) | 2.67 | 9 | n.d. |
| B136 | 396 (a) | 2.73 | 8 | n.d. |
| B137 | 456 (a) | 4.34 | 14 | n.d. |
| B138 | 303 (a) | 0.591 | 13 | n.d. |
| B139 | 352 (a) | 0.530 | 13 | n.d. |
| B140 | 444 (a) | 0.685 | 13 | n.d. |
| B141 | 335 (a) | 2.41 | 8 | n.d. |
| B142 | 315 (a) | 2.70 | 8 | n.d. |
| B143 | 376 (a) | 0.543 | 13 | n.d. |
| B144 | 376 (a) | 0.559 | 13 | n.d. |
| B145 | 375 (a) | 0.533 | 13 | n.d. |
| B146 | 375 (a) | 0.788 | 13 | n.d. |
| B147 | 376 (a) | 0.641 | 13 | n.d. |
| B148 | 337 (a) | 1.73 | 6 | >300 |
| B149 | 358 (a) | 1.94 | 6 | 88.5 |
| B150 | 337 (a) | 1.48 | 6 | >300 |
| B151 | 355 (a) | 1.39 | 6 | 150 |
| B152 | 355 (a) | 1.71 | 6 | n.d. |
| B153 | 325 (a) | 0.53 | 13 | n.d. |
| B154 | 325 (a) | 0.51 | 13 | n.d. |
| B155 | 339 (a) | 0.60 | 13 | n.d. |
| B156 | 375 (a) | 2.67 | 10 | 198.1 |
| B157 | 340 (a) | 3.18 | 10 | n.d. |
| B158 | 339 (a) | 2.57 | 10 | n.d. |
| B159 | 342 (a) | 0.65 | 13 | n.d. |
| B160 | 337 (a) | 0.72 | 13 | n.d. |
| B161 | 341 (a) | 0.63 | 13 | n.d. |
| B162 | 337 (a) | 0.68 | 13 | n.d. |

*"n.d." indicates that the parameter was "not determined" for the indicated compound

8. Generation of Human mGluR5 Stable Cell Line

Human mGluR5a cDNA in pCMV6-XL6 mammalian expression plasmid was purchased from OriGene Technologies, Inc. (catalogue number SC326357) and subcloned into pcDNA3.1(−). Human embryonic kidney (HEK) 293A cells were then transfected with human mGluR5a pcDNA3.1(−) using LipofectAmine 2000 (Invitrogen) and monoclones were selected and tested for functional response using a $Ca^{2+}$ mobilization assay. Monoclones were named for the species ("H" for human) plus the location on the plate (e.g. "10H").

9. Cell-Based Functional Assay

HEK cells transfected with the human mGluR5a receptor were plated at 15,000 cells/well in clear-bottomed poly-D-lysine-coated assay plates (BD Falcon) in glutamate-glutamine-free growth medium and incubated overnight at 37° C. and 5% $CO_2$. The cell-line used to obtain the data reported herein was the H10H cell-line expressing the human mGluR5 receptor. Although the H10H cell-line was used to obtain the data shown herein, the H12H cell-line expressing the human mGluR5 receptor can also be used in these assays. The following day, the growth medium was removed and the cells were washed with assay buffer containing 1× Hank's balanced salt solution (Invitrogen, Carlsbad, Calif.), 20 mM HEPES, 2.5 mM probenecid, pH 7.4 and left with 20 µL of this reagent. Following this step, the cells were loaded with calcium indicator dye, fluo-4 AM, to a final concentration of 2 µM and incubated for 40-45 min at 37° C. The dye solution was removed and replaced with assay buffer. Cell plates were held for 10-15 min at room temperature and were then loaded into the Functional Drug Screening System 6000 (FDSS 6000, Hamamatsu, Japan).

After establishment of a fluorescence baseline for about 3 seconds, the compounds of the present invention were added to the cells, and the response in cells was measured. 2.3 minutes later an $EC_{20}$ concentration of the mGluR5 receptor agonist glutamate was added to the cells, and the response of the cells was measured for about 1.7 minutes. All test compounds were dissolved and diluted to a concentration of 10 mM in 100% DMSO and then serially diluted into assay buffer for a 2× stock solution in 0.6% DMSO; stock compounds were then added to the assay for a final DMSO concentration of 0.3% after the first addition to the assay well. Calcium fluorescence measures were recorded as fold over basal fluorescence; raw data was then normalized to the maximal response to glutamate. Potentiation of the agonist response of the mGluR5 receptor in the present invention was observed as an increase in response to submaximal concentrations of glutamate in the presence of compound compared to the response to glutamate in the absence of compound.

10. Data Analysis

The concentration-response curves of compounds of the present invention, obtained in the presence of $EC_{20}$ of mGluR5 receptor agonist glutamate to determine positive allosteric modulation, were generated using Microsoft Excel with IDBS XLfit add-ins. The raw data file containing all time points was used as the data source in the analysis template. This was saved by the FDSS as a tab-delimited text file. Data were normalized using a static ratio function ($F/F_0$) for each measurement of the total 350 values per well divided by each well's initial value. Data was then reduced as to peak amplitudes (Max−Initial Min) using a time range that starts approximately 1 second after the glutamate $EC_{20}$ addition and continues for approximately 40 seconds. This is sufficient time to capture the peak amplitude of the cellular calcium response. Individual amplitudes were expressed as % $E_{max}$ by multiplying each amplitude by 100 and then dividing the product by the mean of the amplitudes derived from the glutamate $EC_{Max}$-treated wells. $pEC_{50}$ values for test compounds were generated by fitting the normalized values versus the log of the test compound concentration (in mol/L) using a 4 parameter logistic equation where none of the parameters were fixed. Each of the three values collected at each concentration of test compound were weighted evenly. Individual values falling outside the 95% prediction limits of the curve fit were automatically excluded from the fit. A compound was designated as a positive allosteric modulator if the compound showed a concentration-dependent increase in the glutamate $EC_{20}$ addition. % $E_{max}$ for compounds may be estimated using the resulting corresponding parameter value determined using the curve fit or by taking an average of the overall maximum response at a single concentration. These two methods are in good agreement for curves with a clear plateau at the high concentration range. For data that show an increase in the $EC_{20}$ response, but, do not hit a plateau, the average of the maximum response at a single concentration is preferred. For consistency purposes across the range of potencies observed, all $E_{max}$ values reported in this application are calculated using the maximum average response at a single concentration. The % $E_{Max}$ value for each compound reported in this application is defined as the maximum % effect obtained in a concentration-response curve of that compound expressed as a percent of the response of a maximally effect concentration of glutamate. Table IV below shows the pharmacological data obtained for a selected set of compounds. For compounds showing a lower potency (e.g. as indicated by a lack of a plateau in the concentration response curve), but with a greater than a 20% increase in glutamate response, a potency of >10 µM ($pEC_{50}$<5) was estimated.

11. Activity of Compounds in Cell-Based Assays

Table IV below lists specific compounds as well as experimentally determined mGluR5 activity determined in a cell-based. The mGluR5 activity was determined using the metabotropic glutamate receptor activity assays in human embryonic kidney cells as described herein, wherein the human embryonic kidney cells were transfected with human mGluR5. The data in Table IV were obtained using the H10H cell-line which expresses recombinant human mGluR5. The compounds in Table IV were synthesized with methods identical or analogous to those described herein. The compound number corresponds to the compound numbers used in Tables I or II.

TABLE IV

| No. | $E_{max}$ (%) | $pEC_{50}$ |
|---|---|---|
| B1 | 84 | 6.42 |
| B2 | 58 | 5.45 |
| B3 | 47 | 6.88 |
| B4 | 76 | 5.47 |
| B5 | 64 | 6.06 |
| B6 | 92 | 6.30 |
| B7 | 80 | 6.95 |
| B8 | 74 | 6.66 |
| B9 | 68 | 6.31 |
| B10 | 75 | 6.18 |
| B11 | 60 | 6.19 |
| B12 | 69 | 6.06 |
| B13 | 68 | 5.94 |
| B14 | 48 | 5.81 |
| B15 | 74 | 6.43 |
| B16 | 82 | 6.43 |
| B17 | 86 | 6.60 |
| B18 | 69 | 5.33 |
| B19 | 69 | 5.32 |
| B20 | 72 | 5.82 |
| B21 | 81 | 6.05 |
| B22 | 65 | 5.79 |
| B23 | 54 | <5 |
| B24 | 53 | <5 |
| B25 | 83 | 6.35 |
| B26 | 80 | 6.60 |
| B27 | 76 | 6.73 |

TABLE IV-continued

| No. | $E_{max}$ (%) | $pEC_{50}$ |
|---|---|---|
| B28 | 72 | 6.24 |
| B29 | 75 | 6.62 |
| B30 | 44 | 6.83 |
| B31 | 47 | 5.74 |
| B32 | 39 | 5.52 |
| B33 | 69 | 5.70 |
| B34 | 10 | 6.05 |
| B35 | 57 | <5 |
| B36 | 56 | 6.30 |
| B37 | 57 | 5.62 |
| B38 | 60 | 5.39 |
| B39 | 49 | 6.82 |
| B40 | 67 | 5.53 |
| B41 | 50 | 5.22 |
| B42 | 58 | <5 |
| B43 | 64.5 | 6.53 |
| B44 | 64 | 5.7 |
| B45 | 66 | 5.51 |
| B46 | 63 | 5.79 |
| B47 | 56 | <5 |
| B48 | 62 | 5.49 |
| B49 | 58 | 5.51 |
| B50 | 57 | 6.43 |
| B51 | 61 | 5.92 |
| B52 | 51 | 5.24 |
| B53 | 66.5 | 5.90 |
| B54 | 24 | 5.38 |
| B55 | 14 | 5.98 |
| B56 | 50 | <5 |
| B57 | 57 | 7.14 |
| B58 | 31 | 6.22 |
| B59 | 40.5 | 5.53 |
| B60 | 39.5 | 5.70 |
| B61 | 52.5 | 6.52 |
| B62 | 34 | 6.47 |
| B63 | 47.5 | 5.37 |
| B64 | 59 | 6.09 |
| B65 | 49 | 5.43 |
| B66 | 63 | 5.92 |
| B67 | 49 | 5.52 |
| B68 | 71 | 5.62 |
| B69 | 72 | 5.85 |
| B70 | 56 | <5 |
| B71 | 21 | 6.48 |
| B72 | 21 | 6.92 |
| B73 | 73 | 5.78 |
| B74 | 57 | <5 |
| B75 | 70 | 6.03 |
| B76 | 75 | 6.15 |
| B77 | 62 | 6.00 |
| B78 | 71 | 6.48 |
| B79 | 59 | 5.74 |
| B80 | 60 | 5.72 |
| B81 | 63 | 5.72 |
| B82 | 62 | 5.7 |
| B83 | 67 | 6.3 |
| B84 | 53 | 6.59 |
| B85 | 57 | 6.66 |
| B86 | 53 | <5 |
| B87 | 72 | 5.89 |
| B88 | 53 | 5.75 |
| B89 | 61 | 5.66 |
| B90 | 58 | 5.66 |
| B91 | 59 | 5.63 |
| B92 | 52 | 6.73 |
| B93 | 52 | 5.73 |
| B94 | 68 | 5.95 |
| B95 | 64 | <5 |
| B96 | 51 | <5 |
| B97 | 81 | 5.98 |
| B98 | 73 | 6.13 |
| B99 | 57 | 6.11 |
| B100 | 60.5 | 6.61 |
| B101 | 67 | 5.48 |
| B102 | 66 | 6.34 |
| B103 | 78 | 6.44 |
| B104 | 62 | <5 |

TABLE IV-continued

| No. | $E_{max}$ (%) | $pEC_{50}$ |
|---|---|---|
| B105 | 22 | <4.52 |
| B106 | 61 | 7.07 |
| B107 | 65 | <5 |
| B108 | n.t. | n.t. |
| B109 | 73.5 | 7.18 |
| B110 | 57 | 6.70 |
| B111 | 70 | 6.54 |
| B112 | 12 | <4.52 |
| B113 | 45 | 6.58 |
| B114 | 92 | 6.30 |
| B115 | 46 | <5 |
| B116 | 33 | <5 |
| B117 | 69 | 6.60 |
| B118 | 37 | <5 |
| B119 | 22 | <5 |
| B120 | 67 | <5 |
| B121 | 51 | 6.72 |
| B122 | 68 | 6.67 |
| B123 | 45 | 6.77 |
| B124 | 56 | 6.37 |
| B125 | 45 | <5 |
| B126 | 72 | 6.41 |
| B127 | 40 | <5 |
| B128 | 25 | <4.52 |
| B129 | 27 | <4.52 |
| B130 | 22 | <4.52 |
| B131 | 24 | <4.52 |
| B132 | 49 | <5 |
| B133 | 32 | <5 |
| B134 | 61 | 5.92 |
| B135 | 36 | <5 |
| B136 | 45 | <5 |
| B137 | 24 | <4.52 |
| B138 | 27 | <4.52 |
| B139 | 10 | <4.52 |
| B140 | 58 | 5.77 |
| B141 | 35 | <4.52 |
| B142** | — | — |
| B143 | 68 | 5.85 |
| B144 | 39 | >5 |
| B145 | 50 | <5 |
| B146 | 61 | 6.39 |
| B147 | 74 | 6.44 |
| B148 | 43 | <5 |
| B149 | 31 | <4.52 |
| B150 | 44 | <5 |
| B151 | 28 | <5 |
| B152 | 36 | <5 |
| B153 | 32 | <4.52 |
| B154 | 26 | <4.52 |
| B155 | 30 | <4.52 |
| B156 | 14 | <4.52 |
| B157 | 45 | <5 |
| B158 | 27 | <4.52 |
| B159 | 23 | <4.52 |
| B160 | 16 | <4.52 |
| B161 | 20 | <5 |
| B162 | 17 | <4.52 |

*"n.t." indicates that the indicated compound was not tested in the assay.
**The indicated compound is a mGluR5 antagonist.

12. Prospective In Vitro Effects

The compounds provided in the present invention are allosteric modulators of mGluR5, in particular, positive allosteric modulators of mGluR5. These compounds appear to potentiate glutamate responses by binding to an allosteric site other than the glutamate binding site. The response of mGluR5 to a concentration of glutamate is increased when compounds of the formula given below are present. These compounds are expected to have their effect substantially at mGluR5 by virtue of their ability to enhance the function of the receptor. The behaviour of positive allosteric modulators was tested at mGluR5 using the intracellular $Ca^{2+}$ mobilization assay method described below which is suitable for the identification of such compounds. For example, disclosed compounds as described hereinbefore, or a pharmaceutically acceptable salt, hydrate, solvate, or polymorph thereof, are expected to show such in vitro effects. Moreover, compounds prepared using the disclosed synthetic methods are also expected to show such in vitro effects.

13. 5-[(4-fluorophenyl)carbonyl]-2-(phenoxymethyl)-4,5,6,7-tetrahydro[1,3]oxazolo[5,4-c]pyridine Activity in a Induced Hyperlocomotion Animal Model

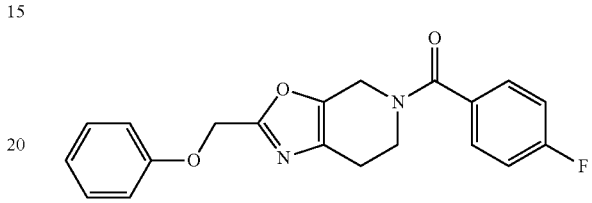

Locomotor activity was assessed as mean distance traveled (cm) in standard 16×16 photocell testing chambers measuring 43.2 cm (Length)×43.2 cm (Width)×30.5 cm (Height) (Med Associates, St. Albans, Vt.). Animals were habituated to individual activity chambers for at least 30 min prior to drug administration. Following administration of drug or vehicle, activity was recorded for a 90 minute time period. Data was expressed as the mean (±SEM) distance traveled recorded in 5 min intervals over the test period. The data was analyzed using repeated measures analysis of variance (ANOVA) followed by post-hoc testing using Dunnett's test, when appropriate. A difference was considered significant when $p \leq 0.05$.

Amphetamine sulfate was obtained from Sigma (Cat#A5880-1G; St. Louis, Mo.) and 10 mg was dissolved in 10 ml of water. The test compound, 5-[(4-fluorophenyl)carbonyl]-2-(phenoxymethyl)-4,5,6,7-tetrahydro[1,3]oxazolo[5,4-c]pyridine (labeled as "Example B1" in FIG. 4), was formulated in a volume of 10 ml with an amount of drug appropriate to the dosage indicated. The appropriate amount of compound was mixed into a 20% (w/v) 2-hydroxypropyl-β-cyclodextrin (2-HP-β-CD; indicated as "BCD" in FIG. 4) aqueous solution. The solution was formulated so that animals were injected with a volume equal to about 10× body weight. The mixture was then ultrahomogenized on ice for 2-3 minutes using the Dismembrator (Fisher Scientific Model 150T). Then the pH was checked using 0-14 EMD strips and adjusted to a pH of 6-7 if necessary. The mixture was then vortexed and stored in a warm sonication bath until time to be injected. Animals were administered samples of the following: (a) Amphetamine sulfate, 1 mg/kg, administered subcutaneously; and, (b) test compound, 5-(4-fluorobenzoyl)-4,5,6,7-tetrahydro-2-(phenoxymethyl)-oxazolo[5,4-c]pyridine, was administered at the doses indicated in FIG. 4 (indicated as "Example" therein), and was administered by oral gavage.

The study was carried out using male Sprague-Dawley rats weighing 225 g-275 g, between 2-3 months old (Harlan, Inc., Indianapolis, Ind.), were used. They were kept in the animal care facility certified by the American Association for the Accreditation of Laboratory Animal Care (AALAC) under a 12-hour light/dark cycle (lights on: 6 a.m.; lights off: 6 p.m.) and had free access to food and water. The experimental protocols performed during the light cycle were approved by the Institutional Animals Care and Use Committee of Vanderbilt University and conformed to the guidelines established by the National Research Council Guide for the Care and Use of Laboratory Animals.

The animals were habituated in Smart Open Field locomotor activity test chambers (Hamilton-Kinder, San Diego, Calif.) with 16×16 photobeams to automatically record locomotor activity for 30 min and then dosed with vehicle or test compound. The rats were then placed into cages. At 60 min, all rats were injected subcutaneously with 1 mg/kg amphetamine or vehicle and then monitored for an additional 60 min. Animals are monitored for a total of 120 minutes. Data are expressed as changes in ambulation defined as total number of beam breaks per 5 min periods.

Figure 4:
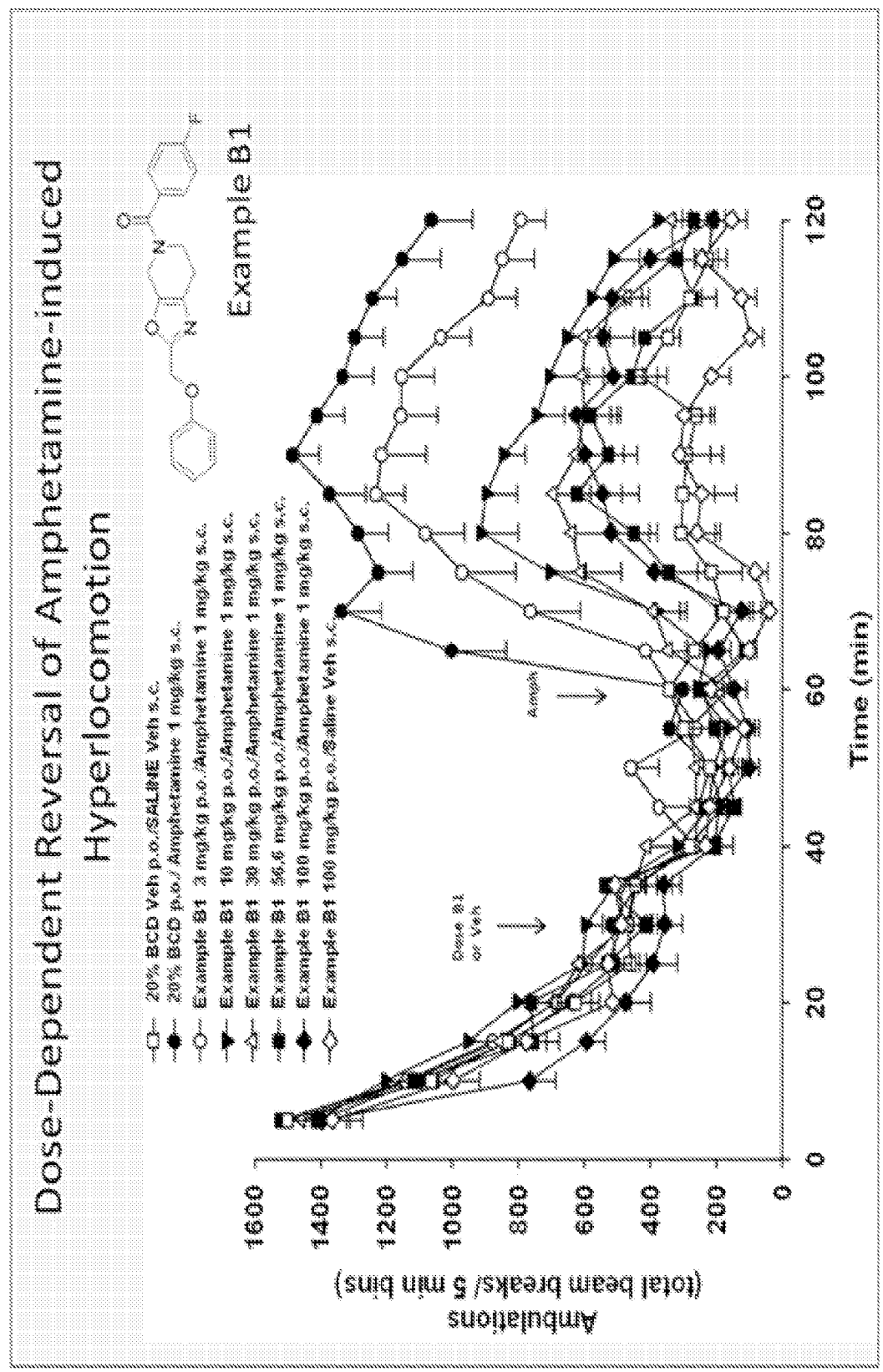
FIG. 4 shows a representative study demonstrating the dose-dependent reversal of amphetamine-induced hyperlocomotion by a representative disclosed compound.

The data for the dose-response studies were analyzed by a between-group analysis of variance. If there was a main effect of dose, then each dose group was compared with the BCD vehicle/amphetamine group. The calculations were performed using JMP IN 8 (SAS Institute, Cary, N.C.) statistical software and graphed using SigmaPlot9 (Saugua, Mass.). Dose-dependent results for reversal of amphetamine-induced hyperlocomotion by 5-[(4-fluorophenyl)carbonyl]-2-(phenoxymethyl)-4,5,6,7-tetrahydro[1,3]oxazolo[5,4-c]pyridine are shown in FIG. 4. The following abbreviations are used: (a) "Example B 1" refers to 5-[(4-fluorophenyl)carbonyl]-2-(phenoxymethyl)-4,5,6,7-tetrahydro[1,3]oxazolo[5,4-c]pyridine; (b) subcutaneous administration of compound is indicated by "sc"; (c) oral gavage administration is indicated by "po"; and (d) amphetamine sulfate is indicated as "Amphetamine." The time of administration of amphetamine sulfate is indicated in FIG. 4 by "AMP" and the corresponding arrow. The vehicle for test compound is 20% wt/v HP-β-CD (indicated as "BCD" in FIG. 4), and the vehicle for amphetamine is sterile water.

14. 5-[(3-fluorophenyl)carbonyl]-2-(phenoxymethyl)-4,5,6,7-tetrahydro[1,3]oxazolo[5,4-c]pyridine Activity in a Induced Hyperlocomotion Animal Model

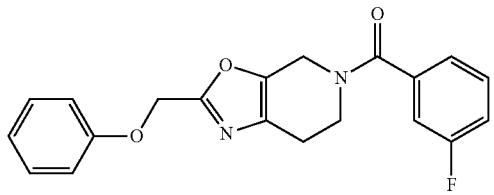 [SMILES: O=C(c1cccc(F)c1)N1CCc2nc(COc3ccccc3)oc2C1]

Figure 5:
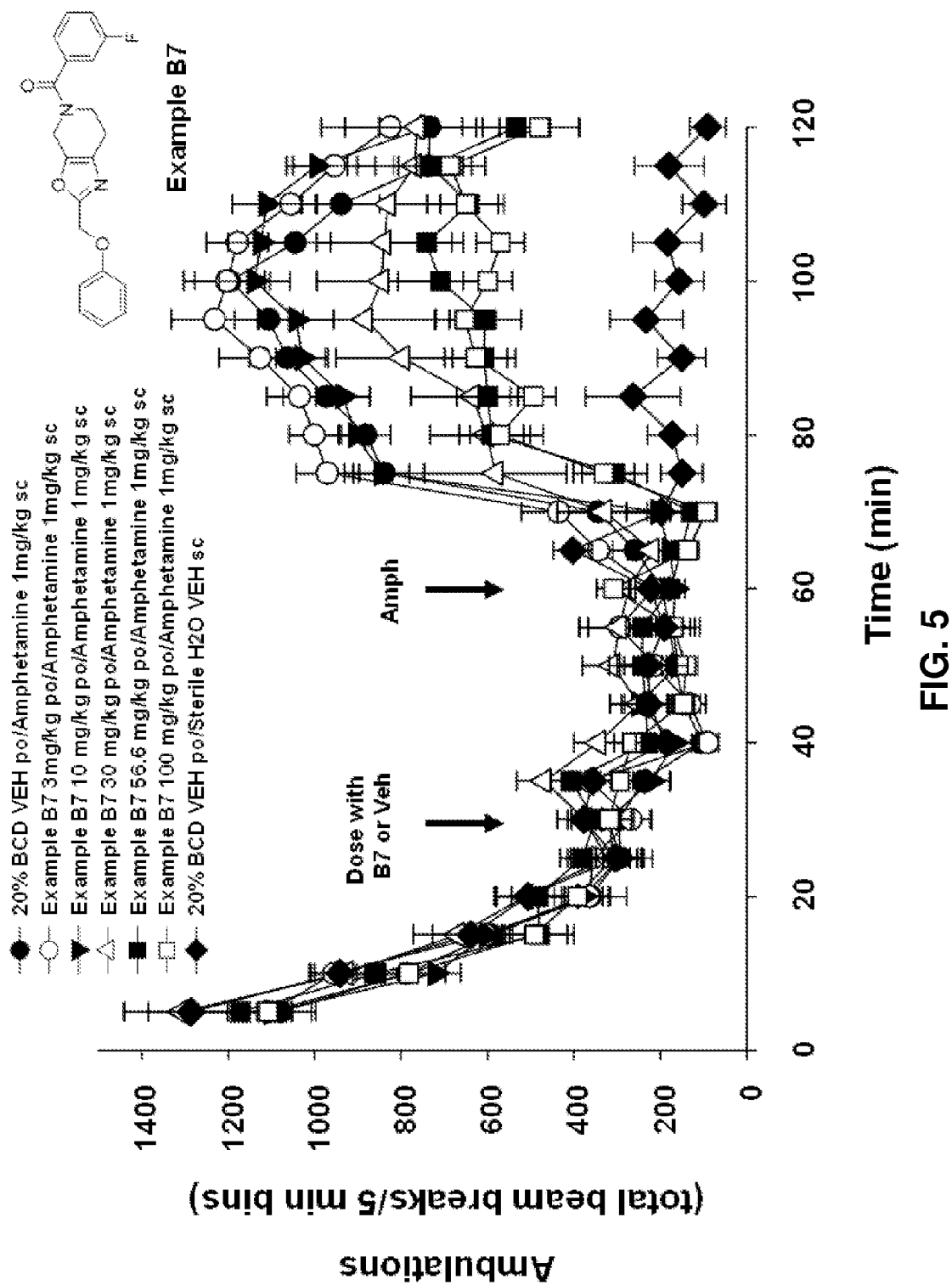
FIG. 5 shows a representative study demonstrating the dose-dependent reversal of amphetamine-induced hyperlocomotion by a representative disclosed compound.

The activity of 5-[(3-fluorophenyl)carbonyl]-2-(phenoxymethyl)-4,5,6,7-tetrahydro[1,3]oxazolo[5,4-c]pyridine (labeled as "Example B7" in FIG. 5) to reverse induced in hyperlocomotion in rats was determined using the conditions and protocol as described in the preceding example. The data are provided in FIG. 5.

15. 5-(4-fluorobenzoyl)-2-[(3-fluorophenoxy)methyl]-4,5,6,7-tetrahydro-oxazolo[5,4-c]pyridine Activity in a Induced Hyperlocomotion Animal Model

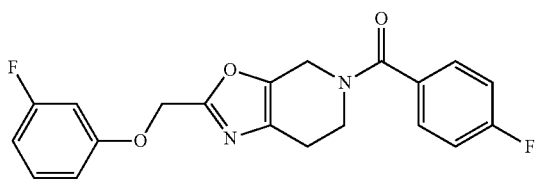 [SMILES: O=C(c1ccc(F)cc1)N1CCc2nc(COc3cccc(F)c3)oc2C1]

Figure 6:
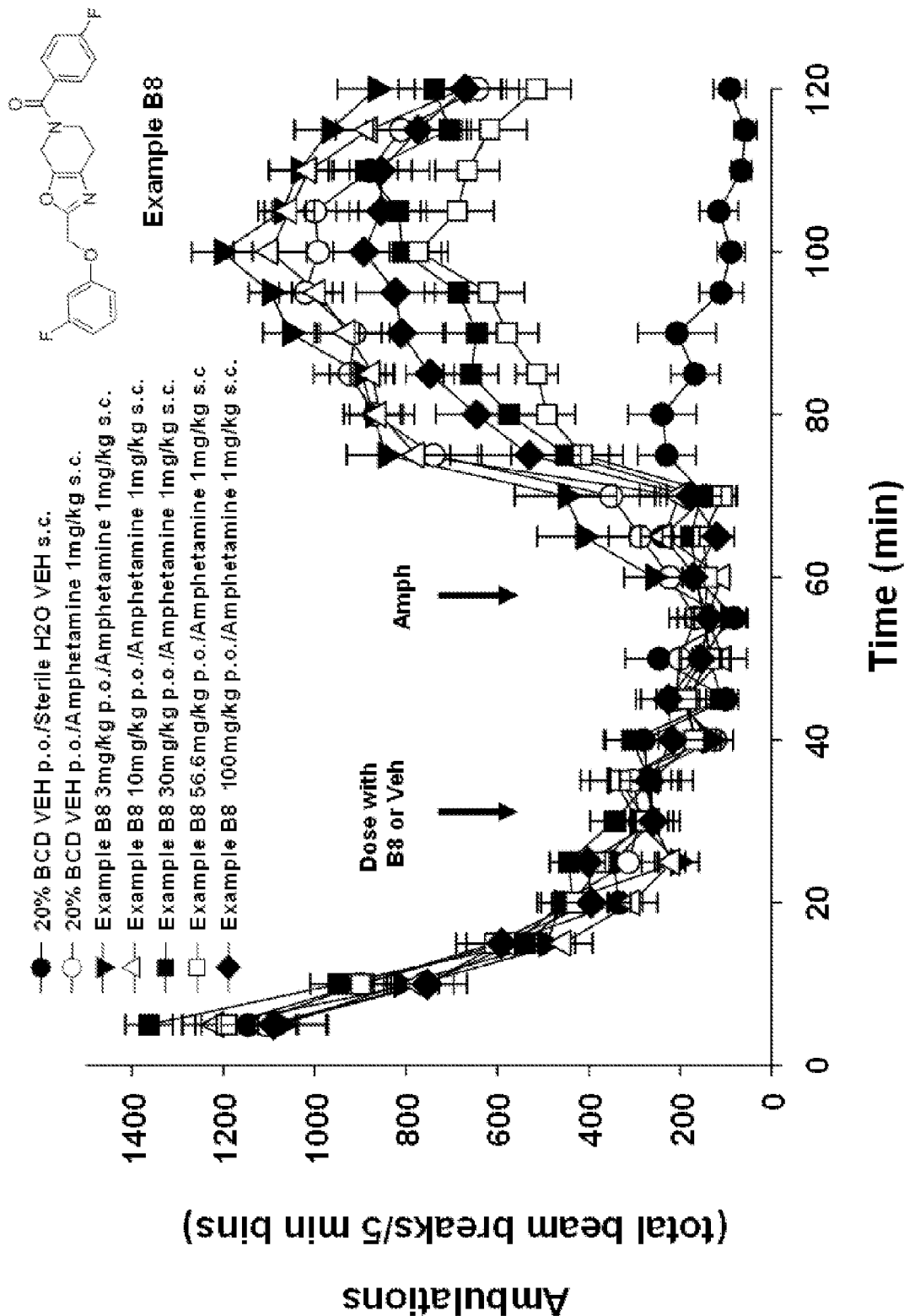
FIG. 6 shows a representative study demonstrating the dose-dependent reversal of amphetamine-induced hyperlocomotion by a representative disclosed compound.

The activity of 5-(4-fluorobenzoyl)-2-[(3-fluorophenoxy) methyl]-4,5,6,7-tetrahydro-oxazolo[5,4-c]pyridine (labeled as "Example B8" in FIG. 6) to reverse induced in hyperlocomotion in rats was determined using the conditions and protocol as described in the preceding example. The data are provided in FIG. 6.

16. Prospective In Vivo Effects

Generally clinically relevant antipsychotic agents (both typical and atypical) display efficacy in preclinical behavior challenge models. The compounds described in the preceding examples are expected to show in vivo effects in various animal behavioural challenge models known to the skilled person, such as amphetamine-induced or phencyclidine (PCP)-induced hyperlocomotion, and other models, such as NMDA receptor antagonist MK-801-induced locomotor activity conducted in rodent, such as rat or mouse, but may be conducted in other animal species as is convenient to the study goals. Compounds, products, and compositions disclosed herein are expected to show in vivo effects in various animal behavioural challenge models known to the skilled person, such as amphetamine-induced or phencyclidine (PCP)-induced hyperlocomotion in rodent, and other models, such as NMDA receptor antagonist MK-801-induced locomotor activity. These models are typically conducted in rodent, such as rat or mouse, but may be conducted in other animal species as is convenient to the study goals.

Compounds of the present invention are expected as a class to show in vivo efficacy in a preclinical rat behavioral model, where known, clinically useful antipsychotics display similar positive responses. For example, 5-[(4-fluorophenyl)carbonyl]-2-(phenoxymethyl)-4,5,6,7-tetrahydro[1,3]oxazolo[5,4-c]pyridine (Example B1), which is viewed as representative of the compounds of the present invention was tested in reverse amphetamine-induced hyperlocomotion in male Sprague-Dawley rates at doses ranging from 1 to 100 mg/kg by oral gavage (see discussion below).

For example, disclosed compounds as described hereinbefore, or a pharmaceutically acceptable salt, hydrate, solvate, or polymorph thereof, are expected to show such in vivo effects. Moreover, compounds prepared using the disclosed synthetic methods are also expected to show such in vivo effects.

17. Prophetic Pharmaceutical Composition Examples

"Active ingredient" as used throughout these examples relates to one or more disclosed compounds or products of disclosed methods of making as described hereinbefore, or a pharmaceutically acceptable salt, hydrate, solvate, or polymorph thereof. The following examples of the formulation of the compounds of the present invention in tablets, suspension, injectables and ointments are prophetic. Typical examples of recipes for the formulation of the invention are as given below.

a. Tablets

A tablet can be prepared as follows:

| Component | Amount |
|---|---|
| Active ingredient | 5 to 50 mg |
| Di-calcium phosphate | 20 mg |
| Lactose | 30 mg |

-continued

| Component | Amount |
| --- | --- |
| Talcum | 10 mg |
| Magnesium stearate | 5 |
| Potato starch | add to make total weight 200 mg |

In this Example, active ingredient can be replaced with the same amount of any of the compounds according to the present invention, in particular by the same amount of any of the exemplified compounds.

b. Suspension

An aqueous suspension is prepared for oral administration so that each 1 mL contains 1 to 5 mg of one of the active compounds, 50 mg of sodium carboxymethyl cellulose, 1 mg of sodium benzoate, 500 mg of sorbitol and water ad 1 ml.

c. Injectable

A parenteral composition is prepared by stirring 1.5% by weight of active ingredient of the invention in 10% by volume propylene glycol in water.

d. Ointment

An ointment can be prepared as follows:

| Component | Amount |
| --- | --- |
| Active ingredient | 5 to 1000 mg |
| Stearyl alcohol | 3 g |
| Lanoline | 5 g |
| White petroleum | 15 g |
| Water | add to make total weight 100 g |

In this Example, active ingredient can be replaced with the same amount of any of the compounds according to the present invention, in particular by the same amount of any of the exemplified compounds.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

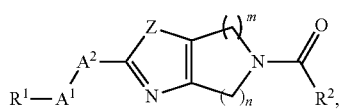

wherein Z is O or S;
wherein each of m and n is independently selected from 1, 2, and 3;
wherein -$A^1$-$A^2$- is —$OCH_2$—;
wherein $R^1$ is aryl or heteroaryl and substituted with 0, 1, 2, or 3 groups each independently selected from cyano, halo, hydroxyl, trialkylsiloxyl, $C_{1-4}$-alkyl, $C_{1-4}$-alkyloxy, monohalo-$C_{1-4}$-alkyl, and polyhalo-$C_{1-4}$-alkyl;
wherein $R^2$ is selected from $C_{1-6}$-alkyl, ($C_{1-6}$-alkyloxy)-$C_{1-6}$-alkyl, monohalo-$C_{1-6}$-alkyl, polyhalo-$C_{1-6}$-alkyl, $C_{3-8}$-cycloalkyl, ($C_{3-8}$-cycloalkyl)-$C_{1-6}$-alkyl, and —$OR^3$; and substituted with 0, 1, 2, or 3 groups each independently selected from cyano, halo, —$NH_2$, $C_{1-4}$-alkyl, $C_{1-4}$-alkyloxy, monohalo-$C_{1-4}$-alkyl, polyhalo-$C_{1-4}$-alkyl, $C_{1-4}$-alkyloxycarbonylamino, aryloxy-$C_{1-4}$-alkyl, aryloxy-$C_{1-4}$-alkyl, aryl-$C_{3-8}$-cycloalkyl, polyhalo-$C_{1-4}$-alkyloxy, $C_{1-4}$-alkyloxy-$C_{1-4}$-alkyl, $C_{1-4}$-alkyloxy-$C_{1-4}$-alkylheterocyclyl, and heterocyclyl substituted with carbonyl;
or wherein $R^2$ is selected from $Ar^1$, $Ar^1$-$C_{1-6}$-alkyl-, $Ar^1$-$C_{3-8}$-cycloalkyl-, $Ar^1$-oxy-$C_{1-4}$-alkyl; $Ar^2$, $Ar^2$-$C_{1-6}$-alkyl-, $Ar^2$-$C_{3-8}$-cycloalkyl-, $Ar^2$-oxy-$C_{1-4}$-alkyl; $Ar^3$, $Ar^3$-$C_{1-6}$-alkyl-, $Ar^1$-oxy-$C_{1-4}$-alkyl; $Ar^3$-$C_{3-8}$-cycloalkyl-, and $Ar^3$-oxy-$C_{1-4}$-alkyl;
wherein $Ar^1$, when present, is phenyl substituted with 0, 1, 2, or 3 groups each independently selected from halo, cyano, —$NH_2$, monoalkylamino, dialkylamino, $C_{1-4}$-alkyl, $C_{1-4}$-alkyloxy, $C_{1-4}$-alkyloxy-$C_{1-4}$-alkyl, monohalo-$C_{1-4}$-alkyl, polyhalo-$C_{1-4}$-alkyl, polyhalo-$C_{1-4}$-alkyloxy, and pentafluorosulfanyl;
wherein $Ar^2$, when present, is monocyclic heterocyclyl substituted with 0, 1, 2, or 3 groups each independently selected from halo, cyano, —$NH_2$, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl;
wherein $Ar^3$, when present, is bicyclic heterocyclyl substituted with 0, 1, 2, or 3 groups each independently selected from halo, cyano, amino, monoalkylamino, dialkylamino, $C_{1-4}$-alkyl, $C_{1-4}$-alkyloxy, and monohalo-$C_{1-4}$-alkyl, polyhalo-$C_{1-4}$-alkyl, and pentafluorosulfanyl;
wherein $R^3$ is selected from $Ar^4$ and $Ar^4$-$C_{1-6}$-alkyl-;
wherein $Ar^4$, when present, is phenyl substituted with 0, 1, 2, or 3 groups each independently selected from halo, cyano, $C_{1-4}$-alkyl, $C_{1-4}$-alkyloxy, monohalo-$C_{1-4}$-alkyl, and polyhalo-$C_{1-4}$-alkyl;
or a pharmaceutically acceptable salt thereof.

2. The compound of claim 1, wherein, $R^1$ is six-membered monocyclic aryl or six-membered monocyclic heteroaryl.

3. The compound of claim 2, wherein, $R^1$ is selected from phenyl, pyridinyl, pyrazinyl, pyridazinyl and pyrimidinyl, and substituted with 0, 1, 2, or 3 groups each independently selected from halo, C1-4-alkyl, C1-4-alkyloxy, monohalo-C1-4-alkyl, and polyhalo-C1-4-alkyl.

4. The compound of claim 1, wherein Z is O.

5. The compound of claim 1, wherein:
$R^1$ is phenyl substituted with 0, 1, 2, or 3 groups each independently selected from halo, $C_{1-4}$alkyl, $C_{1-4}$alkyloxy, and mono- and poly-halo$C_{1-4}$alkyl;
$R^2$ is selected from $C_{1-6}$alkyl, ($C_{1-6}$alkyloxy)$C_{1-6}$alkyl, mono- and polyhalo-$C_{1-6}$alkyl, $C_{3-8}$cycloalkyl, ($C_{3-8}$cycloalkyl)$C_{1-6}$alkyl, —$OR^3$, $Ar^1$, and heteroaryl;
$Ar^1$, when present, is phenyl substituted with 0, 1, 2, or 3 groups each independently selected from halo, cyano, $C_{1-4}$alkyl, $C_{1-4}$alkyloxy, and mono- and polyhalo-$C_{1-4}$alkyl; and
heteroaryl is pyridinyl; and optionally substituted with 1, 2 or 3 groups each independently selected from halo, $C_{1-4}$alkyl, cyano, $C_{1-4}$alkyloxy and mono- and polyhalo-$C_{1-4}$alkyl.

6. The compound of claim 1, having a structure represented by a formula:
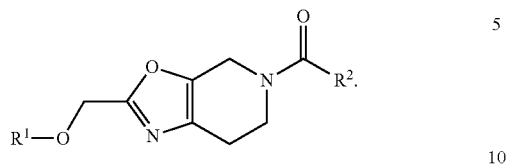
7. A pharmaceutical composition comprising a therapeutically effective amount of a compound of claim 1 and a pharmaceutically acceptable carrier.
* * * * *